US012497628B2

(12) United States Patent
Gordon-Kamm et al.

(10) Patent No.: US 12,497,628 B2
(45) **Date of Patent: *Dec. 16, 2025**

(54) METHODS AND COMPOSITIONS FOR THE INTRODUCTION AND REGULATED EXPRESSION OF GENES IN PLANTS

(71) Applicants: CORTEVA AGRISCIENCE LLC, Indianapolis, IN (US); PIONEER HI-BRED INTERNATIONAL, INC., Johnston, IA (US)

(72) Inventors: William James Gordon-Kamm, Urbandale, IA (US); Theodore M Klein, Wilmington, DE (US); Keith S Lowe, Johnston, IA (US); Kevin E McBride, Davis, CA (US); Christopher J Scelonge, Ankeny, IA (US); Ning Wang, Johnston, IA (US)

(73) Assignees: PIONEER HI-BRED INTERNATIONAL, INC.; CORTEVA AGRISCIENCE LLC

( * ) Notice: Subject to any disclaimer, the term of this patent is extended or adjusted under 35 U.S.C. 154(b) by 336 days.

This patent is subject to a terminal disclaimer.

(21) Appl. No.: 18/047,714

(22) Filed: Oct. 19, 2022

(65) Prior Publication Data

US 2023/0265448 A1 Aug. 24, 2023

Related U.S. Application Data

(63) Continuation of application No. 17/181,136, filed on Feb. 22, 2021, now Pat. No. 11,512,321, which is a continuation of application No. 15/673,609, filed on Aug. 10, 2017, now Pat. No. 10,968,458, which is a continuation of application No. 14/087,775, filed on Nov. 22, 2013, now Pat. No. 9,765,352, which is a continuation of application No. 12/982,180, filed on Dec. 30, 2010, now abandoned.

(60) Provisional application No. 61/291,257, filed on Dec. 30, 2009.

(51) Int. Cl.
*C12N 15/82* (2006.01)

(52) U.S. Cl.
CPC ..... *C12N 15/8241* (2013.01); *C12N 15/8213* (2013.01); *C12N 15/8216* (2013.01); *C12N 15/8262* (2013.01)

(58) Field of Classification Search
None
See application file for complete search history.

(56) References Cited

U.S. PATENT DOCUMENTS

| | | | |
|---|---|---|---|
| 5,451,513 | A | 9/1995 | Maliga et al. |
| 5,545,818 | A | 8/1996 | McBride et al. |
| 5,888,732 | A | 3/1999 | Hartley et al. |
| 6,093,874 | A | 7/2000 | Jofuku et al. |
| 6,143,557 | A | 11/2000 | Hartley et al. |
| 6,171,861 | B1 | 1/2001 | Hartley et al. |
| 6,270,969 | B1 | 8/2001 | Hartley et al. |
| 6,512,165 | B1 | 1/2003 | Ross et al. |
| 6,717,861 | B2 | 4/2004 | Jeong et al. |
| 7,151,170 | B1 | 12/2006 | Boutilier et al. |
| 7,253,000 | B2 | 8/2007 | Sivasankar et al. |
| 7,256,322 | B2 | 8/2007 | Lowe et al. |
| 7,348,468 | B1 | 3/2008 | Cahoon et al. |
| 7,402,734 | B2 | 7/2008 | Martinell et al. |
| 7,414,172 | B2 | 8/2008 | Pages et al. |
| 7,491,813 | B2 | 2/2009 | Wu et al. |
| 7,579,529 | B2 | 8/2009 | Gordon-Kamm et al. |
| 7,595,434 | B2 | 9/2009 | Fischer et al. |
| 7,700,829 | B2 | 4/2010 | Zuo et al. |
| 7,816,580 | B2 | 10/2010 | Zuo et al. |
| 8,420,893 | B2 | 4/2013 | Gordon-Kamm et al. |
| 9,765,352 | B2 | 9/2017 | Gordon-Kamm et al. |
| 10,968,458 | B2 * | 4/2021 | Gordon-Kamm ............ C12N 15/8213 |
| 11,512,321 | B2 * | 11/2022 | Gordon-Kamm ............ C12N 15/8216 |
| 2003/0049835 | A1 | 3/2003 | Helliwell et al. |
| 2003/0082813 | A1 | 5/2003 | Zuo et al. |
| 2003/0135889 | A1 | 7/2003 | Ross et al. |
| 2004/0101880 | A1 | 5/2004 | Rozwadowski |
| 2004/0166563 | A1 | 8/2004 | Lowe et al. |
| 2004/0247620 | A1 | 12/2004 | Julien |
| 2005/0044595 | A1 | 2/2005 | Arias et al. |

(Continued)

FOREIGN PATENT DOCUMENTS

| | | | |
|---|---|---|---|
| CA | 2554644 | A1 | 8/2005 |
| CA | 2 554 644 | C | 6/2015 |

(Continued)

OTHER PUBLICATIONS

Ahmadabadi et al 2007 (Transgenic Research 16: p. 437-448) (Year: 2007).*

(Continued)

*Primary Examiner* — Matthew R Keogh

(57) ABSTRACT

Compositions and methods are provided for the introduction and the regulated expression of genes in plants. Compositions include promoter constructs that provide a level of activity useful for the regulated expression of site-specific recombinases, while avoiding premature excision. Further provided are isolated polynucleotides encoding novel baby-boom polypeptides, expression cassettes, and plants comprising the same. Methods for the introduction of genes into plants are provided, including methods for plastid transformation and methods for the transformation of tissues from mature seeds and leaves.

3 Claims, 17 Drawing Sheets

Specification includes a Sequence Listing.

(56) References Cited

U.S. PATENT DOCUMENTS

| | | | |
|---|---|---|---|
| 2005/0257289 A1* | 11/2005 | Gordon-Kamm ............ C12N 15/8231 435/468 |
| 2006/0026716 A1 | 2/2006 | Sivasankar |
| 2007/0271628 A1 | 11/2007 | Lowe et al. |
| 2009/0041331 A1 | 2/2009 | Prakash |
| 2009/0094717 A1 | 4/2009 | Troukhan et al. |
| 2009/0235391 A1 | 9/2009 | Allen et al. |
| 2009/0328252 A1 | 12/2009 | Gordon-Kamm et al. |
| 2011/0167516 A1 | 7/2011 | Gordon-Kamm et al. |

FOREIGN PATENT DOCUMENTS

| | | |
|---|---|---|
| CN | 101445809 A | 6/2009 |
| EP | 1 033 405 A2 | 9/2000 |
| EP | 1 54 891 A1 | 11/2000 |
| EP | 1 057 891 A | 12/2000 |
| EP | 1 094 112 A2 | 4/2001 |
| EP | 1 185 656 A1 | 3/2002 |
| WO | 95/06722 A1 | 3/1995 |
| WO | 98/07842 A | 2/1998 |
| WO | 99/15178 | 4/1999 |
| WO | 99/21574 | 5/1999 |
| WO | 99/25841 A1 | 5/1999 |
| WO | 99/41974 | 8/1999 |
| WO | 00/40694 A | 7/2000 |
| WO | 00/75330 | 12/2000 |
| WO | 03/001902 A2 | 1/2001 |
| WO | 01/23575 A2 | 4/2001 |
| WO | 02/059294 A1 | 8/2002 |
| WO | 02/097059 A2 | 12/2002 |
| WO | 03/002751 A | 1/2003 |
| WO | 2005/049842 A2 | 6/2005 |
| WO | 02/063990 A2 | 7/2005 |
| WO | 2005/063990 A2 | 7/2005 |
| WO | 2005122750 A2 | 12/2005 |
| WO | 2007092992 A1 | 8/2007 |
| WO | 2007/137114 A2 | 11/2007 |
| WO | 2008/145757 A1 | 12/2008 |
| WO | 2009000013 A1 | 12/2008 |
| WO | 20090132057 A1 | 10/2009 |
| WO | 2009/154639 A2 | 12/2009 |

OTHER PUBLICATIONS

U.S. Appl. No. 14/215,110, filed Mar. 17, 2014, now U.S. Pat. No. 9,926,571.
U.S. Appl. No. 15/890,698, filed Feb. 7, 2018, now U.S. Pat. No. 10,443,064.
U.S. Appl. No. 16/540,889, filed Aug. 14, 2019.
U.S. Appl. No. 12/982,013, filed Dec. 30, 2010, now U.S. Pat. No. 8,704,041.
Cai, et al., "Targeted transgene integration in plant cells using designed zinc finger nucleases," Plant Mol Biol, Dec. 27, 2008 (Dec. 27, 2008), vol. 69, No. 6, pp. 699-709.
Cotsaftis, O., et al., "Enhancing gene targeting efficiency in higher plants: rice is on the move," Transgenic Research, Feb. 1, 2005 (Feb. 1, 2005), vol. 14, No. 1, pp. 1-14.
Deng, et al., "A novel method for induction of plant regeneration via somatic embryogenesis," Plant Science, Jul. 1, 2009 (Jul. 1, 2009), vol. 177, No. 1, pp. 43-48.
De Pater, S., et al., "ZFN-induced mutagenesis and gene-targeting in *Arabidopsis* through Agrobacterium-mediated floral dip transformation," Plant Biotechnology Journal, Oct. 2009 (Oct. 2009), vol. 7, No. 7245, pp. 821-835.
Puchta, Holger, "Gene replacement by homologous recombination in plants," Plant Molecular Biology, Jan. 1, 2002 (Jan. 1, 2002), vol. 48, No. 1/02, pp. 173-182.
Shukla, et al., "Precise genome modification in the crop species *Zea mays* using zinc-finger hucleases," Nature, May 2009 (May 2009), vol. 459, No. 7245, pp. 437-443.
International Search Report and Written Opinion for International Application PCT/US2010/062515, Mailed Aug. 11, 2011.
U.S. Appl. No. 13/790,641, filed Mar. 8, 2013, now U.S. Pat. No. 9,340,796.
U.S. Appl. No. 15/131,181, filed Apr. 18, 2016, now U.S. Pat. No. 10,113,175.
U.S. Appl. No. 15/956,794, filed Apr. 19, 2018.
U.S. Appl. No. 15/097,566, filed Apr. 13, 2016, now U.S. Pat. No. 10,125,372.
U.S. Appl. No. 16/142,766, filed Sep. 26, 2018.
U.S. Appl. No. 16/143,635, filed Sep. 27, 2018.
Written Opinion and Search Report for International Application PCT/US2010/062531.
U.S. Appl. No. 12/503,482, filed Jul. 15, 2009, now U.S. Pat. No. 8,420,893.
U.S. Appl. No. 11/045,802, filed Jan. 28, 2005, now U.S. Pat. No. 7,579,529.
U.S. Appl. No. 60/541,122, filed Feb. 2, 2004.
W. Zhang, et al. Cre/lox-mediated marker gene excision in transgenic maize (*Zea mays* L.) plants; Theoretical and Applied Genetics, 2003 pp. 1159-1168, vol. 107.
Katzen, Expert Opinions in Drug Discovery, 2007, pp. 571-589, 2:4.
Partial European Search Report, EP16167143, dated Aug. 8, 2016.
European Search Report—Application No. 16167143—Date of completion of the search—Aug. 1, 2006, Letter from EP Agent date Nov. 11, 2016.
Al-Abed, et al. 2006 (Planta 223: p. 1355-1360).
Ahmadabadi, et al. 2007 (Transgenic Research 16: p. 437-448).
Invitrogen Corporation, "Gateway® pDONR™ Vectors," User Manual, Version E, 2007, retrieved from http://wolfson.huji.ac.il/expression/gateway_pdonr_vectors.pdf, XP002627486.
Srinivasan, C., et al., "Heterologous expression of the BABY BOOM AP2/ERF transcription factor enhances the regeneration capacity of tobacco (*Nicotiana tabacum* L.)," Planta, 2007, vol. 225, pp. 341-351.
Al-Abed, D., et al., "Split-seed: a new tool for maize researchers," Planta, 2006, vol. 223, pp. 1355-1360.
Boutilier, K., et al., "Ectopic Expression of BABY BOOM Triggers a Conversation from Vegetative to Embryonic Growth," The Plant Cell, 2002, pp. 1737-1749, vol. 14.
Bowie, J.U., et al., "Deciphering the Message in Protein Sequences: Tolerance to Amino Acid Substitutions," Science. 1990, pp. 1306-1310, vol. 247.
Busk, P., et al., "Regulatory elements in vivo in the promoter of the abscisic acid responsive gene rab17 from maize," The Plant Journal, 1997, vol. 11(6), pp. 1285-1295.
El Ouakfaoui, et al., "Control of somatic embryogenesis and embryo development by AP2 transcription factors," Plant Mol Biol, published on-line 2010, 14 pages.
Feng, Q., et al., "Sequence and Analysis of Rice Chromosome 4," Nature, 2002, pp. 316-320, vol. 420.
Juang, X.-Q., et al., "High-frequency plant regeneration through callus initiation from mature embryos of maize (*Zea mays* L.)," Plant Cell Rep, 2004, vol. 22, pp. 793-800.
Kizis, D., et al., "Role of AP2/EREBP Transcription Factors in Gene Regulation During Abiotic Stress," FEBS Letters, 2001, pp. 187-189, vol. 498.
Marsch-Martinez, N., et al., "BOLITA, an *Arabidopsis* AP2/ERF-Like Transcription Factor that Affects Cell Expansion and Proliferation/Differentiation Pathway," Plant Mol Biol., 2006, pp. 825-843, vol. 62.
McConnell, J.R., et al., "Role of PHABULOSA and PHAVOLUTA in determining Radial Patterning in Shoots," Nature, 2001 pp. 709-713, vol. 411.
Mizukami, Y., and Robert L. Fischer, "Plant Organ Size Control: AINTEGUMENTA Regulates Growth and Cell Numbers During Organogenesis," PNAS, 2000, pp. 942-947, vol. 97(2).
Morcillo, et al., "EgAP2-1, an AINTEGUMENTA-like (AIL) gene expressed in meristematic and proliferating tissues of embryos in oil palm," Planta, 2007, vol. 226, pp. 1353-1362.
Riechmann, J. L., et al., "The AP2/EREBP Family of Plant Transcription Factors," Biological Chemistry, 1998, pp. 633-646, vol. 379.

(56) References Cited

OTHER PUBLICATIONS

Sasakl, T., et al. "The Genome Sequence and Structure of Rice Chromosome 1," Nature, 2002, pp. 312-316, vol. 420.
Sato, S., et al., "Structural Analysis of Arabidopsis Thaliana Chromosome 3. I. Sequence Features of the Regions of 4,504,864 bp Covered by Sixty P1 and TAC Clones," DNA Research, 2000, pp. 131-135, vol. 7.
Srinivasan, et al., "Heterologous expression of the BABY BOOM AP2/ERF transcription factor enhances the regeneration capacity of tobacco (*Nicotiana tabacum* L.)," Planta, 2007, vol. 225, pp. 341-351.
Staub, J, et al., "Accumulation of D1 polypeptide in tobacco plastids is regulated via the untranslated region of the psbA mRNA," The EMBO Journal, 1993, vol. 12(2), pp. 601-606.
Svab, Z., et al., "Stable transformation of plastids in higher plants," Proc. Natl. Acad. Sci. USA, 1990, vol. 87, pp. 8526-8530.
Svab, Z, et al., "High-frequency plastid transformation in tobacco by selection for a chimeric aadA gene," Proc. Natl. Acad. Sci. USA, 1993, vol. 90, pp. 913-917.
Theologis, A., et al. "Sequence and Analysis of Chromosome 1 of the Plant *Arabidopsis thaliana*," Nature, 2000, pp. 816-820, vol. 408.
Töpfer, R., et al., "Uptake and Transient Expression of Chimeric Genes in Seed-Derived Embryos," The Plant Cell, 1989, vol. 1, pp. 133-139.
Vilardell, et al., "Gene sequence, developmental expression, and protein phosphorylation of RAB-17 in maize," Plant Molecular Biology, 1990, vol. 14, pp. 423-432.
Vilardell, et al., "Regulation of the maize rab17 gene promoter in transgenic heterologous systems," Plant Molecular Biology, 1991, vol. 17, pp. 985-993.
Wang, Andrew S., "Callus induction and plant generation from maize mature embryos," Plant Cell Reports, 1987, vol. 6, pp. 360-362.
GenBank Report for Accession No. AAD30633, Direct Submission on Oct. 30, 2002.
GenBank Report for Accession No. AAL47205, Direct Submission on May 31, 2002.
GenBank Report for Accession No. AAM33800, Direct Submission on Oct. 10, 2002.
GenBank Report for Accession No. AAM33801, Direct Submission on Oct. 10, 2002.
GenBank Report for Accession No. AAM33803, Direct Submission on Oct. 10, 2002.
GenBank Report for Accession No. AY062108, Direct Submission on Oct. 31, 2001.
GenBank Report for Accession No. AY062180, Direct Submission on Oct. 31, 2001.
GenBank Report for Accession No. BAB02492, Direct Submission on Feb. 14, 2004.
GenBank Report for Accession No. BAB89946, Direct Submission on Aug. 31, 2004.
GenBank Report for Accession No. CAE02944, Direct Submission on Apr. 16, 2005.
GenBank Report for Accession No. CAE05555, Direct Submission on Apr. 16, 2005.
GenBank Report for Accession No. CC603221, 2003.
GenBank Report for Accession No. CC667986, Jun. 20, 2003.
GenBank Report for Accession No. CL960366, Sep. 22, 2004.
GenBank Report for Accession No. F96549, Direct Submission on Mar. 31, 2001.
GenBank Report for Accession No. NP175530, Direct Submission on Feb. 23, 2005.
GenBank Report for Accession No. NP197245, Direct Submission on Feb. 23, 2005.
Genbank Accession No. XM_00245882; Jul. 13, 2009.
Genbank Accession No. AY899909; Nov. 17, 2010.
"Rice Genome Annotation Project; Funded by the NSF," http://rice.plantbiology.msu.edu/cgibin/ORG_infopage.cgi?prf=LOC_Os02g40070.1, 2011, pp. 1-3.
Gidoni, D., et al., "Embryonal Recombination and Germline Inheritance of Recombined FRT Loci Mediated by Constitutively Expressed FLP in Tobacco," Euphytica, 2001, pp. 145-156, vol. 121.
Nardmann, J., andW.Werr, "The Shoot Stem Cell Niche in Angiosperms: Expression Patterns ofWUS Orthologues in Rice and Maize ImplyMajor Modifications in the Course of Mono- and Dicot Evolution," Mol. Biol. Evol., 2006, pp. 2492-2504, vol. 23(12).
International Preliminary Report on Patentability for International Application No. PCT/US2010/062531, mailed Jul. 12, 2012, 12 Pages.
International Search Report and Written Opinion for International Application No. PCT/US2005/003135, mailed Nov. 10, 2005, 14 Pages.
Ishida Y., et al., "Agrobacterium-Mediated Transformation of Maize," Nature Protocols, Nature Publishing Group, GB, Jul. 1, 2007, vol. 2, No. 7, pp. 1614-1621, Published online Jun. 21, 2007, DOI:10.1038/NPROT.2007.241, ISSN 1750-2799, XP009148413.
Bingkai H., et al., "Plastid Gene Transformation in Higher Plants," Advances in Bioengineering, Dec. 31, 2000, vol. 20, No. 1, pp. 70-73.

* cited by examiner

| | SEQ ID NO: | | |
|---|---|---|---|
| GmPLT3b | 70 | ( 221) | YEKELEEMKNMTRQEFVASLRRKSSGFSRGA |
| GmPLT3a | 71 | ( 217) | YEKELEEMKNMTRQEFVASLRRKSSGFSRGA |
| OsBBM | 14 | ( 353) | YEKELEEMKHMTRQEFVASLRRKSSGFSRGA |
| VvBBM | 6 | ( 278) | YEKEIEEMKHMTRQEYVASLRRKSSGFSRGA |
| GmBBM | 2 | ( 339) | YEKELEEMKHMTRQEYVASLRRKSSGFSRGA |
| ZmPLT3b | 72 | ( 210) | YEKELEEMKSMTRQEFIASLRRKSSGFSRGA |
| AtBBM | 22 | ( 280) | YEKEVEEMKHMTRQEYVASLRRKSSGFSRGA |
| OsPLT3 | 73 | ( 214) | YEKELEEMKHMTRQEFVASLRRKSSGFSRGA |
| ZmBBM | 10 | ( 343) | YEKELEDMKHMTRQEFVASLRRKSSGFSRGA |
| BnBBM2 | 26 | ( 280) | YEKEIEEMKHMTRQEYVASLRRKSSGFSRGA |
| BnBBM1 | 24 | ( 280) | YEKEVEEMKHMTRQEYVASLRRKSSGFSRGA |
| OsBBM1 | 16 | ( 238) | YEKELDEMKHMNRQEFVASLRRKSSGFSRGA |
| AtPLT3/AIL5 | 74 | ( 273) | YESELEEMKHMTRQEFVASLRRKSSGFSRGA |
| AtPLT2 | 75 | ( 260) | YEKEVEEMKNMTRQEFVASIRRKSSGFSRGA |
| SbPLT3b | 76 | ( 205) | YEKELEEMKSMTRQEFIASLRRKSSGFSRGA |
| OsAIL1 | 77 | ( 323) | YEKELEEMKHMTRQEFIAHLRRNSSGFSRGA |
| SbBBM | 4 | ( 347) | YEKELEDMKHMTRQEFVASLRRKSSGFSRGA |
| MtBBM | 8 | ( 329) | YEKEVEEMKHMTRQEYVASLRRKSSGFSRGA |
| SbBBM2 | 28 | ( 356) | YEKELEEMKHMTRQEYIAYLRRNSSGFSRGA |
| ZmBBM2 | 12 | ( 349) | YEKELEEMKHMTRQEYIAYLRRNSSGFSRGA |
| GmPLT2 | 78 | ( 234) | YEKELDEMKHMTRQEFVAAIRRKSSGFSRGA |
| OsBBM3 | 20 | ( 349) | YEKELEEMKHMTRQEYIAHLRRNSSGFSRGA |
| MtPLT3 | 79 | ( 229) | YEKEIDDMKNMTRQEFVASLRRKSSGFSRGA |
| ZmPLT3 | 80 | ( 197) | YEKEVEEMKNMTRQEFVASLRRKSSGFSRGA |
| OsPLT3b | 81 | ( 200) | YETELEEMKSMTRQEFIASLRRKSSGFSRGA |
| GmPLT1 | 82 | ( 239) | YEKELDEMKHMTRQEFVAAIRRKSSGFSRGA |
| AtPLT1 | 83 | ( 251) | YEKEVEEMKHMTRQEFVAAIRRKSSGFSRGA |
| OsBBM2 | 18 | ( 370) | YEKELDEMKHMTRQEYIAYLRRNSSGFSRGA |
| MtPLT1/2 | 84 | ( 233) | YEKEIDEMKHMTRQEFVASIRRKSSGFSRGA |
| ZmAIL1 | 85 | ( 341) | YEKELEEMKHMSRQEFIAHLRRNSSGFSRGA |
| GmAIL1 | 86 | ( 272) | YEKELEEMKHMTRQEFVANLRRKSSGFSRGA |
| SbPLT3 | 87 | ( 208) | YEKELEEMKTMTRQEFVASLRRKSSGFSRGA |
| GmAIL6 | 88 | ( 291) | YSKEVEEMKHVTKQEFIASLRRKSSGFSRGA |
| AtAIL6 | 89 | ( 323) | YSKEVEEMKHMTKQEFIASLRRKSSGFSRGA |
| MtAIL1 | 90 | ( 318) | YDKELEEMKHMTRQEFVANLRRKSSGFSRGA |
| SbAIL1 | 91 | ( 333) | YEKELEEMKHMSRQEFIAHLRRNSSGFSRGA |
| AtANT | 92 | ( 353) | YQKEIEDMKNMTRQEYVAHLRRKSSGFSRGA |
| SbANT | 93 | ( 353) | YQEELEEMKNMTRQEYVAHLRRKSSGFSRGA |
| GmAIL7 | 94 | ( 290) | YSKEVEEMKHVTKQEFIASLRRKSSGFSRGA |
| ZmANT | 67 | ( 372) | YREELEEMKNMTRQEYVAHLRRKSSGFSRGA |
| OsANT | 95 | ( 372) | YQEELEEMKNMSRQEYVAHLRRKSSGFSRGA |
| AtAIL7 | 96 | ( 243) | YSKELEEMNHMTKQEFIASLRRKSSGFSRGA |
| ZmANT2 | 97 | ( 354) | YRDELEEMKGMTRQEFVAHLRRRSSGFSRGA |
| MtANT | 98 | ( 380) | YQNQLEEMKNMTRQEYVAHLRRKSSGFSRGA |
| GmANT | 99 | ( 334) | YQVQLEEMKNMSRQEYVAHLRRKSSGFSRGA |
| AtAIL1 | 100 | ( 293) | YEKEIEELNNMNRQEFVAMLRRNSSGFSRGA |
| ZmANTr | 101 | ( 218) | YIREIQDMQNMNRRDVVASLRRKSSGFSRGA |
| AtWRI1 | 102 | ( 135) | YTKELEEMQRVTKEEYLASLRRQSSGFSRGV |
| AtAP2 | 103 | ( 191) | YDDDLKQMTNLTKEEFVHVLRRQSTGFPRGS |
| AtRAP2.7 | 104 | ( 213) | YEEDMKQVQNLSKEEFVHILRRQSTGFSRGS |
| Consensus | 48 | | YEKELEEMK1MTRQE23A4LRRKSSGFSRGA |

1= H or N; 2= F or Y; 3= V or I; 4=S or H

FIG. 2A

| | SEQ ID NO: | | |
|---|---|---|---|
| SbBBM | 4 | ( 378) | SIYRGVTRHHQHGRWQARIGRVAGNKDLYLGTFSTQEEAA |
| OsBBM | 13 | ( 384) | SIYRGVTRHHQHGRWQARIGRVAGNKDLYLGTFSTQEEAA |
| ZmBBM | 10 | ( 374) | SIYRGVTRHHQHGRWQARIGRVAGNKDLYLGTFSTQEEAA |
| GmPLT3b | 70 | ( 252) | SIYRGVTRHHQHGRWQARIGRVAGNKDLYLGTFSTQEEAA |
| GmPLT3a | 71 | ( 248) | SIYRGVTRHHQHGRWQARIGRVAGNKDLYLGTFSTQEEAA |
| MtPLT3 | 79 | ( 260) | SIYRGVTRHHQHGRWQARIGRVAGNKDLYLGTFSTQEEAA |
| AtPLT3/AIL5 | 74 | ( 304) | SMYRGVTRHHQHGRWQARIGRVAGNKDLYLGTFSTQEEAA |
| SbBBM2 | 28 | ( 387) | SKYRGVTRHHQHGRWQARIGRVAGNKDLYLGTFSTEEEAA |
| OsBBM2 | 18 | ( 401) | SKYRGVTRHHQHGRWQARIGRVAGNKDLYLGTFSTEEEAA |
| ZmBBM2 | 12 | ( 380) | SKYRGVTRHHQHGRWQARIGRVAGNKDLYLGTFSTEEEAA |
| GmPLT2 | 78 | ( 265) | SMYRGVTRHHQHGRWQARIGRVAGNKDLYLGTFSTEEEAA |
| GmPLT1 | 82 | ( 270) | SMYRGVTRHHQHGRWQARIGRVAGNKDLYLGTFSTEEEAA |
| ZmPLT3b | 72 | ( 241) | SIYRGVTRHHQHGRWQARIGRVAGNKDLYLGTFSTQEEAA |
| AtAIL1 | 100 | ( 324) | SVYRGVTRHHQHGRWQARIGRVAGNKDLYLGTFSTQEEAA |
| SbPLT3b | 76 | ( 236) | SIYRGVTRHHQHGRWQARIGRVAGNKDLYLGTFSTQEEAA |
| OsPLT3b | 81 | ( 231) | SIYRGVTRHHQHGRWQARIGRVAGNKDLYLGTFSTQEEAA |
| OsBBM1 | 16 | ( 269) | SIYRGVTRHHQHGRWQARIGRVAGNKDLYLGTFGTQEEAA |
| MtPLT1/2 | 84 | ( 264) | SMYRGVTRHHQHGRWQARIGRVAGNKDLYLGTFSTEEEAA |
| SbAIL1 | 91 | ( 364) | SMYRGVTRHHQHGRWQARIGRVAGNKDLYLGTFSTQEEAA |
| OsAIL1 | 77 | ( 354) | SMYRGVTRHHQHGRWQARIGRVAGNKDLYLGTFSTQEEAA |
| ZmAIL1 | 85 | ( 372) | SMYRGVTRHHQHGRWQARIGRVAGNKDLYLGTFSTQEEAA |
| AtPLT2 | 75 | ( 291) | SMYRGVTRHHQHGRWQARIGRVAGNKDLYLGTFSTEEEAA |
| AtPLT1 | 83 | ( 282) | SMYRGVTRHHQHGRWQARIGRVAGNKDLYLGTFSTEEEAA |
| OsBBM3 | 20 | ( 380) | SKYRGVTRHHQHGRWQARIGRVAGNKDIYLGTFSTEEEAA |
| VvBBM | 6 | ( 309) | SIYRGVTRHHQHGRWQARIGRVAGNKDLYLGTFSTQEEAA |
| GmANT | 99 | ( 365) | SIYRGVTRHHQHGRWQARIGRVAGNKDLYLGTFSTQEEAA |
| GmBBM | 2 | ( 370) | SIYRGVTRHHQHGRWQARIGRVAGNKDLYLGTFSTQEEAA |
| MtBBM | 8 | ( 360) | SIYRGVTRHHQHGRWQARIGRVAGNKDLYLGTFSTQEEAA |
| SbANT | 93 | ( 384) | SMYRGVTRHHQHGRWQARIGRVSGNKDLYLGTFSTQEEAA |
| GmAIL1 | 86 | ( 303) | SVYRGVTRHHQHGRWQARIGRVAGNKDLYLGTFSTQEEAA |
| MtAIL1 | 90 | ( 349) | SVYRGVTRHHQHGRWQARIGRVAGNKDLYLGTFSTQEEAA |
| SbPLT3 | 87 | ( 239) | SIYRGVTRHHQHGRWQARIGRVAGNKDLYLGTFSTEEEAA |
| ZmPLT3 | 80 | ( 228) | SIYRGVTRHHQHGRWQARIGRVAGNKDLYLGTFSTEEEAA |
| AtBBM | 22 | ( 311) | SIYRGVTRHHQHGRWQARIGRVAGNKDLYLGTFGTQEEAA |
| OsANT | 95 | ( 403) | SIYRGVTRHHQHGRWQARIGRVSGNKDLYLGTFSTQEEAA |
| BnBBM2 | 26 | ( 311) | SIYRGVTRHHQHGRWQARIGRVAGNKDLYLGTFGTQEEAA |
| BnBBM1 | 24 | ( 311) | SIYRGVTRHHQHGRWQARIGRVAGNKDLYLGTFGTQEEAA |
| MtANT | 98 | ( 412) | SMYRGVTRHHQHGRWQARIGRVAGNKDLYLGTFSTQEEAA |
| AtANT | 92 | ( 384) | SIYRGVTRHHQHGRWQARIGRVAGNKDLYLGTFGTQEEAA |
| AtAIL6 | 89 | ( 354) | SIYRGVTRHHQQGRWQARIGRVAGNKDLYLGTFATEEEAA |
| ZmANT | 67 | ( 403) | SIYRGVTRHHQHGRWQARIGRVSGNKDLYLGTFSTQEEAA |
| OsPLT3 | 73 | ( 245) | SIYRGVTRHHQHGRWQARIGRVAGNKDLYLGTFGTEEEAA |
| GmAIL7 | 94 | ( 321) | SIYRGVTRHHQQGRWQARIGRVAGNKDLYLGTFATEEEAA |
| GmAIL6 | 88 | ( 322) | SIYRGVTRHHQQGRWQARIGRVAGNKDLYLGTFATEEEAA |
| AtAIL7 | 96 | ( 274) | SIYRGVTRHHQQGRWQARIGRVAGNKDLYLGTFATEEEAA |
| ZmANT2 | 97 | ( 385) | SIYRGVTRHHQQGRWQSRIGRVAGNKDLYLGTFTTQEEAA |
| ZmANTr | 101 | ( 249) | SIYRGVTKHHQHGRWQARIGRVAGNKDLYLGTFATEQEAA |
| AtWRI1 | 102 | ( 166) | SKYRGVARHHHNGRWEARIGRVFGNKYLYLGTYNTQEEAA |
| Consensus | 49 | | S1YRGVTRHHQHGRWQARIGRVAGNKDLYLGTFST2EEAA |

FIG. 2B

| | SEQ ID NO: | | |
|---|---|---|---|
| SbBBM | 4 | ( 418) | EAYDIAAIKFRGLNAVTNFDMSR |
| OsBBM | 14 | ( 424) | EAYDIAAIKFRGLNAVTNFDMSR |
| ZmBBM | 10 | ( 414) | EAYDIAAIKFRGLNAVTNFDMSR |
| GmPLT3b | 70 | ( 292) | EAYDIAAIKFRGLNAVTNFDMSR |
| GmPLT3a | 71 | ( 288) | EAYDIAAIKFRGLNAVTNFDMSR |
| MtPLT3 | 79 | ( 300) | EAYDIAAIKFRGLNAVTNFDMSR |
| AtPLT3/AIL5 | 74 | ( 344) | EAYDIAAIKFRGLNAVTNFDISR |
| SbBBM2 | 28 | ( 427) | EAYDIAAIKFRGLNAVTNFDMSR |
| OsBBM2 | 18 | ( 441) | EAYDIAAIKFRGLNAVTNFDMSR |
| ZmBBM2 | 12 | ( 420) | EAYDIAAIKFRGLNAVTNFDMSR |
| GmPLT2 | 78 | ( 305) | EAYDIAAIKFRGLNAVTNFDMSR |
| GmPLT1 | 82 | ( 310) | EAYDIAAIKFRGLNAVTNFDMSR |
| ZmPLT3b | 72 | ( 281) | EAYDIAAIKFRGLNAVTNFDMSR |
| AtAIL1 | 100 | ( 364) | EAYDIAAIKFRGLNAVTNFDINR |
| SbPLT3b | 76 | ( 276) | EAYDIAAIKFRGLNAVTNFDMSR |
| OsPLT3b | 81 | ( 271) | EAYDIAAIKFRGLNAVTNFDMSR |
| OsBBM1 | 16 | ( 309) | EAYDIAAIKFRGLNAVTNFDMSR |
| MtPLT1/2 | 84 | ( 304) | EAYDIAAIKFRGLNAVTNFDMTR |
| SbAIL1 | 91 | ( 404) | EAYDIAAIKFRGLNAVTNFDISK |
| OsAIL1 | 77 | ( 394) | EAYDIAAIKFRGLNAVTNFDISK |
| ZmAIL1 | 85 | ( 412) | EAYDIAAIKFRGLNAVTNFDISK |
| AtPLT2 | 75 | ( 331) | EAYDIAAIKFRGLNAVTNFEINR |
| AtPLT1 | 83 | ( 322) | EAYDIAAIKFRGLNAVTNFEINR |
| OsBBM3 | 20 | ( 420) | EAYDIAAIKFRGLNAVTNFDMSR |
| VvBBM | 6 | ( 349) | EAYDIAAIKFRGLNAVTNFDMSR |
| GmANT | 99 | ( 405) | EAYDIAAIKFRGANAVTNFDISR |
| GmBBM | 2 | ( 410) | EAYDVAAIKFRGLSAVTNFDMSR |
| MtBBM | 8 | ( 400) | EAYDVAAIKFRGLSAVTNFDMSR |
| SbANT | 93 | ( 424) | EAYDIAAIKFRGLNAVTNFDITR |
| GmAIL1 | 86 | ( 343) | EAYDIAAIKFRGTSAVTNFDISR |
| MtAIL1 | 90 | ( 389) | EAYDIAAIKFRGTSAVTNFDISR |
| SbPLT3 | 87 | ( 279) | EAYDIAAIKFRGLNAVTNFEISR |
| ZmPLT3 | 80 | ( 268) | EAYDIAAIKFRGLNAVTNFEISR |
| AtBBM | 22 | ( 351) | EAYDIAAIKFRGLSAVTNFDMNR |
| OsANT | 95 | ( 443) | EAYDVAAIKFRGLNAVTNFDITR |
| BnBBM2 | 26 | ( 351) | EAYDIAAIKFRGLTAVTNFDMNR |
| BnBBM1 | 24 | ( 351) | EAYDIAAIKFRGLTAVTNFDMNR |
| MtANT | 98 | ( 452) | EAYDIAAIKFRGANAVTNFDIIK |
| AtANT | 92 | ( 424) | EAYDVAAIKFRGTNAVTNFDITR |
| AtAIL6 | 89 | ( 394) | EAYDIAAIKFRGINAVTNFEMNR |
| ZmANT | 67 | ( 443) | EAYDVAAIKFRGLSAVTNFDITR |
| OsPLT3 | 73 | ( 285) | EAYDIAAIKFRGLNAVTNFEIGR |
| GmAIL7 | 94 | ( 361) | EAYDIAAIKFRGANAVTNFEMNR |
| GmAIL6 | 88 | ( 362) | EAYDIAAIKFRGANAVTNFEMNR |
| AtAIL7 | 96 | ( 314) | EAYDIAAIKFRGINAVTNFEMNR |
| ZmANT2 | 97 | ( 425) | EAYDIAAIKFRGLNAVTNFDIAR |
| ZmANTr | 101 | ( 289) | EAYDIAALKFRGENAVTNFEPSR |
| AtWRI1 | 102 | ( 206) | AAYDMAAIEYRGANAVTNFDISN |
| Consensus | 49 | | EAYD3AAIKFRGLNAVTNF456R |

1= I or M; 2= Q or E; 3= I or V; 4= D or E; 5=M or I; 6=S or N

FIG. 2B (continued)

| | SEQ ID NO: | | |
|---|---|---|---|
| SbBBM | 4 | ( 276) | SIYRGVTRHRWTGRYEAHLWDNSCRREGQTRK |
| ZmBBM | 10 | ( 272) | SIYRGVTRHRWTGRYEAHLWDNSCRREGQTRK |
| VvBBM | 6 | ( 207) | SIYRGVTRHRWTGRYEAHLWDNSCRREGQTRK |
| GmBBM | 2 | ( 268) | SIYRGVTRHRWTGRYEAHLWDNSCRREGQTRK |
| OsBBM | 14 | ( 282) | SIYRGVTRHRWTGRYEAHLWDNSCRREGQTRK |
| MtBBM | 8 | ( 261) | SIYRGVTRHRWTGRYEAHLWDNSCRREGQTRK |
| SbBBM2 | 28 | ( 285) | SIYRGVTRHRWTGRYEAHLWDNSCRREGQSRK |
| OsBBM3 | 20 | ( 278) | SIYRGVTRHRWTGRYEAHLWDNSCRREGQSRK |
| OsBBM2 | 18 | ( 302) | SIYRGVTRHRWTGRYEAHLWDNSCRREGQSRK |
| ZmBBM2 | 12 | ( 278) | SIYRGVTRHRWTGRYEAHLWDNSCRREGQSRK |
| GmPLT3b | 70 | ( 150) | SIYRGVTRHRWTGRYEAHLWDNSCRREGQSRK |
| GmPLT3a | 71 | ( 146) | SIYRGVTRHRWTGRYEAHLWDNSCRREGQSRK |
| MtPLT3 | 79 | ( 161) | SIYRGVTRHRWTGRYEAHLWDNSCRREGQSRK |
| ZmANT | 67 | ( 301) | SQYRGVTRHRWTGRYEAHLWDNSCRKEGQTRK |
| GmAIL1 | 86 | ( 204) | SQYRGVTRHRWTGRYEAHLWDNSCRKEGQTRK |
| MtAIL1 | 90 | ( 250) | SQYRGVTRHRWTGRYEAHLWDNSCRKEGQTRK |
| SbANT | 93 | ( 285) | SQYRGVTRHRWTGRYEAHLWDNSCKKEGQTRK |
| OsANT | 95 | ( 304) | SQYRGVTRHRWTGRYEAHLWDNSCKKEGQTRK |
| GmANT | 99 | ( 267) | SQYRGVTRHRWTGRYEAHLWDNSCKKEGQTRK |
| GmAIL6 | 88 | ( 223) | SIYRGVTRHRWTGRYEAHLWDNSCRREGQARK |
| MtANT | 98 | ( 312) | SQYRGVTRHRWTGRYEAHLWDNSCKKEGQSRK |
| BnBBM2 | 26 | ( 209) | SIYRGVTRHRWTGRYEAHLWDNSCKREGQTRK |
| BnBBM1 | 24 | ( 209) | SIYRGVTRHRWTGRYEAHLWDNSCKREGQTRK |
| AtBBM | 22 | ( 209) | SIYRGVTRHRWTGRYEAHLWDNSCKREGQTRK |
| SbPLT3 | 87 | ( 140) | SIYRGVTRHRWTGRYEAHLWDNSCRREGQSRK |
| ZmPLT3 | 80 | ( 126) | SIYRGVTRHRWTGRYEAHLWDNSCRREGQSRK |
| GmPLT2 | 78 | ( 163) | SIYRGVTRHRWTGRYEAHLWDNSCRREGQSRK |
| GmPLT1 | 82 | ( 168) | SIYRGVTRHRWTGRYEAHLWDNSCRREGQSRK |
| OsPLT3 | 73 | ( 143) | SIYRGVTRHRWTGRYEAHLWDNSCRREGQSRK |
| GmAIL7 | 94 | ( 223) | SIYRGVTRHRWTGRYEAHLWDNSCRREGQARK |
| AtAIL6 | 89 | ( 253) | SIYRGVTRHRWTGRYEAHLWDNSCRREGQARK |
| AtPLT2 | 75 | ( 189) | SIYRGVTRHRWTGRYEAHLWDNSCRREGQSRK |
| OsPLT3b | 81 | ( 129) | SIYRGVTRHRWTGRYEAHLWDNSCRREGQSRK |
| AtPLT1 | 83 | ( 180) | SIYRGVTRHRWTGRYEAHLWDNSCRREGQSRK |
| AtPLT3/AIL5 | 74 | ( 202) | SIYRGVTRHRWTGRYEAHLWDNSCRREGQSRK |
| SbPLT3b | 76 | ( 134) | SIYRGVTRHRWTGRYEAHLWDNSCRREGQSRK |
| ZmPLT3b | 72 | ( 139) | SIYRGVTRHRWTGRYEAHLWDNSCRREGQSRK |
| ZmANT2 | 97 | ( 283) | SRYRGVTRHRWTGRYEAHLWDNSCRKDGQTRK |
| AtAIL7 | 96 | ( 172) | SIYRGVTRHRWTGRYEAHLWDNSCRREGQARK |
| MtPLT1/2 | 84 | ( 165) | SIYRGVTKHRWTGRYEAHLWDNSCRREGQSRK |
| SbAIL1 | 91 | ( 265) | SQFRGVTRHRWTGRYEAHLWDNTCRKEGQTRK |
| OsAIL1 | 77 | ( 252) | SQFRGVTRHRWTGRYEAHLWDNTCRKEGQTRK |
| ZmAIL1 | 85 | ( 270) | SQFRGVTRHRWTGRYEAHLWDNTCRKEGQTRK |
| OsBBM1 | 16 | ( 167) | SIYRGVTKHRWTGRYEAHLWDNSCRREGQTRK |
| AtAIL1 | 100 | ( 222) | SQYRGVTRHRWTGRYEAHLWDNSCKKEGQTRR |
| AtANT | 92 | ( 282) | SQYRGVTRHRWTGRYEAHLWDNSFKKEGHSRK |
| ZmANTr | 101 | ( 147) | SIYRGVTRHRWTGRYEAHLWDNTCRKEGQKRK |
| AtWRI1 | 102 | ( 64) | SIYRGVTRHRWTGRFEAHLWDKSSWNSIQNKK |
| Consensus | 50 | | S0YRGVTRHRWTGRYEAHLWDNSCR1EGQ2RK |

FIG. 2C

| | SEQ ID NO: | | |
|---|---|---|---|
| SbBBM | 4 | ( 308) | GRQGGYDKEEKAARAYDLAALKYWGPTTTTNFPVNN |
| ZmBBM | 10 | ( 307) | VYLGGYDKEEKAARAYDLAALKYWGATTTTNFPVSN |
| VvBBM | 6 | ( 242) | VYLGGYDKEEKAARAYDLAALKYWGTTTTTNFPISN |
| GmBBM | 2 | ( 303) | VYLGGYDKEEKAARAYDLAALKYWGTTTTTNFPISH |
| OsBBM | 14 | ( 317) | VYLGGYDKEEKAARAYDLAALKYWGPTTTTNFPVNN |
| MtBBM | 8 | ( 293) | GRQGGYDKEEKAARAYDLAALKYWGTTTTTNFPISH |
| SbBBM2 | 28 | ( 320) | VYLGGYDKEDKAARAYDLAALKYWGTTTTTNFPISN |
| OsBBM3 | 20 | ( 313) | VYLGGYDKEDKAARAYDLAALKYWGTTTTTNFPMSN |
| OsBBM2 | 18 | ( 334) | GRQGGYDKEDKAARAYDLAALKYWGTTTTTNFPISN |
| ZmBBM2 | 12 | ( 313) | VYLGGYDKEDKAARAYDLAALKYWGTTTTTNFPISN |
| GmPLT3b | 70 | ( 185) | VYLGGYDKEDKAARAYDLAALKYWGPTTTTNFPISN |
| GmPLT3a | 71 | ( 181) | VYLGGYDKEDKAARAYDLAALKYWGPTTTTNFPISN |
| MtPLT3 | 79 | ( 193) | GRQGGYDKEEKAARAYDLAALKYWGPTTTTNFPISN |
| ZmANT | 67 | ( 336) | VYLGGYDVEEKAARAYDLAALKYWGTSTHVNFPVED |
| GmAIL1 | 86 | ( 236) | GRQGGYDKEEKAAKAYDLAALKYWGPTTHINFPLST |
| MtAIL1 | 90 | ( 282) | GRQGGYDKEEKAAKAYDLAALKYWGPTTHINFPLST |
| SbANT | 93 | ( 317) | GRQGGYDMEEKAARAYDLAALKYWGPSTHINFPLED |
| OsANT | 95 | ( 336) | GRQGGYDMEEKAARAYDLAALKYWGPSTHINFPLED |
| GmANT | 99 | ( 298) | GRQGGYDMEEKAARAYDLAALKYWGPSTHINFSIEN |
| GmAIL6 | 88 | ( 255) | GRQGGYDKEEKAARAYDLAALKYWGPTATTNFPVSN |
| MtANT | 98 | ( 344) | GRQGGYDMEEKAARAYDQAALKYWGPSTHINFPLEN |
| BnBBM2 | 26 | ( 244) | VYLGGYDKEEKAARAYDLAALKYWGTTTTTNFPMSE |
| BnBBM1 | 24 | ( 244) | VYLGGYDKEEKAARAYDLAALKYWGTTTTTNFPMSE |
| AtBBM | 22 | ( 244) | VYLGGYDKEEKAARAYDLAALKYWGPTTTTNFPLSE |
| SbPLT3 | 87 | ( 172) | GRQGGYDKEEKAARAYDLAALKYWGSSTTTNFPVAE |
| ZmPLT3 | 80 | ( 161) | VYLGGYDKEEKAARAYDLAALKYWGSSTTTNFPVAE |
| GmPLT2 | 78 | ( 198) | VYLGGYDKEEKAARAYDLAALKYWGTSTTTNFPISN |
| GmPLT1 | 82 | ( 203) | VYLGGYDKEEKAARSYDLAALKYWGTSTTTNFPISN |
| OsPLT3 | 73 | ( 178) | VYLGGYDKEEKAARAYDLAALKYWGPSTTTNFPVAE |
| GmAIL7 | 94 | ( 254) | GRQGGYDKEEKAARSYDLAALKYWGPTATTNFPVSN |
| AtAIL6 | 89 | ( 287) | VYLGGYDKEDKAARAYDLAALKYWNATATTNFPITN |
| AtPLT2 | 75 | ( 224) | VYLGGYDKEEKAARAYDLAALKYWGPSTTTNFPITN |
| OsPLT3b | 81 | ( 164) | VYLGGYDKEEKAARAYDLAALKYWGPTTTTNFPVAN |
| AtPLT1 | 83 | ( 215) | VYLGGYDKEDKAARSYDLAALKYWGPSTTTNFPITN |
| AtPLT3/AIL5 | 74 | ( 237) | VYLGGYDKEDKAARAYDLAALKYWGPTTTTNFPISN |
| SbPLT3b | 76 | ( 169) | VYLGGYDKEEKAARAYDLAALKYWGATTTTNFPVSN |
| ZmPLT3b | 72 | ( 174) | VYLGGYDKEEKAARAYDLAALKYWGPTTTTNFPVSN |
| ZmANT2 | 97 | ( 318) | VYLGGYDTEDKAARAYDLAALKYWGPATHVNFPVEN |
| AtAIL7 | 96 | ( 207) | VYLGGYDKEDRAARAYDLAALKYWGSTATTNFPVSS |
| MtPLT1/2 | 84 | ( 197) | GRQGGYDKEEKAARSYDLAALKYWGTSTTTNFPVSN |
| SbAIL1 | 91 | ( 297) | GRQGGYDREEKAARAYDLAALKYWGPSTHINFPLSH |
| OsAIL1 | 77 | ( 287) | VYLGGYDKEEKAARAYDLAALKYWGPTTHINFPLST |
| ZmAIL1 | 85 | ( 305) | VYLGGYDREEKAARAYDLAALKYWGPSTHINFPLSH |
| OsBBM1 | 16 | ( 202) | VYLGGYDKEEKAARAYDLAALKYWGTTTTTNFPVSN |
| AtAIL1 | 100 | ( 257) | VYLGGYDEEEKAARAYDLAALKYWGPTTHLNFPLSN |
| AtANT | 92 | ( 317) | VYLGGYDMEEKAARAYDLAALKYWGPSTHTNFSAEN |
| ZmANTr | 101 | ( 182) | VYLGGYDKEDKAARAYDIAALKYWGDNATTNFPREN |
| AtWRI1 | 102 | ( 99) | VYLGAYDSEEAAAHTYDLAALKYWGPDTILNFPAET |
| Consensus | 50 | | 345GGYDKE6KAARAYDLAALKYWG72T89NFP*SN |

0=I or Q; 1=R or K; 2= S or T; 3= V or G; 4= Y or R; 5=L or Q; 6=E or D; 7= P or T; 8=T or H; 9=T or I; *=I, V, or L

FIG. 2C (continued)

| | SEQ ID NO: | | |
|---|---|---|---|
| SbBBM2 | 28 | ( 113) | AVEDSEPKLEDFLGGNSFVSEH |
| OsBBM2 | 18 | ( 108) | AVEETEPKLEDFLGGNSFVSEQ |
| ZmBBM2 | 12 | ( 110) | AVEDSEPKLEDFLGGNSFVSDQ |
| SbBBM | 4 | ( 55) | SALVAEPKLEDFLGGISFSEQH |
| ZmBBM | 10 | ( 56) | SALVAEPKLEDFLGGISFSEQH |
| OsBBM | 14 | ( 61) | SALVAEPKLEDFLGGISFSEQQ |
| GmAIL6 | 88 | ( 77) | HVPPPPPKLEDFLGDSSAVMRY |
| MtBBM | 8 | ( 106) | NNQQAQPKLENFLGGHSFTDHQ |
| GmAIL7 | 94 | ( 75) | SVSHAPPKLEDFLGDSSAVMRY |
| MtAIL1 | 90 | ( 85) | NSNEEGPKLEDFLGCYSNQNQN |
| GmANT | 99 | ( 97) | MVPTSSPKLEDFLGGATMGTHE |
| AtAIL6 | 89 | ( 71) | HSQNHIPKLEDFLGDSSSIVRY |
| VvBBM | 6 | ( 103) | NLENQEPKLENFLGCRSFADHE |
| GmBBM | 2 | ( 107) | QQQQQQPKLENFLGGHSFGEHE |
| ZmANT2 | 97 | ( 106) | MVPSSPPKLEDFLGGGNGGGQE |
| BnBBM2 | 26 | ( 89) | NDEQDGPKLENFLGRTTTIYNT |
| BnBBM1 | 24 | ( 89) | NDEQDGPKLENFLGRTTTIYNT |
| OsPLT3 | 73 | ( 37) | AGAAPPPKLEDFLGGGCNGGSS |
| GmAIL1 | 86 | ( 50) | NSNEEGPKLEDFLGCYSNSPAK |
| AtBBM | 22 | ( 91) | NNEQNGPKLENFLGRTTTIYNT |
| GmPLT2 | 78 | ( 54) | HSSNEIPKVADFLGVSKSENQS |
| MtPLT1/2 | 84 | ( 54) | HNSNEVPKVADFLGVCKSENHS |
| GmPLT3b | 70 | ( 68) | SIFTGGPKFEDFLGGSAATATT |
| SbPLT3 | 87 | ( 35) | AGAAPPPKLEDFLGGGVINGES |
| ZmPLT3 | 80 | ( 36) | AGAAPPPKLEDFLGGGVATGGP |
| GmPLT3a | 71 | ( 64) | SIFTGAPKFEDFLGGSSATATA |
| GmPLT1 | 82 | ( 54) | HSSSEVPKVADFLGVSKSENES |
| AtPLT3/AIL5 | 74 | ( 95) | SVYPGGPKLENFLGGGASTTTT |
| AtAIL7 | 96 | ( 13) | HSQTQIPKLEDFLGDSFVRYSD |
| SbAIL1 | 91 | ( 72) | AAEANGPKLEDFMSVTCSSNNK |
| OsBBM1 | 16 | ( 47) | GEETAAPKLEDFLGMQVQQETA |
| AtPLT2 | 75 | ( 58) | GEGGEVPKVADFLGVSKSGDHH |
| ZmAIL1 | 85 | ( 76) | AAEAKGPKLEDFMSITCSNKSS |
| ZmANT | 67 | ( 123) | VVSSSSPKLEDFLGASASTAMA |
| OsAIL1 | 77 | ( 66) | HAEAKDPKLEDFMSVSYSNKSS |
| AtPLT1 | 83 | ( 52) | DEGGEVPKVADFLGVSKPDENQ |
| OsBBM3 | 20 | ( 109) | DGVGEAPKLENFLDGNSFSDVH |
| MtANT | 98 | ( 110) | MSTTSAPKLENFLGNEAMGTPH |
| SbANT | 93 | ( 103) | QPDHHGPKLEDFLGAAAAQSQA |
| AtANT | 92 | ( 108) | HHQDSSPKVEDFFGTHHNNTSH |
| OsANT | 95 | ( 124) | VVVSASPKLEDFLGAGPAMALS |
| MtPLT3 | 79 | ( 79) | SIFTGGHKFEDFLGSSVAPTRT |
| AtAIL1 | 100 | ( 41) | HHDEDVPKVEDLLSNSHQTEYP |
| OsPLT3b | 81 | ( 42) | GPAEGAPKMEDFLGGLGGGGGA |
| ZmPLT3b | 72 | ( 44) | AVEESPRTVEDFLGGVGGAGAP |
| SbPLT3b | 76 | ( 45) | TVEESPKMVEDFLGGVGGAGAP |
| Consensus | 51 | | PK123FLG |

1= L or V; 2= E or A; 3= D or N

FIG. 2D

| | SEQ ID NO: | | |
|---|---|---|---|
| VvBBM | 6 | ( 377) | ILESSTLPIGGAAKRL |
| MtBBM | 8 | ( 428) | ILESSTLPIGGAAKRL |
| GmBBM | 2 | ( 438) | ILESTTLPIGGAAKRL |
| SbBBM2 | 28 | ( 455) | ILESSTLPVGGAARRL |
| OsBBM2 | 18 | ( 469) | ILESSTLPVGGAARRL |
| ZmBBM2 | 12 | ( 448) | ILESSTLPVGGAARRL |
| AtPLT1 | 83 | ( 350) | ILESSTLPIGGGAAKR |
| OsBBM3 | 20 | ( 448) | ILDSSTLPVGGAARRL |
| GmPLT2 | 78 | ( 333) | ILESNTLPIGGGAAKR |
| GmPLT1 | 82 | ( 338) | ILESNTLPIGGGAAKR |
| MtPLT1/2 | 84 | ( 332) | ILESNTLPIGGGAAKR |
| AtPLT2 | 75 | ( 359) | ILESNTLPIGGGAAKR |
| BnBBM2 | 26 | ( 379) | ILESPSLPIGSAAKRL |
| BnBBM1 | 24 | ( 379) | ILESPSLPIGSAAKRL |
| SbBBM | 4 | ( 446) | ILDSSALPIGSAAKRL |
| ZmBBM | 10 | ( 442) | ILDSSALPIGSAAKRL |
| OsANT | 95 | ( 471) | ILESSTLLPGELARRK |
| AtAIL6 | 89 | ( 421) | AIMKSALPIGGAAKRL |
| AtBBM | 22 | ( 379) | ILESPSLPIGSSAKRL |
| GmAIL7 | 94 | ( 388) | AIMKSSLPVGGAAKRL |
| GmAIL6 | 88 | ( 389) | AIMKSSLPVGGAAKRL |
| SbANT | 93 | ( 452) | IMASNTLLPGDLARRR |
| ZmANT | 67 | ( 471) | IMESSTLLPGEQVRRR |
| SbAIL1 | 91 | ( 432) | ICASTHLIGGGDACRR |
| ZmAIL1 | 85 | ( 440) | ICASTHLIGGGDACRR |
| OsBBM1 | 16 | ( 337) | IIESSNLPIGTGTTRR |
| GmAIL1 | 86 | ( 371) | ICSSSTLIAGDLAKRS |
| OsBBM | 14 | ( 452) | ILDSAALPVGTAAKRL |
| OsAIL1 | 77 | ( 422) | ICSSTHLIGGDLACRR |
| GmANT | 99 | ( 433) | IMASSNLLAGELARRN |
| MtAIL1 | 90 | ( 417) | ICSSSTLITGDLAKRS |
| GmPLT3b | 70 | ( 319) | SIANSTLPIGGLSGKN |
| GmPLT3a | 71 | ( 315) | SIANSTLPIGGLSGKN |
| AtANT | 92 | ( 452) | IMSSNTLLSGELARRN |
| AtAIL7 | 96 | ( 341) | AVMNSSLPVGGAAAKR |
| SbPLT3b | 76 | ( 303) | SILNSDLPVGGGAAGR |
| OsPLT3b | 81 | ( 298) | SILNSDLPVGGGAATR |
| ZmANT2 | 97 | ( 453) | IMESSTLLAVEEARKV |
| MtPLT3 | 79 | ( 327) | SIANCSLPIGGLSNKN |
| ZmPLT3b | 72 | ( 308) | SILSSDLPVGGGASGR |
| OsPLT3 | 73 | ( 312) | SIISSNLPIGSMAGNR |
| MtANT | 98 | ( 480) | IMASSNLLNIEQARRN |
| AtPLT3/AIL5 | 74 | ( 371) | SIASCNLPVGGLMPKP |
| Consensus | 52 | | SSTLP1GG2A334 |

1=I or V; 2= A, L, or G; 3= K or R; 4= L or R

FIG. 2E

| | SEQ ID NO: | | |
|---|---|---|---|
| AtBBM | 22 | ( 4) | MNNWLGFSLSPHDQNH |
| GmANT | 99 | ( 15) | NHNWLGFSLSPHMKME |
| BnBBM2 | 26 | ( 2) | NNNWLGFSLSPYEQNH |
| BnBBM1 | 24 | ( 2) | NNNWLGFSLSPYEQNH |
| VvBBM | 6 | ( 4) | MNNWLGFSLSPRELPP |
| OsBBM | 14 | ( 4) | MNNWLAFSLSPQDQLP |
| SbBBM | 4 | ( 4) | VNNWLAFSLSPQELPP |
| ZmBBM | 10 | ( 4) | VNNWLAFSLSPQELPP |
| MtANT | 98 | ( 16) | ENNWLGFSLSPQMNNI |
| OsBBM2 | 18 | ( 4) | ANNWLGFSLSGQENPQ |
| ZmBBM2 | 12 | ( 4) | ANNWLGFSLSGQDNPQ |
| SbBBM2 | 28 | ( 5) | NNHWLGFSLSGQDNPQ |
| GmAIL1 | 86 | ( 1) | MSNWLGFSLTPHLRID |
| MtAIL1 | 90 | ( 1) | MSNWLGFSLTPHLRID |
| ZmANT2 | 97 | ( 4) | GSNWLGFSLSPHTAME |
| GmAIL6 | 88 | ( 4) | ATNWLSFSLSPMEMLR |
| GmPLT2 | 78 | ( 2) | NNNWLSFPLSPTHSSL |
| GmPLT1 | 82 | ( 2) | NNNWLSFPLSPTHSSL |
| MtPLT1/2 | 84 | ( 2) | NNNWLSFPLSPSHSSL |
| GmAIL7 | 94 | ( 5) | STNWLSFSLSPMDMLR |
| AtPLT1 | 83 | ( 3) | SNNWLGFPLSPNNSSL |
| MtBBM | 8 | ( 3) | SMNLLGFSLSPQEQHP |
| AtPLT2 | 75 | ( 3) | SNNWLAFPLSPTHSSL |
| ZmAIL1 | 85 | ( 4) | NNGWLGFSLSPSAASR |
| OsBBM3 | 20 | ( 4) | ADNWLGFSLSGQGNPQ |
| SbANT | 93 | ( 13) | ASSWLGFSLSPHMASA |
| OsANT | 95 | ( 20) | VGGWLGFSLSPHMATY |
| SbPLT3b | 76 | ( 10) | PHHWLSFSLSNNYHHG |
| OsPLT3b | 81 | ( 10) | PHHWLSFSLSNNYHHG |
| ZmPLT3b | 72 | ( 10) | PHHWLSFSLSNNYHHG |
| SbAIL1 | 91 | ( 4) | NNGWLGFSLSPSAGRG |
| GmBBM | 2 | ( 3) | SMNLLGFSLSPQEHPS |
| AtPLT3/AIL5 | 74 | ( 27) | HQNWLSFSLSNNNNNF |
| GmPLT3b | 70 | ( 13) | NNNSLAFSLSNHFPNP |
| GmPLT3a | 71 | ( 9) | NNNSLAFSLSNHFPNP |
| AtAIL1 | 100 | ( 1) | MKKWLGFSLTPPLRIC |
| ZmANT | 67 | ( 23) | GGSWLGFSLSPHMAAT |
| OsPLT3 | 73 | ( 8) | HYPWLNFSLAHHCEME |
| ZmPLT3 | 80 | ( 7) | YHPWLNFSLAHHCDLE |
| SbPLT3 | 87 | ( 6) | HYPWLNFSLAHHGDLE |
| OsAIL1 | 77 | ( 4) | NSGWLGFSLSSSSARG |
| AtANT | 92 | ( 15) | TTNLLGFSLSSNMMKM |
| OsBBM1 | 16 | ( 4) | ITNWLGFSSSSFSGAG |
| Consensus | 53 | | NWLXFSLSP |

X=G or S

FIG. 2F

```
         SEQ ID NO:
MtBBM    8     ( 159) NNSIGLSMIKTWLRNQPPPPE
BnBBM2   26    ( 130) GGSLGLSMIKTWLRNQPVDNV
BnBBM1   24    ( 130) GGSLGLSMIKTWLRNQPVDNV
SbBBM    4     ( 156) SGSIGLSMIKNWLRSQPAPMQ
SbBBM2   28    ( 157) SNTMELSMIKTWLRNNQVPQP
OsBBM    14    ( 156) NGGIGLSMIKNWLRSQPAPQP
ZmBBM    10    ( 152) GGGIGLSMIKNWLRSQPAPMQ
VvBBM    6     ( 131) YISIGLSMIKTWLRNQPAPTH
ZmBBM2   12    ( 154) SNTMELSMIKTWLRNNQVAQP
GmBBM    2     ( 164) SSSIGLSMIKTWLRNQPPHSE
OsBBM3   20    ( 157) GGTIELSMIKTWLRSNQSQQQ
OsBBM2   18    ( 154) SNTMELSMIKTWLRNNGQVPA
OsBBM1   16    ( 80)  SSVVGLSMIKNWLRSQPPPAV
AtBBM    22    ( 131) GGSLGLSMIKTWLSNHSVANA
Consensus 54              1LSMIK2WLR
1= G or E; 2= T or N
```

FIG. 2G

```
         SEQ ID NO:
SbAIL1     91    ( 527) AGVHQLPVFALWND
OsAIL1     77    ( 536) TVHHQLPVFALWND
ZmAIL1     85    ( 529) PGVHQLPMFALWND
ZmANT      67    ( 624) VSIAHLPVFAAWTD
SbANT      93    ( 664) VSIAHMPVFAAWTD
OsANT      95    ( 638) VSIAHLPMFAAWTD
MtANT      98    ( 642) LSLPQMPVFAAWTD
VvBBM      6     ( 629) AVCHGTPTFTVWND
GmANT      99    ( 532) ISLSHLPVFAAWTD
OsBBM      14    ( 681) GVCHGAQLFSVWND
BnBBM2     26    ( 565) GGGEVAPTFTVWND
BnBBM1     24    ( 565) GGGEVAPTFTVWND
GmAIL1     86    ( 499) GLVNQVPMFALWNE
MtAIL1     90    ( 561) GLVNQVPMFALWNE
ZmANT2     97    ( 637) VVVSHRPVFAAWAD
AtBBM      22    ( 570) GGGEGAPTFSVWND
AtANT      92    ( 541) LTLPQMPVFAAWAD
SbBBM      4     ( 689) VGHGGAQLFSVWND
ZmBBM      10    ( 695) VGHGGAQLFSVWND
GmPLT2     78    ( 540) MQTSNGGVFTMWND
GmPLT1     82    ( 549) MQTSNSGVFTMWND
GmPLT3b    70    ( 92)  CAPPQLPQFSTDNN
GmPLT3a    71    ( 88)  CAPPQLPQFSTDNN
MtPLT3     79    ( 105) CAPTQLQQFSTDND
AtPLT2     75    ( 555) QGSNPGGVFTMWNE
AtPLT1     83    ( 561) QGSNPGGVFTMWNE
MtPLT1/2   84    ( 524) ENMQTADLFTMWND
Consensus 55                   PXFXXWND
X= any amino acid
```

FIG. 2H

| SEQ ID NO: | | | |
|---|---|---|---|
| GmANT | 99 | ( 210) | LQSLSLSMSPGSQSSC |
| AtANT | 92 | ( 194) | QQSLSLSMSPGSQSSC |
| GmPLT2 | 78 | ( 120) | LQSLTLSMGSGKDSTC |
| GmPLT1 | 82 | ( 121) | LQSLTLSMGSGKDSTC |
| MtPLT1/2 | 84 | ( 122) | LQSLTLSMGSGKDSTC |
| MtANT | 98 | ( 250) | LHSLSLSMSPSSQSSC |
| MtBBM | 8 | ( 192) | VQTLSLSMSTGSQSSS |
| GmBBM | 2 | ( 202) | QQTLSLSMSTGSQSST |
| VvBBM | 6 | ( 174) | AQTLSLSMSTGSHQTG |
| SbBBM2 | 28 | ( 221) | SQSLALSMSTGSHLPM |
| OsBBM2 | 18 | ( 234) | SQSLALSMSTGSHSHL |
| ZmBBM2 | 12 | ( 214) | SQSLALSMSTGSHLPM |
| SbANT | 93 | ( 217) | HHALALSMSSGSLSSC |
| ZmBBM | 10 | ( 181) | AQGLSLSMNMAGTTQG |
| GmAIL1 | 86 | ( 150) | FQSLSLTMSPSVQNGV |
| OsBBM | 14 | ( 177) | AQALSLSMNMAGTTTA |
| BnBBM2 | 26 | ( 159) | AKGLSLSMNSSTSCDN |
| BnBBM1 | 24 | ( 159) | AKGLSLSMNSSTSCDN |
| SbBBM | 4 | ( 185) | VQGLSLSMNMAGATQG |
| OsANT | 95 | ( 241) | LHPLTLSMSSAGSQSS |
| MtAIL1 | 90 | ( 191) | FQSLNLTMSPCVQNGV |
| ZmANT | 67 | ( 231) | PHPLALSMSSGTGSQS |
| AtPLT1 | 83 | ( 126) | LQSLTLSMGTTAGNNV |
| AtPLT2 | 75 | ( 129) | LQSLTLSMGSTGAAAA |
| AtBBM | 22 | ( 160) | ARGLSLSMNSSTSDSN |
| OsBBM3 | 20 | ( 220) | GQGLALSMSTGSVAAA |
| ZmANT2 | 97 | ( 202) | TRPLSLSMMSPGTQLS |
| Consensus | 56 | | LXLSM |

X = S, T or A

FIG. 2I

| SEQ ID NO: | | | |
|---|---|---|---|
| SbBBM | 4 | ( 529) | GWCKQEQDHAVIAAAH |
| OsBBM | 14 | ( 534) | GWCKQEQDHAVIAAAH |
| ZmBBM | 10 | ( 531) | GWCKQEQDHAVIAAAH |
| SbBBM2 | 28 | ( 536) | GWCKPEQDAAVAAAAH |
| OsBBM2 | 18 | ( 560) | GWCKPEQDAAVAAAAH |
| ZmBBM2 | 12 | ( 528) | GWCKPEQDAAAAAAHS |
| OsBBM3 | 20 | ( 522) | GWCKPEQDAVIAAGHC |
| MtBBM | 8 | ( 522) | LWCKQEQDSDDHSTYT |
| VvBBM | 6 | ( 453) | VWCKQEQDPDGTHNFQ |
| OsBBM1 | 16 | ( 416) | AWLKQEQDSSVVTAAQ |
| GmBBM | 2 | ( 527) | NWCKQEQDNSDASHSL |
| Consensus | 57 | | WCKXEQD |

X= Q or P

FIG. 2J

```
     SEQ ID NO:
OsBBM2   18    ( 529)  HHHGWPTIAFQQPPPLAVHYPY
SbBBM2   28    ( 508)  GHHAWPTIAFQQPSPLSVHYPY
ZmBBM2   12    ( 501)  GHHGWPTIAFQQPSPLSVHYPY
VvBBM    6     ( 425)  HHHGWPTVAFQQAQPFSMHYPY
SbBBM    4     ( 502)  YHGAWPTIAFQPSAATGLYHPY
ZmBBM    10    ( 500)  HGAAWPTIAFQPGAATTGLYHP
OsBBM    14    ( 502)  AAAAWPTIAFQAAAAPPPHAAG
Consensus 58               WPTIAFQ
```

FIG. 2K

```
     SEQ ID NO:
SbBBM    4     ( 572)  MHGLGSMDNASLEHSTGSNSVVYNG
ZmBBM    10    ( 577)  MHGLASIDSASLEHSTGSNSVVYNG
OsBBM    14    ( 576)  QHGLGSIDNASLEHSTGSNSVVYNG
VvBBM    6     ( 487)  LHNLMSMDSSSMDHSSGSNSVIYSG
MtBBM    8     ( 560)  LQNIMSMDSASMDNSSGSNSVVYGG
GmBBM    2     ( 567)  LHPMLSMDSASIDNSSSSNSVVYDG
Consensus 59                          SXGSNSVVYNG
X= S or T
```

FIG. 2L

```
     SEQ ID NO:
SbBBM2   28    ( 78)   ETQDWNMRGLDY
ZmBBM2   12    ( 75)   ETQDWNMRGLDY
OsBBM2   18    ( 76)   EAQDWNMRGLDY
OsBBM3   20    ( 74)   ETQDWAMRGLDY
SbBBM    4     ( 43)   IPQDWSMRGSEL
OsBBM    14    ( 49)   IPQDWSMRGSEL
ZmBBM    10    ( 44)   IPQDWSMRGSEL
Consensus 60             QDWXMRG
X= S or N
```

FIG. 2M

METHODS AND COMPOSITIONS FOR THE INTRODUCTION AND REGULATED EXPRESSION OF GENES IN PLANTS

CROSS-REFERENCE TO RELATED APPLICATIONS

This application is a continuation of and claims the benefit of U.S. application Ser. No. 17/181,136 filed on Feb. 22, 2021, which is continuation of U.S. application Ser. No. 15/673,609 filed Aug. 10, 2017, now U.S. Pat. No. 10,968,458, which is a continuation of and claims the benefit of U.S. application Ser. No. 14/087,775 filed Nov. 22, 2013, now U.S. Pat. No. 9,765,352, which is a continuation of and claims the benefit of U.S. application Ser. No. 12/982,180 filed Dec. 30, 2010, which claims the benefit of U.S. Provisional Application No. 61/291,257, filed on Dec. 30, 2009, the contents of each of which are hereby incorporated by reference in their entireties.

REFERENCE TO A SEQUENCE LISTING SUBMITTED AS A TEXT FILE VIA EFS-WEB

The official copy of the sequence listing is submitted electronically via EFS-Web as an XML formatted sequence listing with a file named 3650-US-CNT4.xml created on May 10, 2023, and having a size of 296 kilobytes and is filed concurrently with the specification. The sequence listing contained in this ASCII formatted document is part of the specification and is herein incorporated by reference in its entirety.

FIELD OF THE INVENTION

The present invention is drawn to the field of plant genetics and molecular biology. More particularly, the compositions and methods are directed to the introduction and regulated expression of genes in plants.

BACKGROUND OF THE INVENTION

Current transformation technology provides an opportunity to engineer plants with desired traits. Major advances in plant transformation have occurred over the last few years. However, most transformation methods rely on the introduction of polynucleotides into embryonic tissues that are rapidly proliferating. Methods that allow for the transformation of more mature tissues would save considerable time and money. Accordingly, methods are needed in the art to increase transformation efficiencies of plants and allow for the transformation of more mature tissues.

Further, it is often necessary to reduce the activity of a transgene because the transgene may negatively affect the growth or fertility of the plant. Recombination systems can be used to excise the transgene, wherein the expression of a site-specific recombinase is regulated by an inducible promoter. Often, these systems are associated with premature excision. Accordingly, methods are needed in the art to efficiently excise transgenes with limited premature excision.

BRIEF SUMMARY OF THE INVENTION

Compositions and methods are provided for the introduction and regulated expression of genes in plants. Compositions include promoter constructs useful for regulated induction of expression of an operably linked coding sequence. In particular embodiments, the promoter construct comprises a maize rab17 promoter or an active variant or fragment thereof and an attachment B (attB) site. The modified rab17 promoter constructs find use in methods for regulating the expression of various coding sequences, including site-specific recombinases, which can minimize the premature excision of polynucleotides of interest in plants.

Further provided are methods for the transformation of plastids, such as chloroplasts, that involve the introduction of a heterologous polynucleotide encoding a cell proliferation factor, such as a babyboom (BBM) polypeptide. Novel BBM sequences are provided, along with methods of introducing the sequences into plants and plants comprising the novel BBM sequences. Methods for preparing and transforming mature embryo explants and leaf tissues are also provided.

BRIEF DESCRIPTION OF THE FIGURES

FIGS. 2A-2M show the consensus motif sequences 1-10, 14, 15, and 19, respectively, discovered in the analysis described herein, along with the alignments of the regions of various polypeptides used to generate the consensus motifs.

DETAILED DESCRIPTION OF THE INVENTION

Figure 1:
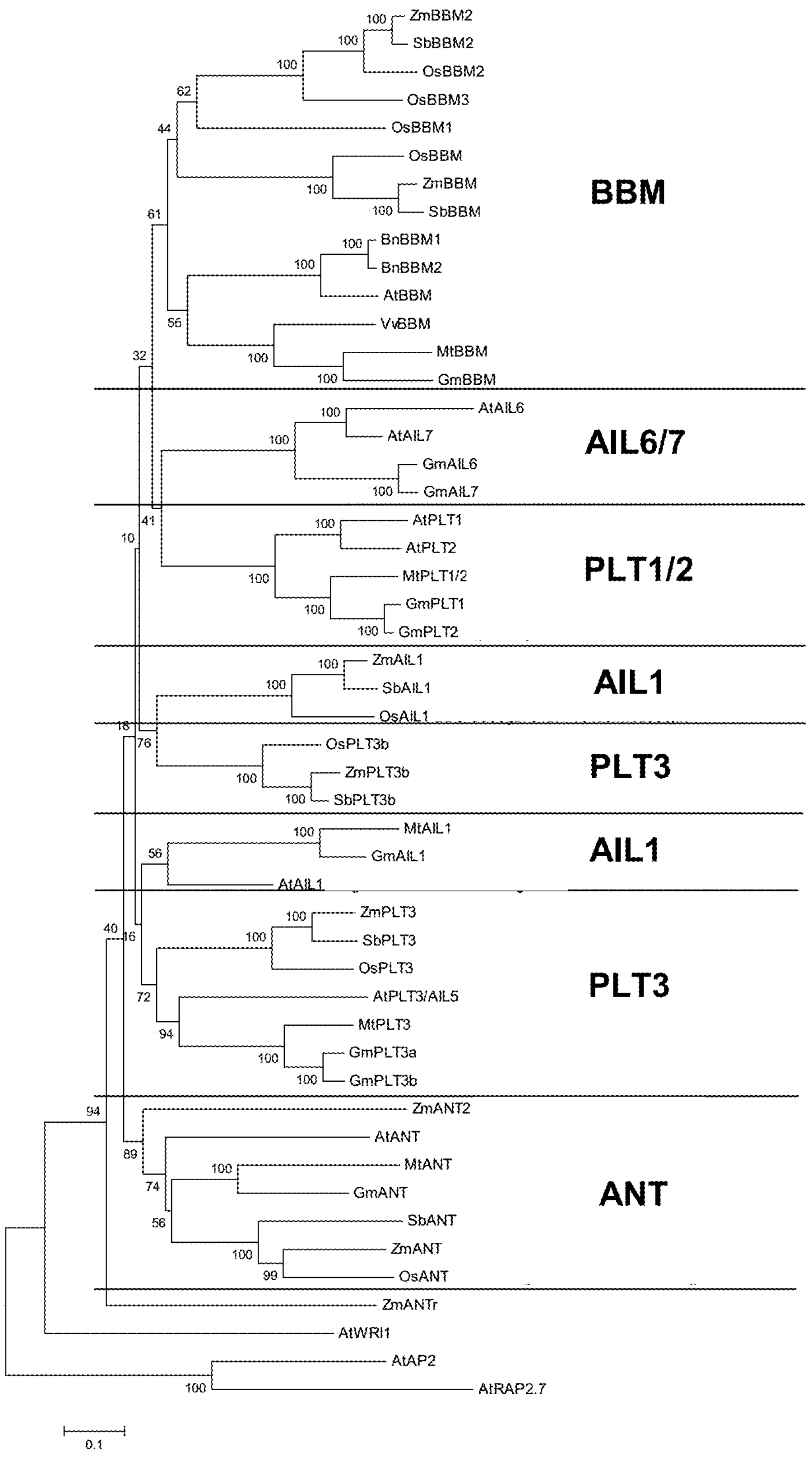
FIG. 1 provides a depiction of a phylogenetic analysis of 50 sequences with homology to maize babyboom (BBM).

The presently disclosed compositions and methods are useful for the introduction and the regulated expression of genes in plants. Compositions comprise promoter constructs that provide a level of activity useful for the regulated expression of various coding sequences, including site-specific recombinases. Further provided are compositions comprising novel babyboom (BBM) polynucleotide and polypeptide sequences and plants comprising the same. Methods for the introduction of genes into plants are provided, including methods for introducing novel BBM polynucleotides and polypeptides into plants, methods for the enhancement of plastid transformation, and methods for the transformation of tissues from mature seeds.

The expression cassette having the sequence set forth in SEQ ID NO: 45, which is comprised of the maize rab17 promoter, an attB site, and the coding sequence for the site-specific recombinase FLP, is capable of expressing FLP upon induction in such a manner as to reduce premature excision. Without being bound by any theory or mechanism of action, it is believed that the presence of the attB site modifies the activity of the promoter, allowing for a tightly regulated induction of expression of an operably linked coding sequence. Therefore, compositions include promoter constructs comprising a modified maize rab17 promoter or an active variant or fragment thereof. In some of these embodiments, the promoter construct comprises the maize rab17 promoter or an active variant or fragment thereof and an attB site or a variant or fragment thereof. In some of these embodiments, the maize rab17 promoter has the sequence set forth in SEQ ID NO: 29 or an active variant or fragment thereof.

As used herein, the term "promoter" includes reference to a region of DNA involved in the recognition and binding of RNA polymerase and other proteins to initiate transcription of a coding sequence. Promoters may be naturally occurring promoters, a variant or fragment thereof, or synthetically derived. A "promoter construct" is a polynucleotide comprising a promoter and optionally, sequences that are not necessary for transcription initiation or part of the coding sequence and are located in between the promoter and the coding sequence in an expression cassette. These intervening sequences can include modulators, restriction sites, sequences of the 5'-untranslated region (5'-UTR), which is the region of a transcript that is transcribed, but is not translated into a polypeptide, and recombination sites.

The promoter in the promoter constructs is the maize rab17 promoter or an active variant or fragment thereof. The maize rab17 (responsive to abscisic acid) gene (GenBank Accession No. X15994; Vilardell et al. (1990) *Plant Mol Biol* 14:423-432; Vilardell et al. (1991) *Plant Mol Biol* 17:985-993; each of which is herein incorporated in its entirety) is expressed in late embryos, but its expression can be induced by exposure to abscisic acid or water stress. The sequence of the maize rab17 promoter corresponds to nucleotides 1-558 of GenBank Accession No. X15994, which was disclosed in Vilardell et al. (1990) *Plant Mol Biol* 14:423-432 and is set forth in SEQ ID NO: 126. An alternative maize rab17 promoter was disclosed in U.S. Pat. Nos. 7,253,000 and 7,491,813, each of which is herein incorporated by reference in its entirety, and is set forth in SEQ ID NO: 29. The rab17 promoter contains 5 putative abscisic acid responsive elements (ABRE) (Busk et al. (1997) *Plant J* 11:1285-1295, which is herein incorporated by reference in its entirety). The putative ABRE elements can be found at about −208 to −203 (nucleotides 304 to 309 of SEQ ID NO: 29), −162 to −157 (nucleotides 348 to 353 of SEQ ID NO: 29), −147 to −142 (nucleotides 363 to 368 of SEQ ID NO: 29), −141 to −136 (nucleotides 369 to 374 of SEQ ID NO: 29), and −96 to −91 (nucleotides 414 to 419 of SEQ ID NO: 29) in the maize rab17 promoter. The rab17 promoter also contains drought-responsive elements (DRE), of which the core sequence is identical to the DRE (drought-responsive) and CRT (cold-response elements) elements in *Arabidopsis*. The drought-responsive elements are found at −213 to −206 (nucleotides 299 to 306 of SEQ ID NO: 29) and −190 to −185 (nucleotides 322 to 327 of SEQ ID NO: 29) of the maize rab17 promoter. The CAAT and TATAA box can be found from nucleotides 395 to 398 and 479 to 484 of SEQ ID NO: 29, respectively.

In some embodiments, the maize rab17 promoter that is part of the presently disclosed promoter constructs has the sequence set forth in SEQ ID NO: 29 or an active variant or fragment thereof. In other embodiments, the maize rab17 promoter that is part of the presently disclosed promoter constructs has the sequence set forth in SEQ ID NO: 125 or 126 or an active variant or fragment thereof.

In some embodiments of the methods and compositions, the promoter constructs comprise active variants or fragments of the maize rab17 promoter. An active variant or fragment of a maize rab17 promoter (e.g., SEQ ID NO: 29, 125, 126) is a polynucleotide variant or fragment that retains the ability to initiate transcription. In some embodiments, an active fragment of a maize rab17 promoter may comprise at least about 50, 100, 150, 200, 250, 300, 350, 400, 450, or 500 contiguous nucleotides of SEQ ID NO: 29, 125, or 126, or may have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to SEQ ID NO: 29, 125, or 126. In particular embodiments, an active variant or fragment of the maize rab17 promoter is one that is capable of initiating transcription in response to abscisic acid (ABA). In some of these embodiments, the promoter comprises at least one ABRE element. In particular embodiments, the promoter of the compositions and methods comprises from about −219 to about −102 of the maize rab17 promoter (corresponding to nucleotides 291 to 408 of SEQ ID NO: 29), which was shown to be sufficient to confer ABA responsiveness (Vilardell et al. (1991) *Plant Mol Biol* 17:985-993, which is herein incorporated by reference in its entirety).

In other embodiments, an active variant or fragment of the maize rab17 promoter is one that is capable of initiating transcription in response to dessication. In some of these embodiments, the promoter comprises at least one DRE element.

In particular embodiments, the active maize rab17 promoter fragment comprises from about −219 to about −80 of the maize rab17 promoter (nucleotides 291 to 430 of SEQ ID NO: 29), which comprises all of the putative DRE and ABRE elements.

Without being bound by any theory or mechanism of action, it is believed that a promoter construct (the sequence of which is set forth in SEQ ID NO: 30) comprising a maize rab17 promoter and a site-specific attachment B (attB) site has a modified level of activity in comparison to the promoter in the absence of the attB site due to the presence and/or the location of the attB site relative to the promoter. Therefore, it is believed the attB site functions as a modulator of the maize rab17 promoter. Accordingly, promoter constructs comprising a maize rab17 promoter or a fragment or variant thereof, and an attB site are provided, and in some of these embodiments, the attB site modifies the activity of the promoter. In other embodiments, the promoter construct comprises a maize rab17 promoter or a fragment or variant thereof and a modulator that modifies the activity of the rab17 promoter.

As used herein, a "modulator" refers to a polynucleotide that when present between a promoter and a coding sequence, serves to increase or decrease the activity of the promoter. Non-limiting examples of modulators include recombination sites, operators, and insulators.

Attachment sites are site-specific recombination sites found in viral and bacterial genomes that facilitate the integration or excision of the viral genome into and out of its host genome. Non-limiting examples of a viral and bacterial host system that utilize attachment sites is the lambda bacteriophage and *E. coli* system (Weisberg and Landy (1983) In Lambda II, eds. Hendrix et al. (Cold Spring Harbor Laboratory, Cold Spring Harbor, N.Y.) pp. 211-250). The modulator of the promoter constructs can be an *E. coli* attachment site B (attB) site. The attB site can be naturally occurring *E. coli* attB sites or an active variants or fragments thereof or a synthetically derived sequence. Synthetically derived attB sites and active variants and fragments of naturally occurring attB sites are those that are capable of recombining with a bacteriophage lambda attachment P site, a process that is catalyzed by the bacteriophage lambda Integrase (Int) and the *E. coli* Integration Host Factor (IHF) proteins (Landy (1989) *Ann Rev Biochem* 58: 913-949, which is herein incorporated by reference in its entirety). AttB sites typically have a length of about 25 nucleotides, with a core 15-base pair sequence that is involved in the actual crossover event. Alternatively, active variants and fragments of naturally occurring attB sites are those that are capable of modulating the activity of a promoter when present within a promoter construct. Non-limiting examples of attB sites that can be used include attB1 (SEQ ID NO: 31), attB2 (SEQ ID NO: 32), attB3 (SEQ ID NO: 33), and attB4 (SEQ ID NO: 34), and variants or fragments thereof. In some embodiments, the modulator is an active variant or fragment of an attB site that is capable of modulating (i.e., increasing, decreasing) the activity of a promoter, but is not capable of recombination with an attachment P site. Non-limiting examples of such active variants of an attB site include those having the sequence set forth in SEQ ID NO: 107, 108, or 109.

In some embodiments, the distance of the modulator from the promoter impacts the ability of the modulator to modify the activity of the promoter. The modulator may be contiguous with the promoter and/or the polynucleotide of interest. In other embodiments, a linker sequence separates the promoter sequence and the modulator. As used herein, a "linker sequence" is a nucleotide sequence that functions to link one functional sequence with another without otherwise contributing to the expression or translation of a polynucleotide of interest when present in a promoter construct. Accordingly, the actual sequence of the linker sequence can vary. The linker sequence can comprise plasmid sequences, restriction sites, and/or regions of the 5'-untranslated region (5'-UTR) of the gene from which the promoter is derived. The linker sequence separating the promoter and the modulator can have a length of about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 400, 500, 1000 nucleotides or greater. In certain embodiments, a linker sequence of about 133 nucleotides separates the promoter and the modulator. In some embodiments, the linker sequence comprises a fragment of the rab17 5'-UTR. The fragment of the 5'-UTR can be about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100 nucleotides, or greater, in length. In certain embodiments, the promoter construct comprises a linker sequence separating the promoter and the modulator that comprises 95 nucleotides of the maize rab17 5'-UTR. In some of these embodiments, the 95 nucleotide sequence has the sequence set forth in SEQ ID NO: 35. In certain embodiments, the linker sequence between the promoter and modulator has the sequence set forth in SEQ ID NO: 36 or a variant or fragment thereof.

In some embodiments, the promoter construct comprises a linker sequence separating the modulator and the polynucleotide of interest. The length and sequence of this linker may also vary and can be about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 400, 500, 1000 nucleotides or greater in length. In certain embodiments, a linker sequence of about 61 nucleotides separates the modulator and the polynucleotide of interest. In certain embodiments, the linker sequence between the modulator and the polynucleotide of interest has the sequence set forth in SEQ ID NO: 37 or a variant or fragment thereof. In other embodiments, a linker sequence of about 25 nucleotides separates the modulator and the polynucleotide of interest. In certain embodiments, the linker sequence between the modulator and the polynucleotide of interest has the sequence set forth in SEQ ID NO: 123.

In certain embodiments, the promoter construct has the sequence set forth in SEQ ID NO: 30 or a variant or fragment thereof.

The promoter constructs can be operably linked to a polynucleotide of interest that encodes a polynucleotide or polypeptide within an expression cassette. "Operably linked" denotes a functional linkage between two or more elements. For example, an operable linkage between a polynucleotide of interest and a promoter is a functional link that allows for expression of the polynucleotide of interest. Operably linked elements may be contiguous or non-contiguous. The expression cassette can comprise other 5' or 3' regulatory elements necessary for expression.

Regulatory elements that can be included in the expression cassette 5' to the polynucleotide of interest include 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods or sequences known to enhance translation can also be utilized, for example, introns, and the like.

The expression cassette may also comprise a transcriptional and/or translational termination region functional in plants. The termination region may be native with the transcriptional initiation region (i.e., promoter), may be native with the operably linked polynucleotide of interest, may be native with the plant host, or may be derived from another source (i.e., foreign to the promoter, the polynucleotide of interest, the plant host, or any combination thereof). Convenient termination regions are available from the potato proteinase inhibitor (PinII) gene or the Ti-plasmid of *A. tumefaciens*, such as the octopine synthase and nopaline synthase termination regions. See also Guerineau et al. (1991)*Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639. In some embodiments, the pinII termination sequence has the sequence set forth in SEQ ID NO: 38 or an active variant or fragment thereof that is capable of terminating transcription and/or translation in a plant cell.

In certain embodiments, the expression cassette can comprise a recombination site, such as an attachment site 3' to the polynucleotide of interest. In some of these embodiments, the recombination site is a second attB site. In some of those embodiments wherein the promoter comprises a first attB site, the second attB site following the polynucleotide of interest and the modulator attB are non-identical. In some of those embodiments wherein the modulator attB site is attB1 (SEQ ID NO: 31), the second attB site 3' of the polynucleotide of interest can have the sequence set forth in SEQ ID NO: 31 (attB1), SEQ ID NO: 32 (attB2), SEQ ID NO: 33 (attB3), or SEQ ID NO: 34 (attB4), or an active variant or fragment thereof.

The recombination site 3' to the polynucleotide of interest can be 5' or 3' to the termination region when present. The recombination site can be contiguous with the polynucleotide of interest and/or the termination sequence, if present. In some embodiments, however, a linker sequence separates the polynucleotide of interest and the recombination site. The length of this linker sequence can vary, but in some embodiments, is about 1, 2, 3, 4, 5, 6, 7, 8, 9, 10, 11, 12, 13, 14, 15, 16, 17, 18, 19, 20, 25, 30, 35, 40, 45, 50, 60, 70, 80, or 90 nucleotides in length. In particular embodiments, the linker sequence separating the recombination site and the polynucleotide of interest is about 16 nucleotides. In certain embodiments, the recombination site and the polynucleotide of interest are separated by a linker sequence having the nucleotide sequence set forth in SEQ ID NO: 39, or a variant or fragment thereof. In other embodiments, the linker sequence separating the recombination site and the polynucleotide of interest is about 8 nucleotides. In certain embodiments, the recombination site and the polynucleotide of interest are separated by a linker sequence having the nucleotide sequence set forth in SEQ ID NO: 124, or a variant or fragment thereof.

In some of those embodiments wherein a termination region is present on the expression cassette and the expression cassette further comprises a recombination site 3' to the polynucleotide of interest, the termination region is 3' to the recombination site and a linker sequence separates the recombination site and the termination region. The length of this linker sequence can vary, but in some embodiments, is about 1, 2, 3, 4, 5, 6, 7, 8, 9, 10, 11, 12, 13, 14, 15, 16, 17, 18, 19, 20, 25, 30, 35, 40, 45, 50, 60, 70, 80, or 90 nucleotides in length. In particular embodiments, the linker sequence separating the recombination site and the termination region is about 14 nucleotides. In certain embodiments, the recombination site and the termination region are separated by a linker sequence having the nucleotide sequence set forth in SEQ ID NO: 40 or a variant or fragment thereof.

The expression cassettes comprise a presently disclosed promoter construct regulating the expression of a polynucleotide of interest. The polynucleotide of interest may be any polynucleotide that encodes a polynucleotide (e.g., antisense, siRNA) or encodes a polypeptide. Where appropriate, the polynucleotide(s) of interest may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In some embodiments, the polynucleotide of interest comprises a polynucleotide that encodes a site-specific recombinase. A site-specific recombinase, also referred to herein as a recombinase, is a polypeptide that catalyzes conservative site-specific recombination between its compatible recombination sites, and includes native polypeptides as well as derivatives, variants and/or fragments that retain activity, and native polynucleotides, derivatives, variants, and/or fragments that encode a recombinase that retains activity. The recombinase used in the methods and compositions can be a native recombinase or a biologically active fragment or variant of the recombinase. For reviews of site-specific recombinases and their recognition sites, see Sauer (1994) *Curr Op Biotechnol* 5:521-527; and Sadowski (1993) *FASEB* 7:760-767, each of which is herein incorporated by reference in its entirety.

Any recombinase system can be used in the methods and compositions. Non-limiting examples of site-specific recombinases include FLP, Cre, SSV1, lambda Int, phi C31 Int, HK022, R, Gin, Tn1721, CinH, ParA, Tn5053, Bxbl, TP907-1, U153, and other site-specific recombinases known in the art, including those described in Thomson and Ow (2006) *Genesis* 44:465-476, which is herein incorporated by reference in its entirety. Examples of site-specific recombination systems used in plants can be found in U.S. Pat. Nos. 5,929,301, 6,175,056, 6,331,661; and International Application Publication Nos. WO 99/25821, WO 99/25855, WO 99/25841, and WO 99/25840, the contents of each are herein incorporated by reference.

In some embodiments, the polynucleotide of interest encodes a recombinase from the Integrase or Resolvase families, including biologically active variants and fragments thereof. The Integrase family of recombinases has over one hundred members and includes, for example, FLP, Cre, lambda integrase, and R. For other members of the Integrase family, see, for example, Esposito et al. (1997) *Nucleic Acids Res* 25:3605-3614; and Abremski et al. (1992) *Protein Eng* 5:87-91; each of which are herein incorporated by reference in its entirety. Other recombination systems include, for example, the Streptomycete bacteriophage phi C31 (Kuhstoss et al. (1991) *J Mol Biol* 20:897-908); the SSV1 site-specific recombination system from *Sulfolobus shibatae* (Maskhelishvili et al. (1993)*Mol Gen Genet* 237:334-342); and a retroviral integrase-based integration system (Tanaka et al. (1998) *Gene* 17:67-76). In some embodiments, the recombinase does not require cofactors or a supercoiled substrate. Such recombinases include Cre, FLP, or active variants or fragments thereof.

The FLP recombinase is a protein that catalyzes a site-specific reaction that is involved in amplifying the copy number of the two-micron plasmid of *S. cerevisiae* during DNA replication. FLP recombinase catalyzes site-specific recombination between two FRT sites. The FLP protein has been cloned and expressed (Cox (1993) *Proc Natl Acad Sci USA* 80:4223-4227, which is herein incorporated by reference in its entirety). The FLP recombinase for use in the methods and compositions may be derived from the genus *Saccharomyces*. In some embodiments, a recombinase polynucleotide modified to comprise more plant-preferred codons is used. A recombinant FLP enzyme encoded by a nucleotide sequence comprising maize preferred codons (FLPm) that catalyzes site-specific recombination events is known (the polynucleotide and polypeptide sequence of which is set forth in SEQ ID NO: 41 and 42, respectively;

see, e.g., U.S. Pat. No. 5,929,301, which is herein incorporated by reference in its entirety). Additional functional variants and fragments of FLP are known (Buchholz et al. (1998) *Nat Biotechnol* 16:657-662; Hartung et al. (1998) *J Biol Chem* 273:22884-22891; Saxena et al. (1997) *Biochim Biophys Acta* 1340:187-204; Hartley et al. (1980) *Nature* 286:860-864; Voziyanov et al. (2002) *Nucleic Acids Res* 30:1656-1663; Zhu & Sadowski (1995) *J Biol Chem* 270: 23044-23054; and U.S. Pat. No. 7,238,854, each of which is herein incorporated by reference in its entirety).

The bacteriophage recombinase Cre catalyzes site-specific recombination between two lox sites. The Cre recombinase is known (Guo et al. (1997) *Nature* 389:40-46; Abremski et al. (1984) *J Biol Chem* 259:1509-1514; Chen et al. (1996) *Somat Cell Mot Genet* 22:477-488; Shaikh et al. (1977) *J Biol Chem* 272:5695-5702; and, Buchholz et al. (1998) *Nat Biotechnol* 16:657-662, each of which is herein incorporated by reference in its entirety). Cre polynucleotide sequences may also be synthesized using plant-preferred codons, for example such sequences (moCre; the polynucleotide and polypeptide sequence of which is set forth in SEQ ID NO: 43 and 44, respectively) are described, for example, in International Application Publication No. WO 99/25840, which is herein incorporated by reference in its entirety. Variants of the Cre recombinase are known (see, for example U.S. Pat. No. 6,890,726; Rufer & Sauer (2002) *Nucleic Acids Res* 30:2764-2772; Wierzbicki et al. (1987) *J Mol Biol* 195:785-794; Petyuk et al. (2004) *J Biol Chem* 279:37040-37048; Hartung & Kisters-Woike (1998) *J Biol Chem* 273: 22884-22891; Santoro & Schultz (2002) *Proc Natl Acad Sci USA* 99:4185-4190; Koresawa et al. (2000) *J Biochem* (Tokyo) 127:367-372; and Vergunst et al. (2000) *Science* 290:979-982, each of which are herein incorporated by reference in its entirety).

In some embodiments, the polynucleotide of interest encodes a chimeric recombinase. A chimeric recombinase is a recombinant fusion protein which is capable of catalyzing site-specific recombination between recombination sites that originate from different recombination systems. For example, if the set of recombination sites comprises a FRT site and a LoxP site, a chimeric FLP/Cre recombinase or active variant or fragment thereof can be used, or both recombinases may be separately provided. Methods for the production and use of such chimeric recombinases or active variants or fragments thereof are described, for example, in International Application Publication No. WO 99/25840; and Shaikh & Sadowski (2000) *J Mol Biol* 302:27-48, each of which are herein incorporated by reference in its entirety.

In other embodiments, a variant recombinase is used. Methods for modifying the kinetics, cofactor interaction and requirements, expression, optimal conditions, and/or recognition site specificity, and screening for activity of recombinases and variants are known, see for example Miller et al. (1980) *Cell* 20:721-9; Lange-Gustafson and Nash (1984) *J Biol Chem* 259:12724-32; Christ et al. (1998) *J Mol Biol* 288:825-36; Lorbach et al. (2000) *J Mol Biol* 296:1175-81; Vergunst et al. (2000) *Science* 290:979-82; Dorgai et al. (1995) *J Mol Biol* 252:178-88; Dorgai et al. (1998) *J Mol Biol* 277:1059-70; Yagu et al. (1995) *J Mol Biol* 252:163-7; Sclimente et al. (2001) *Nucleic Acids Res* 29:5044-51; Santoro and Schultze (2002) *Proc Natl Acad Sci USA* 99:4185-90; Buchholz and Stewart (2001) *Nat Biotechnol* 19:1047-52; Voziyanov et al. (2002) *Nucleic Acids Res* 30:1656-63; Voziyanov et al. (2003) *J Mol Biol* 326:65-76; Klippel et al. (1988) *EMBO J* 7:3983-9; Arnold et al. (1999) *EMBO J* 18:1407-14; and International Application Publication Nos. WO 03/08045, WO 99/25840, and WO 99/25841; each of which is herein incorporated by reference in its entirety.

In particular embodiments, the expression cassette has the sequence set forth in SEQ ID NO: 45 or a variant or fragment thereof.

The expression cassette can be part of a vector that comprises multiple expression cassettes or multiple genes, such as a selectable marker gene. Selectable marker genes may be used to identify transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506-511; Christopherson et al. (1992) *Proc. Natl. Acad Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad Sci. USA* 90:1917-1921; Labow et al. (1990) *Mol. Cell. Biol.* 10:3343-3356; Zambretti et al. (1992) *Proc. Natl. Acad Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used.

In some embodiments, an expression cassette comprising a presently disclosed promoter construct can further comprise a polynucleotide encoding a cell proliferation factor. As used herein, a “cell proliferation factor” is a polypeptide or a polynucleotide capable of stimulating growth of a cell or tissue, including but not limited to promoting progression through the cell cycle, inhibiting cell death, such as apoptosis, stimulating cell division, and/or stimulating embryogenesis. The polynucleotides can fall into several categories, including but not limited to, cell cycle stimulatory polynucleotides, developmental polynucleotides, anti-apoptosis polynucleotides, hormone polynucleotides, or silencing constructs targeted against cell cycle repressors or pro-apoptotic factors. The following are provided as non-limiting examples of each category and are not considered a complete list of useful polynucleotides for each category: 1) cell cycle stimulatory polynucleotides including plant viral replicase genes such as RepA, cyclins, E2F, prolifera, cdc2 and cdc25; 2) developmental polynucleotides such as Lec1, Kn1 family, WUSCHEL, Zwille, BBM, Aintegumenta (ANT), FUS3, and members of the Knotted family, such as Kn1, STM, OSH1, and SbH1; 3) anti-apoptosis polynucleotides such as CED9, Bcl2, Bcl-X(L), Bcl-W, A1, McL-1, Mac1, Boo, and Bax-inhibitors; 4) hormone polynucleotides such as IPT, TZS, and CKI-1; and 5) silencing constructs targeted against cell cycle repressors, such as Rb, CK1, prohibitin, and weel, or stimulators of apoptosis such as APAF-1, bad, bax, CED-4, and caspase-3, and repressors of plant developmental transitions, such as Pickle and WD polycomb genes including FIE and Medea. The polynucleotides can be silenced by any known method such as antisense, RNA interference, cosuppression, chimerplasty, or transposon insertion.

The cell proliferation factors can be introduced into cells through the introduction of a polynucleotide that encodes the proliferation factor. The use of the term "polynucleotide" is not intended to limit compositions to polynucleotides comprising DNA. Polynucleotides can comprise ribonucleotides and combinations of ribonucleotides and deoxyribonucleotides. Such deoxyribonucleotides and ribonucleotides include both naturally occurring molecules and synthetic analogues. The polynucleotides also encompass all forms of sequences including, but not limited to, single-, double-, or multi-stranded forms, hairpins, stem-and-loop structures, circular plasmids, and the like. The polynucleotide encoding the cell proliferation factor may be native to the cell or heterologous. A native polypeptide or polynucleotide comprises a naturally occurring amino acid sequence or nucleotide sequence. "Heterologous" in reference to a polypeptide or a nucleotide sequence is a polypeptide or a sequence that originates from a different species, or if from the same species, is substantially modified from its native form in composition and/or genomic locus by deliberate human intervention.

An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein or biologically active portion thereof is recombinantly produced, optimally culture medium represents less than about 30%, 20%, 10%, 5%, or 1% (by dry weight) of chemical precursors or non-protein-of-interest chemicals.

Any of a number of cell proliferation factors can be used. In certain embodiments, those cell proliferation factors that are capable of stimulating embryogenesis are used to enhance targeted polynucleotide modification. Such cell proliferation factors are referred to herein as embryogenesis-stimulating polypeptides and they include, but are not limited to, babyboom polypeptides.

In some embodiments, the cell proliferation factor is a member of the AP2/ERF family of proteins. The AP2/ERF family of proteins is a plant-specific class of putative transcription factors that regulate a wide variety of developmental processes and are characterized by the presence of an AP2 DNA binding domain that is predicted to form an amphipathic alpha helix that binds DNA (PFAM Accession PF00847). The AP2 domain was first identified in APETALA2, an *Arabidopsis* protein that regulates meristem identity, floral organ specification, seed coat development, and floral homeotic gene expression. The AP2/ERF proteins have been subdivided into distinct subfamilies based on the presence of conserved domains. Initially, the family was divided into two subfamilies based on the number of DNA binding domains, with the ERF subfamily having one DNA binding domain, and the AP2 subfamily having 2 DNA binding domains. As more sequences were identified, the family was subsequently subdivided into five subfamilies: AP2, DREB, ERF, RAV, and others. (Sakuma et al. (2002) *Biochem Biophys Res Comm* 290:998-1009).

Members of the *APETALA2* (AP2) family of proteins function in a variety of biological events, including but not limited to, development, plant regeneration, cell division, embryogenesis, and cell proliferation (see, e.g., Riechmann and Meyerowitz (1998) *Biol Chem* 379:633-646; Saleh and Pages (2003) *Genetika* 35:37-50 and Database of *Arabidopsis* Transciption Factors at daft.cbi.pku.edu.cn). The AP2 family includes, but is not limited to, AP2, ANT, Glossyl5, AtBBM, BnBBM, and maize ODP2/BBM.

Provided herein is an analysis of fifty sequences with homology to a maize BBM sequence (also referred to as maize ODP2 or ZmODP2, the polynucleotide and amino acid sequence of the maize BBM is set forth in SEQ ID NO: 9 and 10, respectively; the polynucleotide and amino acid sequence of another ZmBBM is set forth in SEQ ID NO: 121 and 122, respectively). The analysis identified three motifs (motifs 4-6; set forth in SEQ ID NOs: 51-53), along with the AP2 domains (motifs 2 and 3; SEQ ID NOs: 49 and 50) and linker sequence that bridges the AP2 domains (motif 1; SEQ ID NO: 48), that are found in all of the BBM homologues. Thus, motifs 1-6 distinguish these BBM homologues from other AP2-domain containing proteins (e.g., WRI, AP2, and RAP2.7) and these BBM homologues comprise a subgroup of AP2 family of proteins referred to herein as the BBM/PLT subgroup. In some embodiments, the cell proliferation factor that is used in the methods and compositions is a member of the BBM/PLT group of AP2 domain-containing polypeptides. In these embodiments, the cell proliferation factor comprises two AP2 domains and motifs 4-6 (SEQ ID NOs: 51-53) or a fragment or variant thereof. In some of these embodiments, the AP2 domains have the sequence set forth in SEQ ID NOs: 49 and 50 or a fragment or variant thereof, and in particular embodiments, further comprises the linker sequence of SEQ ID NO: 48 or a fragment or variant thereof. In other embodiments, the cell proliferation factor comprises at least one of motifs 4-6 or a fragment or variant thereof, along with two AP2 domains, which in some embodiments have the sequence set forth in SEQ ID NO: 49 and/or 50 or a fragment or variant thereof, and in particular embodiments have the linker sequence of SEQ ID NO: 48 or a fragment or variant thereof. Based on the phylogenetic analysis provided herein, the subgroup of BBM/PLT polypeptides can be subdivided into the BBM, AIL6/7, PLT1/2, AIL1, PLT3, and ANT groups of polypeptides.

In some embodiments, the cell proliferation factor is a babyboom (BBM) polypeptide, which is a member of the AP2 family of transcription factors. The BBM protein from *Arabidopsis* (AtBBM) is preferentially expressed in the developing embryo and seeds and has been shown to play a central role in regulating embryo-specific pathways. Overexpression of AtBBM has been shown to induce spontaneous formation of somatic embryos and cotyledon-like structures on seedlings. See, Boutiler et al. (2002) *The Plant Cell* 14:1737-1749. The maize BBM protein also induces embryogenesis and promotes transformation (See, U.S. Pat. No. 7,579,529, which is herein incorporated by reference in its entirety). Thus, BBM polypeptides stimulate proliferation, induce embryogenesis, enhance the regenerative capacity of a plant, enhance transformation, and as demonstrated herein, enhance rates of targeted polynucleotide modification. As used herein “regeneration” refers to a morphogenic response that results in the production of new tissues, organs, embryos, whole plants or parts of whole plants that are derived from a single cell or a group of cells. Regeneration may proceed indirectly via a callus phase or directly, without an intervening callus phase. “Regenerative capacity” refers to the ability of a plant cell to undergo regeneration.

In some embodiments, the babyboom polypeptide comprises two AP2 domains and at least one of motifs 7 and 10 (set forth in SEQ ID NO: 54 and 57, respectively) or a variant or fragment thereof. In certain embodiments, the AP2 domains are motifs 3 and 2 (SEQ ID NOs: 50 and 49, respectively) or a fragment or variant thereof, and in particular embodiments, the babyboom polypeptide further comprises a linker sequence between AP2 domain 1 and 2 having motif 1 (SEQ ID NO: 48) or a fragment or variant thereof. In particular embodiments, the BBM polypeptide further comprises motifs 4-6 (SEQ ID NOs 51-53) or a fragment or variant thereof. The BBM polypeptide can further comprise motifs 8 and 9 (SEQ ID NOs: 55 and 56, respectively) or a fragment or variant thereof, and in some embodiments, motif 10 (SEQ ID NO: 57) or a variant or fragment thereof. In some of these embodiments, the BBM polypeptide also comprises at least one of motif 14 (set forth in SEQ ID NO: 58), motif 15 (set forth in SEQ ID NO: 59), and motif 19 (set forth in SEQ ID NO: 60), or variants or fragments thereof. The variant of a particular amino acid motif can be an amino acid sequence having at least about 40%, 50%, 60%, 70%, 75%, 80%, 85%, 90%, 95%, 96%, 97%, 98%, 99%, or greater sequence identity with the motif disclosed herein. Alternatively, variants of a particular amino acid motif can be an amino acid sequence that differs from the amino acid motif by 1, 2, 3, 4, 5, 6, 7, 8, 9, or 10 amino acids.

Non-limiting examples of babyboom polynucleotides and polypeptides that can be used in the methods and compositions include the *Arabidopsis thaliana* AtBBM (SEQ ID NOs: 21 and 22), *Brassica napus* BnBBM1 (SEQ ID NOs: 23 and 24), *Brassica napus* BnBBM2 (SEQ ID NOs: 25 and 26), *Medicago truncatula* MtBBM (SEQ ID NOs: 7 and 8), *Glycine max* GmBBM (SEQ ID NOs: 1 and 2), *Vitis vinifera* VvBBM (SEQ ID NOs: 5 and 6), *Zea mays* ZmBBM (SEQ ID NOs: 9 and 10 and genomic sequence set forth in SEQ ID NO: 68; or SEQ ID NOs: 121 and 122 and genomic sequence set forth in SEQ ID NO: 116) and ZmBBM2 (SEQ ID NOs: 11 and 12), *Oryza sativa* OsBBM (polynucleotide sequences set forth in SEQ ID NOs: 13 and 120; amino acid sequence set forth in SEQ ID NO: 14; and genomic sequence set forth in SEQ ID NO: 117), OsBBM1 (SEQ ID NOs: 15 and 16), OsBBM2 (SEQ ID NOs: 17 and 18), and OsBBM3 (SEQ ID NOs: 19 and 20), *Sorghum bicolor* SbBBM (SEQ ID NOs: 3 and 4 and genomic sequence set forth in SEQ ID NO: 69) and SbBBM2 (SEQ ID NOs: 27 and 28) or active fragments or variants thereof. In particular embodiments, the cell proliferation factor is a maize BBM polypeptide (SEQ ID NO: 10, 122, or 12) or a variant or fragment thereof, or is encoded by a maize BBM polynucleotide (SEQ ID NO: 9, 68, 121, 116, or 11) or a variant or fragment thereof.

Thus, in some embodiments, a polynucleotide encoding a cell proliferation factor has a nucleotide sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to the nucleotide sequence set forth in SEQ ID NO: 1, 3, 5, 7, 9, 11, 13, 15, 17, 19, 21, 23, 25, 27, 68, 116, 117, 120, 121, or 69 or the cell proliferation factor has an amino acid sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence set forth in SEQ ID NO: 2, 4, 6, 8, 10, 12, 14, 16, 18, 20, 22, 24, 26, 122, or 28. In some of these embodiments, the cell proliferation factor has at least one of motifs 7 and 10 (SEQ ID NO: 54 and 57, respectively) or a variant or fragment thereof at the corresponding amino acid residue positions in the babyboom polypeptide. In other embodiments, the cell proliferation factor further comprises at least one of motif 14 (set forth in SEQ ID NO: 58), motif 15 (set forth in SEQ ID NO: 59), and motif 19 (set forth in SEQ ID NO: 60) or a variant or fragment thereof at the corresponding amino acid residue positions in the babyboom polypeptide.

In other embodiments, other cell proliferation factors, such as, Lec1, Kn1 family, WUSCHEL (e.g., WUS1, the polynucleotide and amino acid sequence of which is set forth in SEQ ID NO: 61 and 62; WUS2, the polynucleotide and amino acid sequence of which is set forth in SEQ ID NO: 63 and 64; WUS2 alt, the polynucleotide and amino acid sequence of which is set forth in SEQ ID NO: 114 and 115; WUS3, the polynucleotide and amino acid sequence of which is set forth in SEQ ID NO: 105 and 106), Zwille, and Aintegumeta (ANT), may be used alone, or in combination with a babyboom polypeptide or other cell proliferation factor. See, for example, U.S. Application Publication No. 2003/0135889, International Application Publication No. WO 03/001902, and U.S. Pat. No. 6,512,165, each of which is herein incorporated by reference. When multiple cell proliferation factors are used, or when a babyboom polypeptide is used along with any of the abovementioned polypeptides, the polynucleotides encoding each of the factors can be present on the same expression cassette or on separate expression cassettes. When two or more factors are coded for by separate expression cassettes, the expression cassettes can be provided to the plant simultaneously or sequentially.

In some embodiments, polynucleotides or polypeptides having homology to a known babyboom polynucleotide or polypeptide and/or sharing conserved functional domains can be identified by screening sequence databases using programs such as BLAST. The databases can be queried using full length sequences, or with fragments including, but not limited to, conserved domains or motifs. In some embodiments, the sequences retrieved from the search can be further characterized by alignment programs to quickly identify and compare conserved functional domains, regions of highest homology, and nucleotide and/or amino differences between sequences, including insertions, deletions, or substitutions, including those programs described in more detail elsewhere herein. The retrieved sequences can also be evaluated using a computer program to analyze and output the phylogenetic relationship between the sequences.

In other embodiments, polynucleotides or polypeptides having homology to a known babyboom polynucleotide or polypeptide or one that has been disclosed herein and/or sharing conserved functional domains can be identified using standard nucleic acid hybridization techniques, such as those described in more detail elsewhere herein. Extensive guides on nucleic acid hybridization include Tijssen (1993) Laboratory Techniques in Biochemistry and Molecular Biology—Hybridization with Nucleic Acid Probes, Part I, Chapter 2 (Elsevier, NY); Ausubel et al., eds. (1995) Current Protocols in Molecular Biology, Chapter 2 (Greene Publishing and Wiley-Interscience, NY); and, Sambrook et al. (1989) Molecular Cloning: A Laboratory Manual (2d ed., Cold Spring Harbor Laboratory Press, Plainview, N.Y.).

Compositions further comprise isolated BBM polynucleotides and isolated BBM polypeptides and variants and fragments thereof, expression cassettes comprising the same, and plants comprising the same. Compositions can comprise isolated polynucleotides encoding GmBBM (SEQ ID NO: 1), SbBBM (SEQ ID NO: 3), MtBBM (SEQ ID NO: 7), or OsBBM2 (SEQ ID NO: 17) or an active variant or fragment thereof. Isolated polypeptides include those having SEQ ID NO: 2, 4, 8, or 18 (GmBBM, SbBBM, MtBBM, or OsBBM2, respectively) or an active variant or fragment thereof. The percent identity of the novel BBM polypeptide sequences with those known in the art is presented in Table 1.

PCR primers generally need not encode a biologically active portion of a cell proliferation factor.

"Variants" is intended to mean substantially similar sequences. For polynucleotides, a variant comprises a polynucleotide having deletions at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. For polynucleotides encoding polypeptides conservative variants include those sequences that, because of the degeneracy of the genetic code, encode the amino acid sequence the polypeptide (e.g., cell proliferation factor). Naturally occurring variants such as these can be identified with the use of well-known molecular biology techniques, such as, for example, with polymerase chain reaction (PCR) and hybridization techniques. Variant polynucleotides also include synthetically derived polynucleotides, such as those generated, for example, by using site-directed mutagenesis. Generally, variants of a particular will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters.

TABLE 1

The percent sequence identity between each of 14 babyboom polypeptides.

| | Zm BBM2 | Sb BBM2 | Os BBM2 | Os BBM3 | Os BBM1 | Zm BBM | Sb BBM | Os BBM | Bn BBM1 | Bn BBM2 | At BBM | Mt BBM | Gm BBM | Vv BBM |
|---|---|---|---|---|---|---|---|---|---|---|---|---|---|---|
| ZmBBM2 | 100 | | | | | | | | | | | | | |
| SbBBM2 | 92 | 100 | | | | | | | | | | | | |
| OsBBM2 | 79 | 77 | 100 | | | | | | | | | | | |
| OsBBM3 | 64 | 66 | 67 | 100 | | | | | | | | | | |
| OsBBM1 | 50 | 46 | 46 | 46 | 100 | | | | | | | | | |
| ZmBBM | 43 | 44 | 44 | 47 | 47 | 100 | | | | | | | | |
| SbBBM | 43 | 44 | 42 | 45 | 44 | 90 | 100 | | | | | | | |
| OsBBM | 44 | 44 | 45 | 46 | 49 | 69 | 70 | 100 | | | | | | |
| BnBBM1 | 42 | 41 | 42 | 41 | 40 | 45 | 42 | 43 | 100 | | | | | |
| BnBBM2 | 43 | 41 | 42 | 41 | 39 | 46 | 44 | 44 | 97 | 100 | | | | |
| AtBBM | 43 | 41 | 39 | 42 | 41 | 43 | 43 | 42 | 81 | 82 | 100 | | | |
| MtBBM | 41 | 40 | 40 | 41 | 43 | 42 | 43 | 41 | 47 | 47 | 47 | 100 | | |
| GmBBM | 45 | 44 | 42 | 45 | 44 | 41 | 42 | 44 | 46 | 46 | 43 | 68 | 100 | |
| VvBBM | 51 | 48 | 50 | 48 | 50 | 48 | 47 | 48 | 49 | 49 | 48 | 58 | 62 | 100 |

By "fragment" is intended a portion of the polynucleotide or a portion of an amino acid sequence and hence protein encoded thereby. Fragments of a polynucleotide may retain the biological activity of the native polynucleotide and, for example, have promoter activity (i.e., capable of initiating transcription), or are capable of stimulating proliferation, inducing embryogenesis, or modifying the regenerative capacity of a plant. In those embodiments wherein the polynucleotide encodes a polypeptide, fragments of the polynucleotide may encode protein fragments that retain the biological activity of the native protein. Alternatively, fragments of a polynucleotide that are useful as hybridization probes generally do not retain biological activity or encode fragment proteins that retain biological activity. Thus, fragments of a nucleotide sequence may range from at least about 20, 50, 100, 150, 200, 250, 300, 400, 500 nucleotides, or greater.

A fragment of a polynucleotide that encodes a biologically active portion of a cell proliferation factor, for example, will encode at least 15, 25, 30, 50, 100, 150, 200, 250, 300, 400, 500 contiguous amino acids, or up to the total number of amino acids present in the full-length cell proliferation factor. Fragments of a cell proliferation factor polynucleotide that are useful as hybridization probes or Variants of a particular polynucleotide that encodes a polypeptide can also be evaluated by comparison of the percent sequence identity between the polypeptide encoded by a variant polynucleotide and the polypeptide encoded by the particular polynucleotide. Percent sequence identity between any two polypeptides can be calculated using sequence alignment programs and parameters. Where any given pair of polynucleotides is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion of one or more amino acids at the N-terminal and/or C-terminal end of the native protein; deletion and/or addition of one or more amino acids at one or more internal sites in the native protein; and/or substitution of one or more amino acids at one or more sites in the native protein. Variant proteins retain the desired biological activity of the native protein. For example, variant cell proliferation factors stimulate proliferation and variant babyboom polypeptides are capable of stimulating proliferation, inducing embryogenesis, modifying the regenerative capacity of a plant, increasing the transformation efficiency in a plant, increasing or maintaining the yield in a plant under abiotic stress, producing asexually derived embryos in a plant, and/or enhancing rates of targeted polynucleotide modification. Such variants may result from, for example, genetic polymorphism or from human manipulation. Biologically active variants of a native cell proliferation factor will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters. A biologically active variant of a cell proliferation factor protein may differ from that protein by as few as 1-15 amino acid residues, as few as 1-10, such as 6-10, as few as 5, as few as 4, 3, 2, or even 1 amino acid residue.

In some embodiments, variants or fragments of the BBM polypeptide have amino acid residues valine, tyrosine, and leucine at the positions corresponding to positions 311, 312, and 313, respectively, of SEQ ID NO: 4 or variants or fragments of the BBM polynucleotide encodes a polypeptide having amino acid residues valine, tyrosine, and leucine at the positions corresponding to positions 311, 312, and 313, respectively, of SEQ ID NO: 4. In certain embodiments, variants or fragments of the BBM polypeptide have amino acid residues valine, tyrosine, and leucine at the positions corresponding to positions 337, 338, and 339, respectively, of SEQ ID NO: 18 or variants or fragments of the BBM polynucleotide encodes a polypeptide having amino acid residues valine, tyrosine, and leucine at the positions corresponding to positions 337, 338, and 339, respectively, of SEQ ID NO: 18. In other embodiments, variants or fragments of the BBM polypeptide have amino acid residues methionine, alanine, and serine at the positions corresponding to positions 1, 2, and 3, respectively, of SEQ ID NO: 8 or variants or fragments of the BBM polynucleotide encodes a polypeptide having amino acid residues methionine, alanine, and serine at the positions corresponding to positions 1, 2, and 3, respectively of SEQ ID NO: 8.

The babyboom polynucleotides and polypeptides can be introduced into a plant or plant cell in order to stimulate embryogenesis, modify the regenerative capacity of the plant, increase the transformation efficiency of the plant, increase or maintain the yield in the plant under abiotic stress, and/or to enhance targeted polynucleotide modification. The babyboom polynucleotide or polypeptide can be provided to a plant simultaneously with or prior to the introduction of a polynucleotide of interest in order to facilitate transformation of the plant with the polynucleotide of interest. Further, a haploid plant cell can be provided a novel babyboom polynucleotide or polypeptide to produce a haploid plant embryo (see U.S. Pat. No. 7,579,529, which is herein incorporated by reference in its entirety).

The cell proliferation factor polynucleotide can be operably linked to a promoter active in a plant. Various promoters can be used for the regulation of the expression of the cell proliferation factor. The promoter may be selected based on the desired outcome or expression pattern (for a review of plant promoters, see Potenza et al. (2004) *In Vitro Cell Dev Biol* 40:1-22).

Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), the *Agrobacterium* nopaline synthase (NOS) promoter (Bevan et al. (1983) *Nucl. Acids Res.* 11:369-385), and the like. Other constitutive promoters are described in, for example, U.S. Pat. Nos. 5,608,149; 5,608,144; 5,604,121; 5,569,597; 5,466,785; 5,399,680; 5,268,463; 5,608,142; and 6,177,611.

In some embodiments, an inducible promoter can be used, such as from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference. Promoters that are expressed locally at or near the site of pathogen infection include, for example, Marineau et al. (1987) *Plant Mol. Biol.* 9:335-342; Matton et al. (1989) *Mol Plant-Microbe Interact* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Additional promoters include the inducible promoter for the maize PRms gene, whose expression is induced by the pathogen *Fusarium moniliforme* (see, for example, Cordero et al. (1992) *Physiol. Mol. Plant Path.* 41:189-200). Wound-inducible promoters include potato proteinase inhibitor (pin II) gene (Ryan (1990) *Ann. Rev. Phytopath.* 28:425-449; Duan et al. (1996) *Nat Biotechnol* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225: 1570-1573); WIP1 (Rohmeier et al. (1993) *Plant Mol. Biol.* 22:783-792; Eckelkamp et al. (1993) *FEBS Lett* 323:73-76); MPI gene (Corderok et al. (1994) *Plant J.* 6:141-150); and the like, herein incorporated by reference. Another inducible promoter is the maize In2-2 promoter (deVeylder et al. (2007) *Plant Cell Physiol* 38:568-577, herein incorporated by reference).

Chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners (De Veylder et al. (1997) *Plant Cell Physiol.* 38:568-77), the maize GST promoter (GST-II-27, WO 93/01294), which is activated by hydrophobic electrophilic compounds that are used as pre-emergent herbicides, the PR-1 promoter (Cao et al. (2006) *Plant Cell Reports* 6:554-60), which is activated by BTH or benxo(1,2,3)thiaidazole-7-carbothioic acid s-methyl ester, the tobacco PR-la promoter (Ono et al. (2004) *Biosci. Biotechnol. Biochem.*

68:803-7), which is activated by salicylic acid, the copper inducible ACE1 promoter (Mett et al. (1993) *PNAS* 90:4567-4571), the ethanol-inducible promoter AlcA (Caddick et al. (1988) *Nature Biotechnol* 16:177-80), an estradiol-inducible promoter (Bruce et al. (2000) *Plant Cell* 12:65-79), the XVE estradiol-inducible promoter (Zao et al. (2000) *Plant J* 24:265-273), the VGE methoxyfenozide inducible promoter (Padidam et al. (2003) *Transgenic Res* 12:101-109), and the TGV dexamethasone-inducible promoter (Bohner et al. (1999) *Plant J* 19:87-95). Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237; Gatz et al. (1992) *Plant J* 2:397-404; and U.S. Pat. Nos. 5,814,618 and 5,789,156), herein incorporated by reference.

Tissue-preferred promoters can be utilized to target enhanced expression of a sequence of interest within a particular plant tissue. Tissue-preferred promoters include Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Lam (1994) *Results Probl. Cell Differ.* 20:181-196; and Guevara-Garcia et al. (1993) *Plant* 4(3):495-505.

Leaf-preferred promoters are known in the art. See, for example, Yamamoto et al. (1997) *Plant J.* 12:255-265; Kwon et al. (1994) *Plant Physiol.* 105:357-67; Yamamoto et al. (1994) *Plant Cell Physiol.* 35:773-778; Gotor et al. (1993) *Plant J.* 3:509-18; Orozco et al. (1993) *Plant Mol. Biol.* 23:1129-1138; and Matsuoka et al. (1993) *Proc. Natl. Acad. Sci. USA* 90:9586-9590. In addition, promoter of cab and rubisco can also be used. See, for example, Simpson et al. (1958) *EMBO J* 4:2723-2729 and Timko et al. (1988) *Nature* 318:57-58.

Root-preferred promoters are known and can be selected from the many available. See, for example, Hire et al. (1992) *Plant Mol. Biol.* 20:207-218 (soybean root-specific glutamine synthase gene); Keller and Baumgartner (1991) *Plant Cell* 3:1051-1061 (root-specific control element in the GRP 1.8 gene of French bean); Sanger et al. (1990) *Plant Mol. Biol.* 14:433-443 (root-specific promoter of the mannopine synthase (MAS) gene of *Agrobacterium tumefaciens*); and Miao et al. (1991) *Plant Cell* 3:11-22 (full-length cDNA clone encoding cytosolic glutamine synthase (GS), which is expressed in roots and root nodules of soybean). See also Bogusz et al. (1990) *Plant Cell* 2:633-641, where two root-specific promoters isolated from hemoglobin genes from the nitrogen-fixing nonlegume *Parasponia andersonii* and the related non-nitrogen-fixing nonlegume *Trema tomentosa* are described. Leach and Aoyagi (1991) describe their analysis of the promoters of the highly expressed rolC and rolD root-inducing genes of *Agrobacterium rhizogenes* (see *Plant Sci* (Limerick) 79:69-76). Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue (see *EMBO J* 8:343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29:759-772); and rolB promoter (Capana et al. (1994) *Plant Mol. Biol.* 25:681-691. See also U.S. Pat. Nos. 5,837,876; 5,750,386; 5,633,363; 5,459,252; 5,401,836; 5,110,732; and 5,023,179. Another root-preferred promoter includes the promoter of the phaseolin gene (Murai et al. (1983) *Science* 23:476-482 and Sengopta-Gopalen et al. (1988) *Proc. Natl. Acad. Sci. USA* 82:3320-3324.

Seed-preferred promoters include both those promoters active during seed development as well as promoters active during seed germination. See Thompson et al. (1989) *BioEssays* 10:108, herein incorporated by reference. Such seed-preferred promoters include, but are not limited to, Cim1 (cytokinin-induced message); cZ19B1 (maize 19 kDa zein); and milps (myo-inositol-1-phosphate synthase); (see WO 00/11177 and U.S. Pat. No. 6,225,529; herein incorporated by reference). For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa gamma zein, waxy, shrunken 1, shrunken 2, globulin 1, oleosin, nuc1, etc. See also WO 00/12733, where seed-preferred promoters from end1 and end2 genes are disclosed; herein incorporated by reference.

Where low-level expression is desired, weak promoters will be used. Generally, by "weak promoter" is intended a promoter that drives expression of a coding sequence at a low level. By low level is intended at levels of about 1/1000 transcripts to about 1/100,000 transcripts to about 1/500,000 transcripts. Alternatively, it is recognized that weak promoters also encompasses promoters that are expressed in only a few cells and not in others to give a total low level of expression. Where a promoter is expressed at unacceptably high levels, portions of the promoter sequence can be deleted or modified to decrease expression levels. Such weak constitutive promoters include, for example, the core promoter of the Rsyn7 promoter (WO 99/43838 and U.S. Pat. No. 6,072,050), the core 35S CaMV promoter, and the like.

Other promoters of interest include the Rab 16 promoter (Mundy et al. (1990) *PNAS* 87: 1406-1410), the *Brassica* LEA3-1 promoter (U.S. Application Publication No. US 2008/0244793), the HVA1s, Dhn8s, and Dhn4s from barley and the wsi18j, rab16Bj from rice (Xiao and Xue (2001) *Plant Cell Rep* 20:667-73), and D 113 from cotton (Luo et al. (2008) *Plant Cell Rep* 27:707-717).

In some embodiments, the polynucleotide encoding a cell proliferation factor (e.g., babyboom polypeptide) is operably linked to a maize ubiquitin promoter or a maize oleosin promoter (e.g., SEQ ID NO: 65 or a variant or fragment thereof).

In some of those embodiments wherein the vector comprises a presently disclosed promoter construct operably linked to a polynucleotide encoding a site-specific recombinase and in some embodiments, a polynucleotide encoding a babyboom polypeptide, the vector can further comprise a polynucleotide encoding a Wuschel polypeptide (see International Application Publication No. WO 01/23575 and U.S. Pat. No. 7,256,322, each of which are herein incorporated by reference in its entirety). In certain embodiments, the polynucleotide encoding the Wuschel polypeptide has the sequence set forth in SEQ ID NO: 61, 63, 114, or 105 (WUS1, WUS2, WUS2 alt, or WUS3, respectively) or an active variant or fragment thereof. In particular embodiments, the Wuschel polypeptide has the sequence set forth in SEQ ID NO: 62, 64, 115, or 106 (WUS1, WUS2, WUS2 alt, or WUS3, respectively) or an active variant or fragment thereof. In some of these embodiments, the polynucleotide encoding a Wuschel polypeptide is operably linked to a promoter active in the plant, including but not limited to the maize In2-2 promoter or a nopaline synthase promoter. In some of these embodiments, the expression cassettes for the site-specific recombinase, the babyboom polypeptide, and the Wuschel polypeptide are all flanked by site-specific recombination sites that are directly repeated and are recognized by the site-specific recombinase whose expression is regulated by a presently disclosed promoter construct, such that expression of the site-specific recombinase results in the excision of the three expression cassettes.

In some embodiments, the vector comprises a promoter disclosed herein (maize Rab17 promoter with an attB1 site) operably linked to a site-specific recombinase (e.g., Cre, FLP); a second promoter operably linked to a cell proliferation factor (e.g., a babyboom polypeptide); and a third promoter operably linked to a polynucleotide of interest, such as those disclosed elsewhere herein (e.g., trait gene), or multiple polynucleotides of interest operably linked to one or more promoters; and in some embodiments, a fourth promoter operably linked to a WUS gene. In some of these embodiments, the expression cassettes for the site-specific recombinase, the cell proliferation factor, and the Wuschel polypeptide are all flanked by site-specific recombination sites that are directly repeated and are recognized by the site-specific recombinase, such that expression of the site-specific recombinase results in the excision of the three expression cassettes, leaving the polynucleotides of interest (e.g., trait genes) behind. In other embodiments, the polynucleotide of interest (e.g., trait gene) is introduced along with or following the vector comprising a presently disclosed promoter operably linked to a site-specific recombinase, and at least one cell proliferation factor (e.g., babyboom polypeptide, Wuschel polypeptide) operably linked to one or more promoters, wherein the polynucleotide of interest is present on a separate vector from the expression cassettes for the site-specific recombinase and cell proliferation factor(s). In some of these embodiments, the expression cassettes for the site-specific recombinase and cell proliferation factor(s) are flanked by recombination sites that are recognized by the site-specific recombinase. Expression of the cell proliferation factors facilitates the transformation of the polynucleotide of interest (e.g., trait gene) and expression of the site-specific recombinase results in the excision of the expression cassettes for the site-specific recombinase and cell proliferation factor(s).

The presently disclosed promoter constructs, expression cassettes, and vectors can be introduced into a host cell. By "host cell" is meant a cell, which comprises a heterologous nucleic acid sequence. Host cells may be prokaryotic cells such as *E. coli*, or eukaryotic cells such as yeast, insect, amphibian, or mammalian cells. In some examples, host cells are monocotyledonous or dicotyledonous plant cells. In particular embodiments, the monocotyledonous host cell is a maize host cell.

An intermediate host cell may be used, for example, to increase the copy number of the cloning vector and/or to mediate transformation of a different host cell. With an increased copy number, the vector containing the nucleic acid of interest can be isolated in significant quantities for introduction into the desired plant cells. In one embodiment, plant promoters that do not cause expression of the polypeptide in bacteria are employed.

Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al. (1977) *Nature* 198:1056), the tryptophan (trp) promoter system (Goeddel et al. (1980) *Nucleic Acids Res.* 8:4057) and the lambda derived P L promoter and N-gene ribosome binding site (Shimatake et al. (1981) *Nature* 292:128). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein are available using *Bacillus* sp. and *Salmonella* (Palva et al. (1983) *Gene* 22:229-235); Mosbach et al. (1983) *Nature* 302:543-545).

Methods for expressing a polynucleotide of interest in a plant comprise introducing an expression cassette or vector. Alternatively, the method can comprise introducing a promoter construct, wherein the promoter construct is stably integrated into the genome of the plant and operably linked to a polynucleotide of interest.

"Introducing" is intended to mean presenting to the organism, such as a plant, or the cell the polynucleotide or polypeptide in such a manner that the sequence gains access to the interior of a cell of the organism or to the cell itself. The methods and compositions do not depend on a particular method for introducing a sequence into an organism or cell, only that the polynucleotide or polypeptide gains access to the interior of at least one cell of the organism. Methods for introducing polynucleotides or polypeptides into plants are known in the art including, but not limited to, stable transformation methods, transient transformation methods, virus-mediated methods, and sexual breeding.

"Stable transformation" is intended to mean that the nucleotide construct introduced into a plant integrates into a genome of the plant and is capable of being inherited by the progeny thereof "Transient transformation" is intended to mean that a polynucleotide is introduced into the plant and does not integrate into a genome of the plant or a polypeptide is introduced into a plant.

Protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in Plant Cell, Tissue, and Organ Culture: Fundamental Methods, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In*

*Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Rep* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Rep* 12:250-255 and Christou and Ford (1995) *Annals of Botany* 75:407-413 (rice); Osjoda et al. (1996) *Nat Biotechnol* 14:745-750 (maize via *Agrobacterium tumefaciens*); all of which are herein incorporated by reference.

In specific embodiments, the sequences can be provided to a plant using a variety of transient transformation methods. Such transient transformation methods include, but are not limited to, the introduction of the polypeptide of interest directly into the plant or the introduction of a polynucleotide encoding the polypeptide of interest into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91:2176-2180 and Hush et al. (1994) *J Cell Sci* 107:775-784, all of which are herein incorporated by reference. Alternatively, the polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which its released to become integrated into the genome is greatly reduced. Such methods include the use particles coated with polyethylimine (PEI; Sigma #P3143).

In other embodiments, the polynucleotide may be introduced into plants by contacting plants with a virus or viral nucleic acids. Generally, such methods involve incorporating a nucleotide construct within a viral DNA or RNA molecule. It is recognized that the cell proliferation factor may be initially synthesized as part of a viral polyprotein, which later may be processed by proteolysis in vivo or in vitro to produce the desired recombinant protein. Further, it is recognized that promoters also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Other methods of introducing polynucleotides into a plant can be used, including plastid transformation methods, and the methods for introducing polynucleotides into tissues from seedlings or mature seeds.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide can be contained in a transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

In specific embodiments, methods are provided for the excision of a polynucleotide of interest from a target site in a plant, wherein the polynucleotide of interest is flanked by a first and a second recombination site that are recombinogenic with respect to one another and that are directly repeated. The method comprises introducing into the plant an expression cassette comprising a presently disclosed promoter construct (e.g., SEQ ID NO: 30 or a variant or fragment thereof) operably linked to a site-specific recombinase, expressing the recombinase, so that the recombinase recognizes and implements recombination at the recombination sites flanking the polynucleotide of interest, thereby excising the polynucleotide of interest. The expression cassette can comprise any of the linker sequences, attB sites, termination regions, etc., such as those described herein.

The terms "target site," and "target sequence," as used interchangeably herein, refer to a polynucleotide sequence present in a cell of an organism, such as a plant, that comprises at least one site-specific recombination site. The target site may be part of the organism's native genome or integrated therein or may be present on an episomal polynucleotide. The genomic target sequence may be on any region of any chromosome, and may or may not be in a region encoding a protein or RNA. The target site may be native to the cell or heterologous. In some embodiments, the heterologous target sequence may have been transgenically inserted into the organism's genome, and may be on any region of any chromosome, including an artificial or satellite chromosome, and may or may not be in a region encoding a protein or RNA. It is recognized that the cell or the organism may comprise multiple target sites, which may be located at one or multiple loci within or across chromosomes.

Alternative methods for excising a polynucleotide of interest from a target site in a plant include providing a plant comprising a target site comprising in operable linkage: a first site-specific recombination site, a first promoter, the polynucleotide of interest, a second promoter, a polynucleotide encoding a site-specific recombinase, and a second site-specific recombination site. The first and the second site-specific recombination sites are recombinogenic with respect to one another and directly repeated. The polynucleotide of interest and its operably linked promoter may precede or follow the polynucleotide encoding the site-specific recombinase and its operably linked promoter. The second promoter is one of the presently disclosed promoter constructs (e.g., SEQ ID NO: 30 or a variant or fragment thereof). The method comprises expressing the site-specific recombinase, whereby the site-specific recombinase recognizes and implements recombination at the first and the second site-specific recombination sites, thereby excising the polynucleotide of interest and the polynucleotide encoding the site-specific recombinase.

In some embodiments, the target site further comprises a third promoter operably linked to a polynucleotide encoding a Wuschel polypeptide. The three expression cassettes may be in any order, but in some embodiments, the target site comprises in operable linkage: the first site-specific recombination site, the third promoter, the polynucleotide encoding a Wuschel polypeptide, the first promoter, the polynucleotide of interest, the second promoter, the polynucleotide encoding the site-specific recombinase, and the second site-specific recombination site, wherein expression of the recombinase results in the excision of all three expression cassettes. The expression cassette can comprise any of the linker sequences, attB sites, termination regions, etc., such as those described herein.

Methods are provided to enhance the efficiency of plastid transformation, which include introducing into a plant cell a heterologous polynucleotide encoding a cell proliferation factor and expressing the heterologous polynucleotide before, during, or immediately following the transformation of the plastid of the plant cell with a polynucleotide of interest. The heterologous polynucleotide encoding a cell proliferation factor can be co-delivered with the polynucleotide of interest or the cell proliferation polynucleotide can first be introduced into the plant, followed by the introduction of the polynucleotide of interest.

As used herein, a "plastid" refers to an organelle present in plant cells that stores and manufactures chemical compounds used by the cell, such as starch, fatty acids, terpenes, and that has been derived from a proplastid. Thus, plastids of plants typically have the same genetic content. Plastids include chloroplasts, which are responsible for photosynthesis, amyloplasts, chromoplasts, statoliths, leucoplasts, elaioplasts, and proteinoplasts.

The plastid genome is circular and varies in size among plant species from about 120 to about 217 kilobase pairs (kb). The genome typically includes a large inverted repeat, which can contain up to about 76 kilobase pairs, but which is more typically in the range of about 20 to about 30 kilobase pairs. The inverted repeat present in the plastid genome of various organisms has been described (Palmer (1990) *Trends Genet* 6:115-120).

Transformation of plastids can result in a homoplasmic state, wherein essentially all of the plastids in a plant cell have the introduced DNA integrated into the plastid genome. This occurs through a selection process, whereby those cells that comprise a sufficient number of transformed plastids having an introduced selectable marker gene survive on the selection medium, and through the reproduction of the transformed plastid genomes. Plastids can be present in a plant cell at a very high copy number, with up to 50,000 copies per cell present for the chloroplast genome (Bendich (1987) *BioEssays* 6:279-282). Thus, through plastid transformation, plant cells can be engineered to maintain an introduced gene of interest at a very high copy number.

While plastid transformation is routine and relatively efficient in tobacco by bombardment of leaves, the application of plastid transformation technology in important crop species is not routine. For example, plastid transformation in maize and wheat has not been reported. Plastid transformation is possible in soybean, but the frequency of transformation with vectors carrying trait genes is low. Plastid transformation is possible in rice, but homoplasmic events have not been recovered.

The introduction and expression of polynucleotides encoding cell proliferation factors may be used to enhance the efficiency of plastid transformation. Any cell proliferation factor known in the art or described elsewhere herein may be used to enhance plastid transformation, including babyboom polypeptides. In certain embodiments, embryogenesis-stimulating polypeptides are used to enhance plastid transformation.

Methods are known in the art for introducing genes into the plastid genome. See, for example, Svab et al. (1990) *Proc. Natl. Acad. Sci. USA* 87: 8526-8530; Svab and Maliga (1993) *Proc. Natl. Acad. Sci. USA* 90: 913-917; Svab and Maliga (1993) *EMBO J.* 12: 601-606; and U.S. Pat. Nos. 5,451,513 and 5,545,818; each of which is herein incorporated by reference in its entirety.

One method involves the integration of a polynucleotide of interest into the plastid genome through homologous recombination. Such methods involve the introduction of a polynucleotide of interest flanked by regions of homology with regions of the plastid genome into a plant cell. Delivery of the polynucleotide of interest into the plant cell can be via any method of transformation known in the art, including those described elsewhere herein. These include, but are not limited to, particle gun delivery (Svab, Z. et al. (1990) *Proc Natl Acad Sci USA* 87:8526-8530; Svab and Maliga (1993) *Proc Natl Acad Sci USA* 90:913-917; and Staub and Maliga (1993) *EMBO J* 12:601-606; and U.S. Pat. Nos. 5,451,513 and 5,545,818; each of which is herein incorporated by reference in its entirety) and *Agrobacterium*-mediated transformation (U.S. Pat. Nos. 5,563,055 and 5,981,840). In some species, protoplasts can also be used for chloroplast transformation (O'Neill et al. (1993) *Plant J* 3:729-38; and Spoerlein et al. (1991) *Theor Appl Gen* 82:717-722; each of which is herein incorporated by reference in its entirety). Once the polynucleotide of interest flanked by the homologous regions enters the cell, the polynucleotide of interest will be integrated within the plastid genome.

The homologous regions flanking the polynucleotide of interest, and in some embodiments, its operably linked promoter, and in particular embodiments, the selectable marker gene as well, may vary in length. In some embodiments, the region of homology with the plastid genome is about 50, 75, 100, 200, 300, 400, 500, 600, 700, 800, 900, 1000 base pairs or greater in length. In most instances, the frequency of recombination and thus the frequency of obtaining plants having transformed plastids decreases with the decreasing size of the homologous regions. In those embodiments wherein the regions of homology are present in the inverted repeat regions of the plastid genome, two copies of the polynucleotide of interest are expected per transformed plastid.

In some embodiments, the polynucleotide of interest can be co-delivered with a selectable marker gene that is active in the plastid. The selectable marker gene and the polynucleotide of interest can be present on a single DNA construct or on separate constructs. A number of markers have been developed for use with plant cells, such as resistance to chloramphenicol, the aminoglycoside G418, hygromycin, or the like. Genes conferring resistance to kanamycin (NPTII or AphA6) have been used as a selectable marker for plastid transformation (Caner et al. (1993)*Mol Gen Genetics* 241: 49-56; and Huang et al. (2002) *Mol Gen Genomics* 268:19-27; each of which is herein incorporated by reference in its entirety). Other genes which encode a product involved in chloroplast metabolism may also be used as selectable markers.

Another example of a selectable marker gene for plastid transformation is a selectable marker gene that confers resistance to a substance which inhibits protein synthesis by the plastids, such that cells which have acquired the phenotype are selected for by contacting the cells with a substance which inhibits protein synthesis by the plastids. The plastid DNA encoding the nonlethal selectable phenotype may comprise 16S ribosomal DNA mutated to confer resistance to the effects of streptomycin, or to spectinomycin, or to both antibiotics simultaneously. Expression of heterologous genes that modify non-lethal antibiotics such as streptomycin or spectinomycin by phosphorylation, adenylation or acetylation also are suitable for the selection of plastid transformation events. Another non-limiting example of a gene that confers resistance to streptomycin and spectinomycin is the bacterial aadA gene that codes for streptomycin/spectinomycin adenyltransferase (Svab et al. (1993) *Proc Natl Acad Sci USA* 90:913-917). The aadA gene product allows for continued growth and greening of cells in the presence of streptomycin or spectinomycin whose chloroplasts comprise the selectable marker gene product. Cells which do not contain the selectable marker gene product are bleached. Selection for the aadA gene marker is thus based on identification of plant cells which are not bleached by the presence of streptomycin or spectinomycin, in the plant growth medium.

Other examples of selectable marker genes are those that confer resistance to an herbicide, including a photosystem II herbicide, such as a triazine herbicide, specifically the triazine herbicide atrazine. This phenotype not only provides nonlethal selection, but also provides herbicide resistance. Genes that provide resistance to plant herbicides such as glyphosate, bromoxynil, or imidazolinone may find use as a selectable marker gene. Such genes have been reported (Stalker et al. (1985) *J Biol Chem* 260:4724-4728 (glyphosate resistant EPSP); Stalker et al. (1985) *J Biol Chem* 263:6310-6314 (bromoxynil resistant nitrilase gene); and Sathasivan et al. (1990) *Nucl Acids Res* 18:2188 (AHAS imidazolinone resistance gene); each of which is herein incorporated by reference in its entirety).

The selectable marker gene and/or the polynucleotide of interest can be placed under the regulatory control of a chloroplast 5' promoter and 3' transcription termination regions, such as the tobacco 16S rRNA promoter rrn region and rps16 3' termination region. Numerous additional promoter regions may also be used to drive expression of the selectable marker gene and/or the polynucleotide of interest, including various plastid promoters and bacterial promoters which have been shown to function in plant plastids. Further, if nuclear expression of the selectable marker gene and/or the polynucleotide of interest is not desired, plastid introns can be incorporated into the selectable marker gene and/or the polynucleotide of interest. Certain classes of plastid introns can not be correctly spliced out in the nucleus, thereby preventing expression of the selectable marker gene and/or the polynucleotide of interest within the nucleus. The polynucleotide of interest and/or the heterologous polynucleotide encoding the cell proliferation factor may be optimized for expression in the chloroplast to account for differences in codon usage between the plant nucleus and this organelle. In this manner, the polynucleotide may be synthesized using chloroplast-preferred codons. See, for example, U.S. Pat. No. 5,380,831, herein incorporated by reference.

An additional method of plastid transformation occurs through the transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91: 7301-7305, which is herein incorporated by reference in its entirety. In these methods, the heterologous polynucleotide encoding the cell proliferation factor is introduced into the cell and expressed prior to, during, or immediately after the expression of the plastid-directed RNA polymerase.

In order to select those cells having transformed plastids, following introduction of the chloroplast transformation vectors, the treated tissue is placed on tissue culture medium containing the appropriate selection agent. After a suitable period of incubation on selection medium, transformed cells can be identified and grown to a stage that allows regeneration of the whole plants. The regeneration processes are basically identical to those used for standard nuclear transformation events. Special care must be taken to ensure that selection and regeneration conditions promote the elimination of most wild-type chloroplast genomes. The status of the proportion of wild-type to transformed chloroplast genomes can be monitored by standard molecular techniques including Southern and PCR analysis.

For tobacco and a number of other species, leaves are a preferred target for plastid transformation. In some embodiments, one or more cell proliferation factors (e.g., babyboom polypeptides) can be used to trigger a tissue culture response from leaves of maize and other species. For boosting chloroplast transformation, polynucleotides encoding cell proliferation factors under the control of inducible promoters can be introduced into the species of interest by standard nuclear transformation protocols. Events that contain the transgene can be characterized for expression of the inducible embryogenesis-stimulating polypeptides. Then, the expression of the polynucleotide encoding the cell proliferation factor is induced, thereby stimulating an embryogenic tissue culture response. For example, leaves from plants transformed with the polynucleotide(s) encoding a cell proliferation factor under the control of the tetracycline-repressor system can be placed on medium containing appropriate concentrations of doxycyline for induction of expression. The leaves can be maintained on the induction medium to allow for cell division and the initiation of embryogenic callus to take place. The plastids of the leaves can be transformed with the polynucleotide of interest, and in certain embodiments, a selectable marker gene just prior to the induction of the polynucleotide(s) encoding cell proliferation factor, during induction, or immediately after induction. Alternatively, leaf tissue can be transformed using the methods disclosed elsewhere herein. After plastid transformation, the plastid transformation events can be selected by incubating the leaves on selection medium. Following selection, the leaves or plant cells are grown on medium that stimulates callus formation.

Methods are provided for the preparation and transformation of dried mature seeds, mature embryos, and mature embryo explants. A mature embryo explant is a tissue dissected from a mature embryo, which is an embryo that has an age of at least about 18 days after pollination. Methods for preparing a mature embryo comprise dissecting a mature embryo from a mature seed and methods for preparing a mature embryo explant further comprise preparing slices (e.g., longitudinal slices) of the mature embryo. The mature embryo explant comprises at least one of the following tissues: leaf primordia, mesocotyl, shoot apical meristem, and root primordia. In some embodiments, the mature embryo explant comprises leaf primordia, mesocotyl, and root primordia. In some of these embodiments, the mature embryo explant further comprises a shoot apical meristem. The slices may be prepared using any method or suitable apparatus known in the art, including slices prepared by hand with a scalpel. In certain embodiments, each mature embryo is sliced into about 3 to 4 thin sections using a scalpel. The use of a dissecting microscope can aid in slicing of the mature embryo.

The mature seed from which the mature embryo or mature embryo explant is derived can be a seed of any plant. In some embodiments, the mature seed is from a monocot. In particular embodiments, the mature seed is from maize, rice, sorghum, barley, wheat, oats, or millet. In certain embodiments, the mature seed is from a recalcitrant plant, such as an elite maize inbred. As used herein, a "recalcitrant tissue" or "recalcitrant plant" is a tissue or a plant that has a low rate of transformation using traditional methods of transformation, such as those disclosed elsewhere herein. In some embodiments, the recalcitrant tissue or plant is unable to be transformed in the absence of the cell proliferation factor. In other embodiments, the recalcitrant tissue or plant has a rate of successful transformation of less than about 20%, less than about 15%, less than about 10%, less than about 5%, less than about 1%, less than about 0.1%, less than about 0.01%, less than about 0.001%, or less.

The mature embryo or mature embryo explant can be prepared from a dried mature seed. The dried mature seed can comprise about 90%, 85%, 80%, 75%, 70%, 65%, 60%, 55%, 50%, 45%, 40%, 35%, 30%, 25%, 20%, 15%, 10%, 5%, 1%, 0.1% or less water than a mature seed that has not been dried. The dried mature seed can be imbibed with an aqueous solution for a sufficient period of time to allow the dried mature seed to soften so that the mature embryo may be dissected from the seed and in some embodiments, mature embryo explant slices prepared from the mature embryo. In some embodiments, the dried mature seed is imbibed in an aqueous solution for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 hours or greater. In certain embodiments, the aqueous solution is water. In certain embodiments, the dried mature seed is imbibed for a sufficient period of time to induce germination of the seed. A germinated seed is one in which the radical has emerged.

Mature embryos and mature embryo explants can be transformed with a polynucleotide of interest through the provision of a cell proliferation factor (e.g., babyboom polypeptide). A heterologous polynucleotide encoding the cell proliferation factor is introduced into the mature embryo explant prior to or at the same time as the introduction of the polynucleotide of interest. The heterologous polynucleotide encoding the cell proliferation factor and the polynucleotide of interest can be provided on the same expression cassette or on separate expression cassettes.

The polynucleotides can be introduced into the mature embryo explant using any method known in the art, including but not limited to, *Agrobacterium*-mediated transformation.

In some embodiments, transformed mature embryo explants can be identified. Any method can be used to identify a plant cell or tissue comprising the polynucleotide of interest. In some examples, plant cells or tissues comprising the polynucleotide of interest are identified using one or more of the following techniques, including but not limited to PCR methods, hybridization methods such as Southern or Northern blots, restriction digest analyses, or DNA sequencing. In some embodiments, the transformed mature embryo explants can be identified by incubating the leaf mature embryo explants under conditions to allow for growth of a callus. In some embodiments, those mature embryo explants that are able to grow into a callus with significant proliferation indicate those mature embryo explants that have been transformed. In other embodiments, the tranformed mature embryo explants can be identified and selected for through the introduction and expression of a selectable marker gene into the mature embryo explant.

Methods are also provided herein for the transformation of leaf tissues, which can be a leaf base. A leaf base is the tissue of a leaf above the first leaf base node. The leaf tissue can be derived from any plant. In some embodiments, the leaf tissue is derived from a monocot. In particular embodiments, the leaf tissue is derived from maize, rice, sorghum, barley, wheat, oats, or millet. In certain embodiments, the leaf tissue is derived from a recalcitrant plant, such as an elite maize inbred.

The leaf base can be from a mature leaf or a leaf from a seedling. As used herein, a "seedling" refers to a germinated seed or germinated embryo, or a plantlet generated in an in vitro system (e.g., from callus). The seedlings can be prepared by germinating seeds or dissecting mature embryos from mature seeds for germination. In some embodiments, the mature embryos are dissected from dried mature seeds that have been imbibed with an aqueous solution, as described herein.

In some embodiments, the coleoptile is removed from the leaf tissue and the leaf fragment is split longitudinally, and then horizontal slices are made to cross-dissect the leaf fragment into leaf tissue pieces. In particular embodiments, the pieces of leaf tissue are about 1 to 2 mm in length.

The leaf tissue can be transformed with a polynucleotide of interest through the provision of a cell proliferation factor (e.g., babyboom polypeptide). The polynucleotides can be introduced into the leaf tissue using any method known in the art, including but not limited to, *Agrobacterium*-mediated transformation. A heterologous polynucleotide of interest encoding the cell proliferation factor is introduced into the leaf tissue prior to or at the same time as the introduction of the polynucleotide of interest. The heterologous polynucleotide encoding the cell proliferation factor is expressed. The heterologous polynucleotide encoding the cell proliferation factor and the polynucleotide of interest can be provided on the same expression cassette or on separate expression cassettes.

In some embodiments, transformed leaf tissues can be identified. Any method can be used to identify a plant cell or tissue comprising the polynucleotide of interest. In some examples, plant cells or tissues comprising the polynucleotide of interest are identified using one or more of the following techniques, including but not limited to PCR methods, hybridization methods such as Southern or Northern blots, restriction digest analyses, or DNA sequencing. In some embodiments, the transformed leaf tissues can be identified by incubating the leaf tissues under conditions to allow for growth of a callus. In some embodiments, those leaf tissues that are able to grow a callus with significant proliferation indicate those leaf tissues that have been transformed. In other embodiments, the transformed leaf tissue can be identified and selected for through the introduction and expression of a selectable marker gene into the leaf tissue.

The cells that have been transformed may be grown into plants in accordance with conventional ways. See, for example, McCormick et al. (1986) *Plant Cell Rep* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, transformed seed (also referred to as "transgenic seed") having a nucleotide construct, for example, an expression cassette, stably incorporated into their genome is provided. Thus, compositions of the invention include plant cells, plant tissues, plant parts, and plants comprising the presently disclosed polynucleotides, polypeptides, promoter constructs, expression cassettes, or vectors. Likewise, the methods of the invention can be performed in plant cells, plant tissues, plant parts, and plants.

In some embodiments, the activity and/or level of the cell proliferation factor (e.g., babyboom polypeptide, Wuschel) is reduced prior to regenerating a plant from a cell or tissue having the polynucleotide of interest. In some of these embodiments, the polynucleotide encoding the cell proliferation factor is excised prior to the regeneration of a plant. In certain embodiments, the promoter and other regulatory elements that are operably linked to the heterologous polynucleotide encoding the cell proliferation factor are excised along with the cell proliferation factor coding sequence. In certain embodiments, the polynucleotide encoding the cell proliferation factor is flanked by recombination sites and an appropriate site-specific recombinase is introduced into the mature embryo explant or callus grown therefrom to excise the polynucleotide encoding the cell proliferation factor prior to regeneration of the mature embryo explant or callus into a plant. In some of those embodiments wherein both a babyboom polypeptide and a Wuschel polypeptide are provided to the plant cell, both the polynucleotide encoding the babyboom polypeptide and the polynucleotide encoding the Wuschel polypeptide are excised. The two polynucleotides can be present on the same or different expression cassettes and, therefore, can be excised in one or two different excision reactions. In some of these embodiments, the polynucleotide encoding the site-specific recombinase for excising the babyboom and Wuschel polynucleotides can be located on the same expression cassette as the babyboom and Wuschel polynucleotides and all three polynucleotides can be excised through the activity of the site-specific recombinase.

In order to control the excision of the cell proliferation factor, the expression of the site-specific recombinase that is responsible for the excision can be controlled by a late embryo promoter or an inducible promoter. In some embodiments, the late embryo promoter is GZ (Uead et al. (1994) *Mol Cell Biol* 14:4350-4359), gamma-kafarin promoter (Mishra et al. (2008)*Mol Biol Rep* 35:81-88), Glb1 promoter (Liu et al. (1998) *Plant Cell Reports* 17:650-655), ZM-LEG1 (U.S. Pat. No. 7,211,712), EEP1 (U.S. Patent Application No. US 2007/0169226), B22E (Klemsdal et al. (1991) *Mol Gen Genet* 228:9-16), or EAP1 (U.S. Pat. No. 7,321,031). In some embodiments, the inducible promoter that regulates the expression of the site-specific recombinase is a heat-shock, light-induced promoter, a drought-inducible promoter, including but not limited to Hval (Straub et al. (1994) *Plant Mol Biol* 26:617-630), Dhn, and WSI18 (Xiao & Xue (2001) *Plant Cell Rep* 20:667-673). In other embodiments, expression of the site-specific recombinase is regulated by the maize rab17 promoter, or one of the presently disclosed promoter constructs (e.g., maize rab17 promoter and an attB site). In some embodiments, the site-specific recombinase that excises the polynucleotide encoding the cell proliferation factor is FLP or Cre.

Any plant species can be transformed, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (Carthamus tinctorius), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos* nucifera), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus* casica), guava (*Psidium guajava*), mango (*Mangifera indica*), olive (*Olea europaea*), *papaya* (*Carica papaya*), cashew (*Anacardium occidentale*), macadamia (Macadamia *integrifolia*), almond (*Prunus* amygdalus), sugar beets (*Beta vulgaris*), sugarcane (*Saccharum* spp.), oats (*Avena*), barley (*Hordeum*), *Arabidopsis*, switchgrass, vegetables, ornamentals, grasses, and conifers.

Vegetables include tomatoes (*Lycopersicon esculentum*), lettuce (e.g., *Lactuca sativa*), green beans (*Phaseolus vulgaris*), lima beans (*Phaseolus* limensis), peas (*Lathyrus* spp.), and members of the genus *Cucumis* such as cucumber (*C. sativus*), cantaloupe (C. cantalupensis), and musk melon (*C. melo*). Ornamentals include azalea (*Rhododendron* spp.), *hydrangea* (*Macrophylla hydrangea*), hibiscus (Hibiscus rosasanensis), roses (Rosa spp.), tulips (Tulipa spp.), daffodils (*Narcissus* spp.), petunias (*Petunia hybrida*), carnation (*Dianthus* caryophyllus), poinsettia (*Euphorbia pulcherrima*), and *chrysanthemum.*

Conifers that may be employed in practicing the present invention include, for example, pines such as loblolly pine (*Pinus taeda*), slash pine (*Pinus* elliotii), *ponderosa* pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean and sugarcane plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

As used herein, the term plant also includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

If the polynucleotide of interest is introduced into an organism, it may impart various changes in the organism, particularly plants, including, but not limited to, modification of the fatty acid composition in the plant, altering the amino acid content of the plant, altering pathogen resistance, and the like. These results can be achieved by providing expression of heterologous products, increased expression of endogenous products in plants, or suppressed expression of endogenous produces in plants.

General categories of polynucleotides of interest include, for example, those genes involved in information, such as zinc fingers, those involved in communication, such as kinases, those involved in biosynthetic pathways, and those involved in housekeeping, such as heat shock proteins. More specific categories of transgenes, for example, include sequences encoding important traits for agronomics, insect resistance, disease resistance, herbicide resistance, sterility, grain characteristics, oil, starch, carbohydrate, phytate, protein, nutrient, metabolism, digestability, kernel size, sucrose loading, and commercial products.

Traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Protein modifications to alter amino acid levels are described in U.S. Pat. Nos. 5,703,049, 5,885,801, 5,885,802, and 5,990,389 and WO 98/20122, herein incorporated by reference.

Insect resistance genes may encode resistance to pests such as rootworm, cutworm, European Corn Borer, and the like. Such genes include, for example, *Bacillus thuringiensis* toxic protein genes (U.S. Pat. Nos. 5,366,892; 5,747,450; 5,737,514; 5,723,756; 5,593,881; and Geiser et al. (1986) *Gene* 48:109); lectins (Van Damme et al. (1994) *Plant Mol. Biol.* 24:825); and the like.

Genes encoding disease resistance traits include detoxification genes, such as against fumonosin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the S4 and/or Hra mutations in ALS), genes coding for resistance to herbicides that act to inhibit action of glutamine synthase, such as phosphinothricin or basta (e.g., the bar gene), genes providing resistance to glyphosate, such as GAT (glyphosate N-acetyltransferase; U.S. Pat. No. 6,395,485), EPSPS (enolpyruvylshikimate-3-phosphate synthase; U.S. Pat. Nos. 6,867,293, 5,188,642, 5,627,061), or GOX (glyphosate oxidoreductase; U.S. Pat. No. 5,463,175), or other such genes known in the art. The nptII gene encodes resistance to the antibiotics kanamycin and geneticin.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

Commercial traits can also be encoded on a gene or genes that could, for example increase starch for ethanol production, or provide expression of proteins.

Reduction of the activity of specific genes (also known as gene silencing, or gene suppression) is desirable for several aspects of genetic engineering in plants. Many techniques for gene silencing are well known to one of skill in the art, including but not limited to antisense technology (see, e.g., Sheehy et al. (1988) *Proc. Natl. Acad. Sci. USA* 85:8805-8809; and U.S. Pat. Nos. 5,107,065; 5,453,566; and 5,759,829); cosuppression (e.g., Taylor (1997) *Plant Cell* 9:1245; Jorgensen (1990) *Trends Biotech.* 8(12):340-344; Flavell (1994) *Proc. Natl. Acad. Sci. USA* 91:3490-3496; Finnegan et al. (1994) *Bio/Technology* 12: 883-888; and Neuhuber et al. (1994) *Mol. Gen. Genet.* 244:230-241); RNA interference (Napoli et al. (1990) *Plant Cell* 2:279-289; U.S. Pat. No. 5,034,323; Sharp (1999) *Genes Dev.* 13:139-141; Zamore et al. (2000) *Cell* 101:25-33; Javier (2003) *Nature* 425:257-263; and, Montgomery et al. (1998) *Proc. Natl. Acad. Sci. USA* 95:15502-15507), virus-induced gene silencing (Burton, et al. (2000) *Plant Cell* 12:691-705; and Baulcombe (1999) *Curr. Op. Plant Bio.* 2:109-113); target-RNA-specific ribozymes (Haseloff et al. (1988) *Nature* 334: 585-591); hairpin structures (Smith et al. (2000) *Nature* 407:319-320; WO 99/53050; WO 02/00904; and WO 98/53083); ribozymes (Steinecke et al. (1992) *EMBO J.* 11:1525; U.S. Pat. No. 4,987,071; and, Perriman et al. (1993) *Antisense Res. Dev.* 3:253); oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art.

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as 32P, or any other detectable marker. Thus, for example, probes for hybridization can be made by labeling synthetic oligonucleotides based on the babyboom polynucleotide. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, New York).

For example, the entire babyboom polynucleotide, or one or more portions thereof, may be used as a probe capable of specifically hybridizing to corresponding babyboom polynucleotide and messenger RNAs. To achieve specific hybridization under a variety of conditions, such probes include sequences that are unique among babyboom polynucleotide sequences and are optimally at least about 10 nucleotides in length, and most optimally at least about 20 nucleotides in length. Such probes may be used to amplify corresponding babyboom polynucleotide from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, New York).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2× SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1× SSC at 55 to 60° C. Exemplary high stringency conditions include hybridization in 50% formamide, 1 M NaCl, 1% SDS at 37° C., and a wash in 0.1× SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology, Chapter* 2 (Greene Publishing and Wiley-Interscience, New York). See Sambrook et al. (1989) *Molecular Cloning: A Laboratory Manual* (2d ed., Cold Spring Harbor Laboratory Press, Plainview, New York).

It is to be noted that the term "a" or "an" entity refers to one or more of that entity; for example, "a polypeptide" is understood to represent one or more polypeptides. As such, the terms "a" (or "an"), "one or more," and "at least one" can be used interchangeably herein.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the presently disclosed subject matter be limited to the specific values recited when defining a range.

The following examples are offered by way of illustration and not by way of limitation.

EXPERIMENTAL

Example 1. A Modified Rab 17 Promoter for the Regulated Expression of Genes

Gateway™ technology (Invitrogen, Carlsbad, Calif.) was used to place Gateway™ recombination sites between a promoter and a coding sequence, and between the coding sequence and a terminator. The product of a Gateway™ reaction set up in this manner leaves attB sites in those locations.

The rab17 promoter was identified as a candidate for regulating the expression of FLP recombinase for excision of polynucleotides encoding cell proliferation factors in tissue culture. It was tested for FLP/FRT excision of cell proliferation factor genes in culture. The PHP31004 plasmid was constructed, which has the following operably linked components: Rab 17 Pro-attB1::FLPm-attB2::PinII+Ubi Pro-FRT1::CFP::PinII+Ubi Pro::ZmBBM::PinII-FRT1::YFP::PinII+Ubi Pro::moPAT::PinII. The sequence of the expression cassette for the FLPm gene in the PHP31004 plasmid is provided in SEQ ID NO: 46.

After excision by the FLP recombinase, the PHP31004 plasmid has the following operably linked components: Rab 17 Pro-attB1::FLPm-attB2::PinII+Ubi Pro-FRT1::YFP::PinII+Ubi Pro::moPAT::PinII.

A plasmid (PHP30642) lacking the attB sites, but comprising the FLPm gene was constructed. The PHP30642 has the following operably linked components: Rab17 pro::FLPm::Gz-W64A term+Ubi pro-FRT1::CFP::PinII+Ubi-Pro::ZmBBM::PinII-FRT1::YFP::PinII+Ubi Pro::moPAT::PinII. The sequence of the expression cassette for the FLPm gene in the PHP30642 plasmid is provided in SEQ ID NO: 47.

After excision by the FLP recombinase, the PHP30642 plasmid has the following operably linked components: Rab17 pro::FLPm::Gz-W64A term+Ubi pro-FRT1::YFP::PinII+Ubi pro::moPAT::PinII. The construct lacking the attB sites resulted in frequent premature excision of the cell proliferation factor genes.

Example 2. Transformation of Maize Immature Embryos

Transformation can be accomplished by various methods known to be effective in plants, including particle-mediated delivery, *Agrobacterium*-mediated transformation, PEG-mediated delivery, and electroporation.

a. Particle-Mediated Delivery

Transformation of maize immature embryos using particle delivery is performed as follows. Media recipes follow below.

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

A plasmid comprising the Zm-BBM (also referred to as Zm-ODP2) coding sequence (set forth in SEQ ID NO: 9) operably linked to a promoter is constructed. This could be a weak promoter such as nos, a tissue-specific promoter, such as globulin-1 or oleosin, an inducible promoter such as In2, or a strong promoter such as ubiquitin plus a plasmid containing the selectable marker gene phosphinothricin N-acetyltransferase (PAT; Wohlleben et al. (1988) *Gene* 70:25-37) that confers resistance to the herbicide bialaphos. The plasmid DNA containing the selectable marker gene PAT and the BBM plasmid are precipitated onto 1.1 μm (average diameter) tungsten pellets using a calcium chloride ($CaCl_2$)) precipitation procedure by mixing 100 μl prepared tungsten particles in water, 10 μl (1 μg) DNA in Tris EDTA buffer (1 μg total DNA), 100 μl 2.5 M $CaCl_2$, and 10 μl 0.1 M spermidine. Each reagent is added sequentially to the tungsten particle suspension, with mixing. The final mixture is sonicated briefly and allowed to incubate under constant vortexing for 10 minutes. After the precipitation period, the tubes are centrifuged briefly, liquid is removed, and the particles are washed with 500 ml 100% ethanol, followed by a 30 second centrifugation. Again, the liquid is removed, and 105 μl 100% ethanol is added to the final tungsten particle pellet. For particle gun bombardment, the tungsten/DNA particles are briefly sonicated. 10 μl of the tungsten/DNA particles is spotted onto the center of each macrocarrier, after which the spotted particles are allowed to dry about 2 minutes before bombardment.

The sample plates are bombarded at level #4 with a Biorad Helium Gun. All samples receive a single shot at 450 PSI, with a total of ten aliquots taken from each tube of prepared particles/DNA.

Following bombardment, the embryos are incubated on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to a lighted culture room. Approximately 7-10 days later, developing plantlets are transferred to 272V hormone-free medium in tubes for 7-10 days until plantlets are well established. Plants are then transferred to inserts in flats (equivalent to a 2.5" pot) containing potting soil and grown for 1 week in a growth chamber, subsequently grown an additional 1-2 weeks in the greenhouse, then transferred to Classic 600 pots (1.6 gallon) and grown to maturity. Plants are monitored and scored for transformation efficiency, and/or modification of regenerative capabilities.

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/12,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature).

Selection medium (560R) comprises 4.0 g/l N6 basal salts (SIGMA C-1416), 1.0 ml/1 Eriksson's Vitamin Mix (1000X SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/1 MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/1 of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.).

Hormone-free medium (272V) comprises 4.3 g/l MS salts (GIBCO 11117-074), 5.0 ml/1 MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

b. *Agrobacterium*-Mediated Transformation

*Agrobacterium*-mediated transformation was performed essentially as described in Djukanovic et al. (2006) *Plant Biotech J* 4:345-57. Briefly, 10-12 day old immature embryos (0.8-2.5 mm in size) were dissected from sterilized kernels and placed into liquid medium (4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.690 g/L L-proline, 68.5 g/L sucrose, 36.0 g/L glucose, pH 5.2). After embryo collection, the medium was replaced with 1 ml *Agrobacterium* at a concentration of 0.35-0.45 $OD_{550}$. Maize embryos were incubated with *Agrobacterium* for 5 min at room temperature, then the mixture was poured onto a media plate containing 4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.690 g/L L-proline, 30.0 g/L sucrose, 0.85 mg/L silver nitrate, 0.1 nM acetosyringone, and 3.0 g/L Gelrite, pH 5.8. Embryos were incubated axis down, in the dark for 3 days at 20° C., then incubated 4 days in the dark at 28° C., then transferred onto new media plates containing 4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.69 g/L L-proline, 30.0 g/L sucrose, 0.5 g/L MES buffer, 0.85 mg/L silver nitrate, 3.0 mg/L Bialaphos, 100 mg/L carbenicillin, and 6.0 g/L agar, pH 5.8. Embryos were subcultured every three weeks until transgenic events were identified. Somatic embryogenesis was induced by transferring a small amount of tissue onto regeneration medium (4.3 g/L MS salts (Gibco 11117), 5.0 ml/L MS Vitamins Stock Solution, 100 mg/L myo-inositol, 0.1 μM ABA, 1 mg/L IAA, 0.5 mg/L zeatin, 60.0 g/L sucrose, 1.5 mg/L Bialaphos, 100 mg/L carbenicillin, 3.0 g/L Gelrite, pH 5.6) and incubation in the dark for two weeks at 28° C. All material with visible shoots and roots were transferred onto media containing 4.3 g/L MS salts (Gibco 11117), 5.0 ml/L MS Vitamins Stock Solution, 100 mg/L myo-inositol, 40.0 g/L sucrose, 1.5 g/L Gelrite, pH 5.6, and incubated under artificial light at 28° C.

One week later, plantlets were moved into glass tubes containing the same medium and grown until they were sampled and/or transplanted into soil.

Example 3. Transient Expression of BBM Enhances Transformation

Parameters of the transformation protocol can be modified to ensure that the BBM activity is transient. One such method involves precipitating the BBM-containing plasmid in a manner that allows for transcription and expression, but precludes subsequent release of the DNA, for example, by using the chemical PEI.

In one example, the BBM plasmid is precipitated onto gold particles with PEI, while the transgenic expression cassette (UBI::moPAT~GFPm::PinII; moPAT is the maize optimized PAT gene) to be integrated is precipitated onto gold particles using the standard calcium chloride method.

Briefly, gold particles were coated with PEI as follows. First, the gold particles were washed. Thirty-five mg of gold particles, 1.0 in average diameter (A.S.I. #162-0010), were weighed out in a microcentrifuge tube, and 1.2 ml absolute EtOH was added and vortexed for one minute. The tube was incubated for 15 minutes at room temperature and then centrifuged at high speed using a microfuge for 15 minutes at 4° C. The supernatant was discarded and a fresh 1.2 ml aliquot of ethanol (EtOH) was added, vortexed for one minute, centrifuged for one minute, and the supernatant again discarded (this is repeated twice). A fresh 1.2 ml aliquot of EtOH was added, and this suspension (gold particles in EtOH) was stored at −20° C. for weeks. To coat particles with polyethylimine (PEI; Sigma #P3143), 250 μl of the washed gold particle/EtOH mix was centrifuged and the EtOH discarded. The particles were washed once in 100 μl $ddH_2O$ to remove residual ethanol, 250 μl of 0.25 mM PEI was added, followed by a pulse-sonication to suspend the particles and then the tube was plunged into a dry ice/EtOH bath to flash-freeze the suspension, which was then lyophilized overnight. At this point, dry, coated particles could be stored at −80° C. for at least 3 weeks. Before use, the particles were rinsed 3 times with 250 μl aliquots of 2.5 mM HEPES buffer, pH 7.1, with 1× pulse-sonication, and then a quick vortex before each centrifugation. The particles were then suspended in a final volume of 250 μl HEPES buffer. A 25 μl aliquot of the particles was added to fresh tubes before attaching DNA. To attach uncoated DNA, the particles were pulse-sonicated, then 1 μg of DNA (in 5 μl water) was added, followed by mixing by pipetting up and down a few times with a Pipetteman and incubated for 10 minutes. The particles were spun briefly (i.e. 10 seconds), the supernatant removed, and 60 μl EtOH added. The particles with PEI-precipitated DNA-1 were washed twice in 60 μl of EtOH. The particles were centrifuged, the supernatant discarded, and the particles were resuspended in 45 μl water. To attach the second DNA (DNA-2), precipitation using TFX-50 was used. The 45 μl of particles/DNA-1 suspension was briefly sonicated, and then 5 μl of 100 ng/μl of DNA-2 and 2.5 μl of TFX-50 were added. The solution was placed on a rotary shaker for 10 minutes, centrifuged at 10,000 g for 1 minute. The supernatant was removed, and the particles resuspended in 60 μl of EtOH. The solution was spotted onto macrocarriers and the gold particles onto which DNA-1 and DNA-2 had been sequentially attached were delivered into scutellar cells of 10 DAP Hi-II immature embryos using a standard protocol for the PDS-1000. For this experiment, the DNA-1 plasmid contained a UBI::RFP::pinII expression cassette, and DNA-2 contained a UBI::CFP::pinII expression cassette. Two days after bombardment, transient expression of both the CFP and RFP fluorescent markers was observed as numerous red & blue cells on the surface of the immature embryo. The embryos were then placed on non-selective culture medium and allowed to grow for 3 weeks before scoring for stable colonies. After this 3-week period, 10 multicellular, stably-expressing blue colonies were observed, in comparison to only one red colony. This demonstrated that PEI-precipitation could be used to effectively introduce DNA for transient expression while dramatically reducing integration of the PEI-introduced DNA and thus reducing the recovery of RFP-expressing transgenic events. In this manner, PEI-precipitation can be used to deliver transient expression of BBM and/or WUS2.

For example, the particles are first coated with UBI::BBM::pinII using PEI, then coated with UBI::moPAT~YFP using TFX-50, and then bombarded into scutellar cells on the surface of immature embryos. PEI-mediated precipitation results in a high frequency of transiently expressing cells on the surface of the immature embryo and extremely low frequencies of recovery of stable transformants (relative to the TFX-50 method). Thus, it is expected that the PEI-precipitated BBM cassette expresses transiently and stimulates a burst of embryogenic growth on the bombarded surface of the tissue (i.e. the scutellar surface), but this plasmid will not integrate. The PAT~GFP plasmid released from the $Ca^{++}$/gold particles is expected to integrate and express the selectable marker at a frequency that results in substantially improved recovery of transgenic events. As a control treatment, PEI-precipitated particles containing a UBI::GUS::pinII (instead of BBM) are mixed with the PAT~GFP/$Ca^{++}$ particles. Immature embryos from both treatments are moved onto culture medium containing 3 mg/l bialaphos. After 6-8 weeks, it is expected that GFP+, bialaphos-resistant calli will be observed in the PEI/BBM treatment at a much higher frequency relative to the control treatment (PEI/GUS).

As an alternative method, the BBM plasmid is precipitated onto gold particles with PEI, and then introduced into scutellar cells on the surface of immature embryos, and subsequent transient expression of the BBM gene elicits a rapid proliferation of embryogenic growth. During this period of induced growth, the explants are treated with *Agrobacterium* using standard methods for maize (see Example 1), with T-DNA delivery into the cell introducing a transgenic expression cassette such as UBI::moPAT~GFPm::pinII. After co-cultivation, explants are allowed to recover on normal culture medium, and then are moved onto culture medium containing 3 mg/l bialaphos. After 6-8 weeks, it is expected that $GFP^+$, bialaphos-resistant calli will be observed in the PEI/BBM treatment at a much higher frequency relative to the control treatment (PEI/GUS).

It may be desirable to "kick start" callus growth by transiently expressing the BBM and/or WUS2 polynucleotide products. This can be done by delivering BBM and WUS2 5'-capped polyadenylated RNA, expression cassettes containing BBM and WUS2 DNA, or BBM and/or WUS2 proteins. All of these molecules can be delivered using a biolistics particle gun. For example 5'-capped polyadenylated BBM and/or WUS2 RNA can easily be made in vitro using Ambion's mMessage mMachine kit. RNA is co-delivered along with DNA containing a polynucleotide of interest and a marker used for selection/screening such as Ubi::moPAT~GFPm::PinII. It is expected that the cells receiving the RNA will immediately begin dividing more rapidly and a large portion of these will have integrated the agronomic gene. These events can further be validated as being transgenic clonal colonies because they will also express the PAT~GFP fusion protein (and thus will display green fluorescence under appropriate illumination). Plants regenerated from these embryos can then be screened for the presence of the polynucleotide of interest.

Example 4. Excision of Genes Encoding Cell Proliferation Factors a. Rab17::CRE The following T-DNA was constructed: RB-Ubi pro-loxP::Rab17 pro-attB1::Cre-attB2::PinII+NOS::ZmWUS2::PinII+Ubi pro::ZmBBM::PinII-loxP::YFP::PinII+Ubi pro::moPAT::PinII-LB. As a control, a T-DNA containing Ubi pro::moPAT::PinII was constructed. These T-DNA are introduced into immature embryos (approximately 0.8-2.5 mm in length) of the maize inbred PHH5G using standard *Agrobacterium*-mediated transformation methods. Non-transformed immature embryos of this inbred swell and initiate a small volume of callus cells, but proliferation does not occur on media compositions typically used for maize tissue culture (for example, 605J media, which comprises 4.3 g/l MS salts, 0.6 g/l Shenk & Hildebrand vitamins, 100 mg/l calcium chloride, 275 mg/l ammonium sulfate, 275 mg/l ammonium sulfate, 240 mg/l potassium phosphate, 100 mg/l magnesium sulfate, 3.4 g/l potassium nitrate, 1.8 mg/l boric acid, 6 mg/l manganese sulfate, 0.15 mg/l sodium molybdate, 0.5 mg/l potassium iodide, 22 mg/l disodium EDTA, 17 mg/l ferrous sulfate, 3.4 mg/l silver nitrate, 1 g/l L-proline, 0.2 mg/l nicotinic acid, 0.4 mg/l thiamine, 0.2 mg/l pyridoxine, 0.8 mg/l glycine, 100 mg/l carbenicillin, 0.8 mg/12-4D, 1.2 mg/l dicamba, 0.3 g/l casein hydrosylate, 20 g/l sucrose, 0.6 g/l glucose, and 6 g/l TC agar, pH 5.8). Likewise, PHH5G immature embryos transformed with Ubi pro::moPAT::PinII alone do not produce healthy, growing callus, irrespective of whether bialaphos selection is provided. Thus, no transformed events were produced after introducing Ubi pro::moPAT::PinII alone (or with Ubi pro::moPAT::PinII+Ubi pro::YFP::PinII). In contrast, when the genes encoding cell proliferation factors (BBM and WUS2)+Ubi pro::moPAT::PinII were introduced into PHH5G immature embryos, vigorously-growing callus transformants were recovered from 45% of the treated embryos. To remove the genes encoding cell proliferation factors, the Rab17 promoter can be induced through exposure to either 20 mM abscisic acid (ABA), 20-30% sucrose, or desiccation. In this experiment, callus was placed on dry filter papers for three days to induce excision, and then transferred to regeneration medium. If callus was not treated to induce the expression of Cre recombinase, excision of the genes encoding cell proliferation factors did not occur and viable plantlets were not regenerated. However, for events that were taken through the desiccation treatment, Cre excision occurred in over 90% of single copy events (activating YFP) and subsequent regeneration was not inhibited. Transgenic plants were screened using combinations of PCR primers designed to detect the presence of the Ubi pro-loxP::YFP junction formed as a result of excision, and moPAT (not effected by excision), and the absence of Cre, WUS2 and BBM. Plants in which excision was complete were grown to maturity and were either selfed or out-crossed to wild-type plants. Transgenic progeny seed were readily identified through the yellow fluorescence phenotype and plants were easily tracked through either BASTA resistance or yellow fluorescence. PCR analysis in both the T1 and T2 generations indicated that only the excised locus was present in a single genomic copy and that no *Agrobacterium* plasmid backbone was present.

Both FLP and Cre recombinase have been successfully used to excise genes encoding cell proliferation factors before regeneration. The following two constructs represent examples of how the recombinases can be used for controlled excision:

PHP32371—FLP/FRT

RB-Ubi-FRT1::CFP::PinII-attB4+Rab17 Pro-attB1::FLP-attB2::PinII+Nos::ZmWUS2::PinII+Ubi::ZmBBM::PinII-FRT1::YFP::PinII+Ubi::moPAT::PinII-LB The T-DNA sequence of PHP32371 is set forth in SEQ ID NO: 110.

PHP35648—Cre/LoxP

RB-Ubi-LoxP::CFP::PinII-attB4+Rab17 Pro-attb1::Cre-attB2::PinII+Nos::ZmWUS2::PinII+Ubi::ZmBBM::PinII-LoxP::YFP::PinII+Ubi::MOPAT::PinII-LB The T-DNA sequence of PHP35648 is set forth in SEQ ID NO: 111.

For both recombinases, expression was controlled by the Rab 17 promoter (Vilardell et al. (1991) *Plant Mol. Biol* 17:985-993) with the attb1 site.

For both constructs, transgenic callus events were readily recovered, and both constructs worked well for excision of the expression cassettes comprising genes encoding cell proliferation factors (see Table 2). Of the total number of calli exposed to the 3-day desiccation treatment, 61% (Cre) and 29% (FLP) of the resultant plants exhibited a normal wild-type phenotype. As confirmation of excision, PCR analysis in both the T1 and T2 generations indicated that only the excised locus was present in a single genomic copy and that no *Agrobacterium* plasmid backbone was present.

TABLE 2

Desiccation-induced excision of the recombinase, BBM & WUS expression cassettes prior to regeneration.

| | # of Callus events exposed to desiccation | # of event swith normal T0 plant phenotype | # of T0 plantlets analyzed using PCR | # of single copy plants | # with a totally-excised DevGene package |
|---|---|---|---|---|---|
| PHP35648 | 180 | 110 (61%) | 168 | 94 (56%) | 81 (86%) |
| PHP32371 | 118 | 34 (29%) | 75 | 51 (68%) | 31 (61%) |

Additional constructs that utilize Cre/LoxP were generated.

PHP46446: RB-LoxP-Rab 17 Pro-attB1::Cre-attB2::PinII+Nos::Zm-WUS2::PinII::GZ-W64A Term-attB2+Ubi::ZmBBM::PinII-LoxP-LB PHP48733: RB-LoxP-Rab 17 Pro-attB1::Cre-attB2::PinII+Nos:ZmWUS2::PinII+Ubi::ZmBBM::PinII-LoxP-LB The T-DNA sequences of PHP46446 and PHP48733 is set forth in SEQ ID NO: 112 and 113, respectively.

Introduction of PHP35648, PHP48733, or PHP46446 into PHH5G immature maize embryos via *Agrobacterium* resulted in a transformation frequency of 46%, 67%, or 37%, respectively (see Table 3).

TABLE 3

Transformation of PHH5G immature maize embryos with maize BBM and WUS2 cell proliferation factors.

| Construct | No. of ears | No. of embryos | No. of callus events | Transformation frequency at callus level |
|---|---|---|---|---|
| PHP35648 | 14 | 589 | 268 | 45.5 |
| PHP48733 | 14 | 584 | 389 | 66.6 |
| PHP46446 | 14 | 547 | 203 | 37.1 |

The use of the PHP35648, PHP48733, PHP46446, and PHP32371 constructs (all of which comprised the Rab17 promoter (Vilardell et al. (1990 *Plant Mol. Biol* 17:985-993) with the attb1 site regulating the expression of the recombinase), did not result in frequent premature excision of the cell proliferation factor genes, similar to the results presented in Example 1 with the PHP31004 construct.

b. Tetracycline-Inducible CRE

A 35S promoter in which three tetracycline operator sequences (Top3) have been introduced in proximity to the TATA box (Gatz et al. (1992) *Plant J* 2:397-404) was operably linked to the CRE structural gene in the following T-DNA which also includes an expression cassette for the tetracycline repressor (TETR), BBM, WUS2, and moPAT, as follows:

RB-loxP-35S::Top3::CRE::PinII+Ubi pro::TETR::PinII+NOS::ZmWUS2::PinII+UBI::ZmBBM::PinII–loxP+UBI::moPAT::PinII-LB After *Agrobacterium*-mediated transformation of 12 DAP PH581 immature embryos, followed by 6 weeks of selection on 3 mg/l bialaphos, embryos into which the control T-DNA was introduced (RB-UBI::moPAT::PinII-LB) produced transformed events at a 1% frequency. In contrast, when the above T-DNA containing ZmBBM & ZmWUS2 was transformed into immature embryos harvested from the same PH581 ears, transgenic calli were recovered at a 15% frequency. Before regenerating plantlets, callus is moved onto medium containing 0.5 mg/l tetracycline for 1 week to induce CRE-mediated excision of CRE, WUS and BBM expression cassettes. Glufosinate ammonium-resistant plants are then readily regenerated.

Example 5. Control of BBM and WUS Expression with Regulated Promoters to Increase Transformation Frequencies a. OLE PRO::BBM In the inbred PH581 maize line, the introduction of UBI::ZmBBM+NOS:ZmWUS2 increased transformation frequencies from <1% in the control treatment (UBI PRO::moPAT::PinII alone) to 15%. However, such strong over-expression of BBM negatively affects the regeneration of plantlets. Therefore, an oleosin promoter having high levels of expression in callus, with little to no activity during vegetative growth was used to express BBM. When OLE::ZmBBM::PinII+NOS::ZmWUS2::PinII was introduced into PH581 on a first T-DNA and UBI PRO::moPAT::PinII was introduced into the same cells on a second T-DNA, callus transformants were recovered at a 25% frequency. Normal, fertile plants were regenerated and crossed to wild-type PH581. T1 progeny in which the cell proliferation gene locus had segregated away from the UBI PRO::moPAT::PinII locus were readily recovered.

b. Tetracycline-Inducible BBM and WUS2

A 35S promoter in which three tetracycline operator sequences have been introduced in proximity to the TATA box (Gatz et al. (1992) *Plant J* 2:397-404) is operably linked to both the BBM and WUS2 genes, and these expression cassettes are put into a T-DNA along with an expression cassette for the tetracycline repressor (TETR) as follows.

RB-35S-Top3::ZmBBM::PinII+35S-Top3::ZmWUS2::PinII+UBI::moPAT::PinII-LB

Following *Agrobacterium*-mediated transformation of Hi-II immature maize embryos, the embryos are transferred to selection medium 560R with 3 mg/l bialaphos +/−0.5 mg/l tetracycline. In the control treatment in which only the UBI::moPAT::PinII expression cassette is introduced, the transformation frequency is typically around 5-10%. For embryos in which the inducible BBM and WUS2 genes are introduced, transformation frequency is expected to be greatly increased upon the addition of tetracycline to the medium.

Example 6. Regulated Expression of BBM and WUS2 for Re-Transformation

Stable transgenic events in PHH5G are produced that express ZmBBM and ZmWUS2 in a regulated fashion, for example, having BBM and WUS2 under the control of the OLE and NOS promoters, respectively, or having them being driven by a tetracycline-inducible promoter. Immature embryos are then harvested and re-transformed using *Agrobacterium* to deliver UBI::moPAT::PinII. PHH5G embryos not expressing BBM and WUS2 (i.e. wild-type control embryos) produce no transformation events. However, embryos expressing OLE PRO::ZmBBM::PinII and NOS PRO::ZmWUS2::PinII are expected to produce a much higher frequency of bialaphos-resistant events. Regulated expression of the genes encoding cell proliferation factors is expected to enhance the regeneration frequency of normal fertile plants, and the cell proliferation gene locus should readily segregate away from the newly-generated "trait" locus (represented here by the UBI::moPAT::PinII locus). Likewise, when the expression of tetracycline-inducible genes encoding cell proliferation factors are stimulated by the addition of 0.5 mg/l tetracycline, *Agrobacterium*-mediated transformation to deliver the RB-UBI::moPAT::PinII-LB T-DNA is expected to result in enhanced transformation frequencies.

Example 7. Two T-DNA Co-Transformation to Deliver Genes Encoding Cell Proliferation Factors and Trait Genes Separately An *Agrobacterium* was modified to contain two engineered plasmids, each containing a separate T-DNA. T-DNA-1 was PHP35648 (see Example 4 for description), and T-DNA-2 (PHP41877) contained RB-attB4-UBI::moPAT::PinII+UBI-FRT1::RFP::PinII-attB1+UBI::GAT::PinII-attB2-FRT87-attB3-LB (GAT=glyphosate-N-acetyltransferase) representing the T-DNA that will contain the desired stack of trait genes). *Agrobacterium*-mediated transformation of PHH5G immature maize embryos was followed by glyphosate selection. Only embryos that have integrated T-DNA-1 grew since growth in culture for PHH5G only occurred when the ZmWUS2 and ZmBBM genes were present. Only embryos containing T-DNA-2 were glyphosate-resistant and exhibited red fluorescence. Thus, only embryos that were co-transformed with both T-DNAs grew on glyphosate.

Example 8. Identification of BBM Motifs

Fifty genes from different plant species were identified through a homology search using the maize BBM amino acid sequence (SEQ ID NO: 10) queried against annotated protein sequences (see FIG. 1). The gene structure and sequences of these BBM homologs were manually inspected and compared with EST/cDNA alignments whenever possible. The fifty polypeptides are set forth in SEQ ID NOs: 2, 4, 6, 8, 10, 12, 14, 16, 18, 20, 22, 24, 26, 28, 67, and 70-104. To systematically identify possible motifs within the BBM homologs, protein sequences of these fifty homologs were submitted to the MEME web server, available on the world wide web at meme.nbcr.net/meme4_1/cgi-bin/meme.cgi, with the following specific parameters:

Number of different motifs: 20
Minimum motif width: 5
Maximum motif width: 300
Minimum number of sites: 5

Default values were applied for all other parameters. The raw results from MEME were manually compared with multiple sequence alignments generated by clustalw. Only those candidates showing good consensus with the sequence alignments were considered as motifs for further analysis.

Figure 3:
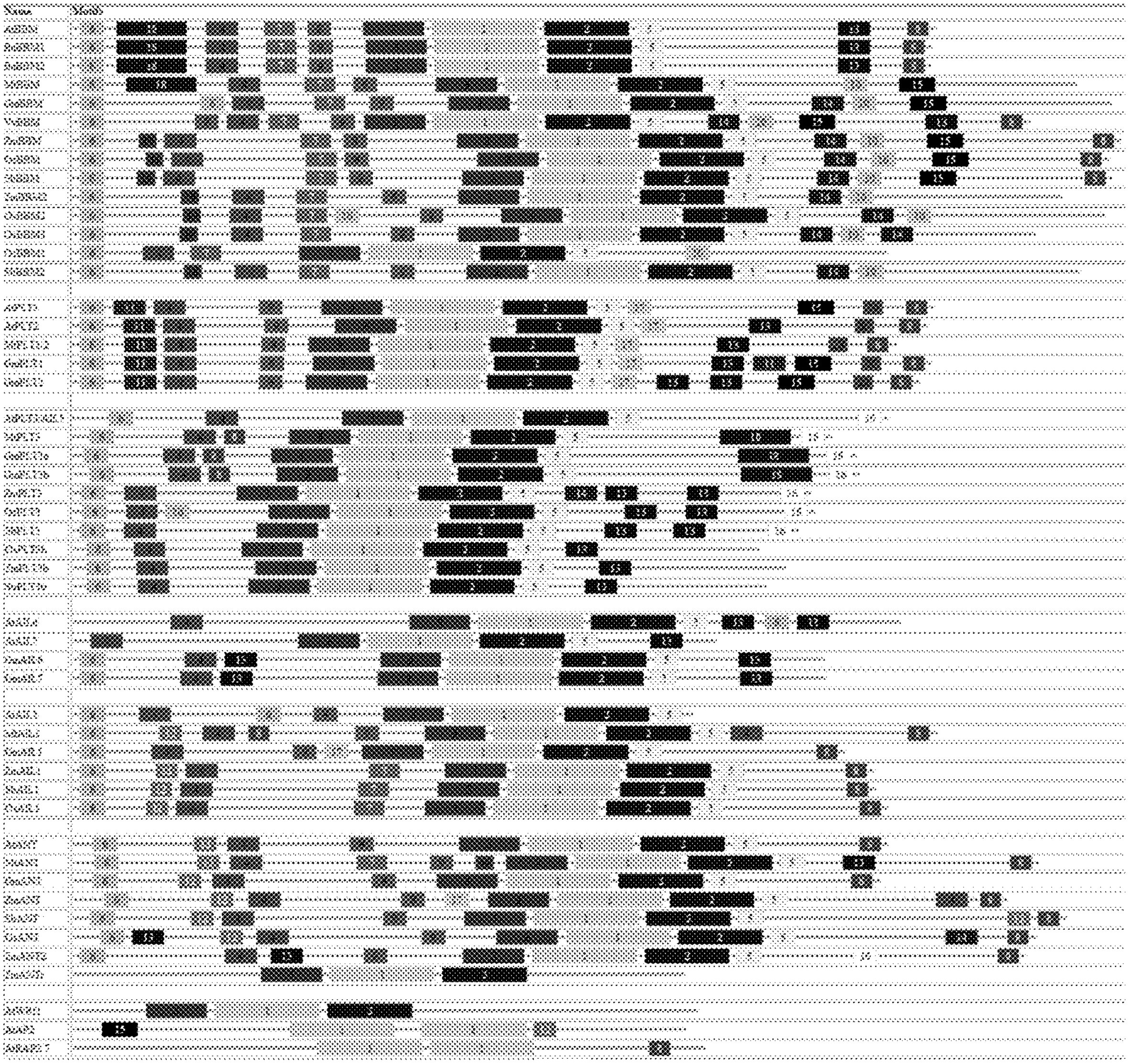
FIG. 3 depicts the motifs found within 50 sequences with homology to maize BBM (ZmBBM).
Figures 1, 4:
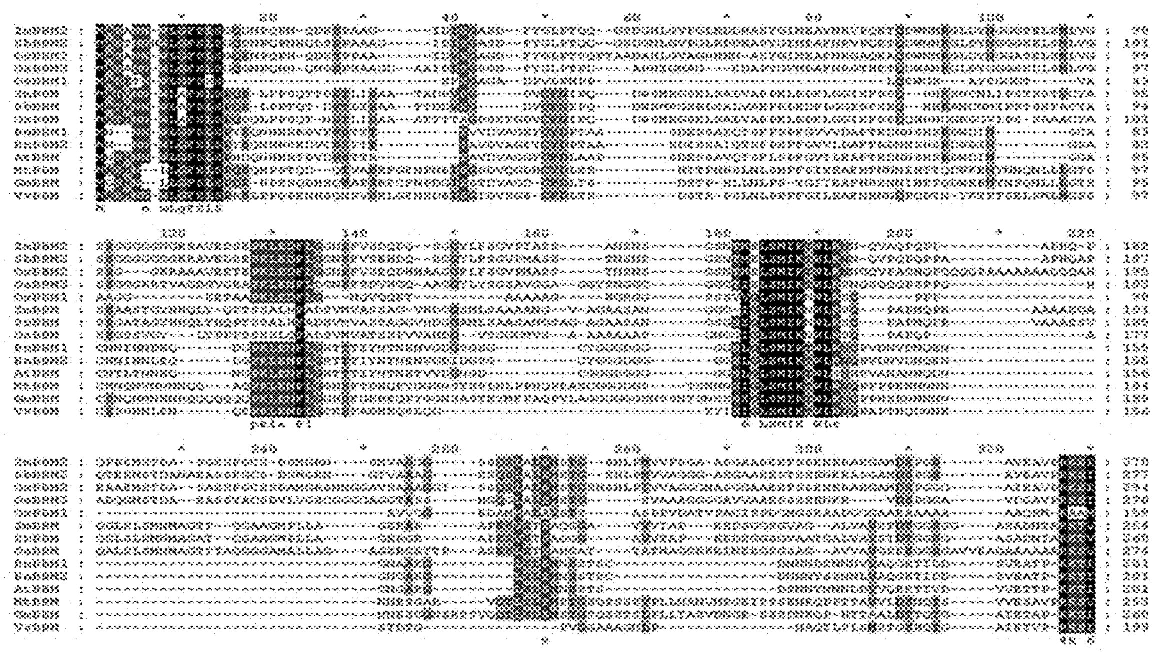
FIG. 4 shows an alignment of the amino acid sequence of various BBM polypeptides: maize babyboom 2 (ZmBBM2; SEQ ID NO: 12), sorghum babyboom 2 (SbBBM2; SEQ ID NO: 28), rice babyboom 2 (OsBBM2; SEQ ID NO: 18), rice babyboom 3 (OsBBM3; SEQ ID NO: 20), rice babyboom 1 (OsBBM1; SEQ ID NO: 16), maize babyboom (ZmBBM; SEQ ID NO: 10), sorghum babyboom (SbBBM; SEQ ID NO: 4), rice babyboom (OsBBM; SEQ ID NO: 14), *Brassica* babyboom 1 (BnBBM1; SEQ ID NO: 24), *Brassica* babyboom 2 (BnBBM2; SEQ ID NO: 26), *Arabidopsis* babyboom (AtBBM; SEQ ID NO: 22), *medicago* babyboom (MtBBM; SEQ ID NO: 8), soybean babyboom (GmBBM; SEQ ID NO: 2), and grape babyboom (VvBBM; SEQ ID NO: 6).
Figures 2, 4:
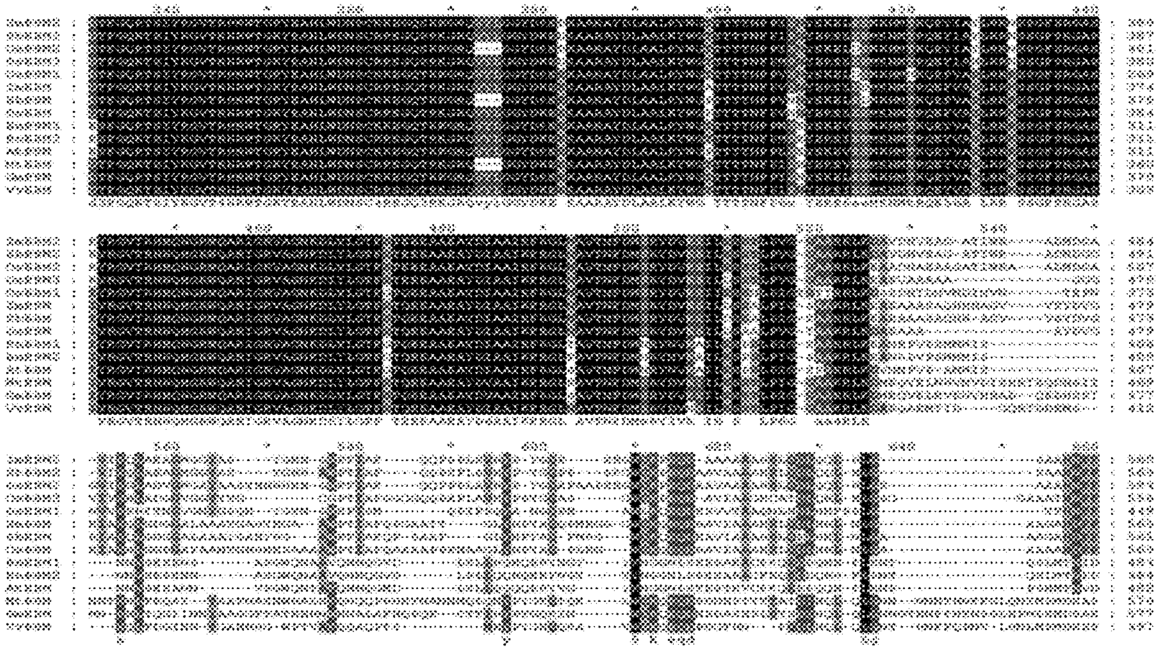
Figures 3, 4:
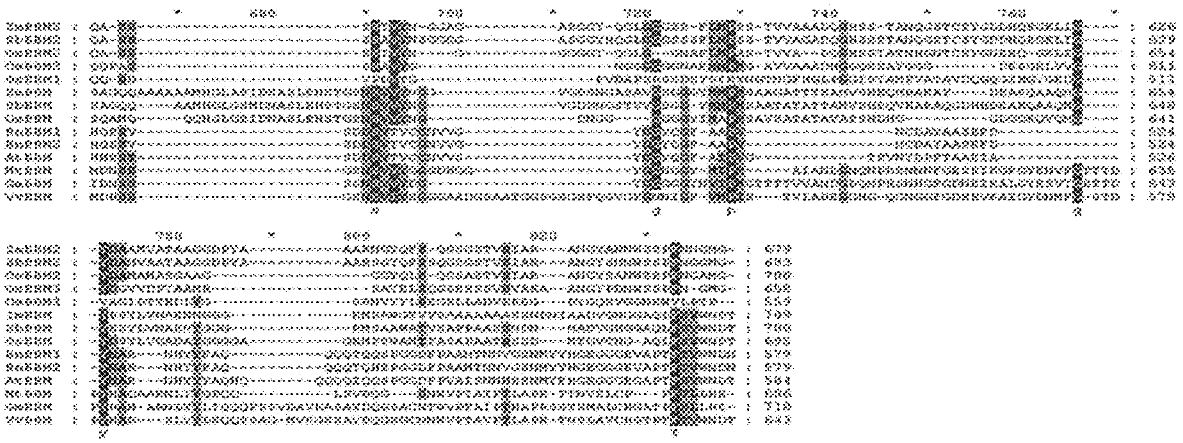

The fifty genes were subjected to a phylogenetic analysis and a total of six subgroups were identified, including BBM, PLT3, PLT1/2, AIL6/7, AIL1, and ANT (see FIG. 1). FIG. 3 depicts all 50 sequences with each of the motifs that were identified using the MEME web server. FIG. 2 provides the motif consensus sequences along with alignments of the various polypeptides used by the MEME web server to generate the consensus motif. With a few exceptions, motifs 1-6, as defined immediately hereinbelow, are present in all 50 genes. This includes motifs 1-3 (SEQ ID NOs 48-50, respectively), which represent the two AP2 domains and a sequence linking the two domains (linker sequence). Motif 4, with the consensus sequence of PK[L/V][E/A][D/N]FLG (SEQ ID NO: 51) is amino-terminal to the two AP2 domains. Motif 5 (SEQ ID NO: 52) flanks the two AP2 domains on the carboxy terminal end of the polypeptides. Near the amino terminus of the polypeptides is motif 6, with the consensus sequence of NWL[G/S]FSLSP (SEQ ID NO: 53).

There were motifs that were relatively specific for the BBM subgroup of the homologous sequences (referred to herein as BBM polypeptides). An alignment of the BBM polypeptides can be found in FIG. 4. Motif 7 is found in all BBM polypeptides at the amino terminus of the polypeptide and has the consensus sequence of [G/E]LSMIK[T/N]WLR (SEQ ID NO: 54). Another motif that is present in all of the BBM polypeptides except for the polypeptides from *Brassica* and from *Arabidopsis*, is Motif 10. Motif 10 has the consensus sequence of WCK[Q/P]EQD (SEQ ID NO: 57) and is located downstream of the AP2 domains.

There are three more motifs specific to the BBM group of polypeptides, including Motif 15 (SEQ ID NO: 59) which appears only in BBM orthologs, but not in the monocot BBM2 polypeptides; a monocot specific motif (Motif 19; SEQ ID NO: 60); and a general BBM specific motif (Motif 14; SEQ ID NO: 58), which appears in BBM homologs except for the *Brassica* and legume branch.

Figure 5:
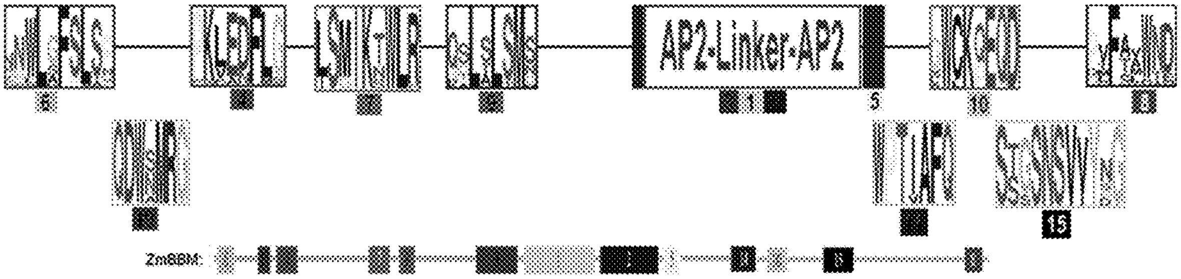
FIG. 5 provides a depiction of the motifs found in babyboom polypeptides.

FIG. 5 provides a summary of the motif structure of the BBM homologs. The amino terminal motifs 4 and 6 and the AP2 flanking motif 5 distinguish the BBM homologous sequences from other two AP2 domain-containing homologs, such as WRI, AP2, and RAP2.7. Therefore, motifs 1-6 can be considered as core BBM/PLT family motifs. Many subgroups of the BBM/PLT family (BBM, PLT1/2, AIL1, and ANT) also have a carboxy-terminal motif (motif 8; SEQ ID NO: 55) and the third amino terminal motif (motif 9; SEQ ID NO: 56).

The BBM polypeptides all have one additional motif (motif 7; SEQ ID NO: 54) in the amino terminus, and all but the *Brassica* and *Arabidopsis* BBM homologs have an AP2 downstream motif (motif 10; SEQ ID NO: 57). Some other BBM/PLT family members (e.g., monocot AIL1) may have a similar motif as motif 7, but none of them also have motif 9. Motif 10 appears only in BBM polypeptides. In summary, the MEME predicted motifs 1-10 can be regarded as BBM polypeptide motifs. All monocot BBM polypeptides (corn, sorghum, and rice) also have motif 14, 15, and 19 (see FIG. 3). Some dicot BBM polypeptides and the second monocot BBM group (BBM2) have one or two of these motifs, but none have all three motifs.

Example 9. Use of Maize BBM and WUS2 to Increase Transformation in Rice a. *Oryza sativa* L. Ssp. Indica Mature and immature Indica embryos were transformed using *Agrobacterium* with a T-DNA comprising the PHP46911 plasmid (control for immature embryos; see immediately hereinbelow for a description), the PHP32269 plasmid (control for mature embryosl; see immediately hereinbelow for a description), or PHP35648.

PHP46911: RB-CaMV35S::Hyg::Nos term+Ubi-FRT1::Zs-yellow1::PinII-FRT87-LB

PHP32269: RB-Ubi::PMI::PinII+Ubi::mo-PAT~Zs-yellow1::PinII-LB (PMI=phosphomannose isomerase)

i. Immature Embryo Transformation

Immature embryos of proprietary Indica strain 851G were transformed using the methods disclosed in International Application Publication No. WO/1995/06722 and Hiei and Komari (2006) *Plant Cell, Tissue and Organ Culture* 85:271-283, each of which is herein incorporated by reference in its entirety. Results are shown hereinbelow in Table 4.

TABLE 4

Transformation events in *Oryza sativa* L. ssp. *Indica* 851G immature embryos infected with *Agrobacterium* containing PHP35648.

| Embryo No. | No. of Pieces/Embryo | Total No. of Events/Embryo |
|---|---|---|
| 1 | 2 | 1 (100%) |
| 2 | 3 | 1 (100%) |
| 3 | 6 | 3 (300%) |
| 4 | 2 | 2 (200%) |
| 5 | 3 | 3 (300%) |
| 6 | 3 | 2 (200%) |
| 7 | 6 | 2 (200%) |
| 8 | 7 | 2 (200%) |
| 9 | 11 | 6 (600%) |
| 10 | 3 | 3 (300%) |

TABLE 4-continued

Transformation events in *Oryza sativa* L. ssp. *Indica* 851G immature embryos infected with *Agrobacterium* containing PHP35648.

| Embryo No. | No. of Pieces/Embryo | Total No. of Events/Embryo |
|---|---|---|
| 11 | 5 | 3 (300%) |
| 12 | 3 | 3 (300%) |
| TOTAL | 54 | 31 (258%) |

In total, infection of 12 immature Indica embryos with *Agrobacterium* containing the PHP35648 plasmid resulted in 31 transformation events, a transformation frequency of 258% events/embryo. The 31 events were derived from 54 pieces of embryo, for a transformation frequency of 57% events/embryo pieces. On the other hand, the infection of nine embryos with *Agrobacterium* containing PHP46911 resulted in only one single transformation event and an overall transformation frequency of 11%.

ii. Mature Embryo Transformation

Mature embryos of Indica strains IRV95 and 851G were transformed using the following protocol. Healthy rice seeds were dehusked and soaked in 50 ml of sterile water with a drop of Tween 20 for 5 minutes. The seeds were sterilized with 75% ethanol for 2-3 minutes, followed by a soak in 50 ml sodium hypochlorite and a drop of Tween 20 for 15-20 minutes. The seeds were rinsed and then callus was initiated in callus induction medium (4.3 g/l MS salts, 10 ml/1 B5 vitamins (100X), 2 mg/l 2,4-D, 500 mg/l L-proline, 30 g/l sucrose, 0.3 g/casein hydrolysate, 3 g/l Gelrite (added after bringing to volume with D-I $H_2O$ and adjusting pH to 5.8) under continuous light at 32° C. for 12 days.

Established callus was transformed using *Agrobacterium* by incubating the callus with the *Agrobacterium* for 10-15 minutes. The *Agrobacterium* solution was then decanted and 12-15 seeds were placed onto a filter paper disk that had been pre-moistened with 0.5 ml of AAM medium (50 ml/1 AA macro elements (20X), 10 ml/1 AA microelements (B5 microelements; 100X), 10 ml/1 AA vitamins (B5 vitamins; 100X), 5 ml/1 Fe-EDTA-B5 (200X), 1 mg/L 2,4-D, 100 ml/1 amino acids, 68.5 g/l sucrose, 36 g/l glucose, 500 mg/l cas amino acid at pH 5.2) containing 50 μM acetosyringone. The seeds and pre-moistened filter papers were cultured in the dark at 21° C. for 72 hours in ACCM medium (4.3 g/l MS salts, 10 ml/1 B5 vitamins (100X), 2 mg/l 2,4-D, 20 g/l sucrose, 10 g/l glucose, 0.5 g/l casein hydrolysate, 3 g/l Gelrite (added after bringing to volume with D-I $H_2O$ and adjusting pH to 5.2) containing 20011M acetosyringone. The calli were washed and then transferred to resting ASM medium (100 ml/1 580S major salts (10X), 10 ml/1 580S minor salts (100X), 5 ml/1 580S FeETDA-L (200X), 5 ml/l 580S vitamins (200X), 100 mg/l myo-inositol, 300 mg/l casein hydrolysate, 30 g/l maltose, 2 mg/12,4-D, 500 mg/l L-proline, 0.5 g/l MES buffer, 8 g/l agar (added after bringing to volume with D-I $H_2O$ and adjusting pH to 5.8) containing 250 mg/l carbenicillin for 15 days. Following the 15 day incubation, the calli were transferred to selection medium (100 ml/1 580S major salts (10X), 10 ml/1 580S minor salts (100X), 5 ml/1 580S FeEDTA-L (200X), 5 ml/l 580S vitamins (200X), 100 mg/l myo-inositol, 300 mg/l casein hydrolysate, 30 g/l sucrose, 2 mg/12,4-D, 500 mg/l L-proline, 0.5 g/l IVIES buffer, 8 g/l agar (added after bringing to volume with D-I $H_2O$ and adjusting pH to 5.8) with 200 mg/l carbenicillin and 2 mg/l bialaphos and subcultured every 15 days until transformation events arose.

The event was then dessicated on filter paper at 28° C. for 48 hours to excise the developmental genes. Dessicated events were identified based on the expression of Zs-yellow visualized under the microscope. The dessicated event was transferred to regeneration medium (100 ml/l N6 major salts (10X), 10 ml/l FeEDTA (100X), 10 ml/l B5 minor salts (100X), 10 ml/l B5 vitamins (100X), 1 mg/l 1-naphthalene acetic acid, 3 mg/l 6-benzyl amino purine, 30 g/L maltose, 0.3 g/l proline, 0.3 g/l vitamin assay casamino acids, 4 g/l agarose type 1, 30 mg/l glutamine (added after adjusting pH to 5.8 and sterilization) and grown at 32° C. under light. After 1-1.5 months, green shoots emerged from the callus and it was transferred to rooting medium (100 ml/l MS major salts (10X), 10 ml/l FeEDTA (100X), 10 ml/l MS minor salts (100X), 10 ml/l MS vitamins (100X), 2 mg/l indole-3-butyric acid, 15 g/l sucrose, 1 g/l vitamin assay casamino acids, 10X AA amino acid at pH 5.8). After another 15-20 days, the rooted plants are hardened in Y-medium (1.25 ml/l Stock A (9.14 g/100 ml ammonium nitrate (HIMEDIA RM5657)), 1.25 ml/l Stock B (4.03 g/100 ml sodium hydrogen phosphate (HIMEDIA 58282)), 1.25 ml/l Stock C (7.14 g/100 ml potassium sulfate (HIMEDIA 29658-4B)), 1.25 ml/l Stock D (8.86 g/100 ml calcium chloride (HIMEDIA C5080)), 1.25 ml/l Stock E (3.234 g/100 ml magnesium sulfate (HIMEDIA RM683)), 1.25 ml/l Stock F (15 mg/100 ml magnesium chloride tetra hydrate (HIMEDIA 10149), 6.74 mg/100 ml ammonium molybdate (HIMEDIA 271974), 9.34 mg/100 ml boric acid (SIGMA 136768), 0.35 mg/100 ml zinc sulfate helpta hydrate (HIMEDIA RM695), 0.31 mg/100 ml copper sulfate hepta hydrate (HIMEDIA C8027), 0.77 mg/100 ml ferric chloride hexa hydrate (SIGMA 236489), 119 mg/100 ml citric acid monohydrate (HIMEDIA C4540)) at pH 5.2.

Results are shown hereinbelow in Table 5.

TABLE 5

Transformation events in Oryza sativa L. ssp. Indica 851G and IRV95 mature embryo-derived callus.

| Seed No | Variety | Construct | No. of infected calli | No. of events | % of events | No. of events regenerated | % of regenerated events/infected calli |
|---|---|---|---|---|---|---|---|
| 1 | 851G | PHP35648 | 100 | 8 | 8.00% | 5 | 5.00% |
| | | PHP32269 | 50 | 1 | 2.00% | 0 | 0.00% |
| 2 | 851G | PHP35648 | 130 | 18 | 13.85% | N/A[a] | N/A |
| | | PHP32269 | 50 | 1 | 2.00% | N/A | N/A |
| 3 | IRV95 | PHP35648 | 128 | 20 | 15.63% | N/A | N/A |
| | | PHP32269 | 50 | 1 | 2.00% | N/A | N/A |

[a]N/A: data not available; calli are currently being dessicated, so no data on number or percentage of regenerated events are available b. Nipponbare Rice (Cv. Kitake)

Callus was initiated from mature embryos of *Oryza sativa*, var. Nipponbare, cv. Kitake, and established callus was transformed using *Agrobacterium* strain LBA4404 containing UBI::ZmBBM::PinII and NOS PRO::ZmWUS2::PinII between the T-DNA borders. Callus culture medium for rice consisted of N6 salts, Eriksson's vitamins, 0.5 mg/l thiamine, 2 mg/lo 2,4-D, 2.1 g/l proline, 30 g/l sucrose, 300 mg/l casein hydrolysate, 100 mg/l myo-inositol, and 3 g/l gelrite at pH 5.8. Five days after Agro-infection, callus was observed under an epifluorescent dissecting microscope. For calli that were transformed with UBI::ZS-GREEN::PinII alone, all the visible fluorescent foci were single cells, with a few possible 2-4 cell foci. When callus was transformed with NOS::ZmWUS2::PinII+UBI::ZmBBM::PinII+UBI::ZS-GREEN::PinII and observed 5 days later, numerous rapidly-growing, green-fluorescent, multicellular colonies were present.

Example 10. The Rice, Sorghum and Grape BBM Genes Increase Transformation Frequency in Maize Growth assays were performed to test whether BBM genes from various species would stimulate growth in maize. For these experiments, 10-13 DAP embryos of the genotype PH581 were bombarded with a first plasmid containing a UBI PRO::moPAT~GFP::pinII expression cassette plus either a plasmid contining 35S::GUS::pinII (control treatment) or a BBM gene driven by the ubiquitin promoter. To attach the DNAs to gold particles, a 25 μl aliquot of 0.6 μm particles (0.01 mg/μl) was added to fresh tubes before attaching DNA. To attach uncoated DNA, the particles were pulse-sonicated, then 500 ng of each DNA (in 5 μl water) was added, followed by mixing (pipetting up and down a few times with a Pipetteman). Then 2.5 μl of TFX-50 was added, and the solution was placed on a rotary shaker for 10 minutes. After centrifugation at 10,000 g for 1 minute, the supernatant was removed, and the particles were resuspended in 60 μl of EtOH, followed by a 10 minute incubation. The particles were spun briefly (i.e., 10 seconds), the supernatant removed, and 60 μl EtOH added. The solution was spotted onto macrocarriers and the gold particles onto which DNA had been attached were delivered into scutellar cells of 10-13 DAP immature embryos using a standard protocol for the DuPont PDS-1000 Helium Gun. After 4-5 weeks on culture medium, the embryos were examined and the number of GFP-expressing multicellular colonies were counted.

a. OsBBM

Based on the rice BBM genomic sequence (SEQ ID NO: 117), TIGR software was used to predict intron splicing and the resultant cDNA sequence (OsBBM (MOD1) is set forth in SEQ ID NO: 118). A plasmid containing an expression cassette for the rice BBM (MOD1) gene (UBI PRO::OsBBM (MOD1)::PinII) was co-delivered with UBI::moPAT~GFP::PinII into 13 DAP PH581 immature embryos using the particle gun. When the UBI PRO::moPAT~GFP::pinII cassette was introduced with 35S::GUS, few multicellular growing sectors were observed (see Tables 6-10). When UBI::ZmBBM::PinII was introduced along with UBI::moPAT~GFP::PinII, a stimulation of growth was observed as indicated by the total number of growing multicellular colonies observed as well as the number of embryos with multiple growing colonies. Despite many conserved amino acid motifs between the encoded maize protein and the protein encoded by the predicted OsBBM (MOD1) cDNA, when the rice expression cassette UBI::OsBBM (MOD1)::PinII, was introduced along with the moPAT~GFP cassette, no stimulation of growth was observed relative to the control treatment (35S::GUS) (see Tables 6 and 7). Based on a comparison of the maize and rice MOD1 amino acid sequences, and a more careful analysis of the rice genomic sequence, it was determined that the TIGR software failed to predict the splicing around a 9-bp exon that encodes the amino acids VYL in the first AP2 domain. Upon including this 9 bp exon in a re-synthesized rice cDNA (OsBBM (MOD2); set forth in SEQ ID NO: 120), and introducing this in the expression cassette UBI::OsBBM (MOD2)::PinII, a growth stimulation similar to that observed for the maize BBM gene was observed (Table 7, 8, 9 and 10).

TABLE 6

Number of green-fluorescent multicellular colonies six weeks after bombardment with UBI::moPAT~GFP plus the plasmid indicated in each treatment.

| | GFP+ Colonies/Bombarded Embryo | | | | | | | | | | | Total Number of Multicellular |
|---|---|---|---|---|---|---|---|---|---|---|---|---|
| TRT | 0 | 1 | 2 | 3 | 4 | 5 | 6 | 7 | 8 | 9 | 10 | Colonies |
| 35S::GUS | 44 | | | | | | | | | | | 0 |
| UBI::ZmBBM | 15 | 10 | 5 | 4 | 3 | 1 | 1 | | | 1 | | 25 |
| UBI::OsBBM (MOD1) | 42 | | | | | | | | | | | 0 |
| OLE::ZmBBM | 14 | 16 | 6 | 1 | | | | | | | | 14 |
| OLE::ZmANT | 44 | | | | | | | | | | | 0 |

TABLE 7

Number of green-fluorescent multicellular colonies five weeks after bombardment with UBI::moPAT~GFP plus the plasmid indicated in each treatment.

| | GFP+ Colonies/Bombarded Embryo | | | | | | | | | Total Number of Multicellular |
|---|---|---|---|---|---|---|---|---|---|---|
| TRT | 0 | 1 | 2 | 3 | 4 | 5 | 6 | 7 | 8 | Colonies |
| 35S::GUS | 70 | 5 | 0 | 3 | | | | | | 8 |
| UBI::ZmBBM | 19 | 24 | 17 | 7 | 3 | 1 | | | | 52 |
| UBI::OsBBM (MOD1) | 70 | 4 | 2 | | | | | | | 6 |
| UBI::OsBBM (MOD2) | 28 | 29 | 11 | 3 | 1 | 1 | | | | 45 |
| OLE::ZmBBM | 28 | 24 | 11 | 9 | 2 | 1 | 2 | | | 49 |
| OLE::ZmANT | 55 | 16 | 1 | 1 | 1 | | | | | 19 |

TABLE 8

Number of green-fluorescent multicellular colonies five weeks after bombardment with UBI::moPAT~GFP plus the plasmid indicated in each treatment.

| | Number of GFP+ Colonies per Scored Embryo | | | | | | | Total Number of Multicellular |
|---|---|---|---|---|---|---|---|---|
| Treatment | 0 | 1 | 2 | 3 | 4 | 5 | 6 | Colonies |
| 35S::GUS | 70 | 5 | 0 | 3 | 0 | 0 | 0 | 8 |
| UBI::ZmBBM | 19 | 24 | 17 | 7 | 3 | 1 | 0 | 52 |
| UBI::OsBBM (MOD2) | 28 | 29 | 11 | 3 | 1 | 1 | 0 | 73 |

TABLE 8-continued

Number of green-fluorescent multicellular colonies five weeks after bombardment with UBI::moPAT~GFP plus the plasmid indicated in each treatment.

| | Number of GFP+ Colonies per Scored Embryo | | | | | | | Total Number of Multicellular |
|---|---|---|---|---|---|---|---|---|
| Treatment | 0 | 1 | 2 | 3 | 4 | 5 | 6 | Colonies |
| OLE::ZmBBM | 28 | 24 | 11 | 9 | 2 | 1 | 2 | 49 |
| OLE::ZmANT | 55 | 16 | 1 | 1 | 1 | 0 | 0 | 19 |

TABLE 9

Number of green-fluorescent multicellular colonies five weeks after bombardment with UBI::moPAT~GFP plus the plasmid indicated in each treatment.

| | Number of GFP+ Colonies per Scored Embryo | | | | | | | Total Number of Multicellular |
|---|---|---|---|---|---|---|---|---|
| Treatment | 0 | 1 | 2 | 3 | 4 | 5 | 6 | Colonies |
| 35S::GUS | 61 | 6 | 1 | 0 | 0 | 0 | 0 | 7 |
| UBI::ZmBBM | 21 | 29 | 12 | 3 | 2 | 0 | 0 | 46 |
| UBI::OsBBM (MOD2) | 27 | 29 | 5 | 2 | 0 | 1 | 0 | 37 |

TABLE 9-continued

Number of green-fluorescent multicellular colonies five weeks after bombardment with UBI::moPAT~GFP plus the plasmid indicated in each treatment.

| | Number of GFP+ Colonies per Scored Embryo | | | | | | | Total Number of Multicellular |
|---|---|---|---|---|---|---|---|---|
| Treatment | 0 | 1 | 2 | 3 | 4 | 5 | 6 | Colonies |
| UBI::VvBBM | 32 | 21 | 6 | 0 | 1 | 0 | 0 | 28 |
| UBI::ZmBBM (genomic) | 9 | 36 | 13 | 6 | 3 | 0 | 10 | 58 |

TABLE 10

Number of green-fluorescent multicellular colonies five weeks after bombardment with UBI::moPAT~GFP plus the plasmid indicated in each treatment.

| | GFP+ Colonies/Scored Embryo | | | | | | | | | | | Total Number of Multicellular |
|---|---|---|---|---|---|---|---|---|---|---|---|---|
| TRT | 0 | 1 | 2 | 3 | 4 | 5 | 6 | 7 | 8 | 9 | 10 | Colonies |
| 35S::GUS | 80 | 11 | | | | | | | | | | 11 |
| UBI::ZmBBM | 43 | 28 | 13 | 5 | 2 | | | | | | | 48 |
| UBI::OsBBM (MOD2) | 45 | 32 | 11 | 3 | | | | | | | | 46 |
| UBI::SbBBM (MOD1) | 81 | 10 | | | | | | | | | | 10 |

b. SbBBM

Based on the sorghum genomic BBM sequence (SEQ ID NO: 69), TIGR software was used to predict intron splicing and the resultant cDNA sequence (SbBBM (MOD1) is set forth in SEQ ID NO: 3). A plasmid containing an expression cassette for the sorghum BBM (MOD1) gene (UBI PRO::SbBBM (MOD1)::PinII) was co-delivered with UBI::moPAT~GFP::PinII into 13 DAP PH581 immature embryos using the particle gun. When the UBI PRO::moPAT~GFP::PinII cassette was introduced with 35S::GUS, few multicellular growing sectors were observed (see Table 10). Unlike UBI::ZmBBM and UBI::OsBBM (MOD2), which in this experiment produced a similar positive growth stimulation, UBI::SbBBM (MOD1)::PinII failed to simulate growth. Assuming there was some unknown defect in the SbBBM (MOD1) synthetic cDNA, the sorghum genomic BBM was cloned using PCR and sequenced to verify fidelity. In an earlier experiment, the maize genomic BBM (SEQ ID NO: 116) was placed behind the UBI promoter and when compared to the UBI::ZmBBM cDNA construct it produced a similar degree of growth stimulation (Table 9). Using the genomic sorghum clone [UBI::SbBBM (GEN)], a similar level of growth stimulation was also observed (Tables 11 and 12).

TABLE 11

Number of green-fluorescent multicellular colonies five weeks after bombardment with UBI::moPAT~GFP plus the plasmid indicated in each treatment.

| | GFP+ Colonies/Scored Embryo | | | | | | | | | Total Number of Multicellular |
|---|---|---|---|---|---|---|---|---|---|---|
| Treatment | 0 | 1 | 2 | 3 | 4 | 5 | 6 | 7 | 8 | Colonies * |
| 35S::GUS | 57 | 3 | | | | | | | | 3 |
| UBI:VvBBM-NoVYL | 57 | 3 | | | | | | | | 3 |

TABLE 11-continued

Number of green-fluorescent multicellular colonies five weeks after bombardment with UBI::moPAT~GFP plus the plasmid indicated in each treatment.

| | GFP+ Colonies/Scored Embryo | | | | | | | | | Total Number of Multicellular |
|---|---|---|---|---|---|---|---|---|---|---|
| Treatment | 0 | 1 | 2 | 3 | 4 | 5 | 6 | 7 | 8 | Colonies * |
| UBI:VvBBM | 36 | 15 | 4 | 1 | 1 | 1 | | | | 22 |
| UBI:SbBBM (Genomic) | 10 | 19 | 11 | 11 | 4 | 3 | 2 | | | 50 |
| UBI:ZmBBM | 12 | 18 | 8 | 10 | 4 | 3 | 1 | | 1 | 45 |

TABLE 12

Number of green-fluorescent multicellular colonies five weeks after bombardment with UBI::moPAT~GFP plus the plasmid indicated in each treatment.

| | GFP+ Colonies/Scored Embryo | | | | | | Total Number of Multicellular |
|---|---|---|---|---|---|---|---|
| TRT | 0 | 1 | 2 | 3 | 4 | 5 | Colonies |
| 35S::GUS | 60 | | | | | | 0 |
| UBI::ZmBBM | 19 | 18 | 11 | 7 | 4 | 1 | 41 |
| UBI::SbBBM (Genomic) | 20 | 15 | 14 | 6 | 5 | | 60 |
| UBI::VvBBM | 46 | 11 | 3 | | | | 14 |
| UBI::VvBBM - No VYL | 60 | | | | | | 0 |

c. VvBBM

A nucleotide sequence was derived that provided good codon usage for maize, but expressed the amino acid sequence of a grape BBM (VvBBM; SEQ ID NO: 5). A plasmid containing an expression cassette for a synthetic grape BBM gene (UBI PRO::VvBBM::PinII) was co-delivered with UBI:moPAT~GFP::PinII into 10 DAP PH581 immature maize embryos using the particle gun. When the UBI PRO::moPAT~GFP::PinII cassette was introduced alone, no (Table 12) or very few (Tables 9 and 11) multicellular growing sectors were observed. When UBI::VvBBM::PinII+UBI::moPAT~GFP::PinII were co-delivered, numerous RFP+multicellular colonies were observed growing on the surface of bombarded embryo after 4 weeks. As with growth stimulation by the maize, rice and sorghum BBM genes, the growth stimulation imparted by the UBI::VvBBM::PinII cassette was manifested by an increase in the overall number of multicellular colonies, and also an increase in the number of multicellular colonies growing on single embryos (see Tables 9, 11 and 12). When a construct comprising the VvBBM sequence, in which the 9-bp sequence encoding VYL in the AP2 domain was removed, was introduced into maize, there was no observed growth stimulation (Tables 11 and 12), similar to the observations made with the rice BBM gene lacking this same exon.

d. Maize ANT Gene

The following constructs were used for comparison: OLE PRO::ZmBBM::pinII, and OLE PRO::ZmANT::pinII. The nucleotide and amino acid sequences of ZmANT are set forth in SEQ ID NOs: 66 and 67. Each of these plasmids was co-delivered with UBI::moPAT~GFP::pinII into 10 or 13 DAP PH581 immature embryos using the particle gun. When the UBI PRO::moPAT~GFP::pinII cassette was introduced alone, no (Table 6) or few multicellular growing sectors (Tables 7 and 8) were observed. When OLE:: ZmBBM::pinII+UBI::moPAT~GFP::pinII were co-delivered, a substantial increase in the number of embryos with GFP+multicellular colonies were observed growing on the surface of each bombarded embryo after 5 weeks (i.e. relative to the control treatment). In addition, the number of embryos supporting multiple GFP+colonies increased. Embryos co-bombarded with OLE::ZmANT::pinII+UBI:: moPAT::pinII appeared identical (Table 6, with no multicellular colonies in either treatment) or similar to the control treatment (FIGS. 6 and 7, with only a 2-fold increase in colony formation and numerous single GFP+ cells (indicating only transient expression but no division) and a reduced number of GFP+colonies relative to the BBM treatment. In a second experiment with the same treatments (control with no BBM or ANT, Ole::BBM or Ole::ANT), out of 44 embryos shot per treatment, the control and ANT treatments produced no multicellular GFP+colonies after 3 weeks while the BBM treatment produced 14 colonies.

Example 11. Expression of the Maize BBM and WUS Genes Improves Transformation in Sorghum

*Agrobacterium tumefaciens* LBA4404 and a super-binary vector constructed with pSB1 and pSB11 (Komari et al. (1996) *Plant J* 10:165-174; Thompson et al. (1987) *EMBO J* 6:2519-2523) can be used for sorghum transformation (Zhao (2006) In "Agrobacterium Protocols," vol. 1, Kan Wang, ed. Hamana Press, Totowa, N.J.; U.S. Pat. No. 6,369,298; and International Application Publication No. WO 98/49332). The super-binary vector contained a selectable marker gene, bar (Chalfie et al. (1994) *Science* 263: 802-805) and a visible marker gene, such as red fluorescent protein (RFP), yellow fluorescent protein (YFP), or intron-GFP (Jefferson et al. (1986) *Proc Natl Acad Sci USA* 83:8447-8451).

Minimal AB media included 50 ml/l Stock A, 50 ml/l Stock B, 5 g/l glucose, 9 g/l Phytagar. For the *Agrobacterium* strain used in this protocol, 50 mg/l spectinomycin is added after autoclaving. Stock A included 60 g/l $K_2HPO_4$, and 20 g/l $NaH_2PO_4$, pH 7.0. Stock B is 20 g/l $NH_4Cl$, 6 g/l $MgSO_4$ $7H_2O$, 3 g/l KCl, 0.2 g/l $CaCl_2$, and 0.5 g/l $FeSO_4$ $H_2O$. YP medium contained 5 g/l yeast extract, 10 g/l peptone, 5 g/l NaCl, and 15 g/l Bacto-agar. For the *Agrobacterium* stain used in this protocol, 50 mg/l spectinomycin was added after autoclaving.

PHI-I media included 4.3 g/l MS salts (GIBCO BRL catalog no. 11117-874), 0.5 mg/l nicotinic acid, 0.5 mg/l pyridoxine HCl, 1 mg/l thiamine HCl, 0.1 g/l myo-inositol, 1 g/l vitamin assay casamino acids, 1.5 mg/12,4-D, 68.5 g/l sucrose, 36 g/l glucose, pH 5.2. 100 μM acetosyringone is added before using.

PHI-T media included PHI-I with sucrose reduced to 20 g/l and glucose reduced to 10 g/l, 2, 4-D increased to 2 mg/1, and with 0.5 g/l IVIES buffer, 0.7 g/l L-proline, 10 mg/l ascorbic acid, 100 μM acetosyringone and 8 g/l agar, pH 5.8 added.

PHI-U media included PHI-T without glucose and acetosyringone, and with 1.5 mg/12,4-D, 100 mg/l carbenicillin, and 5 mg/l PPT (glufosinate-HN4) added.

PHI-RF media included 4.3 g/L MS salts (GIBCO BRL 11117-074), 0.5 mg/L nicotinic acid, 0.1 mg/L thiamine HCl, 0.5 mg/L pyridoxine HCl, 2.0 mg/L glycine, 0.1 g/L myo-inositol, 0.49 μM cupric sulfate, 0.5 mg/L zeatin (Sigma Z-0164), 1 mg/L IAA, 26.4 μg/L ABA, 0.1 mg/L thidiazuron, 60 g/L sucrose, 3 mg/L bialaphos, 100 mg/L carbenicillin, and 8 g/L agar, pH 5.6.

PHI-Z media included 2.15 g/L MS salts, 2.5 ml/L MS vitamin mix, 20 g/L sucrose, and 3 g/L gelrite, pH 5.6

Suspension for immature embryo infection consisted of 100 μM acetosyringone in PHI-I medium (pre-warmed to room temperature). Bacteria were scraped off a working plate with a sterile bacteria loop and placed in PHI-I with 100 μM acetosyringone. The suspension was vigorously vortexed to break clumps and form a uniform suspension as determined by visual inspection. 1 ml of Agro-suspension was taken to measure optical density at 550 nm. The suspension was diluted with PHI-I plus 100 μM acetosyringone to $10^9$ cfu/ml (OD at 0.7).

Sorghum plants were grown under greenhouse, growth chamber, or field conditions. Healthy sorghum plants were always important for a successful transformation. Immature panicles were harvested 9-13 days post-pollination depending on the growing conditions. The size of immature zygotic embryos used in transformation ranged from 0.8 to 2.5 mm in length. Immature kernels were removed from the panicles and sterilized with 50% bleach and 0.1% Tween-20 for 30 min. with vacuum, then the kernels were rinsed three times with sterile water. The kernels were kept in sterile water before isolating embryos. Embryos were aseptically dissected from each sterilized sorghum kernel and placed in a 2-ml microtube containing 2 ml PHI-I with 100 μM acetosyringone. Usually, about 100 embryos were placed in each tube.

PHI-I liquid medium was removed from the tube comprising the embryos with a 1 ml micropipettor and replaced with 1 ml of the *Agrobacterium* suspension. The tube was gently inverted a few times to mix well and incubated 5 minutes at room temperature. The *Agrobacterium* suspension was removed from the tube with a 1 ml micropipettor. The embryos were scraped from the tube using a sterile spatula. Immature embryos were transferred to a plate of PHI-T medium in a 100×15 mm Petri dish. The embryos were oriented with embryonic axis down on the surface of the medium. These embryos were incubated at 21-25° C. in the dark for 3 days. The embryos were transferred to PHI-U minus PPT with the same orientation and incubated at 28° C. in the dark for 4 days.

The embryos were transferred to PHI-U medium and incubated at 28° C. in the dark for 2-3 weeks and were subcultured every two to three weeks for about 10-20 weeks to obtain enough callus for regeneration into plants.

These calli were transferred to PHI-RF medium and incubated at 28° C. in the dark for approximately 2-3 weeks to develop shoots. When shoots formed, these cultures were moved to a lighted culture room under conditions of 16 hours light (270 μE $m^{-2}$ $sec^{-1}$) and 8 hours dark at 25° C. Shoots (about 3-5 cm tall) were transferred to plastic boxes (10×9×10 cm) containing PHI-Z medium. These shoots were cultured under the same light and temperature conditions for 3-5 days. Each box contained shoots derived from a single embryo. When the plantlets reached about 8-10 cm tall with healthy roots, these plantlets were transferred to pots with Universal Mix (Strong-Lite, Seneca, IL61360) in the greenhouse.

Embryos were harvested from developing sorghum seed and transformed using *Agrobacterium*, delivering the PHP32371 T-DNA (see Example 4). As a control treatment, embryos were transformed with RB-Ubi::moPAT+Ubi:CFP-LB. Callus was selected on 3 mg/l bialaphos, and monitored for fluorescence to aid in identifying transgenic sectors. Sorghum transformation frequencies using Ubi:moPAT+

Ubi:CFP averaged 0.5%. By comparison, in six experiments, a total of 393 embryos were transformed with PHP32371, producing an average transformation frequency of 18.3% (see Table 13). Callus from the first experiment (30 events from a starting total of 140 embryos) was used to test the desiccation-induced excision controlled by the Rab17 promoter, and subsequent plant regeneration. Twenty-one events were desiccated for three days on dry filter papers and then taken through the standard regeneration protocol. Fifteen of the 21 events produced a total of 81 plants, with multiple plants being regenerated for many of the individual events. Of these, 60% contained a single copy of the integrated DNA, and of the single copy events, 91% produced PCR results indicating complete excision of the genes encoding cell proliferation factors. From excised events, normal phenotype plants lacking FLP and WUS2 were readily regenerated.

TABLE 13

Transformation efficiencies after *Agrobacterium*-mediated transformation with PHP32371.

| Experiment ID | Number of Embryos | Number of Transformation Events | Transformation Frequency (%) |
|---|---|---|---|
| 1 | 140 | 30 | 21.4 |
| 2 | 40 | 3 | 7.5 |
| 3 | 60 | 8 | 13.3 |
| 4 | 40 | 7 | 17.5 |
| 5 | 61 | 12 | 19.7 |
| 6 | 52 | 12 | 23.1 |
| Average | | | 18.3 |

Example 12. Expression of the Maize BBM and WUS Genes Improves Transformation in Sugarcane A developmental gene binary vector with the ZmBBM/ZmWUS2 gene cassette was compared with a standard vector containing moPAT plus either DsRED or YFP without the ZmBBM/ZmWUS2 gene cassette for transformation frequency using two *Agrobacterium* strains, AGL1 and LBA4404, in CP89-2376 and CP01-1372 sugarcane cultivars. The developmental gene binary vector contains Ubi::LoxP::CFP+Rab17Pro-attB1::Cre-attB2::PinII+Nos::ZmWUS2::PinII+Ubi::ZmBBM::PinII-LoxP::YFP+Ubi::MOPAT::PinII. The Lox cassette containing CFP::Cre::WUS::BBM can be excised by Cre recombinase controlled by the Rab 17 promoter. Callus tissues of both CP89-2376 and CP01-1372 cultivars were induced and maintained on DBC3 medium. Tissues were infected with *Agrobacterium* containing the developmental gene binary vector in 10 mM MgSO4 plus 100 uM acetosyringone and then cocultivated with liquid DBC3(M5G) medium plus 100 uM acetosyringone on the filter paper in Petri dishes at 21° C. in the dark. Three days after cocultivation, the tissues were transferred to DBC3 containing 100 mg/L cefotaxime and 150 mg/L timentin for AGL1, and DBC3 containing 100 mg/L carbenicillin for LBA4404, and incubated at 26° C. (±1° C.) in the dark or dim light for 3-7 days. Afterwards, the tissues were transferred to the same media as the previous step plus 3 or 5 mg/L bialaphos. After two months from the initiation of the experiment, transformation frequency was calculated by the number of tissues showing CFP expression divided by the number of explants infected by *Agrobacterium*. Table 14 demonstrated that AGL1 was even more efficient in transformation than LBA4404 in both CP89-2376 and CP01-1372. There was also a genotype difference in transformation frequency; CP89-2376 had much higher transformation frequencies than CP01-1372 using either of the *Agrobacterium* strains.

AGL1 containing the developmental gene vector was also used to test sugarcane germplasm screening in another set of experiments using 5 different cultivars (CP96-1252, CP01-1372, CP89-2376, CPCL97-2730 and HoCP85-845). Callus tissues of all 5 cultivars tested were induced and maintained on DBC3 medium and tissues were infected with AGL1 containing the developmental gene binary vector. The use of developmental genes dramatically increased transformation frequency in all 5 cultivars tested. Transformation frequencies in the most amenable cultivar, CP89-2376, using a standard binary vector averaged 116.7% (56/48) (Table 14). In contrast, an average transformation frequency in this cultivar from 5 experiments was >2,512.5% (>1,005 events/40 tissues infected) using the developmental gene binary vector. Similar results were obtained from the remaining 4 cultivars, CP96-1252, CPO1-1372, CPCL97-2730 and HoCP85-845; transformation frequencies ranged from 62.5% to 187.5% in these 4 cultivars while no transgenic events were obtained using the standard vector without the BBM/WUS gene cassette from these cultivars.

TABLE 14

Transformation frequency in sugarcane using the developmental genes ZmBBM and ZmWUS2.

| *Agrobacterium* Strain | Binary Vector | Sugarcane Cultivar CP96-1252 | CP01-1372 | CP89-2376 | CPCL97-2730 | HoCP85-845 |
|---|---|---|---|---|---|---|
| AGL1 | DG[a] | n.t. [c] | 37.5% (3/8) | n.t. | n.t. | n.t. |
| LBA4404 | DG | n.t. | 0% (0/8) | n.t. | n.t. | n.t. |
| AGL1 | DG | n.t. | >1,250.0% (>100/8) | >6,250.0% (>500/8) | n.t. | n.t. |
| LBA4404 | DG | n.t. | 12.5% (1/8) | >1,500% (>120/8) | n.t. | n.t. |
| AGL1 | DG | n.t. | n.t. | 687.5% (>55/8) | n.t. | n.t. |
| AGL1 | DG | n.t. | n.t. | >2,500% (>200/8) | 175.0% (14/8) | n.t. |

TABLE 14-continued

Transformation frequency in sugarcane using the developmental genes ZmBBM and ZmWUS2.

| *Agrobacterium* | | Sugarcane Cultivar | | | | |
|---|---|---|---|---|---|---|
| Strain | Binary Vector | CP96-1252 | CP01-1372 | CP89-2376 | CPCL97-2730 | HoCP85-845 |
| AGL1 | DG | 150.0% (12/8) | 62.5% (5/8) | >625.0% (>50/8) | 62.5% (6/8) | n.t. |
| AGL1 | DG | n.t. | n.t. | >2,500% (>200/8) | n.t. | 187.5% (15/8) |
| AGL1 | Std[b] | 0% (0/8) | 0% (0/8) | 116.7% (56/48) | 0% (0/8) | 0% (0/8) |

Each transformation treatment had 8 pieces of callus tissues 0.4-0.5 cm in size.
DG[a]: developmental gene vector with BBM/WUS gene cassette
Std[b]: standard vector without BBM/WUS gene cassette
n.t. [c]: not tested Transgenic callus tissues were desiccated on dry filter papers for three days to induce excision of the Lox cassette containing CFP::Cre::WUS::BBM by Cre recombinase driven by the Rab17 promoter. Excision was monitored by observing YFP expression on desiccated transgenic callus events by the presence of the UBI:loxP:YFP junction formed as a result of excision. Cre excision occurred at 83 of 87 transgenic events (95.4%) (Table 15). Plants from some transgenic events after excision are being regenerated on MSB plus 1 mg/L bialaphos and antibiotics.

TABLE 15

Excision efficiency of the BBM/WUS gene cassette in transgenic sugarcane events by desiccation.

| Sugarcane Cultivar | *Agrobacterium* Strain | Binary Vector | Excision Efficiency (%) |
|---|---|---|---|
| CP89-2376 | AGL1 | DG[a] | 93% (40/43) |
| CP89-2376 | LBA4404 | DG | 100% (25/25) |
| CP01-1372 | AGL1 | DG | 100% (13/13) |
| CP01-1372 | LBA4404 | DG | 0% (0/1) |
| CP89-2376 | AGL1 | DG | 100% (5/5) |
| | Average | | 95.4% (83/87) |

DG[a]: developmental gene vector with BBM/WUS gene cassette

Example 13. Complementation of Separately Transformed BBM and WUS2 Genes

Nos::ZmWUS2::PinII and Rab17-attB1::CRE::PinII are integrated into the genome of an inbred maize plant. LoxP-UBI::BBM::PinII-LoxP+a trait gene operably linked to a promoter are re-transformed into the inbred as a single T-DNA. The BBM and WUS2 genes will complement each other, stimulating rapid growth only in the cells where both are present. BBM is then excised and normal fertile plants are regenerated. Later, the WUS2/CRE locus is segregated away from the genome.

Example 14. Transformation of Mature Dried Maize Seed

Cell proliferation factors can be used to increase transformation and/or recovery frequencies in recalcitrant plants and/or target tissues, such as mature seed.

A T-DNA containing an excisable construct comprising a maize BBM and a maize WUS gene was constructed:

PHP38333: RB-Ubi-LoxP::CFP::PinII-attB4+Rab 17 Pro-attb1::Cre-attB2::PinII+Nos::ZmWUS2::PinII+Ubi::ZmBBM::PinII-LoxP::YFP::PinII+Ubi::moPAT::PinII-LB As a control treatment, embryos were transformed with PHP32269: RB-Ubi::moPAT-YFP::PinII-LB.

The glycerol stock of a thymidine-auxotrophic mutant *Agrobacterium* strain LBA4404 with vector PHP38333, or the control vector were stored at −80° C. before use. A master plate was made by dipping an inoculation loop into a glycerol stock and streaking onto 12V solid medium with 50 mg/l thymidine in a 100x15 Petri dish (for PHP38333) or onto 12S solid medium with 50 mg/l spectinomycin (for the control plasmid). Plates were incubated (inverted) at 28° C. in the dark for 2-3 days to produce single colonies. Master plates were stored at 4° C. for up to 4 weeks and are used for initiating fresh culture for transformation. Several colonies were picked from the master plates and streaked onto 810F solid medium with 50 mg/l thymidine and incubated at 28° C., in the dark for 1 day and fresh *Agrobacterium* was used for transformation.

To make the *Agrobacterium* suspension, 20 ml of 700 liquid medium with 50 mg/l thymidine was added into a 50 ml snap cap tube. A stock solution of acetosyringone (AS) was added to achieve a final concentration of 200 uM and a stock solution of Silwet L-77 was added to achieve a final concentration of 0.04%. *Agrobacterium* was collected from a 1-day culture plate and suspended in the 700 liquid medium. The tube was vortexed until the *Agrobacterium* culture clumps were completely broken up and evenly dispersed throughout the solution. One ml of the suspension was transferred to a spectrophotometer tube and the OD of the suspension was adjusted to 0.7 at 550 nm by adding either more *Agrobacterium* or more of the same suspension medium.

Maize inbred line PHN46 was used as the initial genotype for transformation tests. Dry seeds were placed in a covered glass jar, in an 80% ethanol solution with stirring for 5 min. The ethanol was decanted and a 50% bleach solution with a few drops of the surfactant Tween-20 were added and seeds in the bleach solution were stirred for 30 min and washed three times with sterile water in a sterile flow hood. Surface sterilized seed were soaked in the sterile water for approximately 24 h at room temperature, which is sufficient to trigger germination. After 24 hours, the softened seeds were sterilized once again with a 50% bleach solution for 5 min, and then washed three times with sterile water in a sterile flow hood.

Mature embryos were dissected out of the softened and sterilized kernels. Each mature embryo was sliced into 3-4 thin sections by hand using a No. 10 surgical scalpel under the dissecting microscope. Each explant contained exposed leaf primordia, mesocotyl and root primordia regions. These regions on the embryo chips were the target area for T-DNA delivery during *Agrobacterium*-mediated transformation and contain cells that are culture responsive. Sliced explants were transferred into a 6-well culture plate containing 4 ml 700 liquid medium. About 45 explants were placed into each well for *Agrobacterium* infection.

Liquid medium in the 6-well plate was removed from the explants and replaced with 4 ml of prepared *Agrobacterium* suspension. The 6-well plate was transferred into a transparent polycarbonate desiccator container. The desiccator was covered and placed on a platform shaker rotating at a speed of 100 RPM and connected to an in-house vacuum system for 30 min. After infection, the *Agrobacterium* suspension was drawn off from the wells and the explants were transferred onto solid 7101 co-cultivation medium with 50 mg/l thymidine. The infected embryo explants on the solid medium were incubated at 21° C. in the dark for 3 days. The number of infected explants was recorded to later calculate transformation efficiencies.

To evaluate T-DNA delivery efficiency, both the control vector without genes encoding cell proliferation factors and the vector with the genes encoding cell proliferation factors were used to infect embryo explants. After 3d co-cultivation, all of the chips were transferred onto 605J medium for continuous culture. T-DNA delivery was evaluated around 5d after *Agrobacterium* infection. Transient expression of the color marker YFP (control vector) or CFP (test vector PHP38333) was a reliable indicator of the T-DNA delivery efficiency. In general, 30%-50% of the infected explants showed T-DNA delivery in the right target tissues or cells. Using an optimized infection medium and protocol, 70%-80% T-DNA delivery efficiency to the target area was achieved. Infected explants were sub-cultured to fresh medium every 3 weeks. After 6 weeks of culture, healthy, vigorously growing, embryogenic type I callus could be identified from those explants that had been infected with vector PHP38333 containing the genes encoding cell proliferation factors. These growing calli represented transformed events confirmed by the color marker (CFP) expression. Non-transformed tissues showed either no growth or very limited growth. Embryogenic type I callus were picked and transferred onto fresh culture medium to let the callus proliferate before plant regeneration (10-12 weeks). Transformation efficiency for PHP38333 at the callus level ranged from 12% to 20% calculated as the number events recovered per total number of infected explants (Table 16). Embryo explants that were infected with control vector PHP32269 also showed good T-DNA delivery based on transient YFP expression in the infected cells. However, these cells did not show significant proliferation and no healthy callus was formed during continuous culture.

TABLE 16

Transformation frequency of PHP38333 in PHN46 embryo chips.

| Experiment No. | Number of Chips infected | Number of CFP(+) Events | Transformation Frequency (%) |
|---|---|---|---|
| 1 | 137 | 23 | 16.8% |
| 2 | 134 | 19 | 14.2% |
| 3 | 149 | 20 | 13.4% |
| 4 | 140 | 25 | 17.9% |
| 5 | 148 | 18 | 12.2% |
| 6 | 137 | 26 | 19.0% |
| 7 | 129 | 27 | 20.9% |
| 8 | 136 | 20 | 14.7% |
| 9 | 137 | 21 | 15.3% |
| 10 | 147 | 24 | 16.3% |
| Total | 1393 | 223 | 16.0% |

Transformed callus tissues were treated with either one of the following two desiccation methods to induce excision of the genes encoding cell proliferation factors before plant regeneration.

1) Desiccation by natural air exchange: Transformed callus tissues were transferred to an empty 60 mm×25 mm Petri dish containing a piece of autoclaved glass filter paper and covered with a lid but not sealed. Petri dishes with callus tissues were placed into a culture box with a loose cover. The box was kept at 28° C. in the dark for 3 days.

2) Desiccation in chambers containing a saturated salt solution: Transformed callus tissues were transferred to an empty 60 mm×25 mm Petri dish containing a piece of autoclaved glass filter paper and covered with a lid. The Petri dishes with callus tissues were placed into a container with a tight sealing cover. A glass jar containing saturated $(NH_4)_2SO_4$ salt solution without a cover was placed in the container. The container was kept at 28° C. in the dark for 3 days (as the moisture in the air inside the container was absorbed by the saturated salt solution, the callus tissue gradually lost water and experienced desiccation stress).

After 3 days of desiccation treatment, the callus tissues were transferred to 289L regeneration media for 2-3 weeks in the dark. When shoots formed with a length of about 1-2 cm, callus tissues with shoots were transferred to hormone-free 272V medium for further development of shoots and roots in the light culture room. When plantlets had formed well-developed shoots and roots, plant regeneration efficiency was evaluated. The plant regeneration frequency (number of callus producing plants out of total number of callus events for plant regeneration) varied from 45% to 75% among 10 initial experiments. At this stage, leaf samples were collected from the plantlets derived from each callus event for molecular analysis. Detailed PCR analyses were performed to determine the copy number of transgenes as well as to confirm that the genes encoding proliferation factors were excised and were not present in the regenerated transgenic plants.

Based on the molecular analysis of 316 TO plants from 162 events, about 60% of the transgenic plants contain a single copy of the transgenes. These single-copy transgenic plants showed very efficient excision of the genes encoding cell proliferation factors from the desiccation-treatment-induction (see results in Table 17). In general, plants with complete excision of genes encoding cell proliferation factors displayed normal phenotype in the tube and also in later developmental stages in the greenhouse. In contrast, TO plants in which excision did not occur (or where it was incomplete) displayed an abnormal phenotype, such as thickened roots.

Based on PCR analysis results, chimeric or incomplete excision TO plants can be eliminated and only complete-excision (free of genes encoding cell proliferation factors) events were sent to the greenhouse.

TABLE 17

Analysis of T0 plants for excision of genes encoding cell proliferation factors.

| Number of Events/T0 Plants | Single Copy | Complete Excision |
|---|---|---|
| 162 (Events) | 103 (63.6%) | 94 (91.3%) |
| 316 (Plants) | 189 (59.8%) | 173 (91.5%) |

Example 15. Transformation of Leaf Tissues a. Preparation of *Agrobacterium* and Maize Leaf Explants

*Agrobacterium* suspensions were prepared as described in Example 14. Pioneer maize inbred lines PHN46, PHRO3 and PHEJW were used as the initial genotypes for transformation tests. Dry seed was sterilized and imbibed overnight as described above.

Sterilized seeds were placed onto 272V solid medium for direct germination. Alternatively, mature embryos were dissected from softened and sterilized seeds and placed onto 272V solid medium for faster germination. Plates with seeds or isolated embryos were placed in a culture box and incubated at 28° C. in the dark for 3-7 days. Shoot segments of about 2-3 cm long above the first leaf base node of the seedling were excised under sterile conditions. The coleoptile was removed and the leaf fragment was split longitudinally first, then cross-dissected into smaller segments (0.5 to 2 mm). Alternatively, the 2-3 cm-long segment above the first leaf base node of the seedling was simply diced with the scalpel to produce small leaf segments. Small leaf segments were transferred into a 6-well culture plate containing 4 ml of 700 liquid medium.

Liquid medium in the 6-well plate with leaf pieces were drawn off and replaced with 4 ml prepared *Agrobacterium* suspension. The 6-well plate was transferred into a transparent polycarbonate desiccator container. The desiccator was covered and placed on a platform of the shaker with a speed of 100 RPM and connected to an in-house vacuum system for 15 min. After infection, the *Agrobacterium* suspension was drawn off from the wells and the leaf tissues were transferred onto solid 7101 co-cultivation medium with 50 mg/l thymidine and were incubated at 21° C. in the dark for 3 days.

After 3d co-cultivation, all of the leaf tissues were transferred to 13152C culture medium. T-DNA delivery was evaluated about 5d after *Agrobacterium* infection. Transient expression of the color marker YFP (control vector) or CFP (test vector PHP38333) was a reliable indicator of the T-DNA delivery efficiency. 10%-25% of infected leaf segments showed multiple fluorescent cells along the cut edges or surface of leaf segments in all three inbred lines tested. Infected leaf tissues were sub-cultured every 2 weeks. After 6-8 weeks of culture, stable transformed callus events could be identified. The transgenic nature of these stable callus events was indicated by the expression of the fluorescent gene. Callus events with significant proliferation were subjected to desiccation treatment, and transferred onto regeneration medium for 2-4 weeks. Stable transgenic plantlets were regenerated from two tested maize inbreds, PHN46 and PHR03. Results from numerous experiments clearly demonstrated that stable transgenic plants could be produced form transformation of seedling tissue by using the vector that expresses the genes encoding cell proliferation factors. Leaf tissues infected with the control vector also showed good T-DNA delivery based on transient YFP expression, but the infected cells did not exhibit any subsequent proliferation and no stable callus events were identified from this treatment.

Example 16. The Utilization of Cell Proliferation Factors for Enhancing Chloroplast Transformation For tobacco and a number of other species, leaves are a preferred target for chloroplast transformation. Cell proliferation factors are used to trigger a tissue culture response from leaves of maize and other species. For boosting chloroplast transformation, cell proliferation factor genes under the control of inducible promoters are introduced into the species of interest by standard nuclear transformation protocols. Events that contain the transgene are characterized for expression of the inducible cell proliferation factor genes. For example, leaves of maize from plants transformed with the cell proliferation factor genes under the control of the tetracycline-repressor system are placed on medium containing appropriate concentrations of doxycyline. The doxycyline then activates the cell proliferation factor genes and thereby induces an embryogenic tissue culture response. The leaves are maintained on this medium for about 7-21 days during which time cell division and the initiation of embryogenic callus will take place. The leaves are bombarded with chloroplast transformation vectors carrying the aadA selectable marker gene and trait gene just prior to induction of the cell proliferation genes, during induction or just after induction. One to seven days after bombardment with the chloroplast transformation vector, the tissue is placed in petri plates containing agarose-solidified media supplemented with spectinomycin. The plates are then incubated at 28° C. in the light. The tissue is transferred to fresh medium every two weeks. After about 8 weeks of incubation, green callus is observed. This tissue can be further proliferated on 13152 medium (4.3 g/l MS salts, 0.25 g/l myo-inositol, 1.0 g/l casein hydrolysate, 1 mg/l thiamine, 1 mg/12,4-D, 30 g/l maltose, 0.69 g/l proline, 1.2 mg/l cupric sulfate, and 3.5 g/l phytagel, pH 5.8) and the tissue analyzed for the presence of the transgene using appropriate methods including PCR and Southern analysis.

In an alternative approach, expression cassettes containing the tetracycline-inducible BBM and WUS genes are co-bombarded along with the chloroplast transformation vectors carrying the aadA gene for selection. Either leaf explants or established green tissue callus are used as the target tissue for bombardment. Tetracycline or doxycycline at a concentration of 0.5 to 2.0 mg/l is added to the culture medium (13152) after particle bombardment. Expression of BBM and WUS in cells that have received DNA stimulate callus growth rates during the period while tetracycline (or doxycycline) is present in the medium. The accelerated growth that is stimulated by BBM & WUS will result in improved recovery of homoplastic transgenic events, and the nuclear-integrated BBM/WUS genes can be removed by outcrossing TO plants to wild-type plants and selecting BBM/WUS null plants in the Ti generation.

In another variation on the particle gun approach for delivery of BBM and WUS, a UBI::BBM::PinII and a nos::WUS2::pinII are co-delivered along with the chloroplast transformation vectors.

In another alternative approach, the cell proliferation factor genes are delivered into leaf tissue by vacuum infiltration of an *Agrobacterium* solution. The cell proliferation factor genes are under the control of strong constitutive promoters such as ubi or act or viral promoters such as 35S (Gardner et al. (1981) *Nucl Acids Res* 9:2871-2888), MMV (Dey and Maiti (1999) *Plant Mol Biol* 40:771-782), or BSV (Shenk et al. (2001) *Plant Mol Biol* 47:399-412). The cell proliferation factor genes are carried on binary vectors that facilitate transfer from the bacteria to plant cells. Following vacuum infiltration, the tissue is incubated for an appropriate period of time to allow expression of the cell proliferation factor genes in the leaf tissue. Transient expression from the cell proliferation factor genes delivered by *Agrobacterium* is expected to provide a strong boost in cell division and tissue culture response. After vacuum infiltration with *Agrobacterium*, the tissue is bombarded with a chloroplast transformation vector carrying the aadA selectable marker gene. The tissue is then transferred to media containing spectinomycin and transgenic events selected. It is expected that the *Agrobacterium*-delivered cell proliferation factor genes will not be integrated into the nuclear genome of most of the events that are recovered.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for introducing by *Agrobacterium*-mediated transformation of a polynucleotide of interest into a monocot leaf tissue explant, said method comprising:

a) providing the monocot leaf tissue explant, wherein the leaf tissue explant is obtained from a leaf segment excised from a leaf above the leaf base node;

b) incubating the leaf segments of the leaf tissue explant with *Agrobacterium* comprising the polynucleotide of interest;

c) introducing into said monocot leaf segments of the leaf tissue explant:

i) a heterologous polynucleotide encoding a Babyboom cell proliferation factor and a heterologous polynucleotide encoding a Wuschel cell proliferation factor; and expressing said heterologous polynucleotide encoding said Babyboom cell proliferation factor and said heterologous polynucleotide encoding said Wuschel cell proliferation factor; and ii) a polynucleotide of interest; and d) regenerating a monocot plant comprising the polynucleotide of interest.

2. The method of claim 1, further comprising excising said heterologous polynucleotide encoding said Babyboom cell proliferation factor and said heterologous polynucleotide encoding said Wuschel cell proliferation factor.

3. The method of claim 1, wherein the monocot is selected from the group consisting of maize, sorghum, sugarcane, rice, and wheat.

* * * * *

SEQUENCE LISTING

```
Sequence total quantity: 126
SEQ ID NO: 1            moltype = DNA  length = 2133
FEATURE                 Location/Qualifiers
source                  1..2133
                        mol_type = genomic DNA
                        organism = Glycine max
CDS                     1..2133
SEQUENCE: 1
atggggtcta tgaatttgtt aggtttttct ctctctcctc aagaacaccc ttctagtcaa  60
gatcactctc aaacggcacc ttctcgtttt tgcttcaacc ctgatggaat ctcaagcact  120
gatgtagcag gagactgctt tgatctcact tctgactcaa ctcctcattt actcaacctt  180
ccctcttacg gcatatacga agcttttcat aggagcaaca atattcacac cactcaagat  240
tggaaggaga actacaacag ccaaaacttg ctattgggaa cttcatgcag caaccaaaac  300
atgaaccaca accatcagca acaacaacaa caacagccaa agcttgaaaa cttcctcggt  360
ggacactcat ttggtgaaca tgagcaaccc tacggtggta actcagcctc tacagaatac  420
atgttcccgg ctcagccggt attggccggt ggcggcggcg gtggtagcaa tagcagcaac  480
acaagcaaca gtagctccat agggttatcc atgataaaga catggttgag gaaccaacca  540
ccacactcag aaaacaacaa taacaacaac aatgaaagtg gtggcaatag tagaagcagt  600
gtgcagcaga ctctatcact ttccatgagt actggttcac aatcaagcac atcactaccc  660
cttctcactg ctagtgtgga taatggagag agttcttctg ataacaaaca accacatacc  720
acggctgcac ttgatacaac ccaaaccgga gccattgaaa ctgcacccag aaagtccatt  780
gacacttttg gacagagaac ttctatctac cgtggtgtaa caaggcatag gtggacgggg  840
aggtatgagg ctcacctgtg ggataatagt tgtagaagag agggacaaac tcgcaaagga  900
aggcaagttt acttgggagg ttatgacaaa gaagaaaagg cagctagagc ctacgatttg  960
gcagcactaa aatactgggg aacaactacg acaacaaatt ttccaattag ccactatgag  1020
aaagagttgg aagaaatgaa gcacatgact aggcaagagt acgttgcgtc attgagaagg  1080
aagagtagtg ggttttctcg cggggcatcc atttatcgag gtgtgacgag acaccatcaa  1140
catggaagat ggcaagcgag gattggaaga gttgctggca acaaggatct ctacttggga  1200
actttcagca cccaagagga ggcagcagaa gcatatgatg tagcagcaat caaattcaga  1260
ggactaagtg ctgttacaaa ctttgacatg agcagatatg acgtgaaaag catacttgag  1320
agcaccactt tgccaattgg tggtgctgca aagcgtttga aggatatgga gcaggtggaa  1380
ctgagggtgg agaatgttca tagagcagat caagaagatc atagtagcat catgaactct  1440
cacttaactc aaggaatcat taacaactat gcagcaggag gaacaacagc gactcatcat  1500
cataactggc acaatgctct tgcattccac caacctcaac cttgcaccac catacactac  1560
ccttatggac aaagaattaa ttggtgcaag caagaacaag acaactctga tgcctctcac  1620
tctttgtctt attcagatat tcatcaacta cagctaggga acaatggcac acacaacttc  1680
tttcacacaa attcagggtt gcaccctatg ttaagcatgg attctgcttc cattgacaat  1740
agctcttcat ctaactctgt tgtttatgat ggttatggag gtggtggggg ctataatgtg  1800
attcctatgg ggactactac tactgttgtt gcaaatgatg gtgatcaaaa tccaagaagc  1860
aatcatggtt ttggtgataa tgagataaag gcacttggtt atgaaagtgt gtatggttct  1920
acaactgatc cttatcatgc acatgcaagg aacttgtatt atcttactca acagcaacca  1980
tcttctgttg atgcagtgaa ggctagtgca tatgatcaag gatctgcatg caatacttgg  2040
gttccaactg ctattccaac tcatgcacca aggtctagta ctagtatggc tctctgccat  2100
ggtgctacgc ccttctcttt attgcatgaa tag                              2133

SEQ ID NO: 2            moltype = AA  length = 710
FEATURE                 Location/Qualifiers
source                  1..710
                        mol_type = protein
                        organism = Glycine max
SEQUENCE: 2
MGSMNLLGFS LSPQEHPSSQ DHSQTAPSRF CFNPDGISST DVAGDCFDLT SDSTPHLLNL  60
PSYGIYEAFH RSNNIHTTQD WKENYNSQNL LLGTSCSNQN MNHNHQQQQQ QQPKLENFLG  120
```

```
GHSFGEHEQP YGGNSASTEY MFPAQPVLAG GGGGGSNSSN TSNSSSIGLS MIKTWLRNQP  180
PHSENNNNNN NESGGNSRSS VQQTLSLSMS TGSQSSTSLP LLTASVDNGE SSSDNKQPHT  240
TAALDTTQTG AIETAPRKSI DTFGQRTSIY RGVTRHRWTG RYEAHLWDNS CRREGQTRKG  300
RQVYLGGYDK EEKAARAYDL AALKYWGTTT TTNFPISHYE KELEEMKHMT RQEYVASLRR  360
KSSGFSRGAS IYRGVTRHHQ HGRWQARIGR VAGNKDLYLG TFSTQEEAAE AYDVAAIKFR  420
GLSAVTNFDM SRYDVKSILE STTLPIGGAA KRLKDMEQVE LRVENVHRAD QEDHSSIMNS  480
HLTQGIINNY AAGGTTATHH HNWHNALAFH QPQPCTTIHY PYGQRINWCK QEQDNSDASH  540
SLSYSDIHQL QLGNNGTHNF FHTNSGLHPM LSMDSASIDN SSSSNSVVYD GYGGGGGYNV  600
IPMGTTTTVV ANDGDQNPRS NHGFGDNEIK ALGYESVYGS TTDPYHAHAR NLYYLTQQQP  660
SSVDAVKASA YDQGSACNTW VPTAIPTHAP RSSTSMALCH GATPFSLLHE             710

SEQ ID NO: 3            moltype = DNA  length = 2112
FEATURE                 Location/Qualifiers
source                  1..2112
                        mol_type = genomic DNA
                        organism = Sorghum bicolor
CDS                     1..2112
SEQUENCE: 3
atggctactg tgaacaactg gctcgctttc tccctctccc cgcaggagct gccgcccacc  60
cagacggact ccaccctcat ctctgccgcc accaccgacg atgtctccgg cgatgtctgc  120
ttcaacatcc cccaagattg gagcatgagg ggatccgagc tttcggcgct cgtcgccgag  180
ccgaagctgg aggacttcct cggcggaatc tccttctccg agcagcacca caaggccaac  240
tgcaacatga tccccagcac tagcagcaca gcttgctacg cgagctcggg tgctaccgcc  300
ggctaccatc accagctgta ccaccagccc accagctccg cgctccactt cgctgactcc  360
gtcatggtgg cctcctcggc cggcggcgtc cacgacggag gtgccatgct cagcgcggcc  420
agcgctaatg gtagcgctgg cgctggcgct gccagtgcca atggcagcgg cagcatcggg  480
ctgtccatga tcaagaactg gctgcggagc caaccagctc ccatgcagcc gagggtggcg  540
gcggctgaga gcgtgcaggg gctctctttg tccatgaaca tggcgggggc gacgcaaggc  600
gccgctggca tgccacttct tgctggagag cgcggccggg cgcccgagag tgtctcgacg  660
tcggcacagg gtggagccgt cgtcacggct ccaaaggagg atagcggtgg cagcggtgtt  720
gccgccaccg gcgccctagt agccgtgagc acggacacgg gtggcagcgg cgcgtcggct  780
gacaacacgg caaggaagac ggtggacacg ttcgggcagc gcacgtcgat ttaccgtggc  840
gtgacaaggc atagatggac tgggagatat gaagcacatc tgtgggacaa cagttgcaga  900
agggaaggac aaactcgcaa gggtcgtcaa gtctatttag gtggctatga taaagaggag  960
aaagctgcta gggcttatga tctggctgct cttaagtact ggggtcccac gacaacaaca  1020
aattttccag tgaataacta cgaaaaggag ctggaggata tgaagcacat gacaaggcag  1080
gagtttgtag cgtctctgag aaggaagagc agtggtttct ccagaggtgc atccatttac  1140
aggggagtga ctaggcatca ccagcatgga agatggcaag cacggattgg acgagttgca  1200
gggaacaagg atctctactt gggcaccttc agcacgcagg aggaggcagc ggaggcatac  1260
gacattgcgg cgatcaagtt ccgcggcctc aacgccgtca caaacttcga catgagccgc  1320
tacgacgtca agagcatcct ggacagcagt gcgctcccca tcggcagcgc cgccaagcgt  1380
ctcaaggagg ccgaggccgc cgcgtccgca cagcaccatg ccggcgtggt gagctacgac  1440
gtcggccgca tagcctcaca gctcggcgac ggcggcgccc tggcggcggc gtacggcgcg  1500
cactaccatg gcgcctggcc gaccatcgcg ttccagccga gcgcggccac gggcctgtac  1560
cacccgtacg cgcagccgat gcgcgggtgg tgcaagcagg agcaggacca cgcggtgatc  1620
gcggccgcgc acagcctgca ggagctccac cacctgaacc tgggtgctgc cgccggcgcg  1680
cacgacttct tctcggcggg gcagcaggcg gcgatgcacg gcctgggtag catggacaat  1740
gcatcactcg agcacagcac cggctccaac tccgtcgtgt acaacggtgt tggtgatagc  1800
aacggcagca ccgtcgtcgg cagtggtggc tacatgatgc ctatgagcgc tgccacggcg  1860
acggctacca cggcaatggt gagccacgag caggtgcatg cacgggcaca gggtgatcac  1920
cacgacgaag ccaagcaggc tgctcagatg gggtacgaga gctacctggt gaacgcagag  1980
aactatggcg gcgggaggat gtctgcggcc tgggcgactg tctcagcgcc accggcggca  2040
agcagcaacg ataacatggc ggacgtcggc catggcggcg cacagctctt cagtgtctgg  2100
aacgatactt aa                                                      2112

SEQ ID NO: 4            moltype = AA  length = 703
FEATURE                 Location/Qualifiers
source                  1..703
                        mol_type = protein
                        organism = Sorghum bicolor
SEQUENCE: 4
MATVNNWLAF SLSPQELPPT QTDSTLISAA TTDDVSGDVC FNIPQDWSMR GSELSALVAE  60
PKLEDFLGGI SFSEQHHKAN CNMIPSTSST ACYASSGATA GYHHQLYHQP TSSALHFADS  120
VMVASSAGGV HDGGAMLSAA SANGSAGAGA ASANGSGSIG LSMIKNWLRS QPAPMQPRVA  180
AAESVQGLSL SMNMAGATQG AAGMPLLAGE RGRAPESVST SAQGGAVVTA PKEDSGGSGV  240
AATGALVAVS TDTGGSGASA DNTARKTVDT FGQRTSIYRG VTRHRWTGRY EAHLWDNSCR  300
REGQTRKGRQ VYLGGYDKEE KAARAYDLAA LKYWGPTTTT NFPVNNYEKE LEDMKHMTRQ  360
EFVASLRRKS SGFSRGASIY RGVTRHHQHG RWQARIGRVA GNKDLYLGTF STQEEAAEAY  420
DIAAIKFRGL NAVTNFDMSR YDVKSILDSS ALPIGSAAKR LKEAEAAASA QHHAGVVSYD  480
VGRIASQLGD GGALAAAYGA HYHGAWPTIA FQPSAATGLY HPYAQPMRGW CKQEQDHAVI  540
AAAHSLQELH HLNLGAAAGA HDFFSAGQQA AMHGLGSMDN ASLEHSTGSN SVVYNGVGDS  600
NGSTVVGSGG YMMPMSAATA TATTAMVSHE QVHARAQGDH HDEAKQAAQM GYESYLVNAE  660
NYGGGRMSAA WATVSAPPAA SSNDNMADVG HGGAQLFSVW NDT                    703

SEQ ID NO: 5            moltype = DNA  length = 1932
FEATURE                 Location/Qualifiers
source                  1..1932
                        mol_type = genomic DNA
                        organism = Vitis vinifera
```

-continued

```
CDS                     1..1932
SEQUENCE: 5
atggcttcca tgaacaactg gttgggtttc tctttgtccc ctcgagaact tccaccacag  60
cctgaaaatc actcacagaa cagtgtctct agacttggtt tcaactctga tgaaatctct  120
gggactgatg tgtcaggtga gtgttttgat ctcacttcag attccactgc tccctctctc  180
aacctccctc cccttttgg gatacttgaa gcattcaaca ggaataatca gccccaagat  240
actaactaca aaaccaccac ttctgagctc tccatgctca tgggtagttc atgcagtagt  300
catcataacc tcgaaaacca agaacccaaa cttgaaaatt tcctgggctg ccgctctttt  360
gctgatcatg agcagaaact tcaagggtac tacatttcca ttggtttatc catgatcaag  420
acatggctgc ggaaccaacc tgcacccacc catcaggata acaacaagag tactgatact  480
gggcctgtcg gtggagccgc cgctgggaac ctacccaatg cacagacctt atcgttgtcc  540
atgagcaccg gctcgcacca gaccggtgcc attgaaacgg tgccaaggaa gtccattgat  600
acatttggac agaggacatc catataccgt ggtgtaacaa ggcatagatg gacgggtaga  660
tatgaggctc atctatggga caacagttgc agaagagaag gacaaactcg aaagggaagg  720
caagtttatt taggtggtta tgacaaagaa gaaaaggcag ctagggctta cgatttagca  780
gcactgaagt attggggtac caccaccaca acaaatttcc ctattagcaa ctatgaaaaa  840
gagatagagg agatgaagca catgacaagg caggagtacg tagcatctct gcgaaggaag  900
agtagcgggt ttctcgtgg agcatccata tatagaggag tgaccagaca ccatcagcat  960
gggagatggc aggcaaggat tggaagagtc gcaggcaaca aagatcttta cttgggaact  1020
ttcagcaccc aagaggaagc agcagaggcc tatgacattg ctgccattaa gtttcgagga  1080
ttgaatgcgg tgaccaactt tgatatgagt agatatgatg ttaatagcat tctagagagc  1140
agtaccttgc cgattggtgg agctgcaaag cggttgaaag atgctgagca ggctgaaatg  1200
actatagatg gacagaggac agacgatgag atgagctcac agctgactga tggaatcaac  1260
aactatggag cacaccacca tggctggcct actgttgcat tccaacaagc tcagccattt  1320
agcatgcact acccttatgg ccatcagcag agggctgttt ggtgtaagca agagcaagac  1380
cctgatggca cacacaactt tcaagatctt caccaactac aattgggaaa cactcacaac  1440
ttcttccagc ctaatgttct gcacaacctc atgagcatgg actcttcttc aatggaccat  1500
agctcaggct ccaattcagt catctatagc ggtggtggag ccgctgatgg cagcgctgca  1560
actggcggca gtggcagtgg gagcttccaa ggggtaggtt atgggaacaa cattggcttt  1620
gtgatgccca taagcaccgt catcgctcat gaaggcggcc atggccaggg aaatggtggc  1680
tttggagata gcgaagtgaa ggcgattggt tacgacaaca tgtttggatc gacagatcct  1740
taccatgcta ggagcttgta ctatctttca cagcaatcat ctgcaggcat ggtgaagggc  1800
agtagtgcat atgatcaggg gtcagggtgt aacaactggg ttccaactgc agttccaacc  1860
ctagctccaa ggactaacag cttggcagta tgccatggaa cacctacatt cacagtatgg  1920
aatgatacat aa                                                    1932

SEQ ID NO: 6            moltype = AA  length = 643
FEATURE                 Location/Qualifiers
source                  1..643
                        mol_type = protein
                        organism = Vitis vinifera
SEQUENCE: 6
MASMNNWLGF SLSPRELPPQ PENHSQNSVS RLGFNSDEIS GTDVSGECFD LTSDSTAPSL  60
NLPPPFGILE AFNRNNQPQD TNYKTTTSEL SMLMGSSCSS HHNLENQEPK LENFLGCRSF  120
ADHEQKLQGY YISIGLSMIK TWLRNQPAPT HQDNNKSTDT GPVGGAAAGN LPNAQTLSLS  180
MSTGSHQTGA IETVPRKSID TFGQRTSIYR GVTRHRWTGR YEAHLWDNSC RREGQTRKGR  240
QVYLGGYDKE EKAARAYDLA ALKYWGTTTT TNFPISNYEK EIEEMKHMTR QEYVASLRRK  300
SSGFSRGASI YRGVTRHHQH GRWQARIGRV AGNKDLYLGT FSTQEEAAEA YDIAAIKFRG  360
LNAVTNFDMS RYDVNSILES STLPIGGAAK RLKDAEQAEM TIDGQRTDDE MSSQLTDGIN  420
NYGAHHHGWP TVAFQQAQPF SMHYPYGHQQ RAVWCKQEQD PDGTHNFQDL HQLQLGNTHN  480
FFQPNVLHNL MSMDSSSMDH SSGSNSVIYS GGGAADGSAA TGGSGSGSFQ GVGYGNNIGF  540
VMPISTVIAH EGGHGQGNGG FGDSEVKAIG YDNMFGSTDP YHARSLYYLS QQSSAGMVKG  600
SSAYDQGSGC NNWVPTAVPT LAPRTNSLAV CHGTPTFTVW NDT                  643

SEQ ID NO: 7            moltype = DNA  length = 2070
FEATURE                 Location/Qualifiers
source                  1..2070
                        mol_type = genomic DNA
                        organism = Medicago truncatula
CDS                     1..2070
SEQUENCE: 7
atggcctcta tgaacttgtt aggtttctct ctatctccac aagaacaaca tccatcaaca  60
caagatcaaa cggtggcttc ccgttttggg ttcaacccta atgaaatctc aggctctgat  120
gttcaaggag atcactgcta tgatctctct tctcacacaa ctcctcatca ttcactcaac  180
ctttctcatc ctttttccat ttatgaagct ttccacacaa ataacaacat tcacaccact  240
caagattgga aggagaacta caacaaccaa aacctactat tgggaacatc atgcatgaac  300
caaaatgtga acaacaacaa ccaacaagca caaccaaagc tagaaaactt cctcggtgga  360
cactctttca ccgaccatca agaatacggt ggtagcaact catactcttc attacacctc  420
ccacctcatc agccggaagc atcctgtggc ggtggtgatg gtagtacaag taacaataac  480
tcaataggtt tatctatgat aaaaacatgg ctcagaaacc aaccaccacc accagaaaac  540
aacaacaata acaacaatga aagtggtgca cgtgtgcaga cactatcact ttctatgagt  600
actggctcac agtcaagttc atctgtgcct cttctcaatg caaatgtgat gagtggtgag  660
atttcctcat cggaaaacaa acaaccaccc acaactgcag ttgtacttga tagcaaccaa  720
acaagtgtcg ttgaaagtgc tgtgcctaga aaatccgttg atacatttgg acaaagaact  780
tccatttacc gtggtgtaac aaggcataga tggacaggga gatatgaagc tcacctttgg  840
gataatagtt gtagaagaga ggggcagact cgcaaaggaa ggcaagttta cttgggaggt  900
tatgacaaag aagaaaaagc agctagagcc tatgatttgg cagcactaaa atattgggga  960
acaactacta caacaaattt tccaattagc cattatgaaa aagaagtgga agaaatgaag  1020
catatgacaa ggcaagagta cgttgcgtca ttgagaagga aaagtagtgg tttttcacga  1080
```

```
ggtgcatcca tttaccgagg agtaacaaga catcatcaac atggtagatg gcaagctagg  1140
attggaagag ttgcaggcaa caaagatctc tacctaggaa ctttcagcac tcaagaagag  1200
gcagcagagg catatgatgt ggcagcaata aaattcagag gactgagtgc agttacaaac  1260
tttgacatga gcagatatga tgtcaaaacc atacttgaga gcagcacatt accaattggt  1320
ggtgctgcaa agcgtttaaa agacatggag caagttgaat tgaatcatgt gaatgttgat  1380
attagccata gaactgaaca agatcatagc atcatcaaca acacttccca tttaacagaa  1440
caagccatct atgcagcaac aaatgcatct aattggcatg cactttcatt ccaacatcaa  1500
caaccacatc atcattacaa tgccaacaac atgcagttac agaattatcc ttatggaact  1560
caaactcaaa agctttggtg caaacaagaa caagattctg atgatcatag tacttatact  1620
actgctactg atattcatca actacagtta gggaataata ataacaatac tcacaatttc  1680
tttggtttac aaaatatcat gagtatggat tctgcttcca tggataatag ttctggatct  1740
aattctgttg tttatggtgg tggagatcat ggtggttatg gaggaaatgg tggatatatg  1800
attccaatgg ctattgcaaa tgatggtaac caaaatccaa gaagcaacaa caattttggt  1860
gagagtgaga ttaaaggatt tggttatgaa aatgtttttg ggactactac tgatccttat  1920
catgcacagg cagcaaggaa cttgtactat cagccacaac aattatctgt tgatcaagga  1980
tcaaattggg ttccaactgc tattccaaca cttgctccaa ggactaccaa tgtctctcta  2040
tgtcctcctt tcactttgtt gcatgaatag                                   2070

SEQ ID NO: 8            moltype = AA  length = 689
FEATURE                 Location/Qualifiers
source                  1..689
                        mol_type = protein
                        organism = Medicago truncatula
SEQUENCE: 8
MASMNLLGFS LSPQEQHPST QDQTVASRFG FNPNEISGSD VQGDHCYDLS SHTTPHHSLN  60
LSHPFSIYEA FHTNNNIHTT QDWKENYNNQ NLLLGTSCMN QNVNNNNQQA QPKLENFLGG  120
HSFTDHQEYG GSNSYSSLHL PPHQPEASCG GGDGSTSNNN SIGLSMIKTW LRNQPPPPEN  180
NNNNNNESGA RVQTLSLSMS TGSQSSSSVP LLNANVMSGE ISSSENKQPP TTAVVLDSNQ  240
TSVVESAVPR KSVDTFGQRT SIYRGVTRHR WTGRYEAHLW DNSCRREGQT RKGRQVYLGG  300
YDKEEKAARA YDLAALKYWG TTTTTNFPIS HYEKEVEEMK HMTRQEYVAS LRRKSSGFSR  360
GASIYRGVTR HHQHGRWQAR IGRVAGNKDL YLGTFSTQEE AAEAYDVAAI KFRGLSAVTN  420
FDMSRYDVKT ILESSTLPIG GAAKRLKDME QVELNHVNVD ISHRTEQDHS IINNTSHLTE  480
QAIYAATNAS NWHALSFQHQ QPHHHYNANN MQLQNYPYGT QTQKLWCKQE QDSDDHSTYT  540
TATDIHQLQL GNNNNNTHNF FGLQNIMSMD SASMDNSSGS NSVVYGGGDH GGYGGNGGYM  600
IPMAIANDGN QNPRSNNNFG ESEIKGFGYE NVFGTTTDPY HAQAARNLYY QPQQLSVDQG  660
SNWVPTAIPT LAPRTTNVSL CPPFTLLHE                                    689

SEQ ID NO: 9            moltype = DNA  length = 2130
FEATURE                 Location/Qualifiers
source                  1..2130
                        mol_type = genomic DNA
                        organism = Zea mays
CDS                     1..2130
SEQUENCE: 9
atggccactg tgaacaactg gctcgctttc tccctctccc cgcaggagct gccgccctcc  60
cagacgacgg actccacgct catctcggcc gccaccgccg accatgtctc cggcgatgtc  120
tgcttcaaca tcccccaaga ttggagcatg aggggatcag agctttcggc gctcgtcgcg  180
gagccgaagc tggaggactt cctcggcggc atctccttct ccgagcagca tcacaagtcc  240
aactgcaact tgatacccag cactagcagc acagtttgct acgcgagctc agctgctagc  300
accggctacc atcaccagct gtaccagccc accagctccg cgctccactt cgcggactcc  360
gtcatggtgg cctcctcggc cggtgtccac gacggcggtt ccatgctcag cgcggccgcc  420
gctaacggtg tcgctggcgc tgccagtgcc aacggcggcg gcatcgggct gtccatgatc  480
aagaactggc tgcggagcca accggcgccc atgcagccga gggcggcggc ggctgagggc  540
gcgcaggggc tctctttgtc catgaacatg gcggggacga cccaaggcgc tgctggcatg  600
ccacttctcg ctggagagcg cgcacgggcg cccgagagtg tatcgacgtc agcacagggt  660
ggtgccgtcg tcgtcacggc gccgaaggag gatagcggtg gcagcggtgt tgccggtgct  720
ctagtagccg tgagcacgga cacgggtggc agcggcggcg cgtcggctga caacacggca  780
aggaagacgg tggacacgtt cgggcagcgc acgtcgattt accgtggcgt gacaaggcat  840
agatggactg ggagatatga ggcacatctt tgggataaca gttgcagaag ggaaggacaa  900
actcgtaagg gtcgtcaagt ctatttaggt ggctatgata aagaggagaa agctgctagg  960
gcttatgatc ttgctgctct gaagtactgg ggtgccacaa caacaacaaa ttttccagtg  1020
agtaactacg aaaaggagct cgaggacatg aagcacatga caaggcagga gtttgtagcg  1080
tctctgagaa ggaagagcag tggtttctcc agaggtgcat ccatttacag gggagtgact  1140
aggcatcacc aacatggaag atggcaagca cggattggac gagttgcagg gaacaaggat  1200
ctttacttgg gcaccttcag cacccaggag gaggcagcgg aggcgtacga catcgcggcg  1260
atcaagttcc gcggcctcaa cgccgtcacc aacttcgaca tgagccgcta cgacgtgaag  1320
agcatcctgg acagcagcgc cctccccatc ggcagcgccg ccaagcgtct caaggaggcc  1380
gaggccgcag cgtccgcgca gcaccaccac gccggcgtgg tgagctacga cgtcggccgc  1440
atcgcctcgc agctcggcga cggcggagcc ctagcggcgg cgtacggcgc gcactaccac  1500
ggcgccgcct ggccgaccat cgcgttccag ccgggcgccg ccaccacagg cctgtaccac  1560
ccgtacgcgc agcagccaat gcgcggcggc gggtggtgca agcaggagca ggaccacgcg  1620
gtgatcgcgg ccgcgcacag cctgcaggac ctccaccact tgaacctggg cgcggccggc  1680
gcgcacgact ttttctcggc agggcagcag gccgccgccg cagctgcgat gcacggcctg  1740
gctagcatcg acagtgcgtc gctcgagcac agcaccggct ccaactccgt cgtctacaac  1800
ggcggggtcg gcgatagcaa cggcgccagc gccgttggca gcggcggtgg ctacatgatg  1860
ccgatgagcg ctgccggagc aaccactaca tcggcaatgg tgagccacga gcagatgcat  1920
gcacgggcct acgacgaagc caagcaggct gctcagatgg ggtacgagag ctacctggtg  1980
aacgcggaga acaatggtgg cggaaggatg tctgcatggg ggaccgtcgt ctctgcagcc  2040
gcggcggcag cagcaagcag caacgacaac attgccgccg acgtcggcca tggcggcgcg  2100
```

```
cagctcttca gtgtctggaa cgacacttaa                             2130

SEQ ID NO: 10          moltype = AA  length = 709
FEATURE                Location/Qualifiers
source                 1..709
                       mol_type = protein
                       organism = Zea mays
SEQUENCE: 10
MATVNNWLAF SLSPQELPPS QTTDSTLISA ATADHVSGDV CFNIPQDWSM RGSELSALVA  60
EPKLEDFLGG ISFSEQHHKS NCNLIPSTSS TVCYASSAAS TGYHHQLYQP TSSALHFADS  120
VMVASSAGVH DGGSMLSAAA ANGVAGAASA NGGGIGLSMI KNWLRSQPAP MQPRAAAAEG  180
AQGLSLSMNM AGTTQGAAGM PLLAGERARA PESVSTSAQG GAVVVTAPKE DSGGSGVAGA  240
LVAVSTDTGG SGGASADNTA RKTVDTFGQR TSIYRGVTRH RWTGRYEAHL WDNSCRREGQ  300
TRKGRQVYLG GYDKEEKAAR AYDLAALKYW GATTTTNFPV SNYEKELEDM KHMTRQEFVA  360
SLRRKSSGFS RGASIYRGVT RHHQHGRWQA RIGRVAGNKD LYLGTFSTQE EAAEAYDIAA  420
IKFRGLNAVT NFDMSRYDVK SILDSSALPI GSAAKRLKEA EAAASAQHHH AGVVSYDVGR  480
IASQLGDGGA LAAAYGAHYH GAAWPTIAFQ PGAATTGLYH PYAQQPMRGG GWCKQEQDHA  540
VIAAAHSLQD LHHLNLGAAG AHDFFSAGQQ AAAAAAMHGL ASIDSASLEH STGSNSVVYN  600
GGVGDSNGAS AVGSGGGYMM PMSAAGATTT SAMVSHEQMH ARAYDEAKQA AQMGYESYLV  660
NAENNGGGRM SAWGTVVSAA AAAAASSNDN IAADVGHGGA QLFSVWNDT            709

SEQ ID NO: 11          moltype = DNA  length = 2040
FEATURE                Location/Qualifiers
source                 1..2040
                       mol_type = genomic DNA
                       organism = Zea mays
CDS                    1..2040
SEQUENCE: 11
atggcttcag cgaacaactg gctgggcttc tcgctctcgg gccaggataa cccgcagcct  60
aaccaggata gctcgcctgc cgccggtatc gacatctccg gcgccagcga cttctatggc  120
ctgcccacgc agcagggctc cgacgggcat ctcggcgtgc cgggcctgcg ggacgatcac  180
gcttcttatg gtatcatgga ggcctacaac agggttcctc aagaaaccca agattggaac  240
atgaggggct tggactacaa cggcggtggc tcggagctct cgatgcttgt ggggtccagc  300
ggcggcggcg ggggcaacgg caagagggcc gtggaagaca gcgagcccaa gctcgaagat  360
ttcctcggcg gcaactcgtt cgtctccgat caagatcagt ccggcggtta cctgttctct  420
ggagtcccga tagccagcag cgccaatagc aacagcggga gcaacaccat ggagctctcc  480
atgatcaaga cctggctacg gaacaaccag gtggcccagc cccagccgcc agctccacat  540
cagccgcagc ctgaggaaat gagcaccgac gccagcggca gcagctttgg atgctcggat  600
tcgatgggaa ggaacagcat ggtggcggct ggtgggagct cgcagagcct ggcgctctcg  660
atgagcacgg gctcgcacct gcccatggtt gtgcccagcg gcgccgccag cggagcggcc  720
tcggagagca catcgtcgga gaacaagcga gcgagcggtg ccatggattc gcccggcagc  780
gcggtagaag ccgtaccgag gaagtccatc gacacgttcg ggcaaaggac ctctatatat  840
cgaggtgtaa caaggcatag atggacaggg cggtatgagg ctcatctatg ggataatagt  900
tgtagaaggg aagggcagag tcgcaagggt aggcaagttt accttggtgg ctatgacaag  960
gaggacaagg cagcaagggc ttatgatttg gcagctctca agtattgggg cactacgaca  1020
acaacaaatt tccctataag caactacgaa aaggagctag aagaaatgaa acatatgact  1080
agacaggagt acattgcata cctaagaaga aatagcagtg gattttctcg tggggcgtca  1140
aagtatcgtg gagtaactag acatcatcag catgggagat ggcaagcaag gatagggaga  1200
gttgcaggaa acaaggatct ctacttgggc acattcagca ccgaggagga ggcggcggag  1260
gcctacgaca tcgccgcgat caagttccgc ggtctcaacg ccgtcaccaa cttcgacatg  1320
agccgctacg acgtgaagag catcctcgag agcagcacac tgcctgtcgg cggtgcggcc  1380
aggcgcctca aggacgccgt ggaccacgtg gaggccggcg ccaccatctg gcgcgccgac  1440
atggacggcg ccgtgatctc ccagctggcc gaagccggga tgggcggcta cgcctcgtac  1500
ggccaccacg gctggccgac catcgcgttc cagcagccgt cgccgctctc cgtccactac  1560
ccgtacggcc agccgtcccg cgggtggtgc aaacccgagc aggacgcggc cgccgccgcg  1620
gcgcacagcc tgcaggacct ccagcagctg cacctcggca gcgcggccca caacttcttc  1680
caggcgtcgt cgagctccac agtctacaac ggcggcgccg gcgccagtgg tgggtaccag  1740
ggcctcggtg gtggcagctc tttcctcatg ccgtcgagca ctgtcgtggc ggcggccgac  1800
caggggcaca gcagcacggc caaccagggg agcacgtgca gctacgggga cgaccaccag  1860
gaggggaagc tcatcggtta cgacgccgcc atggtggcga ccgcagctgg tggagacccg  1920
tacgctgcgg cgaggaacgg gtaccagttc tcgcagggct cgggatccac ggtgagcatc  1980
gcgagggcga acgggtacgc taacaactgg agctctcctt tcaacaacgg catggggtga  2040

SEQ ID NO: 12          moltype = AA  length = 679
FEATURE                Location/Qualifiers
source                 1..679
                       mol_type = protein
                       organism = Zea mays
SEQUENCE: 12
MASANNWLGF SLSGQDNPQP NQDSSPAAGI DISGASDFYG LPTQQGSDGH LGVPGLRDDH  60
ASYGIMEAYN RVPQETQDWN MRGLDYNGGG SELSMLVGSS GGGGGNGKRA VEDSEPKLED  120
FLGGNSFVSD QDQSGGYLFS GVPIASSANS NSGSNTMELS MIKTWLRNNQ VAQPQPPAPH  180
QPQPEEMSTD ASGSSFGCSD SMGRNSMVAA GGSSQSLALS MSTGSHLPMV VPSGAASGAA  240
SESTSSENKR ASGAMDSPGS AVEAVPRKSI DTFGQRTSIY RGVTRHRWTG RYEAHLWDNS  300
CRREGQSRKG RQVYLGGYDK EDKAARAYDL AALKYWGTTT TTNFPISNYE KELEEMKHMT  360
RQEYIAYLRR NSSGFSRGAS KYRGVTRHHQ HGRWQARIGR VAGNKDLYLG TFSTEEEAAE  420
AYDIAAIKFR GLNAVTNFDM SRYDVKSILE SSTLPVGGAA RRLKDAVDHV EAGATIWRAD  480
MDGAVISQLA EAGMGGYASY GHHGWPTIAF QQPSPLSVHY PYGQPSRGWC KPEQDAAAAA  540
AHSLQDLQQL HLGSAAHNFF QASSSSTVYN GGAGASGGYQ GLGGGSSFLM PSSTVVAAAD  600
```

```
QGHSSTANQG STCSYGDDHQ EGKLIGYDAA MVATAAGGDP YAAARNGYQF SQGSGSTVSI  660
ARANGYANNW SSPFNNGMG                                               679

SEQ ID NO: 13          moltype = DNA  length = 2088
FEATURE                Location/Qualifiers
source                 1..2088
                       mol_type = genomic DNA
                       organism = Oryza sativa
CDS                    1..2088
SEQUENCE: 13
atggccacca tgaacaactg gctggccttc tccctctccc cgcaggatca gctcccgccg  60
tctcagacca actccactct catctccgcc gccgccacca ccaccaccgc cggcgactcc  120
tccaccggcg acgtctgctt caacatcccc caagattgga gcatgagggg atcggagctc  180
tcggcgctcg tcgccgagcc gaagctggag gacttcctcg gcggcatctc cttctcggag  240
cagcagcatc atcacggcgg caagggcggc gtgatcccga gcagcgccgc cgcttgctac  300
gcgagctccg gcagcagcgt cggctacctg taccctcctc caagctcatc ctcgctccag  360
ttcgccgact ccgtcatggt ggccacctcc tcgcccgtcg tcgcccacga cggcgtcagc  420
ggcggcggca tggtgagcgc cgccgccgcc gcggcggcca gtggcaacgg cggcattggc  480
ctgtccatga tcaagaactg gctccggagc cagccggcgc cgcagccggc gcaggcgctg  540
tctctgtcca tgaacatggc ggggacgacg acggcgcagg gcggcggcgc catggcgctc  600
ctcgccggcg caggggagcg aggccggacg acgcccgcgt cagagagcct gtccacgtcg  660
gcgcacggag cgacgacggc gacgatggct ggtggtcgca aggagattaa cgaggaaggc  720
agcggcagcg ccggcgccgt ggttgccgtc ggctcggagt caggcggcag cggcgccgtg  780
gtggaggccg gcgcggcggc ggcggcggcg aggaagtccg tcgacacgtt cggccagaga  840
acatcgatct accgcggcgt gacaaggcat agatggacag ggaggtatga ggctcatctt  900
tgggacaaca gctgcagaag agagggccaa actcgcaagg gtcgtcaagt ctatctaggt  960
ggttatgaca aagaggaaaa agctgctaga gcttatgatt tggctgctct caaatactgg  1020
ggcccgacga cgacgacaaa ttttccggta aataactatg aaaaggagct ggaggagatg  1080
aagcacatga caaggcagga gttcgtagcc tctttgagaa ggaagagcag tggtttctcc  1140
agaggtgcat ccatttaccg tggagtaact aggcatcacc agcatgggag atggcaagca  1200
aggataggaa gagttgcagg gaacaaggac ctctacttgg gcaccttcag cacgcaggag  1260
gaggcggcgg aggcgtacga catcgcggcg atcaagttcc gggggctcaa cgccgtcacc  1320
aacttcgaca tgagccgcta cgacgtcaag agcatcctcg acagcgctgc cctccccgtc  1380
ggcaccgccg ccaagcgcct caaggacgcc gaggccgccg ccgcctacga cgtcggccgc  1440
atcgcctcgc acctcggcgg cgacggcgcc tacgccgcgc attacggcca ccaccaccac  1500
tcggccgccg ccgcctggcc gaccatcgcg ttccaggcgg cggcggcgcc gccgccgcac  1560
gccgccgggc tttaccaccc gtacgcgcag ccgctgcgtg ggtggtgcaa gcaggagcag  1620
gaccacgccg tgatcgcggc ggcgcacagc ctgcaggatc tccaccacct caacctcggc  1680
gccgccgccg ccgcgcatga cttcttctcg caggcgatgc agcagcagca cggcctcggc  1740
agcatcgaca acgcgtcgct cgagcacagc accggctcca actccgtcgt ctacaacggc  1800
gacaatggcg gcggaggcgg cggctacatc atggcgccga tgagcgccgt gtcggccacg  1860
gccaccgcgg tggcgagcag ccacgatcac ggcggcgacg gcgggaagca ggtgcagatg  1920
gggtacgaca gctacctcgt cggcgcagac gcctacggcg gcggcggcgc cgggaggatg  1980
ccatcctggg cgatgacgcc ggcgtcggcg ccggccgcca cgagcagcag cgacatgacc  2040
ggagtctgcc atggcgcaca gctcttcagc gtctggaacg acacataa              2088

SEQ ID NO: 14          moltype = AA  length = 695
FEATURE                Location/Qualifiers
source                 1..695
                       mol_type = protein
                       organism = Oryza sativa
SEQUENCE: 14
MATMNNWLAF SLSPQDQLPP SQTNSTLISA AATTTTAGDS STGDVCFNIP QDWSMRGSEL  60
SALVAEPKLE DFLGGISFSE QQHHHGGKGG VIPSSAAACY ASSGSSVGYL YPPPSSSSLQ  120
FADSVMVATS SPVVAHDGVS GGGMVSAAAA AAASGNGGIG LSMIKNWLRS QPAPQPAQAL  180
SLSMNMAGTT TAQGGGAMAL LAGAGERGRT TPASESLSTS AHGATTATMA GGRKEINEEG  240
SGSAGAVVAV GSESGGSGAV VEAGAAAAAA RKSVDTFGQR TSIYRGVTRH RWTGRYEAHL  300
WDNSCRREGQ TRKGRQVYLG GYDKEEKAAR AYDLAALKYW GPTTTTNFPV NNYEKELEEM  360
KHMTRQEFVA SLRRKSSGFS RGASIYRGVT RHHQHGRWQA RIGRVAGNKD LYLGTFSTQE  420
EAAEAYDIAA IKFRGLNAVT NFDMSRYDVK SILDSAALPV GTAAKRLKDA EAAAAYDVGR  480
IASHLGGDGA YAAHYGHHHH SAAAAWPTIA FQAAAAPPPH AAGLYHPYAQ PLRGWCKQEQ  540
DHAVIAAAHS LQDLHHLNLG AAAAAHDFFS QAMQQQHGLG SIDNASLEHS TGSNSVVYNG  600
DNGGGGGGYI MAPMSAVSAT ATAVASSHDH GGDGGKQVQM GYDSYLVGAD AYGGGGAGRM  660
PSWAMTPASA PAATSSSDMT GVCHGAQLFS VWNDT                             695

SEQ ID NO: 15          moltype = DNA  length = 1680
FEATURE                Location/Qualifiers
source                 1..1680
                       mol_type = genomic DNA
                       organism = Oryza sativa
CDS                    1..1680
SEQUENCE: 15
atggcctcca tcaccaactg gctcggcttc tcctcctcct ccttctccgg cgccggcgcc  60
gaccccgtcc tgccccaccc gccgctgcaa gagtggggga gcgcttatga gggcggcggc  120
acggtggcgg ccgccggcgg ggaggagacg gcggcgccga agctggagga cttcctcggc  180
atgcaggtgc agcaggagac ggccgccgcg gcggcggggc acggccgtgg aggcagctcg  240
tcggtcgttg ggctgtccat gatcaagaac tggctacgca gccagccgcc gcccgcggtg  300
gttgggggag aagacgctat gatggcgctc gcggtgtcga cgtcggcgtc gccgccggtg  360
gacgcgacgg tgccggcctg catttcgccg gatgggatgg ggtcgaaggc ggccgacggc  420
```

```
ggcggcgcgg ccgaggcggc ggcggcggcg gcggcgcaga ggatgaaggc ggccatggac  480
acgttcgggc agcggacgtc catctaccgg ggtgtcacca agcacaggtg gacaggaagg  540
tatgaagccc atctttggga taacagctgc agaagagaag gtcagactcg caaaggcaga  600
caagtatatc ttggaggata tgataaggaa gaaaaagctg ctagggctta tgatttggct  660
gcccttaaat actggggcac tacaacgacg acgaattttc cggtaagcaa ctacgaaaaa  720
gagttggatg aaatgaagca catgaatagg caggaatttg ttgcatccct tagaagaaaa  780
agcagtggat tttcacgtgg tgcttccata tatcgtggtg ttacaagaca ccatcagcat  840
ggaaggtggc aagcaaggat aggacgggtg gcaggaaaca aggatctgta tttgggcaca  900
tttggcaccc aagaggaagc tgcagaggca tatgatatcg ctgcaatcaa attccgtggt  960
ctcaatgctg tgacaaactt tgacatgagc cggtacgatg tcaagagcat cattgaaagc  1020
agcaatctcc caattggtac tggaaccacc cggcgattga aggactcctc tgatcacact  1080
gataatgtca tggacatcaa tgtcaatacc gaacccaata atgtggtatc atcccacttc  1140
accaatgggg ttggcaacta tggttcgcag cattatggtt acaatggatg gtcgccaatt  1200
agcatgcagc cgatcccctc gcagtacgcc aacggccagc ccagggcatg gttgaaacaa  1260
gagcaggaca gctctgtggt tacagcggcg cagaacctgc acaatctaca tcattttagt  1320
tccttgggct acacccacaa cttcttccag caatctgatg ttccagacgt cacaggtttc  1380
gttgatgcgc cttcgaggtc cagtgactca tactccttca ggtacaatgg aacaaatggc  1440
tttcatggtc tcccgggtgg aatcagctat gctatgccgg ttgcgacagc ggtggaccaa  1500
ggtcagggca tccatggcta tggagaagat ggtgtggcag gcattgacac cacacatgac  1560
ctgtatggca gccgtaatgt gtactacctt tccgagggtt cgcttcttgc cgatgtcgaa  1620
aaagaaggcg actatggcca atctgtgggg ggcaacagct gggttttgcc gacaccgtag  1680

SEQ ID NO: 16           moltype = AA  length = 559
FEATURE                 Location/Qualifiers
source                  1..559
                        mol_type = protein
                        organism = Oryza sativa
SEQUENCE: 16
MASITNWLGF SSSSFSGAGA DPVLPHPPLQ EWGSAYEGGG TVAAAGGEET AAPKLEDFLG  60
MQVQQETAAA AAGHGRGGSS SVVGLSMIKN WLRSQPPPAV VGGEDAMMAL AVSTSASPPV  120
DATVPACISP DGMGSKAADG GGAAEAAAAA AAQRMKAAMD TFGQRTSIYR GVTKHRWTGR  180
YEAHLWDNSC RREGQTRKGR QVYLGGYDKE EKAARAYDLA ALKYWGTTTT TNFPVSNYEK  240
ELDEMKHMNR QEFVASLRRK SSGFSRGASI YRGVTRHHQH GRWQARIGRV AGNKDLYLGT  300
FGTQEEAAEA YDIAAIKFRG LNAVTNFDMS RYDVKSIIES SNLPIGTGTT RRLKDSSDHT  360
DNVMDINVNT EPNNVVSSHF TNGVGNYGSQ HYGYNGWSPI SMQPIPSQYA NGQPRAWLKQ  420
EQDSSVVTAA QNLHNLHHFS SLGYTHNFFQ QSDVPDVTGF VDAPSRSSDS YSFRYNGTNG  480
FHGLPGGISY AMPVATAVDQ GQGIHGYGED GVAGIDTTHD LYGSRNVYYL SEGSLLADVE  540
KEGDYGQSVG GNSWVLPTP                                              559

SEQ ID NO: 17           moltype = DNA  length = 2112
FEATURE                 Location/Qualifiers
source                  1..2112
                        mol_type = genomic DNA
                        organism = Oryza sativa
CDS                     1..2112
SEQUENCE: 17
atggcttctg caaacaactg gctgggcttc tcgctctccg gccaagagaa tccgcagcct  60
caccaggata gctcgcctcc ggcagccatc gacgtctccg gcgccggcga cttctatggc  120
ctgccgacgt cgcagccgac ggcggccgac gcgcacctcg gcgtggcggg gcatcatcac  180
aacgcctcgt atggcatcat ggaggccttc aataggggag ctcaagaggc acaagattgg  240
aacatgaggg ggctggacta caacggcggc gcctcggagc tgtcgatgct cgtcggctcc  300
agcggcggca agagggcggc ggcggtggag gagaccgagc cgaagctgga ggacttcctc  360
ggcggcaact cgttcgtctc cgagcaagat catcacgcgg cgggggcctt cctcttctcc  420
ggcgtcccga tggccagcag caccaacagc aacagcggga gcaacactat ggagctctcc  480
atgatcaaga cctggctccg gaacaacggc caggtgcccg ccggccacca gccgcagcag  540
cagcagccgg cggccgcggc cgccgccgcg cagcagcagg cgcacgaggc ggcggagatg  600
agcaccgacg cgagcgcgag cagcttcggg tgctcctccg acgcgatggg gaggagtaac  660
aacggcggcg cggtctcggc ggcggccggc gggacgagct cgcagagcct ggcgctctcg  720
atgagcacgg gctcgcactc gcacctgcct atcgtcgtcg ccggcggcgg gaacgccagc  780
ggcggagcgg ccgagagcac atcgtcggag aacaagcggg ccagcggcgc catggattcg  840
ccgggcggtg gcgcgataga ggccgtgccg aggaagtcca tcgacacgtt cgggcaaagg  900
acctcgatat atcgaggtgt aacaaggcat agatggacag ggcgatatga ggctcatctc  960
tgggataata gctgtagaag agaagggcag agtcgcaagg gtaggcaagt ttatcttggt  1020
ggctatgaca aggaggataa agcagcgaga gcttatgatt tggcagctct gaagtattgg  1080
ggcacaacaa caacaacaaa tttcccaata agtaactatg aaaaagagct agatgaaatg  1140
aaacatatga ccaggcagga gtatattgca tacctaagaa ggaatagcag tggattttct  1200
cgtggtgcat cgaaatatcg tggtgtaacc aggcaccatc agcatgggag atggcaagca  1260
aggataggga gggttgcagg aaacaaggac ctctacttag gcaccttcag caccgaggag  1320
gaggcggcgg aggcgtacga catcgcggcg atcaagttcc gggggctcaa cgccgtcacc  1380
aactttgaca tgagccgcta cgacgtcaag agcatcctgg agagcagcac gctgccggtg  1440
ggcggcgcgg cgaggcggct gaaggaggcg gcggaccacg cggaggcggc cggcgccacc  1500
atctggcgcg ccgccgacat ggacggcgcc ggcgtcatct ccggcctggc cgacgtcggg  1560
atgggcgcct acgccgcctc gtaccaccac caccaccacc acggctggcc gaccatcgcg  1620
ttccagcagc cgccgccgct cgccgtgcac tacccgtacg gccaggcgcc ggcggcgccg  1680
tcgcgcgggt ggtgcaagcc cgagcaggac gccgccgtcg ctgccgccgc gcacagcctc  1740
caggacctcc agcagctgca cctcggcagc gccgccgccc acaacttctt ccaggcgtcg  1800
tcgagctcga cggtctacaa cggcggcggc ggcgggtacc agggcctcgg tggcaacgcc  1860
ttcttgatgc cggcgagcac cgtcgtggcc gaccaggggc acagcagcac ggccaccaac  1920
catggaaaca cctgcagcta cggcaacgag gagcagggga agctcatcgg gtacgacgcc  1980
```

```
atggcgatgg cgagcggcgc cgccggcggc gggtaccagc tgtcgcaggg ctcggcgtcg  2040
acggtgagca tcgcgagggc gaacggctac tcggccaact ggagctcgcc tttcaatggc  2100
gccatgggat ga                                                      2112

SEQ ID NO: 18          moltype = AA  length = 703
FEATURE                Location/Qualifiers
source                 1..703
                       mol_type = protein
                       organism = Oryza sativa
SEQUENCE: 18
MASANNWLGF SLSGQENPQP HQDSSPPAAI DVSGAGDFYG LPTSQPTAAD AHLGVAGHHH  60
NASYGIMEAF NRGAQEAQDW NMRGLDYNGG ASELSMLVGS SGGKRAAAVE ETEPKLEDFL  120
GGNSFVSEQD HHAAGGFLFS GVPMASSTNS NSGSNTMELS MIKTWLRNNG QVPAGHQPQQ  180
QQPAAAAAAA QQQAHEAAEM STDASASSFG CSSDAMGRSN NGGAVSAAAG GTSSQSLALS  240
MSTGSHSHLP IVVAGGGNAS GGAAESTSSE NKRASGAMDS PGGGAIEAVP RKSIDTFGQR  300
TSIYRGVTRH RWTGRYEAHL WDNSCRREGQ SRKGRQVYLG GYDKEDKAAR AYDLAALKYW  360
GTTTTTNFPI SNYEKELDEM KHMTRQEYIA YLRRNSSGFS RGASKYRGVT RHHQHGRWQA  420
RIGRVAGNKD LYLGTFSTEE EAAEAYDIAA IKFRGLNAVT NFDMSRYDVK SILESSTLPV  480
GGAARRLKEA ADHAEAAGAT IWRAADMDGA GVISGLADVG MGAYAASYHH HHHHGWPTIA  540
FQQPPPLAVH YPYGQAPAAP SRGWCKPEQD AAVAAAAHSL QDLQQLHLGS AAAHNFFQAS  600
SSSTVYNGGG GGYQGLGGNA FLMPASTVVA DQGHSSTATN HGNTCSYGNE EQGKLIGYDA  660
MAMASGAAGG GYQLSQGSAS TVSIARANGY SANWSSPFNG AMG                    703

SEQ ID NO: 19          moltype = DNA  length = 1977
FEATURE                Location/Qualifiers
source                 1..1977
                       mol_type = genomic DNA
                       organism = Oryza sativa
CDS                    1..1977
SEQUENCE: 19
atggcttctg cagataactg gctaggcttc tcgctctccg gccaaggcaa cccacagcat  60
caccagaacg gctcgccgtc tgccgccggc gacgccgcca tcgacatctc cggctcaggc  120
gacttctatg gtctgccaac gccggacgca caccacatcg gcatggcggg cgaagacgcg  180
ccctatggcg tcatggatgc tttcaacaga ggcacccatg aaacccaaga ttgggcgatg  240
aggggtttgg actacggcgg cggctcctcc gacctctcga tgctcgtcgg ctcgagcggc  300
ggcgggagga ggacggtggc cggcgacggc gtcggcgagg cgccgaagct ggagaacttc  360
ctcgacggca actcattctc cgacgtgcac ggccaagccg ccggcgggta cctctactcc  420
ggaagcgctg tcggcggcgc cggtggttac agtaacggcg gatgcggcgg cggaaccata  480
gagctgtcca tgatcaagac gtggctccgg agcaaccagt cgcagcagca gccatcgccg  540
ccgcagcacg ctgatcaggg catgagcacc gacgccagcg cgagcagcta cgcgtgctcc  600
gacgtgctgg tggggagctg cggcggcggc ggcgccgggg gcacggcgag ctcgcatggg  660
cagggcctgg cgctgtcgat gagcacgggg tcggtggccg ccgccggagg gggcggcgcc  720
gtcgtcgcgg ccgagagctc gtcgtcggag aacaagcggg tggattcgcc gggcggcgcc  780
gtggacggcg ccgtcccgag gaaatccatc gacaccttcg ggcaaaggac gtctatatac  840
cgaggtgtaa caaggcatag atggacagga agatatgaag ctcatctgtg ggataatagc  900
tgtaggagag aaggccaaag tcgcaagggg agacaggttt atttgggcgg ttatgacaaa  960
gaagataagg cggctcgggc ttatgatttg gcagctctaa aatactgggg cacgaccaca  1020
acaacaaatt tcccaatgag taattatgaa aaggagctag aggaaatgaa acacatgacc  1080
aggcaggagt acattgcaca tcttagaagg aatagcagtg gattttctcg tggtgcatcc  1140
aaatatcgtg gtgttactag gcatcatcag catgggagat ggcaggcaag gatagggcga  1200
gttgcaggca acaaggatat ctacctaggc accttcagca ccgaggagga ggccgccgag  1260
gcgtacgaca tcgccgccat caagttccgc gggctcaacg ccgtcaccaa cttcgacatg  1320
agccggtacg acgtcaagag catcctggac agcagcacgc tgccggtcgg cggcgcggcg  1380
cggcggctca aggaggcgga ggtcgccgcc gccgccgcgg gcggcggcgt gatcgtctcc  1440
cacctggccg acggcggtgt gggtgggtac tactacgggt gcggcccgac catcgcgttc  1500
ggcggcggcg gccagcagcc ggcgccgctc gccgtgcact acccgtcgta cggccaggcc  1560
agcgggtggt gcaagccgga gcaggacgcg gtgatcgcgg ccgggcactg cgcgacggac  1620
ctccagcacc tgcacctcgg gagcggcggc gccgccgcca cccacaactt cttccagcag  1680
ccggcgtcaa gctcggccgt ctacggcaac ggcggcggcg gcggcggcaa cgcgttcatg  1740
atgccgatgg gcgccgtggt ggccgccgcc gatcacggcg ggcagagcag cgcctacggc  1800
ggtggcgacg agagcgggag gctcgtcgtg gggtacgacg gcgtcgtcga cccgtacgcg  1860
gccatgagaa gcgcgtacga gctctcgcag ggctcgtcgt cgtcgtcggt gagcgtcgcg  1920
aaggcggcga acgggtaccc ggacaactgg agctcgccgt tcaacggcat gggatga     1977

SEQ ID NO: 20          moltype = AA  length = 658
FEATURE                Location/Qualifiers
source                 1..658
                       mol_type = protein
                       organism = Oryza sativa
SEQUENCE: 20
MASADNWLGF SLSGQGNPQH HQNGSPSAAG DAAIDISGSG DFYGLPTPDA HHIGMAGEDA  60
PYGVMDAFNR GTHETQDWAM RGLDYGGGSS DLSMLVGSSG GGRRTVAGDG VGEAPKLENF  120
LDGNSFSDVH GQAAGGYLYS GSAVGGAGGY SNGGCGGGTI ELSMIKTWLR SNQSQQQPSP  180
PQHADQGMST DASASSYACS DVLVGSCGGG GAGGTASSHG QGLALSMSTG SVAAAGGGGA  240
VVAAESSSSE NKRVDSPGGA VDGAVPRKSI DTFGQRTSIY RGVTRHRWTG RYEAHLWDNS  300
CRREGQSRKG RQVYLGGYDK EDKAARAYDL AALKYWGTTT TTNFPMSNYE KELEEMKHMT  360
RQEYIAHLRR NSSGFSRGAS KYRGVTRHHQ HGRWQARIGR VAGNKDIYLG TFSTEEEAAE  420
AYDIAAIKFR GLNAVTNFDM SRYDVKSILD SSTLPVGGAA RRLKEAEVAA AAAGGGVIVS  480
HLADGGVGGY YYGCGPTIAF GGGGQQPAPL AVHYPSYGQA SGWCKPEQDA VIAAGHCATD  540
```

```
LQHLHLGSGG AAATHNFFQQ PASSSAVYGN GGGGGGNAFM MPMGAVVAAA DHGGQSSAYG  600
GGDESGRLVV GYDGVVDPYA AMRSAYELSQ GSSSSSVSVA KAANGYPDNW SSPFNGMG    658

SEQ ID NO: 21          moltype = DNA  length = 1755
FEATURE                Location/Qualifiers
source                 1..1755
                       mol_type = genomic DNA
                       organism = Arabidopsis thaliana
CDS                    1..1755
SEQUENCE: 21
atgaactcga tgaataactg gttaggcttc tctctctctc ctcatgatca aaatcatcac  60
cgtacggatg ttgactcctc caccaccaga accgccgtag atgttgccgg agggtactgt  120
tttgatctgg ccgctccctc cgatgaatct tctgccgttc aaacatcttt tctttctcct  180
ttcggtgtca ccctcgaagc tttcaccaga gacaataata gtcactcccg agattgggac  240
atcaatggtg gtgcatgcaa tacattaacc aataacgaac aaaatggacc aaagcttgag  300
aatttcctcg gccgcaccac cacgatttac aataccaacg agaccgttgt agatggaaat  360
ggcgattgtg gaggaggaga cggtggtggt ggcggctcac taggcctttc gatgataaaa  420
acatggctga gtaatcattc ggttgctaat gctaatcatc aagacaatgg taacggtgca  480
cgaggcttgt ccctctctat gaattcatct actagtgata gcaacaacta caacaacaat  540
gatgatgtcg tccaagagaa gactattgtt gatgtcgtag aaactacacc gaagaaaact  600
attgagagtt ttggacaaag gacgtctata taccgcggtg ttacaaggca tcggtggaca  660
ggtagatacg aggcacattt atgggacaat agttgcaaaa gagaaggcca gactcgcaaa  720
ggaagacaag tttatctggg aggttatgac aaagaagaaa aagcagctag ggcttacgat  780
ttagccgcac taaagtattg gggacccacc actactacta acttcccctt gagtgaatat  840
gagaaagagg tagaagagat gaagcacatg acgaggcaag agtatgttgc ctctctgcgc  900
aggaaaagta gtggtttctc tcgtggtgca tcgatttatc gaggagtaac aaggcatcac  960
caacatggaa ggtggcaagc taggatcgga agagtcgccg gtaacaaaga cctctacttg  1020
ggaactttcg gcacacagga agaggctgct gaggcttatg acattgcagc cattaaattc  1080
agaggattaa gcgcagtgac taacttcgac atgaacagat acaatgttaa agcaatcctc  1140
gagagcccga gtctacctat tggtagttct gcgaaacgtc tcaaggacgt taacaatccg  1200
gttccagcta tgatgattag taataacgtt tcagagagtg caaataatgt tagcggttgg  1260
caaaacactg cgtttcagca tcatcaggga atggatttga gcttattgca gcaacagcag  1320
gagaggtacg ttggttatta caatggagga aacttgtcta ccgagagtac tagggtttgt  1380
ttcaaacaag aggaggaaca acaacacttc ttgagaaact cgccgagtca catgactaat  1440
gttgatcatc atagctcgac ctctgatgat tctgttaccg tttgtggaaa tgttgttagt  1500
tatggtggtt atcaaggatt cgcaatccct gttggaacat cggttaatta cgatcccttt  1560
actgctgctg agattgctta caacgcaaga aatcattatt actatgctca gcatcagcaa  1620
caacagcaga ttcagcagtc gccgggagga gattttccgg tggcgatttc gaataaccat  1680
agctctaaca tgtactttca cggggaaggt ggtggagaag ggctccaac gttttcagtt  1740
tggaacgaca cttag                                                  1755

SEQ ID NO: 22          moltype = AA  length = 584
FEATURE                Location/Qualifiers
source                 1..584
                       mol_type = protein
                       organism = Arabidopsis thaliana
SEQUENCE: 22
MNSMNNWLGF SLSPHDQNHH RTDVDSSTTR TAVDVAGGYC FDLAAPSDES SAVQTSFLSP  60
FGVTLEAFTR DNNSHSRDWD INGGACNTLT NNEQNGPKLE NFLGRTTTIY NTNETVVDGN  120
GDCGGGDGGG GGSLGLSMIK TWLSNHSVAN ANHQDNGNGA RGLSLSMNSS TSDSNNYNNN  180
DDVVQEKTIV DVVETTPKKT IESFGQRTSI YRGVTRHRWT GRYEAHLWDN SCKREGQTRK  240
GRQVYLGGYD KEEKAARAYD LAALKYWGPT TTTNFPLSEY EKEVEEMKHM TRQEYVASLR  300
RKSSGFSRGA SIYRGVTRHH QHGRWQARIG RVAGNKDLYL GTFGTQEEAA EAYDIAAIKF  360
RGLSAVTNFD MNRYNVKAIL ESPSLPIGSS AKRLKDVNNP VPAMMISNNV SESANNVSGW  420
QNTAFQHHQG MDLSLLQQQQ ERYVGYYNGG NLSTESTRVC FKQEEEQQHF LRNSPSHMTN  480
VDHHSSTSDD SVTVCGNVVS YGGYQGFAIP VGTSVNYDPF TAAEIAYNAR NHYYYAQHQQ  540
QQQIQQSPGG DFPVAISNNH SSNMYFHGEG GGEGAPTFSV WNDT                  584

SEQ ID NO: 23          moltype = DNA  length = 1740
FEATURE                Location/Qualifiers
source                 1..1740
                       mol_type = genomic DNA
                       organism = Brassica napus
CDS                    1..1740
SEQUENCE: 23
atgaataata actggttagg ctttctctc tctccttatg aacaaaatca ccatcgtaag  60
gacgtctact cttccaccac cacaaccgtc gtagatgtcg ccggagagta ctgttacgat  120
ccgaccgctg cctccgatga gtcttcagcc atccaaacat cgtttccttc tccctttggt  180
gtcgtcgtcg atgctttcac cagagacaac aatagtcact cccgagattg ggacatcaat  240
ggttgtgcat gcaataacat ccacaacgat gagcaagatg gaccaaagct tgagaatttc  300
cttggccgca ccaccacgat ttacaacacc aacgaaaacg ttggagatgg aagtggaagt  360
ggctgttatg gaggaggaga cggtggtggt ggctcactag gactttcgat gataaagaca  420
tggctgagaa atcaacccgt ggataatgtt gataatcaag aaaatggcaa tgctgcaaaa  480
ggcctgtccc tctcaatgaa ctcatctact tcttgtgata acaacaacga cagcaataac  540
aacgttgttg cccaagggaa gactattgat gatagcgttg aagctacacc gaagaaaact  600
attgagagtt ttggacagag gacgtctata taccgcggtg ttacaaggca tcggtggaca  660
ggaagatatg aggcacattt atgggataat agttgtaaaa gagaaggcca aacgcgcaaa  720
ggaagacaag tttatttggg aggttatgac aaagaagaaa aagcagctag ggcttatgat  780
ttagccgcac tcaagtattg gggaaccacc actactacta acttccccat gagcgaatat  840
```

```
gaaaaagagg tagaagagat gaagcacatg acaaggcaag agtatgttgc ctcactgcgc  900
aggaaaagta gtggtttctc tcgtggtgca tcgatttatc gtggagtaac aagacatcac  960
caacatggaa gatggcaagc taggatagga agagtcgccg gtaacaaaga cctctacttg  1020
ggaacttttg gcacacaaga agaagctgca gaggcatacg acattgcggc catcaaattc  1080
agaggattaa ccgcagtgac taacttcgac atgaacagat acaacgttaa agcaatcctc  1140
gaaagcccta gtcttcctat tggtagcgcc gcaaaacgtc tcaaggaggc taaccgtccg  1200
gttccaagta tgatgatgat cagtaataac gtttcagaga gtgagaatag tgctagcggt  1260
tggcaaaacg ctgcggttca gcatcatcag ggagtagatt tgagcttatt gcaccaacat  1320
caagagaggt acaatggtta ttattacaat ggaggaaact tgtcttcgga gagtgctagg  1380
gcttgtttca aacaagagga tgatcaacac catttcttga gcaacacgca gagcctcatg  1440
actaatatcg atcatcaaag ttctgtttcg gatgattcgg ttactgtttg tggaaatgtt  1500
gttggttatg gtggttatca aggatttgca gccccggtta actgcgatgc ctacgctgct  1560
agtgagtttg attataacgc aagaaaccat tattactttg ctcagcagca gcagacccag  1620
cagtcgccag gtggagattt tcccgcggca atgacgaata atgttggctc taatatgtat  1680
taccatgggg aaggtggtgg agaagttgct ccaacattta cagtttggaa cgacaattag  1740

SEQ ID NO: 24          moltype = AA  length = 579
FEATURE                Location/Qualifiers
source                 1..579
                       mol_type = protein
                       organism = Brassica napus
SEQUENCE: 24
MNNNWLGFSL SPYEQNHHRK DVYSSTTTTV VDVAGEYCYD PTAASDESSA IQTSFPSPFG  60
VVVDAFTRDN NSHSRDWDIN GCACNNIHND EQDGPKLENF LGRTTTIYNT NENVGDGSGS  120
GCYGGGDGGG GSLGLSMIKT WLRNQPVDNV DNQENGNAAK GLSLSMNSST SCDNNNDSNN  180
NVVAQGKTID DSVEATPKKT IESFGQRTSI YRGVTRHRWT GRYEAHLWDN SCKREGQTRK  240
GRQVYLGGYD KEEKAARAYD LAALKYWGTT TTTNFPMSEY EKEVEEMKHM TRQEYVASLR  300
RKSSGFSRGA SIYRGVTRHH QHGRWQARIG RVAGNKDLYL GTFGTQEEAA EAYDIAAIKF  360
RGLTAVTNFD MNRYNVKAIL ESPSLPIGSA AKRLKEANRP VPSMMMISNN VSESENSASG  420
WQNAAVQHHQ GVDLSLLHQH QERYNGYYYN GGNLSSESAR ACFKQEDDQH HFLSNTQSLM  480
TNIDHQSSVS DDSVTVCGNV VGYGGYQGFA APVNCDAYAA SEFDYNARNH YYFAQQQQTQ  540
QSPGGDFPAA MTNNVGSNMY YHGEGGGEVA PTFTVWNDN                        579

SEQ ID NO: 25          moltype = DNA  length = 1740
FEATURE                Location/Qualifiers
source                 1..1740
                       mol_type = genomic DNA
                       organism = Brassica napus
CDS                    1..1740
SEQUENCE: 25
atgaataata actggttagg cttttctctc tctccttatg aacaaaatca ccatcgtaag  60
gacgtctgct cttccaccac cacaaccgcc gtagatgtcg ccggagagta ctgttacgat  120
ccgaccgctg cctccgatga gtcttcagcc atccaaacat cgtttccttc tccctttggt  180
gtcgtcctcg atgctttcac cagagacaac aatagtcact cccgagattg ggacatcaat  240
ggtagtgcat gtaataacat ccacaatgat gagcaagatg gaccaaaact tgagaatttc  300
cttggccgca ccaccacgat ttacaacacc aacgaaaacg ttggagatat cgatggaagt  360
gggtgttatg gaggaggaga cggtggtggt ggctcactag gactttcgat gataaagaca  420
tggctgagaa atcaacccgt ggataatgtt gataatcaag aaaatggcaa tggtgcaaaa  480
ggcctgtccc tctcaatgaa ctcatctact tcttgtgata acaacaacta cagcagtaac  540
aaccttgttg cccaaggaaa gactattgat gatagcgttg aagctacacc gaagaaaact  600
attgagagtt ttggacagag gacgtctata taccgcggtg ttacaaggca tcggtggaca  660
ggaagatatg aggcacattt atgggataat agttgtaaac gagaaggcca aacgcgcaaa  720
ggaagacaag tttatttggg aggttatgac aaagaagaaa aagcagctag ggcttatgat  780
ttagccgcac tcaagtattg gggaaccacc actactacta acttccccat gagcgaatat  840
gagaaagaga tagaagagat gaagcacatg acaaggcaag agtatgttgc ctcacttcgc  900
aggaaaagta gtggtttctc tcgtggtgca tcgatttatc gtggagtaac aagacatcac  960
caacatggaa gatggcaagc taggatagga agagtcgccg gtaacaaaga cctctacttg  1020
ggaacttttg gcacacaaga agaagctgca gaggcatacg acattgcggc catcaaattc  1080
agaggattaa ccgcagtgac taacttcgac atgaacagat acaacgttaa agcaatcctc  1140
gaaagcccta gtcttcctat tggtagcgcc gcaaaacgtc tcaaggaggc taaccgtccg  1200
gttccaagta tgatgatgat cagtaataac gtttcagaga gtgagaataa tgctagcggt  1260
tggcaaaacg ctgcggttca gcatcatcag ggagtagatt tgagcttatt gcagcaacat  1320
caagagaggt acaatggtta ttattacaat ggaggaaact tgtcttcgga gagtgctagg  1380
gcttgtttca aacaagagga tgatcaacac catttcttga gcaacacgca gagcctcatg  1440
actaatatcg atcatcaaag ttctgtttca gatgattcgg ttactgtttg tggaaatgtt  1500
gttggttatg gtggttatca aggatttgca gccccggtta actgcgatgc ctacgctgct  1560
agtgagtttg actataacgc aagaaaccat tattactttg ctcagcagca gcagacccag  1620
cattcgccag gaggagattt tcccgcggca atgacgaata atgttggctc taatatgtat  1680
taccatgggg aaggtggtgg agaagttgct ccaacattta cagtttggaa cgacaattag  1740

SEQ ID NO: 26          moltype = AA  length = 579
FEATURE                Location/Qualifiers
source                 1..579
                       mol_type = protein
                       organism = Brassica napus
SEQUENCE: 26
MNNNWLGFSL SPYEQNHHRK DVCSSTTTTA VDVAGEYCYD PTAASDESSA IQTSFPSPFG  60
VVLDAFTRDN NSHSRDWDIN GSACNNIHND EQDGPKLENF LGRTTTIYNT NENVGDIDGS  120
GCYGGGDGGG GSLGLSMIKT WLRNQPVDNV DNQENGNGAK GLSLSMNSST SCDNNNYSSN  180
```

```
NLVAQGKTID DSVEATPKKT IESFGQRTSI YRGVTRHRWT GRYEAHLWDN SCKREGQTRK  240
GRQVYLGGYD KEEKAARAYD LAALKYWGTT TTTNFPMSEY EKEIEEMKHM TRQEYVASLR  300
RKSSGFSRGA SIYRGVTRHH QHGRWQARIG RVAGNKDLYL GTFGTQEEAA EAYDIAAIKF  360
RGLTAVTNFD MNRYNVKAIL ESPSLPIGSA AKRLKEANRP VPSMMMISNN VSESENNASG  420
WQNAAVQHHQ GVDLSLLQQH QERYNGYYYN GGNLSSESAR ACFKQEDDQH HFLSNTQSLM  480
TNIDHQSSVS DDSVTVCGNV VGYGGYQGFA APVNCDAYAA SEFDYNARNH YYFAQQQQTQ  540
HSPGGDFPAA MTNNVGSNMY YHGEGGGEVA PTFTVWNDN                        579

SEQ ID NO: 27          moltype = DNA  length = 2082
FEATURE                Location/Qualifiers
source                 1..2082
                       mol_type = genomic DNA
                       organism = Sorghum bicolor
CDS                    1..2082
SEQUENCE: 27
atggcttcga cgaacaacca ctggctgggt ttctcgctct cgggccagga taacccgcag  60
cctaatcatc aggacagctc gcctgccgcc gccggcatcg acatctccgg cgccagcgac  120
ttctatggct tgcccacgca gcagggctcc gacgggaatc tcggcgtgcc gggcctgcgg  180
gacgatcacg cttcttatgg catcatggag gccttcaaca gggttcctca agaaacccaa  240
gattggaaca tgaggggatt ggactacaac ggcggtggct cggaactctc gatgcttgtg  300
gggtccagcg gcggcggcgg gggcggcggc aagagggccg tggaagacag cgagcccaag  360
ctcgaagatt tcctcggcgg caactcgttc gtctccgagc atgatcagtc cggcggttac  420
ctgttctctg gagtcccgat ggccagcagc accaacagca acagcgggag caacaccatg  480
gagctctcca tgatcaagac ctggctccgg aacaaccagg tgccccagcc gcagccgcca  540
gcagctccgc atcaggcgcc gcagactgag gagatgagca ccgacgccaa cgccagcgcc  600
agcagctttg gctgctcgga ttcgatgggg aggaacggca cggtggcggc tgctgggagc  660
tcccagagcc tggcgctctc gatgagcacg ggctcgcacc tgccgatggt tgtggccggc  720
ggcggcgcca gcggagcggc ctcggagagc acgtcatcgg agaacaagcg agcgagcggc  780
gccatggatt cgcccggcag cgcggtagaa gccgtcccga ggaagtccat cgacacgttc  840
gggcaaagga cctctatata tcgaggtgta acaagacata gatggacagg gcgatatgag  900
gctcatctat gggataatag ttgtagaaga gaagggcaga gtcgcaaggg taggcaagtt  960
taccttggtg gctatgacaa ggaagacaag gcagcaaggg cttatgattt ggcagctctc  1020
aagtattggg gcactactac aacaacaaat ttccctataa gcaactatga aaaggagcta  1080
gaggaaatga aacatatgac taggcaggag tatattgcat acctaagaag aaatagcagt  1140
ggatttctc gtggcgcatc aaaatatcgt ggagtaacta gacatcatca gcatgggaga  1200
tggcaagcaa ggataggag agttgcagga aacaaggatc tctacttggg cacattcagc  1260
accgaggagg aggcggcgga ggcctacgac atcgccgcga tcaagttccg cggtctgaac  1320
gccgtcacca acttcgacat gagccgctac gacgtcaaga gcatcctcga gagcagcacg  1380
ctgcctgtcg gcggcgcggc caggcgcctc aaggatgccg tggaccacgt ggaggccggc  1440
gccaccatct ggcgcgccga catggacggc ggcgtgatct cccagctcgc cgaagccggg  1500
atgggcggct acgcctcgta cgggcaccac gcctggccga ccatcgcgtt ccagcagccg  1560
tcgccgctct ccgtccacta cccgtacggg cagccgccgt cccgcgggtg gtgcaagccc  1620
gagcaggacg cggccgtcgc cgccgccgcg cacagcctgc aggacctcca gcagctgcac  1680
ctcggcagcg cggcacacaa cttcttccag gcgtcgtcga gctcggcagt ctacaacagc  1740
ggcggcggcg gcgctagcgg cgggtaccac cagggcctcg gtggcggcag cagctccttc  1800
ctcatgccgt cgagcactgt cgtggcgggg gccgaccagg ggcacagcag cagcacggcc  1860
aaccagggga gcacgtgcag ctacggggac gatcaccagg aagggaagct catcgggtac  1920
gacgccatgg tggcggcgac cgcagccggc ggggacccgt acgccgcggc gaggagcggg  1980
taccagttct cgtcgcaggg ctcgggatcc acggtgagca tcgcgagggc gaacgggtac  2040
tctaacaact ggagctctcc tttcaacggc ggcatggggt ga                     2082

SEQ ID NO: 28          moltype = AA  length = 693
FEATURE                Location/Qualifiers
source                 1..693
                       mol_type = protein
                       organism = Sorghum bicolor
SEQUENCE: 28
MASTNNHWLG FSLSGQDNPQ PNHQDSSPAA AGIDISGASD FYGLPTQQGS DGNLGVPGLR  60
DDHASYGIME AFNRVPQETQ DWNMRGLDYN GGGSELSMLV GSSGGGGGGG KRAVEDSEPK  120
LEDFLGGNSF VSEHDQSGGY LFSGVPMASS TNSNSGSNTM ELSMIKTWLR NNQVPQPQPP  180
AAPHQAPQTE EMSTDANASA SSFGCSDSMG RNGTVAAAGS SQSLALSMST GSHLPMVVAG  240
GGASGAASES TSSENKRASG AMDSPGSAVE AVPRKSIDTF GQRTSIYRGV TRHRWTGRYE  300
AHLWDNSCRR EGQSRKGRQV YLGGYDKEDK AARAYDLAAL KYWGTTTTTN FPISNYEKEL  360
EEMKHMTRQE YIAYLRRNSS GFSRGASKYR GVTRHHQHGR WQARIGRVAG NKDLYLGTFS  420
TEEEAAEAYD IAAIKFRGLN AVTNFDMSRY DVKSILESST LPVGGAARRL KDAVDHVEAG  480
ATIWRADMDG GVISQLAEAG MGGYASYGHH AWPTIAFQQP SPLSVHYPYG QPPSRGWCKP  540
EQDAAVAAAA HSLQDLQQLH LGSAAHNFFQ ASSSSAVYNS GGGGASGGYH QGLGGGSSSF  600
LMPSSTVVAG ADQGHSSSTA NQGSTCSYGD DHQEGKLIGY DAMVAATAAG GDPYAAARSG  660
YQFSSQGSGS TVSIARANGY SNNWSSPFNG GMG                              693

SEQ ID NO: 29          moltype = DNA  length = 508
FEATURE                Location/Qualifiers
source                 1..508
                       mol_type = genomic DNA
                       organism = Zea mays
SEQUENCE: 29
ctatagtatt ttaaaattgc attaacaaac atgtcctaat tggtactcct gagatactat  60
accctcctgt tttaaaatag ttggcattat cgaattatca ttttactttt taatgttttc  120
tcttctttta atatatttta tgaattttaa tgtattttaa aatgttatgc agttcgctct  180
```

```
ggacttttct gctgcgccta cacttgggtg tactgggcct aaattcagcc tgaccgaccg  240
cctgcattga ataatggatg agcaccggta aaatccgcgt acccaacttt cgagaagaac  300
cgagacgtgg cgggccgggc caccgacgca cggcaccagc gactgcacac gtcccgccgg  360
cgtacgtgta cgtgctgttc cctcactggc cgcccaatcc actcatgcat gcccacgtac  420
acccctgccg tggcgcgccc agatcctaat cctttcgccg ttctgcactt ctgctgccta  480
taaatggcgg catcgaccgt cacctgct                                     508

SEQ ID NO: 30          moltype = DNA  length = 665
FEATURE                Location/Qualifiers
misc_feature           1..665
                       note = Promoter construct comprising Zea mays Rab17promoter
                        and attB1 site
source                 1..665
                       mol_type = other DNA
                       organism = synthetic construct
SEQUENCE: 30
ctatagtatt ttaaaattgc attaacaaac atgtcctaat tggtactcct gagatactat  60
accctcctgt tttaaaatag ttggcattat cgaattatca ttttactttt taatgttttc  120
tcttctttta atatatttta tgaattttaa tgtattttaa aatgttatgc agttcgctct  180
ggacttttct gctgcgccta cacttgggtg tactgggcct aaattcagcc tgaccgaccg  240
cctgcattga ataatggatg agcaccggta aaatccgcgt acccaacttt cgagaagaac  300
cgagacgtgg cgggccgggc caccgacgca cggcaccagc gactgcacac gtcccgccgg  360
cgtacgtgta cgtgctgttc cctcactggc cgcccaatcc actcatgcat gcccacgtac  420
acccctgccg tggcgcgccc agatcctaat cctttcgccg ttctgcactt ctgctgccta  480
taaatggcgg catcgaccgt cacctgcttc accaccggcg agccacatcg agaacacgat  540
cgagcacaca agcacgaaga ctcgtttagg agaaaccaca aaccaccaag ccgtgcaagc  600
accaagcttg gtcacccggt ccgggcctag aaggccagct tcaagtttgt acaaaaaagc  660
aggct                                                              665

SEQ ID NO: 31          moltype = DNA  length = 24
FEATURE                Location/Qualifiers
misc_feature           1..24
                       note = attachment B1 site
source                 1..24
                       mol_type = other DNA
                       organism = synthetic construct
SEQUENCE: 31
caagtttgta caaaaaagca ggct                                         24

SEQ ID NO: 32          moltype = DNA  length = 24
FEATURE                Location/Qualifiers
misc_feature           1..24
                       note = attachment B2 site
source                 1..24
                       mol_type = other DNA
                       organism = synthetic construct
SEQUENCE: 32
acccagcttt cttgtacaaa gtgg                                         24

SEQ ID NO: 33          moltype = DNA  length = 22
FEATURE                Location/Qualifiers
misc_feature           1..22
                       note = attachment B3 site
source                 1..22
                       mol_type = other DNA
                       organism = synthetic construct
SEQUENCE: 33
acaactttgt ataataaagt tg                                           22

SEQ ID NO: 34          moltype = DNA  length = 22
FEATURE                Location/Qualifiers
misc_feature           1..22
                       note = attachment B4 site
source                 1..22
                       mol_type = other DNA
                       organism = synthetic construct
SEQUENCE: 34
acaactttgt atagaaaagt tg                                           22

SEQ ID NO: 35          moltype = DNA  length = 95
FEATURE                Location/Qualifiers
source                 1..95
                       mol_type = genomic DNA
                       organism = Zea mays
SEQUENCE: 35
tcaccaccgg cgagccacat cgagaacacg atcgagcaca caagcacgaa gactcgttta  60
ggagaaacca caaaccacca agccgtgcaa gcacc                             95

SEQ ID NO: 36          moltype = DNA  length = 133
```

```
FEATURE                 Location/Qualifiers
misc_feature            1..133
                        note = Plasmid linker sequence
source                  1..133
                        mol_type = other DNA
                        organism = synthetic construct
SEQUENCE: 36
tcaccaccgg cgagccacat cgagaacacg atcgagcaca caagcacgaa gactcgttta  60
ggagaaacca caaaccacca agccgtgcaa gcaccaagct tggtcacccg gtccgggcct  120
agaaggccag ctt                                                     133

SEQ ID NO: 37           moltype = DNA  length = 61
FEATURE                 Location/Qualifiers
misc_feature            1..61
                        note = Plasmid linker sequence
source                  1..61
                        mol_type = other DNA
                        organism = synthetic construct
SEQUENCE: 37
tcgaaggaga tagaaccaat tctctaagga aatacttaac catggtcgac tggatccaac  60
a                                                                  61

SEQ ID NO: 38           moltype = DNA  length = 318
FEATURE                 Location/Qualifiers
misc_feature            1..318
                        note = PinII terminator
source                  1..318
                        mol_type = other DNA
                        organism = synthetic construct
SEQUENCE: 38
agacttgtcc atcttctgga ttggccaact taattaatgt atgaaataaa aggatgcaca  60
catagtgaca tgctaatcac tataatgtgg gcatcaaagt tgtgtgttat gtgtaattac  120
tagttatctg aataaaagag aaagagatca tccatatttc ttatcctaaa tgaatgtcac  180
gtgtctttat aattctttga tgaaccagat gcatttcatt aaccaaatcc atatacatat  240
aaatattaat catatataat taatatcaat tgggttagca aaacaaatct agtctaggtg  300
tgttttgcga attgcggc                                                318

SEQ ID NO: 39           moltype = DNA  length = 16
FEATURE                 Location/Qualifiers
misc_feature            1..16
                        note = Plasmid linker sequence
source                  1..16
                        mol_type = other DNA
                        organism = synthetic construct
SEQUENCE: 39
gtttcgagat atctag                                                  16

SEQ ID NO: 40           moltype = DNA  length = 14
FEATURE                 Location/Qualifiers
misc_feature            1..14
                        note = Plasmid linker sequence
source                  1..14
                        mol_type = other DNA
                        organism = synthetic construct
SEQUENCE: 40
ccgttaacgg atcc                                                    14

SEQ ID NO: 41           moltype = DNA  length = 1272
FEATURE                 Location/Qualifiers
misc_feature            1..1272
                        note = Maize optimized FLP coding sequence
source                  1..1272
                        mol_type = other DNA
                        organism = synthetic construct
CDS                     1..1272
SEQUENCE: 41
atgccccagt tcgacatcct ctgcaagacc cccccccaagg tgctcgtgag gcagttcgtg  60
gagaggttcg agaggccctc cggcgagaag atcgccctct gcgccgccga gctcacctac  120
ctctgctgga tgatcaccca caacggcacc gccattaaga gggccacctt catgtcatac  180
aacaccatca tctccaactc cctctccttc gacatcgtga acaagtccct ccagttcaaa  240
tacaagaccc agaaggccac catcctcgag gcctccctca agaagctcat ccccgcctgg  300
gagttcacca tcatccccta ctacggccag aagcaccagt ccgacatcac cgacatcgtg  360
tcatccctcc agcttcagtt cgagtcctcc gaggaggctg acaagggcaa ctcccactcc  420
aagaagatgc tgaaggccct cctctccgag ggcgagtcca tctgggagat caccgagaag  480
atcctcaact ccttcgagta cacctccagg ttcactaaga ccaagaccct ctaccagttc  540
ctcttcctcg ccaccttcat caactgcggc aggttctcag acatcaagaa cgtggacccc  600
aagtccttca agctcgtgca gaacaagtac ctcggcgtga tcatccagtg cctcgtgacc  660
gagaccaaga cctccgtgtc caggcacatc tacttcttct ccgctcgcgg caggatcgac  720
cccctcgtgt acctcgacga gttcctcagg aactcagagc ccgtgctcaa gagggtgaac  780
```

```
aggaccggca actcctcctc caacaagcag gagtaccagc tcctcaagga caacctcgtg  840
aggtcctaca acaaggccct caagaagaac gccccctact ccatcttcgc catcaagaac  900
ggccccaagt cccacatcgg taggcacctc atgacctcct tcctctcaat gaagggcctc  960
accgagctca ccaacgtggt gggcaactgg tccgacaaga gggcctccgc cgtggccagg  1020
accacctaca cccaccagat caccgccatc cccgaccact acttcgccct cgtgtcaagg  1080
tactacgcct acgaccccat ctccaaggag atgatcgccc tcaaggacga gactaacccc  1140
atcgaggagt ggcagcacat cgagcagctc aagggctccg ccgagggctc catcaggtac  1200
cccgcctgga acggcatcat ctcccaggag gtgctcgact acctctcctc ctacatcaac  1260
aggaggatct ga                                                      1272

SEQ ID NO: 42          moltype = AA  length = 423
FEATURE                Location/Qualifiers
REGION                 1..423
                       note = FLP
source                 1..423
                       mol_type = protein
                       organism = synthetic construct
SEQUENCE: 42
MPQFDILCKT PPKVLVRQFV ERFERPSGEK IALCAAELTY LCWMITHNGT AIKRATFMSY  60
NTIISNSLSF DIVNKSLQFK YKTQKATILE ASLKKLIPAW EFTIIPYYGQ KHQSDITDIV  120
SSLQLQFESS EEADKGNSHS KKMLKALLSE GESIWEITEK ILNSFEYTSR FTKTKTLYQF  180
LFLATFINCG RFSDIKNVDP KSFKLVQNKY LGVIIQCLVT ETKTSVSRHI YFFSARGRID  240
PLVYLDEFLR NSEPVLKRVN RTGNSSSNKQ EYQLLKDNLV RSYNKALKKN APYSIFAIKN  300
GPKSHIGRHL MTSFLSMKGL TELTNVVGNW SDKRASAVAR TTYTHQITAI PDHYFALVSR  360
YYAYDPISKE MIALKDETNP IEEWQHIEQL KGSAEGSIRY PAWNGIISQE VLDYLSSYIN  420
RRI                                                                423

SEQ ID NO: 43          moltype = DNA  length = 1032
FEATURE                Location/Qualifiers
misc_feature           1..1032
                       note = Maize optimized Cre coding sequence
source                 1..1032
                       mol_type = other DNA
                       organism = synthetic construct
CDS                    1..1032
SEQUENCE: 43
atgtccaacc tgctcacggt tcaccagaac cttccggctc ttccagtgga cgcgacgtcc  60
gatgaagtca ggaagaacct catggacatg ttccgcgaca ggcaagcgtt cagcgagcac  120
acctggaaga tgctgctctc cgtctgccgc tcctgggctg catggtgcaa gctgaacaac  180
aggaagtggt tccccgctga gcccgaggac gtgagggatt accttctgta cctgcaagct  240
cgcgggctgg cagtgaagac catccagcaa caccttggac aactgaacat gcttcacagg  300
cgctccggcc tcccgcgccc cagcgactcg aacgccgtga gcctcgtcat gcgccgcatc  360
aggaaggaaa acgtcgatgc cggcgaaagg gcaaagcagg ccctcgcgtt cgagaggacc  420
gatttcgacc aggtccgcag cctgatggag aacagcgaca ggtgccagga cattaggaac  480
ctggcgttcc tcggaattgc atacaacacg ctcctcagga tcgcggaaat tgcccgcatt  540
cgcgtgaagg acattagccg caccgacggc ggcaggatgc ttatccacat tggcaggacc  600
aagacgctcg tttccaccgc aggcgtcgaa aaggccctca gcctcggagt gaccaagctc  660
gtcgaacgct ggatctccgt gtccggcgtc gcggacgacc caaacaacta cctcttctgc  720
cgcgtccgca agaacggggt ggctgcccct agcgccacca gccaactcag cacgagggcc  780
ttggaaggta ttttcgaggc cacccaccgc ctgatctacg gcgcgaagga tgacagcggt  840
caacgctacc tcgcatggtc cgggcactcc gcccgcgttg gagctgctag ggacatggcc  900
cgcgccggtg tttccatccc cgaaatcatg caggcgggtg gatggacgaa cgtgaacatt  960
gtcatgaact acattcgcaa ccttgacagc gagacgggcg caatggttcg cctcctggaa  1020
gatggtgact ga                                                      1032

SEQ ID NO: 44          moltype = AA  length = 343
FEATURE                Location/Qualifiers
REGION                 1..343
                       note = Cre
source                 1..343
                       mol_type = protein
                       organism = synthetic construct
SEQUENCE: 44
MSNLLTVHQN LPALPVDATS DEVRKNLMDM FRDRQAFSEH TWKMLLSVCR SWAAWCKLNN  60
RKWFPAEPED VRDYLLYLQA RGLAVKTIQQ HLGQLNMLHR RSGLPRPSDS NAVSLVMRRI  120
RKENVDAGER AKQALAFERT DFDQVRSLME NSDRCQDIRN LAFLGIAYNT LLRIAEIARI  180
RVKDISRTDG GRMLIHIGRT KTLVSTAGVE KALSLGVTKL VERWISVSGV ADDPNNYLFC  240
RVRKNGVAAP SATSQLSTRA LEGIFEATHR LIYGAKDDSG QRYLAWSGHS ARVGAARDMA  300
RAGVSIPEIM QAGGWTNVNI VMNYIRNLDS ETGAMVRLLE DGD                    343

SEQ ID NO: 45          moltype = DNA  length = 1198
FEATURE                Location/Qualifiers
misc_feature           1..1198
                       note = Expression cassette comprising Zea mays
                        rab17promoter, attB1 site, and FLPm coding sequence
source                 1..1198
                       mol_type = other DNA
                       organism = synthetic construct
SEQUENCE: 45
```

```
ctatagtatt ttaaaattgc attaacaaac atgtcctaat tggtactcct gagatactat  60
accctcctgt tttaaaatag ttggcattat cgaattatca ttttactttt taatgttttc  120
tcttctttta atatatttta tgaattttaa tgtattttaa aatgttatgc agttcgctct  180
ggacttttct gctgcgccta cacttgggtg tactgggcct aaattcagcc tgaccgaccg  240
cctgcattga ataatggatg agcaccggta aaatccgcgt acccaacttt cgagaagaac  300
cgagacgtgg cgggccgggc caccgacgca cggcaccagc gactgcacac gtcccgccgg  360
cgtacgtgta cgtgctgttc cctcactggc cgcccaatcc actcatgcat gcccacgtac  420
acccctgccg tggcgcgccc agatcctaat cctttcgccg ttctgcactt ctgctgccta  480
taaatggcgg catcgaccgt cacctgcttc accaccggcg agccacatcg agaacacgat  540
cgagcacaca agcacgaaga ctcgtttagg agaaaccaca aaccaccaag ccgtgcaagc  600
accaagcttg gtcacccggt ccgggcctag aaggccagct tcaagtttgt acaaaaaagc  660
aggcttcgaa ggagatagaa ccaattctct aaggaaatac ttaaccatgg tcgactggat  720
ccaacaatgc cccagttcga catcctctgc aagaccccc ccaaggtgct cgtgaggcag  780
ttcgtggaga ggttcgagag gccctccggc gagaagatcg ccctctgcgc cgccgagctc  840
acctacctct gctggatgat cacccacaac ggcaccgcca ttaagagggc caccttcatg  900
tcatacaaca ccatcatctc caactccctc tccttcgaca tcgtgaacaa gtccctccag  960
ttcaaataca agacccagaa ggccaccatc ctcgaggcct ccctcaagaa gctcatcccc  1020
gcctgggagt tcaccatcat cccctactac ggccagaagc accagtccga catcaccgac  1080
atcgtgtcat ccctccagct tcagttcgag tcctccgagg aggctgacaa gggcaactcc  1140
cactccaaga agatgctgaa ggccctcctc tccgagggcg agtccatctg ggagatca    1198
```

```
SEQ ID NO: 46          moltype = DNA  length = 2370
FEATURE                Location/Qualifiers
misc_feature           1..2370
                       note = Plasmid PHP31004
source                 1..2370
                       mol_type = other DNA
                       organism = synthetic construct
SEQUENCE: 46
ctatagtatt ttaaaattgc attaacaaac atgtcctaat tggtactcct gagatactat  60
accctcctgt tttaaaatag ttggcattat cgaattatca ttttactttt taatgttttc  120
tcttctttta atatatttta tgaattttaa tgtattttaa aatgttatgc agttcgctct  180
ggacttttct gctgcgccta cacttgggtg tactgggcct aaattcagcc tgaccgaccg  240
cctgcattga ataatggatg agcaccggta aaatccgcgt acccaacttt cgagaagaac  300
cgagacgtgg cgggccgggc caccgacgca cggcaccagc gactgcacac gtcccgccgg  360
cgtacgtgta cgtgctgttc cctcactggc cgcccaatcc actcatgcat gcccacgtac  420
acccctgccg tggcgcgccc agatcctaat cctttcgccg ttctgcactt ctgctgccta  480
taaatggcgg catcgaccgt cacctgcttc accaccggcg agccacatcg agaacacgat  540
cgagcacaca agcacgaaga ctcgtttagg agaaaccaca aaccaccaag ccgtgcaagc  600
accaagcttg gtcacccggt ccgggcctag aaggccagct tcaagtttgt acaaaaaagc  660
aggcttcgaa ggagatagaa ccaattctct aaggaaatac ttaaccatgg tcgactggat  720
ccaacaatgc cccagttcga catcctctgc aagaccccc ccaaggtgct cgtgaggcag  780
ttcgtggaga ggttcgagag gccctccggc gagaagatcg ccctctgcgc cgccgagctc  840
acctacctct gctggatgat cacccacaac ggcaccgcca ttaagagggc caccttcatg  900
tcatacaaca ccatcatctc caactccctc tccttcgaca tcgtgaacaa gtccctccag  960
ttcaaataca agacccagaa ggccaccatc ctcgaggcct ccctcaagaa gctcatcccc  1020
gcctgggagt tcaccatcat cccctactac ggccagaagc accagtccga catcaccgac  1080
atcgtgtcat ccctccagct tcagttcgag tcctccgagg aggctgacaa gggcaactcc  1140
cactccaaga agatgctgaa ggccctcctc tccgagggcg agtccatctg ggagatcacc  1200
gagaagatcc tcaactcctt cgagtacacc tccaggttca ctaagaccaa gaccctctac  1260
cagttcctct tcctcgccac cttcatcaac tgcggcaggt tctcagacat caagaacgtg  1320
gaccccaagt ccttcaagct cgtgcagaac aagtacctcg gcgtgatcat ccagtgcctc  1380
gtgaccgaga ccaagacctc cgtgtccagg cacatctact tcttctccgc tcgcggcagg  1440
atcgaccccc tcgtgtacct cgacgagttc ctcaggaact cagagcccgt gctcaagagg  1500
gtgaacagga ccggcaactc ctcctccaac aagcaggagt accagctcct caaggacaac  1560
ctcgtgaggt cctacaacaa ggccctcaag aagaacgccc cctactccat cttcgccatc  1620
aagaacggcc ccaagtccca catcggtagg cacctcatga cctccttcct ctcaatgaag  1680
ggcctcaccg agctcaccaa cgtggtgggc aactggtccg acaagagggc ctccgccgtg  1740
gccaggacca cctacaccca ccagatcacc gccatccccg accactactt cgccctcgtg  1800
tcaaggtact acgcctacga ccccatctcc aaggagatga tcgccctcaa ggacgagact  1860
aaccccatcg aggagtggca gcacatcgag cagctcaagg gctccgccga gggctccatc  1920
aggtaccccg cctggaacgg catcatctcc caggaggtgc tcgactacct ctcctcctac  1980
atcaacagga ggatctgagt ttcgagatat ctagacccag ctttcttgta caaagtggcc  2040
gttaacggat ccagacttgt ccatcttctg gattggccaa cttaattaat gtatgaaata  2100
aaaggatgca cacatagtga catgctaatc actataatgt gggcatcaaa gttgtgtgtt  2160
atgtgtaatt actagttatc tgaataaaag agaaagagat catccatatt tcttatccta  2220
aatgaatgtc acgtgtcttt ataattcttt gatgaaccag atgcatttca ttaaccaaat  2280
ccatatacat ataaatatta atcatatata attaatatca attgggttag caaaacaaat  2340
ctagtctagg tgtgttttgc gaattgcggc                                    2370
```

```
SEQ ID NO: 47          moltype = DNA  length = 2383
FEATURE                Location/Qualifiers
misc_feature           1..2383
                       note = Plasmid PHP30642
source                 1..2383
                       mol_type = other DNA
                       organism = synthetic construct
SEQUENCE: 47
ctatagtatt ttaaaattgc attaacaaac atgtcctaat tggtactcct gagatactat  60
```

```
accctcctgt tttaaaatag ttggcattat cgaattatca ttttactttt taatgttttc  120
tcttctttta atatatttta tgaattttaa tgtattttaa aatgttatgc agttcgctct  180
ggacttttct gctgcgccta cacttgggtg tactgggcct aaattcagcc tgaccgaccg  240
cctgcattga ataatggatg agcaccggta aaatccgcgt acccaacttt cgagaagaac  300
cgagacgtgg cgggccgggc caccgacgca cggcaccagc gactgcacac gtcccgccgg  360
cgtacgtgta cgtgctgttc cctcactggc cgcccaatcc actcatgcat gcccacgtac  420
accccctgccg tggcgcgccc agatcctaat cctttcgccg ttctgcactt ctgctgccta  480
taaatggcgg catcgaccgt cacctgcttc accaccggcg agccacatcg agaacacgat  540
cgagcacaca agcacgaaga ctcgtttagg agaaaccaca aaccaccaag ccgtgcaagc  600
accatggatc caacaatgcc ccagttcgac atcctctgca agaccccccc caaggtgctc  660
gtgaggcagt tcgtggagag gttcgagagg ccctccggcg agaagatcgc cctctgcgcc  720
gccgagctca cctacctctg ctggatgatc acccacaacg gcaccgccat taagagggcc  780
accttcatgt catacaacac catcatctcc aactccctct ccttcgacat cgtgaacaag  840
tccctccagt tcaaatacaa gacccagaag gccaccatcc tcgaggcctc cctcaagaag  900
ctcatccccg cctgggagtt caccatcatc ccctactacg gccagaagca ccagtccgac  960
atcaccgaca tcgtgtcatc cctccagctt cagttcgagt cctccgagga ggctgacaag  1020
ggcaactccc actccaagaa gatgctgaag gccctcctct ccgagggcga gtccatctgg  1080
gagatcaccg agaagatcct caactccttc gagtacacct ccaggttcac taagaccaag  1140
accctctacc agttcctctt cctcgccacc ttcatcaact gcggcaggtt ctcagacatc  1200
aagaacgtgg accccaagtc cttcaagctc gtgcagaaca agtacctcgg cgtgatcatc  1260
cagtgcctcg tgaccgagac caagacctcc gtgtccaggc acatctactt cttctccgct  1320
cgcggcagga tcgacccccct cgtgtacctc gacgagttcc tcaggaactc agagcccgtg  1380
ctcaagaggg tgaacaggac cggcaactcc tcctccaaca agcaggagta ccagctcctc  1440
aaggacaacc tcgtgaggtc ctacaacaag gccctcaaga agaacgcccc ctactccatc  1500
ttcgccatca agaacggccc caagtcccac atcggtaggc acctcatgac ctccttcctc  1560
tcaatgaagg gcctcaccga gctcaccaac gtggtgggca actggtccga caagagggcc  1620
tccgccgtgg ccaggaccac ctacacccac cagatcaccg ccatccccga ccactacttc  1680
gccctcgtgt caaggtacta cgcctacgac cccatctcca aggagatgat cgccctcaag  1740
gacgagacta accccatcga ggagtggcag cacatcgagc agctcaaggg ctccgccgag  1800
ggctccatca ggtaccccgc ctggaacggc atcatctccc aggaggtgct cgactacctc  1860
tcctcctaca tcaacaggag gatctgagtt ctagttcgaa tgtgagttga tccccggcgg  1920
tgtcccccac tgaagaaact atgtgctgta gtatagccgc tggctagcta gctagttgag  1980
tcatttagcg gcgatgattg agtaataatg tgtcacgcat caccatgcat gggtggcagt  2040
ctcagtgtga gcaatgacct gaatgaacaa ttgaaatgaa aagaaaaaag tattgttcca  2100
aattaaacgt tttaaccttt taataggttt atacaataat tgatatatgt tttctgtata  2160
tgtctaattt gttatcatcc atttagatat agacgaaaaa aaatctaaga actaaaacaa  2220
atgctaattt gaaatgaagg gagtatatat tgggataatg tcgatgagat ccctcgtaat  2280
atcaccgaca tcacacgtgt ccagttaatg tatcagtgat acgtgtattc acatttgttg  2340
cgcgtaggcg tacccaacaa ttttgatcga ctatcagaaa gtc                    2383

SEQ ID NO: 48          moltype = AA  length = 31
FEATURE                Location/Qualifiers
REGION                 1..31
                       note = Consensus sequence motif 1
VARIANT                10
                       note = Xaa = His or Asn
VARIANT                16
                       note = Xaa = Phe or Tyr
VARIANT                17
                       note = Xaa = Val or Ile
VARIANT                19
                       note = Xaa = Ser or His
source                 1..31
                       mol_type = protein
                       organism = synthetic construct
SEQUENCE: 48
YEKELEEMKX MTRQEXXAXL RRKSSGFSRG A                                 31

SEQ ID NO: 49          moltype = AA  length = 63
FEATURE                Location/Qualifiers
REGION                 1..63
                       note = Consensus sequence motif 2
VARIANT                2
                       note = Xaa = Ile or Met
VARIANT                36
                       note = Xaa = Gln or Glu
VARIANT                45
                       note = Xaa = Ile or Val
VARIANT                60
                       note = Xaa = Asp or Glu
VARIANT                61
                       note = Xaa = Met or Ile
VARIANT                62
                       note = Xaa = Ser or Asn
source                 1..63
                       mol_type = protein
                       organism = synthetic construct
SEQUENCE: 49
SXYRGVTRHH QHGRWQARIG RVAGNKDLYL GTFSTXEEAA EAYDXAAIKF RGLNAVTNFX  60
```

```
XXR                                                                        63

SEQ ID NO: 50           moltype = AA  length = 68
FEATURE                 Location/Qualifiers
REGION                  1..68
                        note = Consensus sequence motif 3
VARIANT                 2
                        note = Xaa = Ile or Gln
VARIANT                 26
                        note = Xaa = Arg or Lys
VARIANT                 33
                        note = Xaa = Val or Gly
VARIANT                 34
                        note = Xaa = Tyr or Arg
VARIANT                 35
                        note = Xaa = Leu or Gln
VARIANT                 42
                        note = Xaa = Glu or Asp
VARIANT                 58
                        note = Xaa = Pro or Thr
VARIANT                 61
                        note = Xaa = Thr or His
VARIANT                 62
                        note = Xaa = Thr or Ile
VARIANT                 66
                        note = Xaa = Ile, Val, or Leu
source                  1..68
                        mol_type = protein
                        organism = synthetic construct
SEQUENCE: 50
SXYRGVTRHR WTGRYEAHLW DNSCRXEGQX RKXXXGGYDK EXKAARAYDL AALKYWGXXT  60
XXNFPXSN                                                           68

SEQ ID NO: 51           moltype = AA  length = 8
FEATURE                 Location/Qualifiers
REGION                  1..8
                        note = Consensus sequence motif 4
VARIANT                 3
                        note = Xaa = Leu or Val
VARIANT                 4
                        note = Xaa = Glu or Ala
VARIANT                 5
                        note = Xaa = Asp or Asn
source                  1..8
                        mol_type = protein
                        organism = synthetic construct
SEQUENCE: 51
PKXXXFLG                                                           8

SEQ ID NO: 52           moltype = AA  length = 13
FEATURE                 Location/Qualifiers
REGION                  1..13
                        note = Consensus sequence motif 5
VARIANT                 6
                        note = Xaa = Ile or Val
VARIANT                 9
                        note = Xaa = Ala or Leu
VARIANT                 13
                        note = Xaa = Leu or Arg
source                  1..13
                        mol_type = protein
                        organism = synthetic construct
SEQUENCE: 52
SSTLPXGGXA XXX                                                     13

SEQ ID NO: 53           moltype = AA  length = 9
FEATURE                 Location/Qualifiers
REGION                  1..9
                        note = Consensus sequence motif 6
VARIANT                 4
                        note = Xaa = Gly or Ser
source                  1..9
                        mol_type = protein
                        organism = synthetic construct
SEQUENCE: 53
NWLXFSLSP                                                          9

SEQ ID NO: 54           moltype = AA  length = 10
FEATURE                 Location/Qualifiers
```

```
REGION              1..10
                    note = Consensus sequence motif 7
VARIANT             1
                    note = Xaa = Gly or Glu
VARIANT             7
                    note = Xaa = Thr or Asn
source              1..10
                    mol_type = protein
                    organism = synthetic construct
SEQUENCE: 54
XLSMIKXWLR                                                  10

SEQ ID NO: 55       moltype = AA  length = 8
FEATURE             Location/Qualifiers
REGION              1..8
                    note = Consensus sequence motif 8
source              1..8
                    mol_type = protein
                    organism = synthetic construct
SEQUENCE: 55
PXFXXWND                                                    8

SEQ ID NO: 56       moltype = AA  length = 5
FEATURE             Location/Qualifiers
REGION              1..5
                    note = Consensus sequence motif 9
VARIANT             2
                    note = Xaa = Ser, Thr, or Ala
source              1..5
                    mol_type = protein
                    organism = synthetic construct
SEQUENCE: 56
LXLSM                                                       5

SEQ ID NO: 57       moltype = AA  length = 7
FEATURE             Location/Qualifiers
REGION              1..7
                    note = Consensus sequence motif 10
VARIANT             4
                    note = Xaa = Gln or Pro
source              1..7
                    mol_type = protein
                    organism = synthetic construct
SEQUENCE: 57
WCKXEQD                                                     7

SEQ ID NO: 58       moltype = AA  length = 7
FEATURE             Location/Qualifiers
REGION              1..7
                    note = Consensus sequence motif 14
source              1..7
                    mol_type = protein
                    organism = synthetic construct
SEQUENCE: 58
WPTIAFQ                                                     7

SEQ ID NO: 59       moltype = AA  length = 11
FEATURE             Location/Qualifiers
REGION              1..11
                    note = Consensus sequence motif 15
VARIANT             2
                    note = Xaa = Ser or Thr
source              1..11
                    mol_type = protein
                    organism = synthetic construct
SEQUENCE: 59
SXGSNSVVYN G                                                11

SEQ ID NO: 60       moltype = AA  length = 7
FEATURE             Location/Qualifiers
REGION              1..7
                    note = Consensus sequence motif 19
VARIANT             4
                    note = Xaa = Ser or Asn
source              1..7
                    mol_type = protein
                    organism = synthetic construct
SEQUENCE: 60
QDWXMRG                                                     7
```

```
SEQ ID NO: 61          moltype = DNA  length = 975
FEATURE                Location/Qualifiers
source                 1..975
                       mol_type = genomic DNA
                       organism = Zea mays
CDS                    1..975
SEQUENCE: 61
atggagacgc cacagcagca atccgccgcc gccgccgccg ccgccgccca cgggcaggac  60
gacggcgggt cgccgccgat gtcgccggcc tccgccgcgg cggcggcgct ggcgaacgcg  120
cggtggaacc cgaccaagga gcaggtggcc gtgctggagg ggctgtacga gcacggcctg  180
cgcaccccca gcgcggagca gatacagcag atcacgggca ggctgcggga gcacggcgcc  240
atcgagggca agaacgtctt ctactggttc cagaaccaca aggcccgcca gcgccagagg  300
cagaagcagg acagcttcgc ctacttcagc aggctcctcc gccggccccc gccgctgccc  360
gtgctctcca tgcccccgc gccaccgtac catcacgccc gcgtcccggc gccgcccgcg  420
ataccgatgc cgatggcgcc gccgccgccc gctgcatgca acgacaacgg cggcgcgcgt  480
gtgatctaca ggaacccatt ctacgtggct gcgccgcagg cgcccccctgc aaatgccgcc  540
tactactacc cacagccaca gcagcagcag cagcagcagg tgacagtcat gtaccagtac  600
ccgagaatgg aggtagccgg ccaggacaag atgatgacca gggccgcggc gcaccagcag  660
cagcagcaca acggcgccgg gcaacaaccg ggacgcgccg gccaccccag ccgcgagacg  720
ctccagctgt tcccgctcca gcccaccttc gtgctgcggc acgacaaggg gcgcgccgcc  780
aacggcagta ataacgactc cctgacgtcg acgtcgacgg cgactgcgac agcgacagcg  840
acagcgacag cgtccgcttc catctccgag gactcggatg gcctggagag cggcagctcc  900
ggcaagggcg tcgaggaggc gcccgcgctg ccgttctatg acttcttcgg gctccagtcc  960
tccggaggcc gctga                                                   975

SEQ ID NO: 62          moltype = AA  length = 324
FEATURE                Location/Qualifiers
source                 1..324
                       mol_type = protein
                       organism = Zea mays
SEQUENCE: 62
METPQQQSAA AAAAAAHGQD DGGSPPMSPA SAAAAALANA RWNPTKEQVA VLEGLYEHGL  60
RTPSAEQIQQ ITGRLREHGA IEGKNVFYWF QNHKARQRQR QKQDSFAYFS RLLRRPPPLP  120
VLSMPPAPPY HHARVPAPPA IPMPMAPPPP AACNDNGGAR VIYRNPFYVA APQAPPANAA  180
YYYPQPQQQQ QQQVTVMYQY PRMEVAGQDK MMTRAAAHQQ QQHNGAGQQP GRAGHPSRET  240
LQLFPLQPTF VLRHDKGRAA NGSNNDSLTS TSTATATATA TATASASISE DSDGLESGSS  300
GKGVEEAPAL PFYDFFGLQS SGGR                                         324

SEQ ID NO: 63          moltype = DNA  length = 909
FEATURE                Location/Qualifiers
source                 1..909
                       mol_type = genomic DNA
                       organism = Zea mays
CDS                    1..909
SEQUENCE: 63
atggcggcca atgcgggcgg cggtggagcg ggaggaggca gcggcagcgg cagcgtggct  60
gcgccggcgg tgtgccgccc cagcggctcg cggtggacgc cgacgccgga gcagatcagg  120
atgctgaagg agctctacta cggctgcggc atccggtcgc ccagctcgga gcagatccag  180
cgcatcaccg ccatgctgcg gcagcacggc aagatcgagg gcaagaacgt cttctactgg  240
ttccagaacc acaaggcccg cgagcgccag aagcgccgcc tcaccagcct cgacgtcaac  300
gtgcccgccg ccggcgcggc cgacgccacc accagccaac tcggcgtcct ctcgctgtcg  360
tcgccgccgc cttcaggcgc ggcgcctccc tcgcccaccc tcggcttcta cgccgccggc  420
aatggcggcg gatcggctgt gctgctggac acgagttccg actggggcag cagcggcgct  480
gccatggcca ccgagacatg cttcctgcag gactacatgg gcgtgacgga cacgggcagc  540
tcgtcgcagt ggccacgctt ctcgtcgtcg gacacgataa tggcggcggc cgcggcgcgg  600
gcggcgacga cgcgggcgcc cgagacgctc cctctcttcc cgacctgcgg cgacgacggc  660
ggcagcggta gcagcagcta cttgccgttc tggggtgccg cgtccacaac tgccggcgcc  720
acttcttccg ttgcgatcca gcagcaacac cagctgcagg agcagtacag cttttacagc  780
aacagcaaca gcacccagct ggccggcacc ggcaaccaag acgtatcggc aacagcagca  840
gcagccgccg ccctggagct gagcctcagc tcatggtgct ccccttaccc tgctgcaggg  900
agtatgtga                                                          909

SEQ ID NO: 64          moltype = AA  length = 302
FEATURE                Location/Qualifiers
source                 1..302
                       mol_type = protein
                       organism = Zea mays
SEQUENCE: 64
MAANAGGGGA GGGSGSGSVA APAVCRPSGS RWTPTPEQIR MLKELYYGCG IRSPSSEQIQ  60
RITAMLRQHG KIEGKNVFYW FQNHKARERQ KRRLTSLDVN VPAAGAADAT TSQLGVLSLS  120
SPPPSGAAPP SPTLGFYAAG NGGGSAVLLD TSSDWGSSGA AMATETCFLQ DYMGVTDTGS  180
SSQWPRFSSS DTIMAAAAAR AATTRAPETL PLFPTCGDDG GSGSSSYLPF WGAASTTAGA  240
TSSVAIQQQH QLQEQYSFYS NSNSTQLAGT GNQDVSATAA AAAALELSLS SWCSPYPAAG  300
SM                                                                 302

SEQ ID NO: 65          moltype = DNA  length = 961
FEATURE                Location/Qualifiers
source                 1..961
```

```
                         mol_type = genomic DNA
                         organism = Zea mays
SEQUENCE: 65
gatccgattg actatctcat tcctccaaac ccaaacacct caaatatatc tgctatcggg  60
attggcattc ctgtatccct acgcccgtgt accccctgtt tagagaacct cccaaggtat  120
aagatggcga agattattgt tgtcttgtct ttcatcatat atcgagtctt tccctaggat  180
attattattg gcaatgagca ttacacggtt aatcgattga gagaacatgc atctcacctt  240
cagcaaataa ttacgataat ccatatttta cgcttcgtaa cttctcatga gtttcgatat  300
acaaatttgt tttctggaca ccctaccatt catcctcttc ggagaagaga ggaagtgtcc  360
tcaatttaaa tatgttgtca tgctgtagtt cttcacccaa tctcaacagg taccaagcac  420
attgtttcca caaattatat tttagtcaca ataaatctat attattatta atatactaaa  480
actatactga cgctcagatg cttttactag ttcttgctag tatgtgatgt aggtctacgt  540
ggaccagaaa atagtgagac acggaagaca aaagaagtaa aagaggcccg gactacggcc  600
cacatgagat tcggccccgc cacctccggc aaccagcggc cgatccaacg gaagtgcgcg  660
cacacacaca acctcgtata tatcgccgcg cggaagcggc gcgaccgagg aagccttgtc  720
ctcgacaccc cctacacagg tgtcgcgctg cccccgacac gagtcccgca tgcgtcccac  780
gcggccgcgc cagatcccgc ctccgcgcgt tgccacgccc tctataaaca cccagctctc  840
cctcgccctc atctacctca ctcgtagtcg tagctcaagc atcagcggca gcggcagcgg  900
caggagctct gggcagcgtg cgcacgtggg gtacctagct cgctctgcta gcctacctta  960
a                                                                  961

SEQ ID NO: 66            moltype = DNA  length = 1917
FEATURE                  Location/Qualifiers
source                   1..1917
                         mol_type = genomic DNA
                         organism = Zea mays
CDS                      1..1917
SEQUENCE: 66
atgaccagca acagcagcca gaacatgagc agctgcagca ccggcggaag cgacgcggcg  60
gtcggcggcg gcagctggct cggcttctcg ctgtcgcctc acatggcggc gaccatggac  120
ggcgcggccg acggcgttcc ggtgcagcac caccaccacg aaggcctctt ctaccctccc  180
gtcgtcagct cctcgcccgc gcccttctgc tacgctctcg gcggcggcca agatggcctc  240
gccacggcgg ccgccaatgg tggcgggggg ttctaccccg ggctctcctc tatgccgctc  300
aagtccgacg gctccctatg catcctggag gccctccaca ggagcgagca agaacggcac  360
ggggtggtgg tgtcgtcgtc gtcgcccaaa ctggaggatt tcttgggcgc gagcgcgagc  420
acggcgatgg cgctgagctt ggacagctcc agcttctact acggctgcgg ccacggccac  480
ggccacgacc aaggcgggta cctgcagcca atgcagtgcg cggtgatgcc cggctcgggc  540
gggcacgacg tgtacggcgg cggcacgcg cagatggtgg acgagcagtc cgccgcggca  600
atggcggcga gctggttctc cgcccgcggc aatggcggct acgacgtcga cggcgccggc  660
gccggcgcca tcgtgccgtt gcagggccac ccgcacccgc tcgccctctc catgagctcc  720
gggacggggt cccagtccag cagcgtcacc atgcaagtcg gcagcgccca cgccgacgcc  780
gtcaccgagt acatcgccat ggacgggagc aagaagcgcg gcgccggcaa cggcgctagt  840
gccgggcaga agcagcccac catccaccgc aagaccatcg acacattcgg gcagcgcacg  900
tcgcagtacc gcggcgtcac caggcatagg tggacgggga ggtatgaggc gcacctctgg  960
gacaacagct gcaggaagga agggcagacc cggaaaggcc ggcaagttta tctcggcggg  1020
tatgacgtgg aggagaaggc cgcgagggca tatgacctgg cggcgctcaa gtactggggg  1080
acgtccacgc acgtgaattt cccggtggag gactacaggg aagagctgga ggagatgaag  1140
aacatgacca gacaggagta cgtcgctcac ctgagaagga aaagcagcgg cttctcgcgc  1200
ggcgcttcga tctaccgggg agtcaccagg catcaccagc acgggcggtg gcaggcgcgc  1260
atcggccgcg tctcgggcaa caaggacctc tacctcggaa cgttcagcac ccaggaggag  1320
gcggcggagg cgtacgacgt ggccgcgatc aagttccgcg gcctcagcgc ggtcaccaac  1380
ttcgacatca cgcggtacga cgtggacaag atcatggaga gcagcacgct gctcccgggc  1440
gagcaggtcc ggcgcaggaa ggaaggcgcc gacgccgcgg tctcggaggc cgccgccgcg  1500
ctggtgcagg ccggcaactg catgacggac acctggaaga tccaggcggc gctgccggct  1560
gccgcgcggg ccgacgagcg cggcgccggc cagcagcagc gtcaggactt gctgtcgagc  1620
gaggccttct cgctgctcca cgacatcgtg tccgtcgacg ccgctgctgg tacagggaca  1680
gggggcatgt cgaacgcgtc ctcgtcgctg gcccccagcg tgagcaactc ccgggagcag  1740
agcccggacc ggggcggcgc cagcctcgcc atgctcttcg ccaagcccgc cgcggcgccc  1800
aagctggctt gcccgctgcc gctggggtcc tgggtgtcgc cgtccgcggt gtccgccagg  1860
ccgcccggcg tgtcaatcgc gcacctgccg gtgttcgccg cgtggaccga cgcatga     1917

SEQ ID NO: 67            moltype = AA  length = 638
FEATURE                  Location/Qualifiers
source                   1..638
                         mol_type = protein
                         organism = Zea mays
SEQUENCE: 67
MTSNSSQNMS SCSTGGSDAA VGGGSWLGFS LSPHMAATMD GAADGVPVQH HHHEGLFYPP  60
VVSSSPAPFC YALGGGQDGL ATAAANGGGG FYPGLSSMPL KSDGSLCILE ALHRSEQERH  120
GVVVSSSSPK LEDFLGASAS TAMALSLDSS SFYYGCGHGH GHDQGGYLQP MQCAVMPGSG  180
GHDVYGGGHA QMVDEQSAAA MAASWFSARG NGGYDVDGAG AGAIVPLQGH PHPLALSMSS  240
GTGSQSSSVT MQVGSAHADA VTEYIAMDGS KKRGAGNGAS AGQKQPTIHR KTIDTFGQRT  300
SQYRGVTRHR WTGRYEAHLW DNSCRKEGQT RKGRQVYLGG YDVEEKAARA YDLAALKYWG  360
TSTHVNFPVE DYREELEEMK NMTRQEYVAH LRRKSSGFSR GASIYRGVTR HHQHGRWQAR  420
IGRVSGNKDL YLGTFSTQEE AAEAYDVAAI KFRGLSAVTN FDITRYDVDK IMESSTLLPG  480
EQVRRRKEGA DAAVSEAAAA LVQAGNCMTD TWKIQAALPA AARADERGAG QQQRQDLLSS  540
EAFSLLHDIV SVDAAAGTGT GGMSNASSSL APSVSNSREQ SPDRGGASLA MLFAKPAAAP  600
KLACPLPLGS WVSPSAVSAR PPGVSIAHLP VFAAWTDA                          638
```

```
SEQ ID NO: 68          moltype = DNA  length = 2260
FEATURE                Location/Qualifiers
source                 1..2260
                       mol_type = genomic DNA
                       organism = Zea mays
SEQUENCE: 68
cttccctaac ctttgcactg tccaaaatgg cttcctgatc ccctcacttc ctcgaatcaa  60
tctaagaaga aactcaagcc gcaaccatta ggggcagatt aattgctgca ctttcagata  120
atcaaccatg gccactgtga acaactggct cgctttctcc ctctccccgc aggagctgcc  180
gccctcccag acgacggact ccacactcat ctcggccgcc accgccgacc atgtctccgg  240
cgatgtctgc ttcaacatcc cccaagattg gagcatgagg ggatcagagc tttcggcgct  300
cgtcgcggag ccgaagctgg aggacttcct cggcggcatc tccttctccg agcagcatca  360
caaggccaac tgcaacatga tacccagcac tagcagcaca gtttgctacg cgagctcagg  420
tgctagcacc ggctaccatc accagctgta ccaccagccc accagctcag cgctccactt  480
cgcggactcc gtaatggtgg cctcctcggc cggtgtccac gacggcggtg ccatgctcag  540
cgcggccgcc gctaacggtg tcgctggcgc tgccagtgcc aacggcggcg gcatcgggct  600
gtccatgatt aagaactggc tgcggagcca accggcgccc atgcagccga gggtggcggc  660
ggctgagggc gcgcaggggc tctctttgtc catgaacatg gcggggacga cccaaggcgc  720
tgctggcatg ccacttctcg ctggagagcg cgcacgggcg cccgagagtg tatcgacgtc  780
agcacagggt ggagccgtcg tcgtcacggc gccgaaggag gatagcggtg gcagcggtgt  840
tgccggcgct ctagtagccg tgagcacgga cacgggtggc agcggcggcg cgtcggctga  900
caacacggca aggaagacgg tggacacgtt cgggcagcgc acgtcgattt accgtggcgt  960
gacaaggcat agatggactg ggagatatga ggcacatctt tgggataaca gttgcagaag  1020
ggaagggcaa actcgtaagg gtcgtcaagt ctatttaggt ggctatgata aagaggagaa  1080
agctgctagg gcttatgatc ttgctgctct gaagtactgg ggtgccacaa caacaacaaa  1140
ttttccagtg agtaactacg aaaaggagct cgaggacatg aagcacatga caaggcagga  1200
gtttgtagcg tctctgagaa ggaagagcag tggtttctcc agaggtgcat ccatttacag  1260
gggagtgact aggcatcacc aacatggaag atggcaagca cggattggac gagttgcagg  1320
gaacaaggat ctttacttgg gcaccttcag cacccaggag gaggcagcgg aggcgtacga  1380
catcgcggcg atcaagttcc gcggcctcaa cgccgtcacc aacttcgaca tgagccgcta  1440
cgacgtgaag agcatcctgg acagcagcgc cctccccatc ggcagcgccg ccaagcgcct  1500
caaggaggcc gaggccgcag cgtccgcgca gcaccaccac gccggcgtgg tgagctacga  1560
cgtcggccgc atcgcctcgc agctcggcga cggcggagcc ctggcggcgg cgtacggcgc  1620
gcactaccac ggcgccgcct ggccgaccat cgcgttccag ccgggcgccg ccagcacagg  1680
cctgtaccac ccgtacgcgc agcagccaat gcgcggcggc gggtggtgca agcaggagca  1740
ggaccacgcg gtgatcgcgg ccgcgcacag cctgcaggac ctccaccacc tgaacctggg  1800
cgcggccggc gcgcacgact ttttctcggc agggcagcag gccgccgccg ctgcgatgca  1860
cggcctgggt agcatcgaca gtgcgtcgct cgagcacagc accggctcca actccgtcgt  1920
ctacaacggc ggggtcggcg acagcaacgg cgccagcgcc gtcggcggca gtggcggtgg  1980
ctacatgatg ccgatgagcg ctgccggagc aaccactaca tcggcaatgg tgagccacga  2040
gcaggtgcat gcacgggcct acgacgaagc caagcaggct gctcagatgg ggtacgagag  2100
ctacctggtg aacgcggaga acaatggtgg cggaaggatg tctgcatggg ggactgtcgt  2160
gtctgcagcc gcggcggcag cagcaagcag caacgacaac atggccgccg acgtcggcca  2220
tggcggcgcg cagctcttca gtgtctggaa cgacacttaa                        2260

SEQ ID NO: 69          moltype = DNA  length = 3766
FEATURE                Location/Qualifiers
source                 1..3766
                       mol_type = genomic DNA
                       organism = Sorghum bicolor
SEQUENCE: 69
atggctactg tgaacaactg gctcgctttc tccctctccc cgcaggagct gccgcccacc  60
cagacggact ccaccctcat ctctgccgcc accaccgacg atgtctccgg cgatgtctgc  120
ttcaacatcc cccaaggtat gcatctatcg atcgatatat gtacgtacag tgcgcatata  180
tatatatatc tgcagtttgt ggtacgaata ctgattgaag ctagcatgaa atgtcgtttg  240
ttctttcaga ttggagcatg aggggatccg agctttcggc gctcgtcgcc gagccgaagc  300
tggaggactt cctcggcgga atctccttct ccgagcagca ccacaaggcc aactgcaaca  360
tgatccccag cactagcagc acagcttgct acgcgagctc gggtgctacc gccggctacc  420
atcaccagct gtaccaccag cccaccagct ccgcgctcca cttcgctgac tccgtcatgg  480
tggcctcctc ggccggcggc gtccacgacg gaggtgccat gctcagcgcg gccagcgcta  540
atggtagcgc tggcgctggc gctgccagtg ccaatggcag cggcagcatc gggctgtcca  600
tgatcaagaa ctggctgcgg agccaaccag ctcccatgca gccgagggtg gcggcggctg  660
agagcgtgca ggggctctct ttgtccatga acatggcggg ggcgacgcaa ggcgccgctg  720
gcatgccact tcttgctgga gagcgcggcc gggcgcccga gagtgtctcg acgtcggcac  780
agggtggagc cgtcgtcacg gctccaaagg aggatagcgg tggcagcggt gttgccgcca  840
ccggcgccct agtagccgtg agcacggaca cgggtggcag cggcgcgtcg gctgacaaca  900
cggcaaggaa gacggtggac acgttcgggc agcgcacgtc gatttaccgt ggcgtgacaa  960
ggtaataagg gtccggtatt acaatgaatc gtcacttcgt cagagaacta aactagcaca  1020
aatcagcaat gaatcaagta atatcatgaa atttagaaaa gccgttagca atgcaaggag  1080
ctatcattat agatttgatt gcatctagac agttctgaat taaatgagta gggcaatgtg  1140
tagcctttga tgatctcgct gattattagg agtgccattt gtattggcta tgattgtggt  1200
atatacagca gtagacaatt aacaaaaggc taccactttc gaattatttt aggcatagat  1260
ggactgggag atatgaagca catctgtggg acaacagttg cagaagggaa ggacaaactc  1320
gcaagggtcg tcaaggtacc aatataatgc aatacaccgt atttaaatat atatgctttt  1380
ctgtaattaa gtttatactt tcacaaaact gacattactt cgcattatca tttttggatt  1440
gtcgtcgtca tgattggcgg gattgaaatg aactattgaa tctacagtct atttaggtaa  1500
gcgatttcac ttggttatta atttgggacc aactacttaa tccagtttgt ttttccccta  1560
taaccattat tttttcatct gtgttctcaa ctcttacttt tccatcttgt tccactgata  1620
ggtggctatg ataaagagga gaaagctgct agggcttatg atctggctgc tcttaagtac  1680
```

```
tggggtccca cgacaacaac aaattttcca gtatgtatat gtagaatgca gttttacttc  1740
actgaagatc ataccttttgc tatgtctcaa atgccgttca ttagttagtg gatctgaagt  1800
gaaggttctg taatttttgt taactatgta cattgctgga attgtactta aagtcatttg  1860
tttttgtata tctaggtgaa taactacgaa aaggagctgg aggatatgaa gcacatgaca  1920
aggcaggagt ttgtagcgtc tctgagaagg tcggtcgaac agcattgatt aatcaatgcc  1980
aactctattg aataaacatc tactctgtta attgttaaag tttgagagaa agatctgcat  2040
gttagatctt aatagaccac tgtatatgaa tgcaggaaga gcagtggttt ctccagaggt  2100
gcatccattt acaggggagt gactaggtat gaattcatat aatggcgtca acaaacacac  2160
atacactttg attgaggagg cgaatgcacg catggattga atgtgaatgg tgttttactt  2220
gaactatgta attataggca tcaccagcat ggaagatggc aagcacggat tggacgagtt  2280
gcagggaaca aggatctcta cttgggcacc ttcagtaagt atcagagatg ttttctcatt  2340
gtatatagag gagtacttct atatgtatat atacattcag ttattcacca cacaaaagca  2400
aattgcagtc aactaataac aatctcaacg caatgagaag caagtgttac agctgatagt  2460
acacatttgt agaccttctg catatggatg ttatatatga tgactattaa aaatgtgacc  2520
attgcatcaa gtcatgcaaa gttgcattgc agtagtacat acattactta gtgcatgctc  2580
ctcaagtggc tttttcaaac ctgatcccat gtctggcgct attgttgtct cccattcacc  2640
cgtgcatcag gtcaaaatag tactatgcct caataagaaa cacatgagca tgcactggca  2700
gcagcagact aatcaagttc tatcatttac taataaacta attaggctac agcatccaaa  2760
agattctacc cattaagcca caactgttca tgcatgcatt cataaaccag gataccacca  2820
tgcatgcgtg caccgtgttc gtgcttggaa tattgagctg agccgagtgc acccttgcgt  2880
ggatgcaggc acgcaggagg aggcagcgga ggcatacgac attgcggcga tcaagttccg  2940
cggcctcaac gccgtcacaa acttcgacat gagccgctac gacgtcaaga gcatcctgga  3000
cagcagtgcg ctccccatcg gcagcgccgc caagcgtctc aaggaggccg aggccgccgc  3060
gtccgcacag caccatgccg gcgtggtgag ctacgacgtc ggccgcatag cctcacagct  3120
cggcgacggc ggcgccctgg cggcggcgta cggcgcgcac taccatggcg cctggccgac  3180
catcgcgttc cagccgagcg cggccacggg cctgtaccac ccgtacgcgc agccgatgcg  3240
cgggtggtgc aagcaggagc aggaccacgc ggtgatcgcg gccgcgcaca gcctgcagga  3300
gctccaccac ctgaacctgg gtgctgccgc cggcgcgcac gacttcttct cggcggggca  3360
gcaggcggcg atgcacggcc tgggtagcat ggacaatgca tcactcgagc acagcaccgg  3420
ctccaactcc gtcgtgtaca acggtgttgg tgatagcaac ggcagcaccg tcgtcggcag  3480
tggtggctac atgatgccta tgagcgctgc cacggcgacg gctaccacgg caatggtgag  3540
ccacgagcag gtgcatgcac gggcacaggg tgatcaccac gacgaagcca agcaggctgc  3600
tcagatgggg tacgagagct acctggtgaa cgcagagaac tatggcggcg ggaggatgtc  3660
tgcggcctgg gcgactgtct cagcgccacc ggcggcaagc agcaacgata acatggcgga  3720
cgtcggccat ggcggcgcac agctcttcag tgtctggaac gatact                3766
```

```
SEQ ID NO: 70          moltype = AA  length = 530
FEATURE                Location/Qualifiers
source                 1..530
                       mol_type = protein
                       organism = Glycine max
SEQUENCE: 70
MDSSSSSPPN STNNNSLAFS LSNHFPNPSS SPLSLFHSFT YPSLSLTGSN TVDAPPEPTA  60
GAGPTNLSIF TGGPKFEDFL GGSAATATTV ACAPPQLPQF STDNNNHLYD SELKSTIAAC  120
FPRALAAEQS TEPQKPSPKK TVDTFGQRTS IYRGVTRHRW TGRYEAHLWD NSCRREGQSR  180
KGRQVYLGGY DKEDKAARAY DLAALKYWGP TTTTNFPISN YEKELEEMKN MTRQEFVASL  240
RRKSSGFSRG ASIYRGVTRH HQHGRWQARI GRVAGNKDLY LGTFSTQEEA AEAYDIAAIK  300
FRGLNAVTNF DMSRYDVKSI ANSTLPIGGL SGKNKNSTDS ASESKSHEPS QSDGDPSSAS  360
SVTFASQQQP SSSNLSFAIP IKQDPSDYWS ILGYHNTPLD NSGIRNTTST VTTTTFPSSN  420
NGTASSLTPF NMEFSSAPSS TGSDNNAAFF SGGGIFVQQQ TSHGHGNASS GSSSSSLSCS  480
IPFATPIFSL NSNTSYESSA GYGNWIGPTL HTFQSHAKPS LFQTPIFGME             530
```

```
SEQ ID NO: 71          moltype = AA  length = 528
FEATURE                Location/Qualifiers
source                 1..528
                       mol_type = protein
                       organism = Glycine max
SEQUENCE: 71
MDSCSSPPNN NSLAFSLSNH FPNPSSSPLS LFHSFTYPSL SLTGSHTADA PPEPIAGGGA  60
TNLSIFTGAP KFEDFLGGSS ATATATTCAP PQLPQFSTDN NNHLYDSELK TTIAACFPRA  120
FAAEPTTEPQ KPSPKKTVDT FGQRTSIYRG VTRHRWTGRY EAHLWDNSCR REGQSRKGRQ  180
VYLGGYDKED KAARAYDLAA LKYWGPTTTT NFPISNYEKE LEEMKNMTRQ EFVASLRRKS  240
SGFSRGASIY RGVTRHHQHG RWQARIGRVA GNKDLYLGTF STQEEAAEAY DIAAIKFRGL  300
NAVTNFDMSR YDVKSIANST LPIGGLSGKN KNSTDSASES KSHEASRSDE RDPSAASSVT  360
FASQQQPSSS TLSFAIPIKQ DPSDYWSILG YHNSPLDNTG IRNTTSVTAT SFPSSNNGTT  420
SSLTPFHMEF SNAPTSTGSD NDAAFFSGGG IFVQQQSGHG NGHGSGSSGS SSSSLSCSIP  480
FATPIFSLNS NTSYENSAGY GNWIGPTLHT FQSHAKPSLF QTPIFGME               528
```

```
SEQ ID NO: 72          moltype = AA  length = 488
FEATURE                Location/Qualifiers
source                 1..488
                       mol_type = protein
                       organism = Zea mays
SEQUENCE: 72
MDMDMSSAYP HHWLSFSLSN NYHHGLLEAF SNSSGTPLGD EQGAVEESPR TVEDFLGGVG  60
GAGAPPQPAA AADQDHQLVC GELGSITARF LRHYPAAPAG TTVENPGAVT VAAMSSTDVA  120
GAESDQARRP AETFGQRTSI YRGVTRHRWT GRYEAHLWDN SCRREGQSRK GRQVYLGGYD  180
KEEKAARAYD LAALKYWGPT TTTNFPVSNY EKELEEMKSM TRQEFIASLR RKSSGFSRGA  240
SIYRGVTRHH QHGRWQARIG RVAGNKDLYL GTFSTQEEAA EAYDIAAIKF RGLNAVTNFD  300
```

```
MSRYDVESIL SSDLPVGGGA SGRAPAKFPL DSLQPGSAAA MMLAGAAAAS QATMPPSEKD  360
YWSLLALHYQ QQQEQERQFP ASAYEAYGSG GVNVDFTMGT SSGNNNNNTG SGVMWGATTG  420
AVVVGQQDSS GKQGNGYASN IPYAAAAMVS GSAGYEGSTG DNGTWVTTTT SSNTGTAPHY  480
YNYLFGME                                                         488

SEQ ID NO: 73          moltype = AA  length = 495
FEATURE                Location/Qualifiers
source                 1..495
                       mol_type = protein
                       organism = Oryza sativa
SEQUENCE: 73
MDMDTSHHYP WLNFSLAHHC EMEEEERGAA AELAAIAGAA PPPKLEDFLG GGCNGGSSGG  60
ACPPVQTTAP TAAELYESEL KFLAAGFQLS GAAGAAPPVP ALLPAAALEQ TDETKQLALP  120
PQAAVAPPPE QKKAVDSFGQ RTSIYRGVTR HRWTGRYEAH LWDNSCRREG QSRKGRQVYL  180
GGYDKEEKAA RAYDLAALKY WGPSTTTNFP VAEYEKELEE MKHMTRQEFV ASLRRKSSGF  240
SRGASIYRGV TRHHQHGRWQ ARIGRVAGNK DLYLGTFGTE EEAAEAYDIA AIKFRGLNAV  300
TNFEIGRYNV ESIISSNLPI GSMAGNRSTK AGLELAPSSS ADAIAATEAN HTGVAPPSTL  360
AFTALPMKYD QADYLSYLAL QHHQQGNLQG LGFGLYSSGV NLDFANANGN GAMSNCYTNV  420
SLHEQQQQHQ HQHQQEQQQD QQDDQSQSSN NSCGSIPFAT PIAFSGSYES SMTAAGTFGY  480
YPNVAAFQTP IFGME                                                 495

SEQ ID NO: 74          moltype = AA  length = 558
FEATURE                Location/Qualifiers
source                 1..558
                       mol_type = protein
                       organism = Arabidopsis thaliana
SEQUENCE: 74
MKNNNNKSSS SSSYDSSLSP SSSSSSHQNW LSFSLSNNNN NFNSSSNPNL TSSTSDHHHP  60
HPSHLSLFQA FSTSPVERQD GSPGVSPSDA TAVLSVYPGG PKLENFLGGG ASTTTTRPMQ  120
QVQSLGGVVF SSDLQPPLHP PSAAEIYDSE LKSIAASFLG NYSGGHSSEV SSVHKQQPNP  180
LAVSEASPTP KKNVESFGQR TSIYRGVTRH RWTGRYEAHL WDNSCRREGQ SRKGRQVYLG  240
GYDKEDKAAR AYDLAALKYW GPTTTTNFPI SNYESELEEM KHMTRQEFVA SLRRKSSGFS  300
RGASMYRGVT RHHQHGRWQA RIGRVAGNKD LYLGTFSTQE EAAEAYDIAA IKFRGLNAVT  360
NFDISRYDVK SIASCNLPVG GLMPKPSPAT AAADKTVDLS PSDSPSLTTP SLTFNVATPV  420
NDHGGTFYHT GIPIKPDPAD HYWSNIFGFQ ANPKAEMRPL ANFGSDLHNP SPGYAIMPVM  480
QEGENNFGGS FVGSDGYNNH SAASNPVSAI PLSSTTTMSN GNEGYGGNIN WINNNISSSY  540
QTAKSNLSVL HTPVFGLE                                              558

SEQ ID NO: 75          moltype = AA  length = 568
FEATURE                Location/Qualifiers
source                 1..568
                       mol_type = protein
                       organism = Arabidopsis thaliana
SEQUENCE: 75
MNSNNWLAFP LSPTHSSLPP HIHSSQNSHF NLGLVNDNID NPFQNQGWNM INPHGGGGEG  60
GEVPKVADFL GVSKSGDHHT DHNLVPYNDI HQTNASDYYF QTNSLLPTVV TCASNAPNNY  120
ELQESAHNLQ SLTLSMGSTG AAAAEVATVK ASPAETSADN SSSTTNTSGG AIVEATPRRT  180
LETFGQRTSI YRGVTRHRWT GRYEAHLWDN SCRREGQSRK GRQVYLGGYD KEEKAARAYD  240
LAALKYWGPS TTTNFPITNY EKEVEEMKNM TRQEFVASIR RKSSGFSRGA SMYRGVTRHH  300
QHGRWQARIG RVAGNKDLYL GTFSTEEEAA EAYDIAAIKF RGLNAVTNFE INRYDVKAIL  360
ESNTLPIGGG AAKRLKEAQA LESSRKREEM IALGSNFHQY GAASGSSSVA SSSRLQLQPY  420
PLSIQQPFEH LHHHQPLLTL QNNNDISQYH DSFSYIQTQL HLHQQQTNNY LQSSSHTSQL  480
YNAYLQSNPG LLHGFVSDNN NTSGFLGNNG IGIGSSSTVG SSAEEEFPAV KVDYDMPPSG  540
GATGYGGWNS GESAQGSNPG GVFTMWNE                                   568

SEQ ID NO: 76          moltype = AA  length = 474
FEATURE                Location/Qualifiers
source                 1..474
                       mol_type = protein
                       organism = Sorghum bicolor
SEQUENCE: 76
MDMDMSSAYP HHWLSFSLSN NYHHGLLEAF SNSSSAAPLG DEQGTVEESP KMVEDFLGGV  60
GGAGAPPAAA TAAEDHQLVC GELGSITAGF LRHYPAPGTT VENPGAVTVA AMSTDVAESD  120
QARRPAETFG QRTSIYRGVT RHRWTGRYEA HLWDNSCRRE GQSRKGRQVY LGGYDKEEKA  180
ARAYDLAALK YWGATTTTNF PVSNYEKELE EMKSMTRQEF IASLRRKSSG FSRGASIYRG  240
VTRHHQHGRW QARIGRVAGN KDLYLGTFST QEEAAEAYDI AAIKFRGLNA VTNFDMSRYD  300
VDSILNSDLP VGGGAAGRAS KFPLDSLQPG SAAAMIAGAA SQAMPPSEKD YWSLLALHYQ  360
QQQQQQQFPA SAYEAYGSGV NVDFTMGTSS HSSSNTGSGV MWGTTTGAMG QQDSSSSKQG  420
NGYASNIPYA AAAAAMVSGS AGYEGSTGNN GTWVTSSTST STAPQYYNYL FGME        474

SEQ ID NO: 77          moltype = AA  length = 549
FEATURE                Location/Qualifiers
source                 1..549
                       mol_type = protein
                       organism = Oryza sativa
SEQUENCE: 77
MDMNSGWLGF SLSSSSARGY GDGCGEGNGG GDGDGSCSSP VAASPLVAMP LHSDGSVHYD  60
APDWRHAEAK DPKLEDFMSV SYSNKSSSNL YGSSSSSSCG HADQIKYHHV HDVQAFSTPY  120
FYGHGGSGVG IDINMNAPPA GCTGVLPDHR PPPPQQDHIF LPPHGQYFLG PPNPMAPAPM  180
```

```
YNAGGGGGGV VDGSMSISGI KSWLRQAMYV PERSAAALSL SVPAAPPSEA PLPPAAMPVV  240
RKPAQTFGQR TSQFRGVTRH RWTGRYEAHL WDNTCRKEGQ TRKGRQVYLG GYDKEEKAAR  300
AYDLAALKYW GPTTHINFPL STYEKELEEM KHMTRQEFIA HLRRNSSGFS RGASMYRGVT  360
RHHQHGRWQA RIGRVAGNKD LYLGTFSTQE EAAEAYDIAA IKFRGLNAVT NFDISKYDVK  420
RICSSTHLIG GDLACRRSPT RMLPPDAPAG AAGVDVVVAP GDHQQISAGG GGASDNSDTA  480
SDGHRGAHLL HGLQYAHAMK FEAGESSGGG GGDGATTNWM AAAAAAARPV AGIPTTVHHQ  540
LPVFALWND                                                          549

SEQ ID NO: 78           moltype = AA  length = 553
FEATURE                 Location/Qualifiers
source                  1..553
                        mol_type = protein
                        organism = Glycine max
SEQUENCE: 78
MNNNWLSFPL SPTHSSLPAH DLQATQYHQF SLGLVNENMD NPFQNHDWNL INTHSSNEIP  60
KVADFLGVSK SENQSDLAAL NEIHSNDSDY LFTNNSLVPM QNPVLDTPSN EYQENANSNL  120
QSLTLSMGSG KDSTCETSGE NSTNTTVEVA PRRTLDTFGQ RTSIYRGVTR HRWTGRYEAH  180
LWDNSCRREG QSRKGRQVYL GGYDKEEKAA RAYDLAALKY WGTSTTTNFP ISNYEKELDE  240
MKHMTRQEFV AAIRRKSSGF SRGASMYRGV TRHHQHGRWQ ARIGRVAGNK DLYLGTFSTE  300
EEAAEAYDIA AIKFRGLNAV TNFDMSRYDV KAILESNTLP IGGGAAKRLK EAQALESSRK  360
REEMIALGSS STFQYGTSAS SSRLHAYPLM QHHHQFEQPQ PLLTLQNHDI SSSHFSHQQD  420
PLHHQGYIQT QLQLHQQSGA SSYSFQNNAQ FYNGYLQNHP ALLQGMMNMG SSSSSSSVLE  480
NNNSNNNNNN VGGFVGSGFG MASNATAGNT VGTAEELGLV KVDYDMPAGG YGGWSAADSM  540
QTSNGGVFTM WND                                                     553

SEQ ID NO: 79           moltype = AA  length = 509
FEATURE                 Location/Qualifiers
source                  1..509
                        mol_type = protein
                        organism = Medicago truncatula
SEQUENCE: 79
MDKSSSSPPT NTNNTSLAFS LSNNNFPNPS HSSSSHLSLF HSFTPYPSSI IPPSLTLTGS  60
NNPVEASPEA TDGGTTNLSI FTGGHKFEDF LGSSVAPTRT AAATCAPTQL QQFSTDNDVY  120
NSELKKTIAA CFPGGYPTEP NSEPQKPSPK KTVDTFGQRT SIYRGVTRHR WTGRYEAHLW  180
DNSCRREGQS RKGRQGGYDK EEKAARAYDL AALKYWGPTT TTNFPISNYE KEIDDMKNMT  240
RQEFVASLRR KSSGFSRGAS IYRGVTRHHQ HGRWQARIGR VAGNKDLYLG TFSTQEEAAE  300
AYDIAAIKFR GLNAVTNFDM SRYDVKSIAN CSLPIGGLSN KNNKNSTDCV SETKINEPIQ  360
SDEIDHPSST SSATTLSFAL PIKQDPSTDY WSNILGFHNN PSAVTTTTIP FNMDFSAHVP  420
SNTNSDNPHN AAFFSGSGIF VQQQNMNGSS GSNSSSSSSA STSSIPFATP IFSLNSNSSS  480
YGNGNNWIGH TFQTHAKPSL FQTPIFGME                                    509

SEQ ID NO: 80           moltype = AA  length = 492
FEATURE                 Location/Qualifiers
source                  1..492
                        mol_type = protein
                        organism = Zea mays
SEQUENCE: 80
MDTSHHYHPW LNFSLAHHCD LEEEERGAAA ELAAIAGAAP PPKLEDFLGG GVATGGPEAV  60
APAEMYDSDL KFIAAAGFLG GSAAAAATSP LSSLDQAGSK LALPAAAAAP APEQRKAVDS  120
FGQRTSIYRG VTRHRWTGRY EAHLWDNSCR REGQSRKGRQ VYLGGYDKEE KAARAYDLAA  180
LKYWGSSTTT NFPVAEYEKE VEEMKNMTRQ EFVASLRRKS SGFSRGASIY RGVTRHHQHG  240
RWQARIGRVA GNKDLYLGTF STEEEAAEAY DIAAIKFRGL NAVTNFEISR YNVETIMSSN  300
LPVASMSSSA AAAAGGRSSK ALESPPSGSL DGGGGMPVVE ASTAPPLFIP VKYDQQQQEY  360
LSMLALQQHH QQQQAGNLLQ GPLVGFGGLY SSGVNLDFAN SHGTAAPSSM AHHCYANGTA  420
SASHEHQHQM QQGGENETQP QPQQSSSSCS SLPFATPVAF NGSYESSITA AGPFGYSYPN  480
VAAFQTPIYG ME                                                      492

SEQ ID NO: 81           moltype = AA  length = 469
FEATURE                 Location/Qualifiers
source                  1..469
                        mol_type = protein
                        organism = Oryza sativa
SEQUENCE: 81
MDMDMSSAYP HHWLSFSLSN NYHHGLLEAL STTSAPPLGE EGPAEGAPKM EDFLGGLGGG  60
GGAVAAAPAA APEDQLSCGE LGSIAAGFLR RYPAPENAGG VTIAMATDAA AELADPARRT  120
AETFGQRTSI YRGVTRHRWT GRYEAHLWDN SCRREGQSRK GRQVYLGGYD KEEKAARAYD  180
LAALKYWGPT TTTNFPVANY ETELEEMKSM TRQEFIASLR RKSSGFSRGA SIYRGVTRHH  240
QHGRWQARIG RVAGNKDLYL GTFSTQEEAA EAYDIAAIKF RGLNAVTNFD MSRYDVDSIL  300
NSDLPVGGGA ATRASKFPSD PSLPLPSPAM PPSEKDYWSL LALHYHHHQQ QQQQQQFPAS  360
AFDTYGCSSG VNVDFTMGTS SHSGSNSNSS SSSAIWGTAA GAAMGRQQNG GSSNKQSNSY  420
SGNNIPYAAA AAMTSGSALY GGSTGSNGTW VASNTSTAPH FYNYLFGME              469

SEQ ID NO: 82           moltype = AA  length = 562
FEATURE                 Location/Qualifiers
source                  1..562
                        mol_type = protein
                        organism = Glycine max
SEQUENCE: 82
MNNNWLSFPL SPTHSSLPAH DLQATQYHQF SLGLVNENME NPFQNHDWSL INTHSSSEVP  60
```

```
KVADFLGVSK SENESDLAAS LNEIQSNDSD YLFTNNSLVP MQNPAVDTPS NEYQENANSS  120
LQSLTLSMGS GKDSTCETSG DNSTNTTTTT TVEAAPRRTL DTFGQRTSIY RGVTRHRWTG  180
RYEAHLWDNS CRREGQSRKG RQVYLGGYDK EEKAARSYDL AALKYWGTST TTNFPISNYE  240
KELDEMKHMT RQEFVAAIRR KSSGFSRGAS MYRGVTRHHQ HGRWQARIGR VAGNKDLYLG  300
TFSTEEEAAE AYDIAAIKFR GLNAVTNFDM SRYDVKAILE SNTLPIGGGA AKRLKEAQAL  360
ESSRKREEMI ALGSSTFQYG TTSSNSRLHA YPLMQHHHQF EQPQPLLTLQ NHDISSHFSH  420
QQDPLHQGYI QTQLQLHQQQ SGGSSSYSFQ NNNINNAQFY NGYNLQNHPA LLQGMINMGS  480
SSSSSVLENN NSNNNNVGGF VGSGFGMASN ATSGNTVGTA EELGLVKVDY DMPTGGYGGW  540
SAAAAAESMQ TSNSGVFTMW ND                                           562

SEQ ID NO: 83          moltype = AA  length = 574
FEATURE                Location/Qualifiers
source                 1..574
                       mol_type = protein
                       organism = Arabidopsis thaliana
SEQUENCE: 83
MNSNNWLGFP LSPNNSSLPP HEYNLGLVSD HMDNPFQTQE WNMINPHGGG GDEGGEVPKV  60
ADFLGVSKPD ENQSNHLVAY NDSDYYFHTN SLMPSVQSND VVVAACDSNT PNNSSYHELQ  120
ESAHNLQSLT LSMGTTAGNN VVDKASPSET TGDNASGGAL AVVETATPRR ALDTFGQRTS  180
IYRGVTRHRW TGRYEAHLWD NSCRREGQSR KGRQVYLGGY DKEDKAARSY DLAALKYWGP  240
STTTNFPITN YEKEVEEMKH MTRQEFVAAI RRKSSGFSRG ASMYRGVTRH HQHGRWQARI  300
GRVAGNKDLY LGTFSTEEEA AEAYDIAAIK FRGLNAVTNF EINRYDVKAI LESSTLPIGG  360
GAAKRLKEAQ ALESSRKREA EMIALGSSFQ YGGGSSTGSG STSSRLQLQP YPLSIQQPLE  420
PFLSLQNNDI SHYNNNNAHD SSSFNHHSYI QTQLHLHQQT NNYLQQQSSQ NSQQLYNAYL  480
HSNPALLHGL VSTSIVDNNN NNGGSSGSYN TAAFLGNHGI GIGSSSTVGS TEEFPTVKTD  540
YDMPSSDGTG GYSGWTSESV QGSNPGGVFT MWNE                              574

SEQ ID NO: 84          moltype = AA  length = 543
FEATURE                Location/Qualifiers
source                 1..543
                       mol_type = protein
                       organism = Medicago truncatula
SEQUENCE: 84
MNNNWLSFPL SPSHSSLPSN DLQATQYHHF PLGLVNDNME NPFQNHDWNL MNTHNSNEVP  60
KVADFLGVCK SENHSDLATP NEIQSNDSDY LFTNNNTLMP MQNQMVTTCT NEYQEKASNS  120
NLQSLTLSMG SGKDSTCETS GENSTNTVEV AVPKRTSETF GQRTSIYRGV TKHRWTGRYE  180
AHLWDNSCRR EGQSRKGRQG GYDKEEKAAR SYDLAALKYW GTSTTTNFPV SNYEKEIDEM  240
KHMTRQEFVA SIRRKSSGFS RGASMYRGVT RHHQHGRWQA RIGRVAGNKD LYLGTFSTEE  300
EAAEAYDIAA IKFRGLNAVT NFDMTRYDVK AILESNTLPI GGGAAKRLKE AQALETSRKR  360
EEMLALNSSS FQYGTSSSSN TRLQPYPLMQ YHHQFEQPQP LLTLQNNHES LNSQQFSQHQ  420
GGGYFQTQLE LCQQQNQQPS QNSNIGSFYN GYYQNHPGLF QMNNIGSSSS SSVMGNNGGG  480
SSGIYSNSGG LISNNAVEEF VPVKVDYDMQ GDGSGFGGWS AAGENMQTAD LFTMWNDYET  540
REN                                                                543

SEQ ID NO: 85          moltype = AA  length = 543
FEATURE                Location/Qualifiers
source                 1..543
                       mol_type = protein
                       organism = Zea mays
SEQUENCE: 85
MDMNNGWLGF SLSPSAASRG GYGYGDGGGG ASASACGDGE GSCPSPAAAA SPLPLVAMPL  60
DDSLHYSSAP DWRHGAAEAK GPKLEDFMSI TCSNKSSGRS LYDSCGHHDD EQASKYHEVH  120
GIHPLSCGSY YHGCISSGGG GGGGIGLGIN MNAPPCTGGF PDHQHHQFVP SSHHGQYFLG  180
APAASAGPPA GAAMPMYNAG GGSVVGGSMS ISGIKSWLRE AMYVPPERPA AAALSLAVTD  240
DVPPAEPPQL LPAPLPVHRK PAQTFGQRTS QFRGVTRHRW TGRYEAHLWD NTCRKEGQTR  300
KGRQVYLGGY DREEKAARAY DLAALKYWGP STHINFPLSH YEKELEEMKH MSRQEFIAHL  360
RRNSSGFSRG ASMYRGVTRH HQHGRWQARI GRVAGNKDLY LGTFSTQEEA AEAYDIAAIK  420
FRGLNAVTNF DISKYDVKRI CASTHLIGGG DACRRSPTRP PDAAPALAGG ADRSSDAPGD  480
QAASDNSDTS DGHRGAHLLH GLQYGHPMKL EAGEGSSWMA AAAAARPVPG VHQLPMFALW  540
NDC                                                                543

SEQ ID NO: 86          moltype = AA  length = 512
FEATURE                Location/Qualifiers
source                 1..512
                       mol_type = protein
                       organism = Glycine max
SEQUENCE: 86
MSNWLGFSLT PHLRIDEEFE RENQERGGGI ILFEKKKTKW RYDSAIGGGN SNEEGPKLED  60
FLGCYSNSPA KVFCQDSQPD QNQSQNNVSK INIETGDNLT NPSSLLHSFH AYNDNSHALI  120
PTNGMYKSWL AQTQFSSDGK PSNEANGCNF QSLSLTMSPS VQNGVGAISS VQVNEDSRKR  180
VMAKSHAREP VPRKSIDTFG QRTSQYRGVT RHRWTGRYEA HLWDNSCRKE GQTRKGRQGG  240
YDKEEKAAKA YDLAALKYWG PTTHINFPLS TYEKELEEMK HMTRQEFVAN LRRKSSGFSR  300
GASVYRGVTR HHQHGRWQAR IGRVAGNKDL YLGTFSTQEE AAEAYDIAAI KFRGTSAVTN  360
FDISRYDVKR ICSSSTLIAG DLAKRSPKES PAPPPPLAIT DGEHSDELSN MMWNANNSDE  420
QAQNESGGAE FNNNVTESSS SQQVSPSSNK DALNPQSPNE FGVSGADYGH GYFTLDGPKY  480
DDGNNENDHM STNRLGNLGL VNQVPMFALW NE                                 512

SEQ ID NO: 87          moltype = AA  length = 485
FEATURE                Location/Qualifiers
```

```
source                  1..485
                        mol_type = protein
                        organism = Sorghum bicolor
SEQUENCE: 87
MDTSHHYPWL NFSLAHHGDL EEEERGAAAE LAAIAGAAPP PKLEDFLGGG VINGESARSG  60
GGVPVAAPEV SAPAEMYDSD LKFIAAAGFL GGGSAAGPVA TSPLSSLDQA DPKLALPAAA  120
AAAPAPEQRK AVDSFGQRTS IYRGVTRHRW TGRYEAHLWD NSCRREGQSR KGRQGGYDKE  180
EKAARAYDLA ALKYWGSSTT TNFPVAEYEK ELEEMKTMTR QEFVASLRRK SSGFSRGASI  240
YRGVTRHHQH GRWQARIGRV AGNKDLYLGT FSTEEEAAEA YDIAAIKFRG LNAVTNFEIS  300
RYNVESIMNS NIPMGSMSAG GRSNKALESP PSGSPDAMPV EASTAPLFAA LPVKYDQQQQ  360
DYLSMLALQH HQQGNLQGLG FGLYSSGVNL DFANSHSTAS SMTHCYVNGG TVSSHEQHQH  420
HQQLQDHQQQ GESETQQSSN SCSSLPFATP IAFNGSYESS MTAAGPFGYS YPNVAAFQTP  480
IYGME                                                              485

SEQ ID NO: 88           moltype = AA  length = 507
FEATURE                 Location/Qualifiers
source                  1..507
                        mol_type = protein
                        organism = Glycine max
SEQUENCE: 88
MARATNWLSF SLSPMEMLRT SEPQFLQYDA ASATSSHHYY LDNLYTNGWG NGSLKFEQNL  60
NHSDVSFVES SSQSVGHVPP PPPKLEDFLG DSSAVMRYSD SQTETQDSSL THIYDHHHHH  120
HHHHGSTSYF GGDQQDLKAI TGFQAFSTNS GSEVDDSASI GKAQASEFGT HSIESSGNEF  180
AAFSGGTTGT LSLAVALSSE KAVVAAESNS SKKIVDTFGQ RTSIYRGVTR HRWTGRYEAH  240
LWDNSCRREG QARKGRQGGY DKEEKAARAY DLAALKYWGP TATTNFPVSN YSKEVEEMKH  300
VTKQEFIASL RRKSSGFSRG ASIYRGVTRH HQQGRWQARI GRVAGNKDLY LGTFATEEEA  360
AEAYDIAAIK FRGANAVTNF EMNRYDVEAI MKSSLPVGGA AKRLRLSLES EQKAPPVNSS  420
SQQQNPQCGN VSGSINFSAI HQPIASIPCG IPFDSTTAYY PHNLFQHFHP TNAGAAASAV  480
TSANATALTA LPASAATEFF IWPHQSY                                      507

SEQ ID NO: 89           moltype = AA  length = 569
FEATURE                 Location/Qualifiers
source                  1..569
                        mol_type = protein
                        organism = Arabidopsis thaliana
SEQUENCE: 89
MEMLRSSDQS QFVSYDASSA ASSSPYLLDN FYGWSNQKPQ EFFKEEAQLA AAASMADSTI  60
LTTFVDPQSH HSQNHIPKLE DFLGDSSSIV RYSDNSQTDT QDSSLTQIYD PRHHHNQTGF  120
YSDHHDFKTM AGFQSAFSTN SGSEVDDSAS IGRTHLAGDY LGHVVESSGP ELGFHGGSTG  180
ALSLGVNVNN NTNHRNDNDN HYRGNNNGER INNNNNNDNE KTDSEKEKAV VAVETSDCSN  240
KKIADTFGQR TSIYRGVTRH RWTGRYEAHL WDNSCRREGQ ARKGRQVYLG GYDKEDKAAR  300
AYDLAALKYW NATATTNFPI TNYSKEVEEM KHMTKQEFIA SLRRKSSGFS RGASIYRGVT  360
RHHQQGRWQA RIGRVAGNKD LYLGTFATEE EAAEAYDIAA IKFRGINAVT NFEMNRYDVE  420
AIMKSALPIG GAAKRLKLSL EAAASSEQKP ILGHHQLHHF QQQQQQQQLQ LQSSPNHSSI  480
NFALCPNSAV QSQQIIPCGI PFEAAALYHH HQQQQQHQQQ QQQQNFFQHF PANAASDSTG  540
SNNNSNVQGT MGLMAPNPAE FFLWPNQSY                                    569

SEQ ID NO: 90           moltype = AA  length = 574
FEATURE                 Location/Qualifiers
source                  1..574
                        mol_type = protein
                        organism = Medicago truncatula
SEQUENCE: 90
MSNWLGFSLT PHLRIDEEFG TENQNQNQNH VAEGSEIGRN YVTPSSHPHP HHLSIMPLRS  60
DGSLCVSDSF TPQEWRYENA ITDGNSNEEG PKLEDFLGCY SNQNQNSTTT STMSKINVNV  120
SPSFCTNNNP EIDTRENLTN QSLIHSFHAY NDHSNNNHHA LIHDNSMYKS WMTQTQFSSE  180
GKTTSSDGNG FQSLNLTMSP CVQNGVGGGV GSAISNVQVN EDPRKRSLSK SNAREPVPRK  240
SIDTFGQRTS QYRGVTRHRW TGRYEAHLWD NSCRKEGQTR KGRQGGYDKE EKAAKAYDLA  300
ALKYWGPTTH INFPLSTYDK ELEEMKHMTR QEFVANLRRK SSGFSRGASV YRGVTRHHQH  360
GRWQARIGRV AGNKDLYLGT FSTQEEAAEA YDIAAIKFRG TSAVTNFDIS RYDVKRICSS  420
STLITGDLAK RSPKDSTPPA TTAEDFNSCG SSSTLSQPPP LTITDGEQHS DELSNMVWNS  480
NNDEQKPQNG TNITESSQHG SPSNKNEMNP QSPKCSLGLP NEFGVSGADY GHGYFTLHGP  540
KFDDGSNEND HMNNNRLGNL GLVNQVPMFA LWNE                               574

SEQ ID NO: 91           moltype = AA  length = 541
FEATURE                 Location/Qualifiers
source                  1..541
                        mol_type = protein
                        organism = Sorghum bicolor
SEQUENCE: 91
MDMNNGWLGF SLSPSAGRGG YGDGGASASG DGGDGSCSSP AAAASPVPLV AMPLQPDGSL  60
HYTSAPDWRH GAAEANGPKL EDFMSVTCSS NNKRSSSSSS FYDRCSHAEQ ANKYHEVHDL  120
QPLSCGSYYH GSSGGGGNGI ALGINMNAPP CSGGGFPDHH HHHQFVSSHH GQYFLGAPLN  180
ASPPGAVPMY SAGGGGVGGS MSISGIKSWL REAMYVPPER PVAAAAALSL AVTDDVGAEP  240
PQLLPAAPMP PVHRKPAQTF GQRTSQFRGV TRHRWTGRYE AHLWDNTCRK EGQTRKGRQG  300
GYDREEKAAR AYDLAALKYW GPSTHINFPL SHYEKELEEM KHMSRQEFIA HLRRNSSGFS  360
RGASMYRGVT RHHQHGRWQA RIGRVAGNKD LYLGTFSTQE EAAEAYDIAA IKFRGLNAVT  420
NFDISKYDVK RICASTHLIG GGDACRRSPT QPPDAPALAI DAAGADRSSD APGGGDQAVS  480
DNSDTSAGHR GAHLLHGLQY GHPMKLEAGE GSSWMAAATA AAARPVAGVH QLPVFALWND  540
```

```
C                                                                  541

SEQ ID NO: 92            moltype = AA  length = 555
FEATURE                  Location/Qualifiers
source                   1..555
                         mol_type = protein
                         organism = Arabidopsis thaliana
SEQUENCE: 92
MKSFCDNDDN NHSNTTNLLG FSLSSNMMKM GGRGGREAIY SSSTSSAATS SSSVPPQLVV  60
GDNTSNFGVC YGSNPNGGIY SHMSVMPLRS DGSLCLMEAL NRSSHSNHHQ DSSPKVEDFF  120
GTHHNNTSHK EAMDLSLDSL FYNTTHEPNT TTNFQEFFSF PQTRNHEEET RNYGNDPSLT  180
HGGSFNVGVY GEFQQSLSLS MSPGSQSSCI TGSHHHQQNQ NQNHQSQNHQ QISEALVETS  240
VGFETTTMAA AKKKRGQEDV VVVGQKQIVH RKSIDTFGQR TSQYRGVTRH RWTGRYEAHL  300
WDNSFKKEGH SRKGRQVYLG GYDMEEKAAR AYDLAALKYW GPSTHTNFSA ENYQKEIEDM  360
KNMTRQEYVA HLRRKSSGFS RGASIYRGVT RHHQHGRWQA RIGRVAGNKD LYLGTFGTQE  420
EAAEAYDVAA IKFRGTNAVT NFDITRYDVD RIMSSNTLLS GELARRNNNS IVVRNTEDQT  480
ALNAVVEGGS NKEVSTPERL LSFPAIFALP QVNQKMFGSN MGGNMSPWTS NPNAELKTVA  540
LTLPQMPVFA AWADS                                                   555

SEQ ID NO: 93            moltype = AA  length = 678
FEATURE                  Location/Qualifiers
source                   1..678
                         mol_type = protein
                         organism = Sorghum bicolor
SEQUENCE: 93
MTNNNGNGTN AAASSWLGFS LSPHMASAMD EHHHVQQQQQ HHHHHSLFFP SVTAAAAAAY  60
GLGGSDGGVA TSASPYYTPQ LASMPLKSDG SLCIMEALRR SDQPDHHGPK LEDFLGAAAA  120
QSQAMALSLQ DNPAAAASSF YYYGNGGGGG SGHQHHGGFL QPCADLYGGP SEASLVADDD  180
EAAAAATAMA SWVAARAGES GGVLSAAAAA AGHQHHHHAL ALSMSSGSLS SCVTAHPGAA  240
AADYGVVAAT ASASLDGGRK RGGAAGQKQP VHHRKSIDTF GQRTSQYRGV TRHRWTGRYE  300
AHLWDNSCKK EGQTRKGRQG GYDMEEKAAR AYDLAALKYW GPSTHINFPL EDYQEELEEM  360
KNMTRQEYVA HLRRKSSGFS RGASMYRGVT RHHQHGRWQA RIGRVSGNKD LYLGTFSTQE  420
EAAEAYDIAA IKFRGLNAVT NFDITRYDVD KIMASNTLLP GDLARRRKDD DPAAVIAGAD  480
ASNGGGVTTA AAAAALVQQA AAAAAAGAGG NHSASSSETW IKVAAAAALQ AAGAAPRDGN  540
HHHHHHDVLS GEAFSVLHDL VVTAADGGNG NGNGGHHHHH VHNSAATAQH MSMSSASSLV  600
TSLGNSREGS PDRGGGLSML FSKPPAPAPA ASAHAANKPM SPLMPLGSWA STAAASARAA  660
AAAVSIAHMP VFAAWTDA                                                678

SEQ ID NO: 94            moltype = AA  length = 509
FEATURE                  Location/Qualifiers
source                   1..509
                         mol_type = protein
                         organism = Glycine max
SEQUENCE: 94
MARASTNWLS FSLSPMDMLR TPEPQFVQYD AASDTSSHHY YLDNLYTNGW GNGSLKFEQN  60
LNHSDVSFVQ SSSQSVSHAP PKLEDFLGDS SAVMRYSDSQ TETQDSSLTH IYDHHHHHHH  120
GSSAYFGGDH QDLKAITGFQ AFSTNSGSEV DDSASIGKAQ GSEFGTHSIE SSVNEFAAFS  180
GGTNTGGTLS LAVAQSSEKA VAAAAESDRS KKVVDTFGQR TSIYRGVTRH RWTGRYEAHL  240
WDNSCRREGQ ARKGRQGGYD KEEKAARSYD LAALKYWGPT ATTNFPVSNY SKEVEEMKHV  300
TKQEFIASLR RKSSGFSRGA SIYRGVTRHH QQGRWQARIG RVAGNKDLYL GTFATEEEAA  360
EAYDIAAIKF RGANAVTNFE MNRYDVEAIM KSSLPVGGAA KRLKLSLESE QKALPVSSSS  420
SSSQQQNPQC GNVSASINFS SIHQPIASIP CGIPFDSTTA YYHHNLFQHF HPTNAGTAAS  480
AVTSANANAL TALPPTAAAE FFIWPHQSY                                    509

SEQ ID NO: 95            moltype = AA  length = 652
FEATURE                  Location/Qualifiers
source                   1..652
                         mol_type = protein
                         organism = Oryza sativa
SEQUENCE: 95
MASGNSSSSS GSMAATAGGV GGWLGFSLSP HMATYCAGGV DDVGHHHHHH VHQHQQQHGG  60
GLFYNPAAVA SSFYYGGGHD AVVTSAAGGG SYYGAGFSSM PLKSDGSLCI MEALRGGDQE  120
QQGVVVSASP KLEDFLGAGP AMALSLDNSA FYYGGHGHHQ GHAQDGGAVG GDPHHGGGGF  180
LQCAVIPGAG AGHDAALVHD QSAAAVAAGW AAMHGGGYDI ANAAADDVCA AGPIIPTGGH  240
LHPLTLSMSS AGSQSSCVTV QAAAAGEPYM AMDAVSKKRG GADRAGQKQP VHRKSIDTFG  300
QRTSQYRGVT RHRWTGRYEA HLWDNSCKKE GQTRKGRQGG YDMEEKAARA YDLAALKYWG  360
PSTHINFPLE DYQEELEEMK NMSRQEYVAH LRRKSSGFSR GASIYRGVTR HHQHGRWQAR  420
IGRVSGNKDL YLGTFSTQEE AAEAYDVAAI KFRGLNAVTN FDITRYDVDK ILESSTLLPG  480
ELARRKGKVG DGGGAAAVAD AAAALVQAGN VAEWKMATAA ALPAAARTEQ QQQHGHGGHQ  540
HHDLLPSDAF SVLQDIVSTV DAAGAPPRAP HMSMAATSLG NSREQSPDRG VGGGGGGGVL  600
ATLFAKPAAA SKLYSPVPLN TWASPSPAVS SVPARAGVSI AHLPMFAAWT DA          652

SEQ ID NO: 96            moltype = AA  length = 440
FEATURE                  Location/Qualifiers
source                   1..440
                         mol_type = protein
                         organism = Arabidopsis thaliana
SEQUENCE: 96
MADSTTLSTF FDHSQTQIPK LEDFLGDSFV RYSDNQTETQ DSSSLTPFYD PRHRTVAEGV  60
```

```
TGFFSDHHQP DFKTINSGPE IFDDSTTSNI GGTHLSSHVV ESSTTAKLGF NGDCTTTGGV  120
LSLGVNNTSD QPLSCNNGER GGNSNKKKTV SKKETSDDSK KKIVETLGQR TSIYRGVTRH  180
RWTGRYEAHL WDNSCRREGQ ARKGRQVYLG GYDKEDRAAR AYDLAALKYW GSTATTNFPV  240
SSYSKELEEM NHMTKQEFIA SLRRKSSGFS RGASIYRGVT RHHQQGRWQA RIGRVAGNKD  300
LYLGTFATEE EAAEAYDIAA IKFRGINAVT NFEMNRYDIE AVMNSSLPVG GAAAKRHKLK  360
LALESPSSSS SDHNLQQQQL LPSSSPSDQN PNSIPCGIPF EPSVLYYHQN FFQHYPLVSD  420
STIQAPMNQA EFFLWPNQSY                                              440

SEQ ID NO: 97          moltype = AA  length = 651
FEATURE                Location/Qualifiers
source                 1..651
                       mol_type = protein
                       organism = Zea mays
SEQUENCE: 97
MANGSNWLGF SLSPHTAMEV PSVSEPASTH HAPPPPSSST TISSSSTNNT ISSNFLFSPM  60
ASPYPGYYCV GGAYGDGTSA AGVYYSHLPA MPNKSDDGTL CNMEGMVPSS PPKLEDFLGG  120
GNGGGQETAT YYSHQQQGQE EGASRSDYRQY HYQHQQLVPY NFQPLTEAEM LQEGAAPMEE  180
AMAAAKNFLL ASYGACYSNE ETRPLSLSMM SPGTQLSSCV SAAPQQQHQM AATVATAATA  240
AAALGRSNGD GEQCVGRKRS TGKGGHKQTV HRKSIDTFGQ RTSRYRGVTR HRWTGRYEAH  300
LWDNSCRKDG QTRKGRQVYL GGYDTEDKAA RAYDLAALKY WGPATHVNFP VENYRDELEE  360
MKGMTRQEFV AHLRRRSSGF SRGASIYRGV TRHHQQGRWQ SRIGRVAGNK DLYLGTFTTQ  420
EEAAEAYDIA AIKFRGLNAV TNFDIARYDV DKIMESSTLL AVEEARKVKA VEAASSAPMT  480
HTHSGGKEQL NATTAEETSS AGWRMVLHGS PHQLEAARCP EAADLQSAIM NNDSHPRPSL  540
HGIAGLDIEC AVHDHHDHLD VPAGSRTTAA GSINFSNSSS QVTSLGNSRE GSPERLGLAM  600
MYGKQPSSAV SLAATMSPWT PVAAQTVAHV LKQQPNVVVS HRPVFAAWAD A           651

SEQ ID NO: 98          moltype = AA  length = 656
FEATURE                Location/Qualifiers
source                 1..656
                       mol_type = protein
                       organism = Medicago truncatula
SEQUENCE: 98
MKRMENNDDS VDINNENNWL GFSLSPQMNN IGVSSHTHHH SLPSATATAS EVVPLQASFY  60
HSSPLSNFCY SYGLEHENAG LYSLLPIMPL KSDGSLFEME ALSRSQTQAM STTSAPKLEN  120
FLGNEAMGTP HYACSSTVTE TMPLSLDSMF QNQIQQNMNM NNQQHLSYYN STLRNHELML  180
EGSKQSQTSS GNFHQSNMGE DHGLSGLKNW VLRNFPASHG HDQSKMIVPV VEENEGECGS  240
NIGSMAYGDL HSLSLSMSPS SQSSCVTTSQ NMSSAVVENS VAMDTKKRGS EKFEQKQIVH  300
RKSIDTFGQR TSQYRGVTRH RWTGRYEAHL WDNSCKKEGQ SRKGRQGGYD MEEKAARAYD  360
QAALKYWGPS THINFPLENY QNQLEEMKNM TRQEYVAHLR RKSSGFSRGA SMYRGVTSRH  420
HQHGRWQARI GRVAGNKDLY LGTFSTQEEA AEAYDIAAIK FRGANAVTNF DIIKYDVEKI  480
MASSNLLNIE QARRNKEVVD ISSTQYIDQN KPSSAYDNNS TQEAISMQKS MVLYQSSQHQ  540
QLQQNQPRFE NERTHQTFSS VSLDNMFHQE VVEEASKMRT HVSNASSLAT SLSSSREGTP  600
DRTSLQNLSG IMPSTASKLL VTSAPNSNLN SWDPSQHLRP SLSLPQMPVF AAWTDA      656

SEQ ID NO: 99          moltype = AA  length = 546
FEATURE                Location/Qualifiers
source                 1..546
                       mol_type = protein
                       organism = Glycine max
SEQUENCE: 99
MKRMNESNNT DDGNNHNWLG FSLSPHMKME VTSAATVSDN NVPTTFYMSP SHMSNSGMCY  60
SVGENGNFHS PLTVMPLKSD GSLGILEALN RSQTQVMVPT SSPKLEDFLG GATMGTHEYG  120
NHERGLSLDS IYYNSQNAEA QPNRNLLSHP FRQQGHAPSE EEATKETHVS VMPQMTGGGL  180
QNWILEQQMN CGIWNERSGV SVGTVGCGEL QSLSLSMSPG SQSSCVTAPS GTDSVAVDAK  240
KRGHAKLGQK QPVHRKSIDT FGQRTSQYRG VTRHRWTGRY EAHLWDNSCK KEGQTRKGRQ  300
GGYDMEEKAA RAYDLAALKY WGPSTHINFS IENYQVQLEE MKNMSRQEYV AHLRRKSSGF  360
SRGASIYRGV TRHHQHGRWQ ARIGRVAGNK DLYLGTFSTQ EEAAEAYDIA AIKFRGANAV  420
TNFDISRYDV ERIMASSNLL AGELARRNKD NDPRNEAIDY NKSVFKQETT MKMIRSGRCL  480
SSSREASPEK MGPSLLFPKP PPMETKIVNP IGTSVTSWLP SPTVQMRPSP AISLSHLPVF  540
AAWTDT                                                             546

SEQ ID NO: 100         moltype = AA  length = 415
FEATURE                Location/Qualifiers
source                 1..415
                       mol_type = protein
                       organism = Arabidopsis thaliana
SEQUENCE: 100
MKKWLGFSLT PPLRICNSEE EELRHDGSDV WRYDINFDHH HHDEDVPKVE DLLSNSHQTE  60
YPINHNQTNV NCTTVVNRLN PPGYLLHDQT VVTPHYPNLD PNLSNDYGGF ERVGSVSVFK  120
SWLEQGTPAF PLSSHYVTEE AGTSNNISHF SNEETGYNTN GSMLSLALSH GACSDLINES  180
NVSARVEEPV KVDEKRKRLV VKPQVKESVP RKSVDSYGQR TSQYRGVTRH RWTGRYEAHL  240
WDNSCKKEGQ TRRGRQVYLG GYDEEEKAAR AYDLAALKYW GPTTHLNFPL SNYEKEIEEL  300
NNMNRQEFVA MLRRNSSGFS RGASVYRGVT RHHQHGRWQA RIGRVAGNKD LYLGTFSTQE  360
EAAEAYDIAA IKFRGLNAVT NFDINRYDVK RICSSSTIVD SDQAKHSPTS SGAGH       415

SEQ ID NO: 101         moltype = AA  length = 428
FEATURE                Location/Qualifiers
source                 1..428
                       mol_type = protein
```

```
                         organism = Zea mays
SEQUENCE: 101
MSPPTNGAIS LAYAPSMMLG AGALTNPPLL PFDGFTDEDF LASADAALLG EAGTDQTLLL  60
LPSCPGANCC GGSSSDQGLG ALACEVTTAG SFSLLGQPAP GQVSWEVTTA VAADRNTFSR  120
ARDPAPSPPP SPALPLVQTT SQSQRTSIYR GVTRHRWTGR YEAHLWDNTC RKEGQKRKGR  180
QVYLGGYDKE DKAARAYDIA ALKYWGDNAT TNFPRENYIR EIQDMQNMNR RDVVASLRRK  240
SSGFSRGASI YRGVTKHHQH GRWQARIGRV AGNKDLYLGT FATEQEAAEA YDIAALKFRG  300
ENAVTNFEPS RYNLLAIAQR DIPILGRKLI QKPAPEAEDQ AALSARSFSQ SQQSSNSLPP  360
YFLTNLLQPL PSQHSLAQAL PSYNNLGFGE PSLYWPCPCG DPGEQKVQLG SKLEIVDGLV  420
QLANSAAN                                                          428

SEQ ID NO: 102           moltype = AA  length = 438
FEATURE                  Location/Qualifiers
source                   1..438
                         mol_type = protein
                         organism = Arabidopsis thaliana
SEQUENCE: 102
MKKRLTTSTC SSSPSSSVSS STTTSSPIQS EAPRPKRAKR AKKSSPSGDK SHNPTSPAST  60
RRSSIYRGVT RHRWTGRFEA HLWDKSSWNS IQNKKGKQVY LGAYDSEEAA AHTYDLAALK  120
YWGPDTILNF PAETYTKELE EMQRVTKEEY LASLRRQSSG FSRGVSKYRG VARHHHNGRW  180
EARIGRVFGN KYLYLGTYNT QEEAAAAYDM AAIEYRGANA VTNFDISNYI DRLKKKGVFP  240
FPVNQANHQE GILVEAKQEV ETREAKEEPR EEVKQQYVEE PPQEEEEKEE EKAEQQEAEI  300
VGYSEEAAVV NCCIDSSTIM EMDRCGDNNE LAWNFCMMDT GFSPFLTDQN LANENPIEYP  360
ELFNELAFED NIDFMFDDGK HECLNLENLD CCVVGRESPP SSSSPLSCLS TDSASSTTTT  420
TTSVSCNYLF QGLFVGSE                                               438

SEQ ID NO: 103           moltype = AA  length = 432
FEATURE                  Location/Qualifiers
source                   1..432
                         mol_type = protein
                         organism = Arabidopsis thaliana
SEQUENCE: 103
MWDLNDAPHQ TQREEESEEF CYSSPSKRVG SFSNSSSSAV VIEDGSDDDE LNRVRPNNPL  60
VTHQFFPEMD SNGGGVASGF PRAHWFGVKF CQSDLATGSS AGKATNVAAA VVEPAQPLKK  120
SRRGPRSRSS QYRGVTFYRR TGRWESHIWD CGKQVYLGGF DTAHAAARAY DRAAIKFRGV  180
EADINFNIDD YDDDLKQMTN LTKEEFVHVL RRQSTGFPRG SSKYRGVTLH KCGRWEARMG  240
QFLGKKYVYL GLFDTEVEAA RAYDKAAIKC NGKDAVTNFD PSIYDEELNA ESSGNPTTPQ  300
DHNLDLSLGN SANSKHKSQD MRLRMNQQQQ DSLHSNEVLG LGQTGMLNHT PNSNHQFPGS  360
SNIGSGGGFS LFPAAENHRF DGRASTNQVL TNAAASSGFS PHHHNQIFNS TSTPHQNWLQ  420
TNGFQPPLMR PS                                                     432

SEQ ID NO: 104           moltype = AA  length = 449
FEATURE                  Location/Qualifiers
source                   1..449
                         mol_type = protein
                         organism = Arabidopsis thaliana
SEQUENCE: 104
MLDLNLNADS PESTQYGGDS YLDRQTSDNS AGNRVEESGT STSSVINADG DEDSCSTRAF  60
TLSFDILKVG SSSGGDESPA ASASVTKEFF PVSGDCGHLR DVEGSSSSRN WIDLSFDRIG  120
DGETKLVTPV PTPAPVPAQV KKSRRGPRSR SSQYRGVTFY RRTGRWESHI WDCGKQVYLG  180
GFDTAHAAAR AYDRAAIKFR GVDADINFTL GDYEEDMKQV QNLSKEEFVH ILRRQSTGFS  240
RGSSKYRGVT LHKCGRWEAR MGQFLGKKAY DKAAINTNGR EAVTNFEMSS YQNEINSESN  300
NSEIDLNLGI SLSTGNAPKQ NGRLFHFPSN TYETQRGVSL RIDNEYMGKP VNTPLPYGSS  360
DHRLYWNGAC PSYNNPAEGR ATEKRSEAEG MMSNWGWQRP GQTSAVRPQP PGPQPPPLFS  420
VAAASSGFSH FRPQPPNDNA TRGYFYPHP                                   449

SEQ ID NO: 105           moltype = DNA  length = 663
FEATURE                  Location/Qualifiers
source                   1..663
                         mol_type = genomic DNA
                         organism = Zea mays
CDS                      1..663
SEQUENCE: 105
atggaggcgc tgagcgggcg ggtaggcgtc aagtgcgggc ggtggaaccc tacggcggag  60
caggtgaagg tcctgacgga gctcttccgc gcggggctgc ggacgcccag cacggagcag  120
atccagcgca tctccaccca cctcagcgcc ttcggcaagg tggagagcaa gaacgtcttc  180
tactggttcc agaaccacaa ggcccgcgag cgccaccacc acaagaagcg ccgccgcggc  240
gcgtcgtcgt cctcccccga cagcggcagc ggcaggggaa gcaacaacga ggaagacggc  300
cgtggtgccg cctcgcagtc gcacgacgcc gacgccgacg ccgacctcgt gctgcaaccg  360
ccagagagca agcgggaggc cagaagctat ggccaccatc accggctcgt gacatgctac  420
gtcagggacg tggtggagca gcaggaggcg tcgccgtcgt gggagcggcc gacgagggag  480
gtggagacgc tagagctctt ccccctcaag tcgtacggcg acctcgaggc ggcggagaag  540
gtccggtcgt acgtcagagg catcgccgcc accagcgagc agtgcaggga gttgtccttc  600
ttcgacgtct ccgccggccg ggatccgccg ctcgagctca ggctctgcag cttcggtccc  660
tag                                                               663

SEQ ID NO: 106           moltype = AA  length = 220
FEATURE                  Location/Qualifiers
source                   1..220
```

```
                        mol_type = protein
                        organism = Zea mays
SEQUENCE: 106
MEALSGRVGV KCGRWNPTAE QVKVLTELFR AGLRTPSTEQ IQRISTHLSA FGKVESKNVF  60
YWFQNHKARE RHHHKKRRRG ASSSSPDSGS GRGSNNEEDG RGAASQSHDA DADADLVLQP  120
PESKREARSY GHHHRLVTCY VRDVVEQQEA SPSWERPTRE VETLELFPLK SYGDLEAAEK  180
VRSYVRGIAA TSEQCRELSF FDVSAGRDPP LELRLCSFGP                      220

SEQ ID NO: 107          moltype = DNA  length = 24
FEATURE                 Location/Qualifiers
misc_feature            1..24
                        note = attB1 variant
source                  1..24
                        mol_type = other DNA
                        organism = synthetic construct
SEQUENCE: 107
caagttcgta caaaaaagca ggct                                       24

SEQ ID NO: 108          moltype = DNA  length = 23
FEATURE                 Location/Qualifiers
misc_feature            1..23
                        note = attB1 variant
source                  1..23
                        mol_type = other DNA
                        organism = synthetic construct
SEQUENCE: 108
caagtttgta caaaaaggac tct                                        23

SEQ ID NO: 109          moltype = DNA  length = 24
FEATURE                 Location/Qualifiers
misc_feature            1..24
                        note = attB1 variant
source                  1..24
                        mol_type = other DNA
                        organism = synthetic construct
SEQUENCE: 109
caagtgcata caaaaaggac tgct                                       24

SEQ ID NO: 110          moltype = DNA  length = 17747
FEATURE                 Location/Qualifiers
misc_feature            1..17747
                        note = PHP32371
misc_feature            4310..4817
                        note = Rab17 promoter
misc_feature            4818..4912
                        note = Rab17 5' UTR
misc_feature            4951..4974
                        note = attB1
misc_feature            5036..6496
                        note = FLP
misc_feature            6513..6536
                        note = attB2
misc_feature            6551..6868
                        note = PinII term
source                  1..17747
                        mol_type = other DNA
                        organism = synthetic construct
SEQUENCE: 110
gtttacccgc caatatatcc tgtcaaacac tgatagttta aactgaaggc gggaaacgac  60
aatctgatca tgagcggaga attaagggag tcacgttatg acccccgccg atgacgcggg  120
acaagccgtt ttacgtttgg aactgacaga accgcaacgt tgaaggagcc actcagcaag  180
ctggtacgat tgtaatacga ctcactatag ggcgaattga gcgctgttta aacgctcttc  240
aactggaaga gcggttacca gagctggtca cctttgtcca ccaagatgga actgcggccg  300
ctcattaatt aagtcaggcg cgcctctagt tgaagacacg ttcatgtctt catcgtaaga  360
agacactcag tagtcttcgg ccagaatggc catctggatt cagcaggcct agaaggccat  420
ttaaatcctg aggatctggt cttcctaagg acccgggata tcgctatcaa ctttgtatag  480
aaaagttggg ccgaattcga gctcggtacg gccagaatgg cccggaccgg gttaccgaat  540
tcgagctcgg taccctggga tccggtgcgg gcctcttcgc tattacgcca gctggcgaaa  600
gggggatgtg ctgcaaggcg attaagttgg gtaacgccag ggttttccca gtcacgacgt  660
tgtaaaacga cggccagtgc caagctcaga tcagcttgca tgcctgcagt gcagcgtgac  720
ccggtcgtgc ccctctctag agataatgag cattgcatgt ctaagttata aaaaattacc  780
acatattttt tttgtcacac ttgtttgaag tgcagtttat ctatctttat acatatattt  840
aaactttact ctacgaataa tataatctat agtactacaa taatatcagt gttttagaga  900
atcatataaa tgaacagtta gacatggtct aaaggacaat tgagtatttt gacaacagga  960
ctctacagtt ttatcttttt agtgtgcatg tgttctcctt ttttttgca aatagcttca  1020
cctatataat acttcatcca ttttattagt acatccattt agggtttagg gttaatggtt  1080
tttatagact aattttttta gtacatctat tttattctat tttagcctct aaattaagaa  1140
aactaaaact ctattttagt ttttttattt aataatttag atataaaata gaataaaata  1200
aagtgactaa aaattaaaca aataccottt aagaaattaa aaaaactaag gaaacatttt  1260
```

-continued

```
tcttgtttcg agtagataat gccagcctgt taaacgccgt cgacgagtct aacggacacc  1320
aaccagcgaa ccagcagcgt cgcgtcgggc caagcgaagc agacggcacg gcatctctgt  1380
cgctgcctct ggacccctct cgagagttcc gctccaccgt tggacttgct ccgctgtcgg  1440
catccagaaa ttgcgtggcg gagcggcaga cgtgagccgg cacggcaggc ggcctcctcc  1500
tcctctcacg gcacggcagc tacgggggat tcctttccca ccgctccttc gctttccctt  1560
cctcgcccgc cgtaataaat agacaccccc tccacaccct ctttccccaa cctcgtgttg  1620
ttcggagcgc acacacacac aaccagatct cccccaaatc cacccgtcgg cacctccgct  1680
tcaaggtacg ccgctcgtcc tccccccccc cccctctcta ccttctctag atcggcgttc  1740
cggtccatgg ttagggcccg gtagttctac ttctgttcat gtttgtgtta gatccgtgtt  1800
tgtgttagat ccgtgctgct agcgttcgta cacggatgcg acctgtacgt cagacacgtt  1860
ctgattgcta acttgccagt gtttctcttt ggggaatcct gggatggctc tagccgttcc  1920
gcagacggga tcgatttcat gatttttttt gtttcgttgc atagggtttg gtttgccctt  1980
ttcctttatt tcaatatatg ccgtgcactt gtttgtcggg tcatcttttc atgctttttt  2040
ttgtcttggt tgtgatgatg tggtctggtt gggcggtcgt tctagatcgg agtagaattc  2100
tgtttcaaac tacctggtgg atttattaat tttggatctg tatgtgtgtg ccatacatat  2160
tcatagttac gaattgaaga tgatggatgg aaatatcgat ctaggatagg tatacatgtt  2220
gatgcgggtt ttactgatgc atatacagag atgctttttg ttcgcttggt tgtgatgatg  2280
tggtgtggtt gggcggtcgt tcattcgttc tagatcggag tagaatactg tttcaaacta  2340
cctggtgtat ttattaattt tggaactgta tgtgtgtgtc atacatcttc atagttacga  2400
gtttaagatg gatggaaata tcgatctagg ataggtatac atgttgatgt gggttttact  2460
gatgcatata catgatggca tatgcagcat ctattcatat gctctaacct tgagtaccta  2520
tctattataa taaacaagta tgttttataa ttattttgat cttgatatac ttggatgatg  2580
gcatatgcag cagctatatg tggatttttt tagccctgcc ttcatacgct atttatttgc  2640
ttggtactgt ttcttttgtc gatgctcacc ctgttgtttg gtgttacttc tgcaggtcga  2700
ctctagagga tccaccatgg ctagcgaagt tcctattccg aagttcctat tctctagaaa  2760
gtataggaac ttcagatctg ccctgtccaa caagttcatc ggcgacgaca tgaagatgac  2820
ctaccacatg gacggctgcg tgaacggcca ctacttcacc gtgaagggcg agggcagcgg  2880
caagccctac gagggcaccc agacctccac cttcaaggtg accatggcca acggcggccc  2940
cctggccttc tccttcgaca tcctgtccac cgtgttcatg tacggcaacc gctgcttcac  3000
cgcctacccc accagcatgc ccgactactt caagcaggcc ttccccgacg gcatgtccta  3060
cgagagaacc ttcacctacg aggacggcgg cgtggccacc gccagctggg agatcagcct  3120
gaagggcaac tgcttcgagc acaagtccac cttccacggc gtgaacttcc ccgccgacgg  3180
ccccgtgatg gccaagaaga ccaccggctg ggacccctcc ttcgagaaga tgaccgtgtg  3240
cgacggcatc ttgaagggcg acgtgaccgc cttcctgatg ctgcagggcg gcggcaacta  3300
cagatgccag ttccacacct cctacaagac caagaagccc gtgaccatgc cccccaacca  3360
cgtggtggag caccgcatcg ccagaaccga cctggacaag ggcggcaaca gcgtgcagct  3420
gaccgagcac gccgtggccc acatcacctc cgtggtgccc ttctgaagcg gccgcaacct  3480
agacttgtcc atcttctgga ttggccaact taattaatgt atgaaataaa aggatgcaca  3540
catagtgaca tgctaatcac tataatgtgg gcatcaaagt tgtgtgttat gtgtaattac  3600
tagttatctg aataaaagag aaagagatca tccatatttc ttatcctaaa tgaatgtcac  3660
gtgtctttat aattctttga tgaaccagat gcatttcatt aaccaaatcc atatacatat  3720
aaatattaat catatataat taatatcaat tgggttagca aaacaaatct agtctaggtg  3780
tgttttgcga attcgtaatc atggtcatag ctgtttcctg tgtgaaattg ttatccgctc  3840
acaattccac acaacatacg agccggaagc ataaagtgta aagcctgggg tgcctaatga  3900
gtgagctaac tcacattaat tgcgttgcgc tcactgcccg ctttccagtc gggaaacctg  3960
tcgtgccagc tgcattaatg aatcggccaa cgcgcgggga gaggcggttt gcgtattggg  4020
cgctcttccg atccgatatc gatgggccct ggccgaagct tggtcacccg gtccgggcct  4080
agaaggccag cttcaagttt gtacaaaaaa gcaggctccg gccagaatgg cccggaccgg  4140
gttaccgaat tcgagctcgg taccctggga tccgatatcg atgggccctg gccgaagctg  4200
ggatatcgct atcaactttg tatagaaaag ttgggccgaa ttcgagctcg gtacggccag  4260
aatggcccgg accgggttac cgaattcgag ctcggtaccc tggggatccc tatagtattt  4320
taaaattgca ttaacaaaca tgtcctaatt ggtactcctg agatactata ccctcctgtt  4380
ttaaaatagt tggcattatc gaattatcat tttacttttt aatgttttct cttcttttaa  4440
tatattttat gaattttaat gtattttaaa atgttatgca gttcgctctg gacttttctg  4500
ctgcgcctac acttgggtgt actgggccta aattcagcct gaccgaccgc ctgcattgaa  4560
taatggatga gcaccggtaa aatccgcgta cccaactttc gagaagaacc gagacgtggc  4620
gggccgggcc accgacgcac ggcaccagcg actgcacacg tcccgccggc gtacgtgtac  4680
gtgctgttcc ctcactggcc gcccaatcca ctcatgcatg cccacgtaca cccctgccgt  4740
ggcgcgccca gatcctaatc ctttcgccgt tctgcacttc tgctgcctat aaatggcggc  4800
atcgaccgtc acctgcttca ccaccggcga gccacatcga gaacacgatc gagcacacaa  4860
gcacgaagac tcgtttagga gaaaccacaa accaccaagc cgtgcaagca ccaagcttgg  4920
tcacccggtc cgggcctaga aggccagctt caagtttgta caaaaaagca ggcttcgaag  4980
gagatagaac caattctcta aggaaatact taaccatggt cgactggatc caacaatgcc  5040
ccagttcgac atcctctgca agaccccccc caaggtgctc gtgaggcagt tcgtggagag  5100
gttcgagagg ccctccggcg agaagatcgc cctctgcgcc gccgagctca cctacctctg  5160
ctggatgatc acccacaacg gcaccgccat taagagggcc accttcatgt catacaacac  5220
catcatctcc aactccctct ccttcgacat cgtgaacaag tccctccagt tcaaatacaa  5280
gacccagaag gccaccatcc tcgaggcctc cctcaagaag ctcatccccg cctgggagtt  5340
caccatcatc ccctactacg gccagaagca ccagtccgac atcaccgaca tcgtgtcatc  5400
cctccagctt cagttcgagt cctccgagga ggctgacaag ggcaactccc actccaagaa  5460
gatgctgaag gccctcctct ccgagggcga gtccatctgg gagatcaccg agaagatcct  5520
caactccttc gagtacacct ccaggttcac taagaccaag accctctacc agttcctctt  5580
cctcgccacc ttcatcaact gcggcaggtt ctcagacatc aagaacgtgg accccaagtc  5640
cttcaagctc gtgcagaaca agtacctagg tttgtttctg cttctacctt tgatatatat  5700
ataataatta tcattaatta gtagtaatat aatatttcaa atattttttt caaaataaaa  5760
gaatgtagta tatagcaatt gcttttctgt agtttataag tgtgtatatt ttaatttata  5820
acttttctaa tatatgacca aaacatggtg atgcctaggt gtcatcatcc agtgcctcgt  5880
gaccgagacc aagacctccg tgtccaggca catctacttc ttctccgctc gcggcaggat  5940
cgacccccctc gtgtacctcg acgagttcct caggaactca gagcccgtgc tcaagagggt  6000
```

-continued

```
gaacaggacc ggcaactcct cctccaacaa gcaggagtac cagctcctca aggacaacct  6060
cgtgaggtcc tacaacaagg ccctcaagaa gaacgccccc tactccatct tcgccatcaa  6120
gaacggcccc aagtcccaca tcggtaggca cctcatgacc tccttcctct caatgaaggg  6180
cctcaccgag ctcaccaacg tggtgggcaa ctggtccgac aagagggcct ccgccgtggc  6240
caggaccacc tacacccacc agatcaccgc catccccgac cactacttcg ccctcgtgtc  6300
aaggtactac gcctacgacc ccatctccaa ggagatgatc gccctcaagg acgagactaa  6360
ccccatcgag gagtggcagc acatcgagca gctcaagggc tccgccgagg gctccatcag  6420
gtaccccgcc tggaacggca tcatctccca ggaggtgctc gactacctct cctcctacat  6480
caacaggagg atctgagttt cgagatatct agacccagct ttcttgtaca aagtggccgt  6540
taacggatcc agacttgtcc atcttctgga ttggccaact taattaatgt atgaaataaa  6600
aggatgcaca catagtgaca tgctaatcac tataatgtgg gcatcaaagt tgtgtgttat  6660
gtgtaattac tagttatctg aataaaagag aaagagatca tccatatttc ttatcctaaa  6720
tgaatgtcac gtgtctttat aattctttga tgaaccagat gcatttcatt aaccaaatcc  6780
atatacatat aaatattaat catatataat taatatcaat tgggttagca aaacaaatct  6840
agtctaggtg tgttttgcga attgcggcaa gcttgcggcc gccccagctt ggtcacccgg  6900
tccgggccta gaaggccgat ctcccgggca cccagctttc ttgtacaaag tggccgttaa  6960
cggatcggcc agaatggccc ggaccgggtt accgaattcg agctcggtac cctgggatcg  7020
accgaagctg accgaagctt gcggccgcac actgatagtt taaactgaag gcgggaaacg  7080
acaatctgat catgagcgga gaattaaggg agtcacgtta tgacccccgc cgatgacgcg  7140
ggacaagccg ttttacgttt ggaactgaca gaaccgcaac gattgaagga gccactcagc  7200
cgcgggtttc tggagtttaa tgagctaagc acatacgtca gaaaccatta ttgcgcgttc  7260
aaaagtcgcc taaggtcact atcagctagc aaatatttct tgtcaaaaat gctccactga  7320
cgttccataa attcccctcg gtatccaatt agagtctcat attcactctc ccggggggatc  7380
tcgactctag aggatcgctc aggaaggccg ctgagataga ggcatggcgg ccaatgcggg  7440
cggcggtgga gcgggaggag gcagcggcag cggcagcgtg gctgcgccgg cggtgtgccg  7500
ccccagcggc tcgcggtgga cgccgacgcc ggagcagatc aggatgctga aggagctcta  7560
ctacggctgc ggcatccggt cgcccagctc ggagcagatc cagcgcatca ccgccatgct  7620
gcggcagcac ggcaagatcg agggcaagaa cgtcttctac tggttccaga accacaaggc  7680
ccgcgagcgc cagaagcgcc gcctcaccag cctcgacgtc aacgtgcccg ccgccggcgc  7740
ggccgacgcc accaccagcc aactcggcgt cctctcgctg tcgtcgccgc cgccttcagg  7800
cgcggcgcct ccctcgccca ccctcggctt ctacgccgcc ggcaatggcg gcggatcggc  7860
tgtgctgctg gacacgagtt ccgactgggg cagcagcggc gctgccatgg ccaccgagac  7920
atgcttcctg caggactaca tgggcgtgac ggacacgggc agctcgtcgc agtggccacg  7980
cttctcgtcg tcggacacga taatggcggc ggccgcggcg cgggcggcga cgacgcgggc  8040
gcccgagacg ctccctctct tcccgacctg cggcgacgac ggcggcagcg gtagcagcag  8100
ctacttgccg ttctggggtg ccgcgtccac aactgccggc gccacttctt ccgttgcgat  8160
ccagcagcaa caccagctgc aggagcagta cagcttttac agcaacagca acagcaccca  8220
gctggccggc accggcaacc aagacgtatc ggcaacagca gcagcagccg ccgccctgga  8280
gctgagcctc agctcatggt gctcccctta ccctgctgca gggagtatgt gagagcaacg  8340
cgagctgcca ctgctcttca ctgatgtctc tggaatggaa ggaggaggaa gtgagcatag  8400
cgttggtgcg ttgctgtcaa gggcgaattg taccacatgg ttaacctaga cttgtccatc  8460
ttctggattg gccaacttaa ttaatgtatg aaataaaagg atgcacacat agtgacatgc  8520
taatcactat aatgtgggca tcaaagttgt gtgttatgtg taattactag ttatctgaat  8580
aaaagagaaa gagatcatcc atatttctta tcctaaatga atgtcacgtg tctttataat  8640
tctttgatga accagatgca tttcattaac caaatccata tacatataaa tattaatcat  8700
atataattaa tatcaattgg gttagcaaaa caaatctagt ctaggtgtgt tttgcgaatt  8760
gcggccgcca ccgcggtgga gctcgaattc cggtcagctt gcatgcctgc agtgcagcgt  8820
gacccggtcg tgcccctctc tagagataat gagcattgca tgtctaagtt ataaaaaatt  8880
accacatatt ttttttgtca cacttgtttg aagtgcagtt tatctatctt tatacatata  8940
tttaaacttt actctacgaa taatataatc tatagtacta caataatatc agtgttttag  9000
agaatcatat aaatgaacag ttagacatgg tctaaaggac aattgagtat tttgacaaca  9060
ggactctaca gttttatctt tttagtgtgc atgtgttctc cttttttttt gcaaatagct  9120
tcacctatat aatacttcat ccattttatt agtacatcca tttagggttt agggttaatg  9180
gtttttatag actaattttt ttagtacatc tattttattc tattttagcc tctaaattaa  9240
gaaaactaaa actctatttt agttttttta tttaataatt tagatataaa atagaataaa  9300
ataaagtgac taaaaattaa acaaataccc tttaagaaat taaaaaaact aaggaaacat  9360
ttttcttgtt tcgagtagat aatgccagcc tgttaaacgc cgtcgacgag tctaacggac  9420
accaaccagc gaaccagcag cgtcgcgtcg ggccaagcga agcagacggc acggcatctc  9480
tgtcgctgcc tctggacccc tctcgagagt tccgctccac cgttggactt gctccgctgt  9540
cggcatccag aaattgcgtg gcggagcggc agacgtgagc cggcacggca ggcggcctcc  9600
tcctcctctc acggcaccgg cagctacggg ggattccttt cccaccgctc cttcgctttc  9660
ccttcctcgc ccgccgtaat aaatagacac cccctccaca ccctctttcc ccaacctcgt  9720
gttgttcgga gcgcacacac acacaaccag atctccccca aatccacccg tcggcacctc  9780
cgcttcaagg tacgccgctc gtcctccccc cccccctct ctaccttctc tagatcggcg  9840
ttccggtcca tgcatggtta gggcccggta gttctacttc tgttcatgtt tgtgttagat  9900
ccgtgtttgt gttagatccg tgctgctagc gttcgtacac ggatgcgacc tgtacgtcag  9960
acacgttctg attgctaact tgccagtgtt tctctttggg gaatcctggg atggctctag  10020
ccgttccgca gacgggatcg atttcatgat tttttttgtt tcgttgcata gggtttggtt  10080
tgcccttttc ctttatttca atatatgccg tgcacttgtt tgtcgggtca tcttttcatg  10140
cttttttttg tcttggttgt gatgatgtgg tctggttggg cggtcgttct agatcggagt  10200
agaattctgt ttcaaactac ctggtggatt tattaatttt ggatctgtat gtgtgtgcca  10260
tacatattca tagttacgaa ttgaagatga tggatggaaa tatcgatcta ggataggtat  10320
acatgttgat gcgggtttta ctgatgcata tacagagatg ctttttgttc gcttggttgt  10380
gatgatgtgg tgtggttggg cggtcgttca ttcgttctag atcggagtag aatactgttt  10440
caaactacct ggtgtattta ttaattttgg aactgtatgt gtgtgtcata catcttcata  10500
gttacgagtt taagatggat ggaaatatcg atctaggata ggtatacatg ttgatgtggg  10560
ttttactgat gcatatacat gatggcatat gcagcatcta ttcatatgct ctaaccttga  10620
gtacctatct attataataa acaagtatgt tttataatta ttttgatctt gatatacttg  10680
gatgatggca tatgcagcag ctatatgtgg atttttttag ccctgccttc atacgctatt  10740
```

```
tatttgcttg gtactgtttc ttttgtcgat gctcaccctg ttgtttggtg ttacttctgc  10800
aggtcgactc tagaggatcc atggccactg tgaacaactg gctcgctttc tccctctccc  10860
cgcaggagct gccgccctcc cagacgacgg actccacact catctcggcc gccaccgccg  10920
accatgtctc cggcgatgtc tgcttcaaca tcccccaaga ttggagcatg aggggatcag  10980
agctttcggc gctcgtcgcg gagccgaagc tggaggactt cctcggcggc atctccttct  11040
ccgagcagca tcacaaggcc aactgcaaca tgatacccag cactagcagc acagtttgct  11100
acgcgagctc aggtgctagc accggctacc atcaccagct gtaccaccag ccccaccagct  11160
cagcgctcca cttcgcggac tccgtaatgg tggcctcctc ggccggtgtc cacgacggcg  11220
gtgccatgct cagcgcggcc gccgctaacg gtgtcgctgg cgctgccagt gccaacggcg  11280
gcggcatcgg gctgtccatg attaagaact ggctgcggag ccaaccggcg cccatgcagc  11340
cgagggtggc ggcggctgag ggcgcgcagg ggctctcttt gtccatgaac atggcgggga  11400
cgacccaagg cgctgctggc atgccacttc tcgctggaga gcgcgcacgg gcgcccgaga  11460
gtgtatcgac gtcagcacag ggtggagccg tcgtcgtcac ggcgccgaag gaggatagcg  11520
gtggcagcgg tgttgccggc gctctagtag ccgtgagcac ggacacgggt ggcagcggcg  11580
gcgcgtcggc tgacaacacg gcaaggaaga cggtggacac gttcgggcag cgcacgtcga  11640
tttaccgtgg cgtgacaagg catagatgga ctgggagata tgaggcacat ctttgggata  11700
acagttgcag aagggaaggg caaactcgta agggtcgtca agtctattta ggtggctatg  11760
ataaagagga gaaagctgct agggcttatg atcttgctgc tctgaagtac tggggtgcca  11820
caacaacaac aaattttcca gtgagtaact acgaaaagga gctcgaggac atgaagcaca  11880
tgacaaggca ggagtttgta gcgtctctga gaaggaagag cagtggtttc tccagaggtg  11940
catccattta caggggagtg actaggcatc accaacatgg aagatggcaa gcacggattg  12000
gacgagttgc agggaacaag gatctttact tgggcacctt cagcacccag gaggaggcag  12060
cggaggcgta cgacatcgcg gcgatcaagt tccgcggcct caacgccgtc accaacttcg  12120
acatgagccg ctacgacgtg aagagcatcc tggacagcag cgccctcccc atcggcagcg  12180
ccgccaagcg cctcaaggag gccgaggccg cagcgtccgc gcagcaccac cacgccggcg  12240
tggtgagcta cgacgtcggc cgcatcgcct cgcagctcgg cgacggcgga gccctggcgg  12300
cggcgtacgg cgcgcactac cacggcgccg cctggccgac catcgcgttc cagccgggcg  12360
ccgccagcac aggcctgtac cacccgtacg cgcagcagcc aatgcgcggc ggcgggtggt  12420
gcaagcagga gcaggaccac gcggtgatcg cggccgcgca cagcctgcag gacctccacc  12480
acctgaacct gggcgcggcc ggcgcgcacg actttttctc ggcagggcag caggccgccg  12540
ccgctgcgat gcacggcctg ggtagcatcg acagtgcgtc gctcgagcac agcaccggct  12600
ccaactccgt cgtctacaac ggcggggtcg gcgacagcaa cggcgccagc gccgtcggcg  12660
gcagtggcgg tggctacatg atgccgatga gcgctgccgg agcaaccact acatcggcaa  12720
tggtgagcca cgagcaggtg catgcacggg cctacgacga agccaagcag gctgctcaga  12780
tggggtacga gagctacctg gtgaacgcgg agaacaatgg tggcggaagg atgtctgcat  12840
gggggactgt cgtgtctgca gccgcggcgg cagcagcaag cagcaacgac aacatggccg  12900
ccgacgtcgg ccatggcggc gcgcagctct tcagtgtctg gaacgacact taagcgtacg  12960
tgccggcctg gctctccgaa agggcgaatt ccagcacact ggcggccgtt actagaccca  13020
acctagactt gtccatcttc tggattggcc aacttaatta atgtatgaaa taaaaggatg  13080
cacacatagt gacatgctaa tcactataat gtgggcatca aagttgtgtg ttatgtgtaa  13140
ttactagtta tctgaataaa agagaaagag atcatccata tttcttatcc taaatgaatg  13200
tcacgtgtct ttataattct ttgatgaacc agatgcattt cattaaccaa atccatatac  13260
atataaatat taatcatata taattaatat caattgggtt agcaaaacaa atctagtcta  13320
ggtgtgtttt gcgaatgcgg ccgccaccgc ggtggagctc gaattccggt cgatccgata  13380
tcgatgggcc ctggccgaag ctaattcctg cagtgcagcg tgacccggtc gtgcccctct  13440
ctagtggatc tgagcttcta gcgaagttcc tattccgaag ttcctattct ctagaaagta  13500
taggaacttc agatctgccc acagcaagca cggcctgaag gaggagatga ccatgaagta  13560
ccacatggag ggctgcgtga acggccacaa gttcgtgatc accggcgagg gcatcggcta  13620
ccccttcaag ggcaagcaga ccatcaacct gtgcgtgatc gagggcggcc ccctgccctt  13680
cagcgaggac atcctgagcg ccggcttcaa gtacggcgac cggatcttca ccgagtaccc  13740
ccaggacatc gtggactact tcaagaacag ctgccccgcc ggctacacct ggggccggag  13800
cttcctgttc gaggacggcg ccgtgtgcat ctgtaacgtg gacatcaccg tgagcgtgaa  13860
ggagaactgc atctaccaca agagcatctt caacggcgtg aacttccccg ccgacggccc  13920
cgtgatgaag aagatgacca ccaactggga ggccagctgc gagaagatca tgcccgtgcc  13980
taagcagggc atcctgaagg gcgacgtgag catgtacctg ctgctgaagg acggcggccg  14040
gtaccggtgc cagttcgaca ccgtgtacaa ggccaagagc gtgcccagca agatgcccga  14100
gtggcacttc atccagcaca agctgctgcg ggaggaccgg agcgacgcca agaaccagaa  14160
gtggcagctg accgagcacg ccatcgcctt ccccagcgcc ctggcctgaa gcggccgcaa  14220
cctagacttg tccatcttct ggattggcca acttaattaa tgtatgaaat aaaaggatgc  14280
acacatagtg acatgctaat cactataatg tgggcatcaa agttgtgtgt tatgtgtaat  14340
tactagttat ctgaataaaa gagaaagaga tcatccatat ttcttatcct aaatgaatgt  14400
cacgtgtctt tataattctt tgatgaacca gatgcatttc attaaccaaa tccatataca  14460
tataaatatt aatcatatat aattaatatc aattgggtta gcaaaacaaa tctagtctag  14520
gtgtgttttg cgaattagct tggtcacccg gtccgggcct agaaggccag cttgcggccg  14580
ccccgggcaa ctttattata caaagttgat agatatcgga ccgattaaac tttaattcgg  14640
tccgaagctt gcatgcctgc agtgcagcgt gacccggtcg tgcccctctc tagagataat  14700
gagcattgca tgtctaagtt ataaaaaatt accacatatt ttttttgtca cacttgtttg  14760
aagtgcagtt tatctatctt tatacatata tttaaacttt actctacgaa taatataatc  14820
tatagtacta caataatatc agtgttttag agaatcatat aaatgaacag ttagacatgg  14880
tctaaaggac aattgagtat tttgacaaca ggactctaca gttttatctt tttagtgtgc  14940
atgtgttctc cttttttttt gcaaatagct tcacctatat aatacttcat ccattttatt  15000
agtacatcca tttagggttt agggttaatg gtttttatag actaattttt ttagtacatc  15060
tattttattc tattttagcc tctaaattaa gaaaactaaa actctatttt agttttttta  15120
tttaataatt tagatataaa atagaataaa ataaagtgac taaaaattaa acaaataccc  15180
tttaagaaat taaaaaaact aaggaaacat ttttcttgtt tcgagtagat aatgccagcc  15240
tgttaaacgc cgtcgacgag tctaacggac accaaccagc gaaccagcag cgtcgcgtcg  15300
ggccaagcga agcagacggc acggcatctc tgtcgctgcc tctggacccc tctcgagagt  15360
tccgctccac cgttggactt gctccgctgt cggcatccag aaattgcgtg gcggagcggc  15420
agacgtgagc cggcacggca ggcggcctcc tcctcctctc acggcaccgg cagctacggg  15480
```

```
ggattccttt cccaccgctc cttcgctttc ccttcctcgc ccgccgtaat aaatagacac  15540
cccctccaca ccctctttcc ccaacctcgt gttgttcgga gcgcacacac acacaaccag  15600
atctccccca aatccacccg tcggcacctc cgcttcaagg tacgccgctc gtcctccccc  15660
cccccccctct ctaccttctc tagatcggcg ttccggtcca tgcatggtta gggcccggta  15720
gttctacttc tgttcatgtt tgtgttagat ccgtgtttgt gttagatccg tgctgctagc  15780
gttcgtacac ggatgcgacc tgtacgtcag acacgttctg attgctaact tgccagtgtt  15840
tctctttggg gaatcctggg atggctctag ccgttccgca gacgggatcg atttcatgat  15900
ttttttgtt tcgttgcata gggtttggtt tgccctttc ctttatttca atatatgccg  15960
tgcacttgtt tgtcgggtca tcttttcatg cttttttttg tcttggttgt gatgatgtgg  16020
tctggttggg cggtcgttct agatcggagt agaattctgt ttcaaactac ctggtggatt  16080
tattaatttt ggatctgtat gtgtgtgcca tacatattca tagttacgaa ttgaagatga  16140
tggatggaaa tatcgatcta ggataggtat acatgttgat gcgggtttta ctgatgcata  16200
tacagagatg ctttttgttc gcttggttgt gatgatgtgg tgtggttggg cggtcgttca  16260
ttcgttctag atcggagtag aatactgttt caaactacct ggtgtattta ttaattttgg  16320
aactgtatgt gtgtgtcata catcttcata gttacgagtt taagatggat ggaaatatcg  16380
atctaggata ggtatacatg ttgatgtggg ttttactgat gcatatacat gatggcatat  16440
gcagcatcta ttcatatgct ctaaccttga gtacctatct attataataa acaagtatgt  16500
tttataatta ttttgatctt gatatacttg gatgatggca tatgcagcag ctatatgtgg  16560
attttttag ccctgccttc atacgctatt tatttgcttg gtactgtttc ttttgtcgat  16620
gctcaccctg ttgtttggtg ttacttctgc aggtcgactt taacttagcc taggatccac  16680
acgacaccat gtcccccgag cgccgccccg tcgagatccg cccggccacc gccgccgaca  16740
tggccgccgt gtgcgacatc gtgaaccact acatcgagac ctccaccgtg aacttccgca  16800
ccgagccgca gacccccgcag gagtggatcg acgacctgga gcgcctccag gaccgctacc  16860
cgtggctcgt ggccgaggtg gagggcgtgg tggccggcat cgcctacgcc ggcccgtgga  16920
aggcccgcaa cgcctacgac tggaccgtgg agtccaccgt gtacgtgtcc caccgccacc  16980
agcgcctcgg cctcggctcc accctctaca cccacctcct caagagcatg gaggcccagg  17040
gcttcaagtc cgtggtggcc gtgatcggcc tcccgaacga cccgtccgtg cgcctccacg  17100
aggccctcgg ctacaccgcc cgcggcaccc tccgcgccgc cggctacaag cacggcggct  17160
ggcacgacgt cggcttctgg cagcgcgact tcgagctgcc ggccccgccg cgcccggtgc  17220
gcccggtgac gcagatctga gtcgaaacct agacttgtcc atcttctgga ttggccaact  17280
taattaatgt atgaaataaa aggatgcaca catagtgaca tgctaatcac tataatgtgg  17340
gcatcaaagt tgtgtgttat gtgtaattac tagttatctg aataaaagag aaagagatca  17400
tccatatttc ttatcctaaa tgaatgtcac gtgtctttat aattctttga tgaaccagat  17460
gcatttcatt aaccaaatcc atatacatat aaatattaat catatataat taatatcaat  17520
tgggttagca aaacaaatct agtctaggtg tgttttgcga attgcggccg ccaccgcggt  17580
ggagctcgaa ttcattccga ttaatcgtgg cctcttgctc ttcaggatga agagctatgt  17640
ttaaacgtgc aagcgctact agacaattca gtacattaaa aacgtccgca atgtgttatt  17700
aagttgtcta agcgtcaatt tgtttacacc acaatatatc ctgccac              17747
```

```
SEQ ID NO: 111          moltype = DNA  length = 17373
FEATURE                 Location/Qualifiers
misc_feature            1..17373
                        note = PHP35648
misc_feature            4301..4808
                        note = Rab17 promoter
misc_feature            4809..4903
                        note = Rab17 5' UTR
misc_feature            4942..4965
                        note = attB1
misc_feature            4991..6208
                        note = Cre
misc_feature            6217..6240
                        note = attB2
misc_feature            6255..6572
                        note = PinII term
source                  1..17373
                        mol_type = other DNA
                        organism = synthetic construct
SEQUENCE: 111
gtttacccgc caatatatcc tgtcaaacac tgatagttta aactgaaggc gggaaacgac  60
aatctgatca tgagcggaga attaagggag tcacgttatg acccccgccg atgacgcggg  120
acaagccgtt ttacgtttgg aactgacaga accgcaacgt tgaaggagcc actcagcaag  180
ctggtacgat tgtaatacga ctcactatag ggcgaattga gcgctgttta aacgctcttc  240
aactggaaga gcggttacca gagctggtca cctttgtcca ccaagatgga actgcggccg  300
ctcattaatt aagtcaggcg cgcctctagt tgaagacacg ttcatgtctt catcgtaaga  360
agacactcag tagtcttcgg ccagaatggc catctggatt cagcaggcct agaaggccat  420
ttaaatcctg aggatctggt cttcctaagg acccgggata tcgctatcaa ctttgtatag  480
aaaagttggg ccgaattcga gctcggtacg gccagaatgg cccggaccgg gttaccgaat  540
tcgagctcgg taccctggga tccggtgcgg gcctcttcgc tattacgcca gctggcgaaa  600
gggggatgtg ctgcaaggcg attaagttgg gtaacgccag ggttttccca gtcacgacgt  660
tgtaaaacga cggccagtgc caagctcaga tcagcttgca tgcctgcagt gcagcgtgac  720
ccggtcgtgc ccctctctag agataatgag cattgcatgt ctaagttata aaaaattacc  780
acatattttt tttgtcacac ttgtttgaag tgcagtttat ctatctttat acatatattt  840
aaactttact ctacgaataa tataatctat agtactacaa taatatcagt gttttagaga  900
atcatataaa tgaacagtta gacatggtct aaaggacaat tgagtatttt gacaacagga  960
ctctacagtt ttatcttttt agtgtgcatg tgttctcctt tttttttgca aatagcttca  1020
cctatataat acttcatcca ttttattagt acatccattt agggtttagg gttaatggtt  1080
tttatagact aattttttta gtacatctat tttattctat tttagcctct aaattaagaa  1140
aactaaaact ctattttagt ttttttattt aataatttag atataaaata gaataaaata  1200
```

-continued

```
aagtgactaa aaattaaaca aatacccttt aagaaattaa aaaaactaag gaaacatttt  1260
tcttgtttcg agtagataat gccagcctgt taaacgccgt cgacgagtct aacggacacc  1320
aaccagcgaa ccagcagcgt cgcgtcgggc caagcgaagc agacggcacg gcatctctgt  1380
cgctgcctct ggacccctct cgagagttcc gctccaccgt tggacttgct ccgctgtcgg  1440
catccagaaa ttgcgtggcg gagcggcaga cgtgagccgg cacggcaggc ggcctcctcc  1500
tcctctcacg gcacggcagc tacgggggat tcctttccca ccgctccttc gctttccctt  1560
cctcgcccgc cgtaataaat agacaccccc tccacaccct ctttccccaa cctcgtgttg  1620
ttcggagcgc acacacacac aaccagatct cccccaaatc cacccgtcgg cacctccgct  1680
tcaaggtacg ccgctcgtcc tccccccccc cccctctcta ccttctctag atcggcgttc  1740
cggtccatgg ttagggcccg gtagttctac ttctgttcat gtttgtgtta gatccgtgtt  1800
tgtgttagat ccgtgctgct agcgttcgta cacggatgcg acctgtacgt cagacacgtt  1860
ctgattgcta acttgccagt gtttctcttt ggggaatcct gggatggctc tagccgttcc  1920
gcagacggga tcgatttcat gatttttttt gtttcgttgc atagggtttg gtttgccctt  1980
ttcctttatt tcaatatatg ccgtgcactt gtttgtcggg tcatcttttc atgctttttt  2040
ttgtcttggt tgtgatgatg tggtctggtt gggcggtcgt tctagatcgg agtagaattc  2100
tgtttcaaac tacctggtgg atttattaat tttggatctg tatgtgtgtg ccatacatat  2160
tcatagttac gaattgaaga tgatggatgg aaatatcgat ctaggatagg tatacatgtt  2220
gatgcgggtt ttactgatgc atatacagag atgctttttg ttcgcttggt tgtgatgatg  2280
tggtgtggtt gggcggtcgt tcattcgttc tagatcggag tagaatactg tttcaaacta  2340
cctggtgtat ttattaattt tggaactgta tgtgtgtgtc atacatcttc atagttacga  2400
gtttaagatg gatggaaata tcgatctagg ataggtatac atgttgatgt gggttttact  2460
gatgcatata catgatggca tatgcagcat ctattcatat gctctaacct tgagtaccta  2520
tctattataa taaacaagta tgttttataa ttattttgat cttgatatac ttggatgatg  2580
gcatatgcag cagctatatg tggatttttt tagccctgcc ttcatacgct atttatttgc  2640
ttggtactgt ttcttttgtc gatgctcacc ctgttgtttg gtgttacttc tgcaggtcga  2700
ctctagagga tccaccatgg ctagcataac ttcgtatagc atacattata cgaagttatc  2760
cagatctgcc ctgtccaaca agttcatcgg cgacgacatg aagatgacct accacatgga  2820
cggctgcgtg aacggccact acttcaccgt gaagggcgag ggcagcggca agccctacga  2880
gggcacccag acctccacct tcaaggtgac catggccaac ggcggccccc tggccttctc  2940
cttcgacatc ctgtccaccg tgttcatgta cggcaaccgc tgcttcaccg cctaccccac  3000
cagcatgccc gactacttca agcaggcctt ccccgacggc atgtcctacg agagaacctt  3060
cacctacgag gacggcggcg tggccaccgc cagctgggag atcagcctga agggcaactg  3120
cttcgagcac aagtccacct tccacggcgt gaacttcccc gccgacggcc ccgtgatggc  3180
caagaagacc accggctggg acccctcctt cgagaagatg accgtgtgcg acggcatctt  3240
gaagggcgac gtgaccgcct tcctgatgct gcagggcggc ggcaactaca gatgccagtt  3300
ccacacctcc tacaagacca agaagcccgt gaccatgccc cccaaccacg tggtggagca  3360
ccgcatcgcc agaaccgacc tggacaaggg cggcaacagc gtgcagctga ccgagcacgc  3420
cgtggcccac atcacctccg tggtgccctt ctgaagcggc cgcaacctag acttgtccat  3480
cttctggatt ggccaactta attaatgtat gaaataaaag gatgcacaca tagtgacatg  3540
ctaatcacta taatgtgggc atcaaagttg tgtgttatgt gtaattacta gttatctgaa  3600
taaaagagaa agagatcatc catatttctt atcctaaatg aatgtcacgt gtctttataa  3660
ttctttgatg aaccagatgc atttcattaa ccaaatccat atacatataa atattaatca  3720
tatataatta atatcaattg ggttagcaaa acaaatctag tctaggtgtg ttttgcgaat  3780
tcgtaatcat ggtcatagct gtttcctgtg tgaaattgtt atccgctcac aattccacac  3840
aacatacgag ccggaagcat aaagtgtaaa gcctggggtg cctaatgagt gagctaactc  3900
acattaattg cgttgcgctc actgcccgct ttccagtcgg gaaacctgtc gtgccagctg  3960
cattaatgaa tcggccaacg cgcggggaga ggcggtttgc gtattgggcg ctcttccgct  4020
gatccgatat cgatgggccc tggccgaagc ttggtcaccc ggtccgggcc tagaaggcca  4080
gcttcaagtt tgtacaaaaa agcaggctcc ggccagaatg gcccggaccg ggttaccgaa  4140
ttcgagctcg gtaccctggg atccgatatc gatgggccct ggccgaagct gggatatcgc  4200
tatcaacttt gtatagaaaa gttgggccga attcgagctc ggtacggcca gaatggcccg  4260
gaccgggtta ccgaattcga gctcggtacc ctggggatcc ctatagtatt ttaaaattgc  4320
attaacaaac atgtcctaat tggtactcct gagatactat accctcctgt tttaaaatag  4380
ttggcattat cgaattatca ttttactttt taatgttttc tcttctttta atatatttta  4440
tgaattttaa tgtattttaa aatgttatgc agttcgctct ggacttttct gctgcgccta  4500
cacttgggtg tactgggcct aaattcagcc tgaccgaccg cctgcattga ataatggatg  4560
agcaccggta aaatccgcgt acccaacttt cgagaagaac cgagacgtgg cgggccgggc  4620
caccgacgca cggcaccagc gactgcacac gtcccgccgg cgtacgtgta cgtgctgttc  4680
cctcactggc cgcccaatcc actcatgcat gcccacgtac acccctgccg tggcgcgccc  4740
agatcctaat cctttcgccg ttctgcactt ctgctgccta taaatggcgg catcgaccgt  4800
cacctgcttc accaccggcg agccacatcg agaacacgat cgagcacaca agcacgaaga  4860
ctcgtttagg agaaaccaca aaccaccaag ccgtgcaagc accaagcttg gtcacccggt  4920
ccgggcctag aaggccagct tcaagtttgt acaaaaaagc aggcttcgaa ggagatagaa  4980
ccgatccacc atgtccaacc tgctcacggt tcaccagaac cttccggctc ttccagtgga  5040
cgcgacgtcc gatgaagtca ggaagaacct catggacatg ttccgcgaca ggcaagcgtt  5100
cagcgagcac acctggaaga tgctgctctc cgtctgccgc tcctgggctg catggtgcaa  5160
gctgaacaac aggaagtggt tccccgctga gcccgaggac gtgagggatt accttctgta  5220
cctgcaagcg cgaggtttgt ttctgcttct acctttgata tatatataat aattatcatt  5280
aattagtagt aatataatat ttcaaatatt tttttcaaaa taaaagaatg tagtatatag  5340
caattgcttt tctgtagttt ataagtgtgt atattttaat ttataacttt tctaatatat  5400
gaccaaaaca tggtgatgcc taggtctggc agtgaagacc atccagcaac accttggaca  5460
actgaacatg cttcacaggc gctccggcct cccgcgcccc agcgactcga acgccgtgag  5520
cctcgtcatg cgccgcatca ggaaggaaaa cgtcgatgcc ggcgaaaggg caaagcaggc  5580
cctcgcgttc gagaggaccg atttcgacca ggtccgcagc ctgatggaga acagcgacag  5640
gtgccaggac attaggaacc tggcgttcct cggaattgca tacaacacgc tcctcaggat  5700
cgcggaaatt gcccgcattc gcgtgaagga cattagccgc accgacggcg gcaggatgct  5760
tatccacatt ggcaggacca agacgctcgt ttccaccgca ggcgtcgaaa aggccctcag  5820
cctcggagtg accaagctcg tcgaacgctg gatctccgtg tccggcgtcg cggacgaccc  5880
aaacaactac ctcttctgcc gcgtccgcaa gaacggggtg gctgccccta gcgccaccag  5940
```

-continued

```
ccaactcagc acgagggcct tggaaggtat tttcgaggcc acccaccgcc tgatctacgg  6000
cgcgaaggat gacagcggtc aacgctacct cgcatggtcc gggcactccg cccgcgttgg  6060
agctgctagg gacatggccc gcgccggtgt ttccatcccc gaaatcatgc aggcgggtgg  6120
atggacgaac gtgaacattg tcatgaacta cattcgcaac cttgacagcg agacgggcgc  6180
aatggttcgc ctcctggaag atggtgactg agctagaccc agctttcttg tacaaagtgg  6240
ccgttaacgg atccagactt gtccatcttc tggattggcc aacttaatta atgtatgaaa  6300
taaaaggatg cacacatagt gacatgctaa tcactataat gtgggcatca aagttgtgtg  6360
ttatgtgtaa ttactagtta tctgaataaa agagaaagag atcatccata tttcttatcc  6420
taaatgaatg tcacgtgtct ttataattct ttgatgaacc agatgcattt cattaaccaa  6480
atccatatac atataaatat taatcatata taattaatat caattgggtt agcaaaacaa  6540
atctagtcta ggtgtgtttt gcgaattgcg gcaagcttgc ggccgcccca gcttggtcac  6600
ccggtccggg cctagaaggc cgatctcccg ggcacccagc tttcttgtac aaagtggccg  6660
ttaacggatc ggccagaatg gcccggaccg ggttaccgaa ttcgagctcg gtaccctggg  6720
atcgaccgaa gctgaccgaa gcttgcggcc gcacactgat agtttaaact gaaggcggga  6780
aacgacaatc tgatcatgag cggagaatta agggagtcac gttatgaccc ccgccgatga  6840
cgcgggacaa gccgttttac gtttggaact gacagaaccg caacgattga aggagccact  6900
cagccgcggg tttctggagt ttaatgagct aagcacatac gtcagaaacc attattgcgc  6960
gttcaaaagt cgcctaaggt cactatcagc tagcaaatat ttcttgtcaa aaatgctcca  7020
ctgacgttcc ataaattccc ctcggtatcc aattagagtc tcatattcac tctcccgggg  7080
gatctcgact ctagaggatc gctcaggaag gccgctgaga tagaggcatg gcggccaatg  7140
cgggcggcgg tggagcggga ggaggcagcg gcagcggcag cgtggctgcg ccggcggtgt  7200
gccgccccag cggctcgcgg tggacgccga cgccggagca gatcaggatg ctgaaggagc  7260
tctactacgg ctgcggcatc cggtcgccca gctcggagca gatccagcgc atcaccgcca  7320
tgctgcggca gcacggcaag atcgagggca agaacgtctt ctactggttc cagaaccaca  7380
aggcccgcga gcgccagaag cgccgcctca ccagcctcga cgtcaacgtg cccgccgccg  7440
gcgcggccga cgccaccacc agccaactcg gcgtcctctc gctgtcgtcg ccgccgcctt  7500
caggcgcggc gcctccctcg cccaccctcg gcttctacgc cgccggcaat ggcggcggat  7560
cggctgtgct gctggacacg agttccgact ggggcagcag cggcgctgcc atggccaccg  7620
agacatgctt cctgcaggac tacatgggcg tgacggacac gggcagctcg tcgcagtggc  7680
cacgcttctc gtcgtcggac acgataatgg cggcggccgc ggcgcgggcg gcgacgacgc  7740
gggcgcccga gacgctccct ctcttcccga cctgcggcga cgacggcggc agcggtagca  7800
gcagctactt gccgttctgg ggtgccgcgt ccacaactgc cggcgccact tcttccgttg  7860
cgatccagca gcaacaccag ctgcaggagc agtacagctt ttacagcaac agcaacagca  7920
cccagctggc cggcaccggc aaccaagacg tatcggcaac agcagcagca gccgccgccc  7980
tggagctgag cctcagctca tggtgctccc cttaccctgc tgcagggagt atgtgagagc  8040
aacgcgagct gccactgctc ttcactgatg tctctggaat ggaaggagga ggaagtgagc  8100
atagcgttgg tgcgttgctg tcaagggcga attgtaccac atggttaacc tagacttgtc  8160
catcttctgg attggccaac ttaattaatg tatgaaataa aaggatgcac acatagtgac  8220
atgctaatca ctataatgtg ggcatcaaag ttgtgtgtta tgtgtaatta ctagttatct  8280
gaataaaaga gaaagagatc atccatattt cttatcctaa atgaatgtca cgtgtcttta  8340
taattctttg atgaaccaga tgcatttcat taaccaaatc catatacata taaatattaa  8400
tcatatataa ttaatatcaa ttgggttagc aaaacaaatc tagtctaggt gtgttttgcg  8460
aattgcggcc gccaccgcgg tggagctcga attccggtca gcttgcatgc ctgcagtgca  8520
gcgtgacccg gtcgtgcccc tctctagaga taatgagcat tgcatgtcta agttataaaa  8580
aattaccaca tatttttttt gtcacacttg tttgaagtgc agtttatcta tctttataca  8640
tatatttaaa ctttactcta cgaataatat aatctatagt actacaataa tatcagtgtt  8700
ttagagaatc atataaatga acagttagac atggtctaaa ggacaattga gtattttgac  8760
aacaggactc tacagtttta tctttttagt gtgcatgtgt tctccttttt ttttgcaaat  8820
agcttcacct atataatact tcatccattt tattagtaca tccatttagg gtttagggtt  8880
aatggttttt atagactaat ttttttagta catctatttt attctatttt agcctctaaa  8940
ttaagaaaac taaaactcta ttttagtttt tttatttaat aatttagata taaaatagaa  9000
taaaataaag tgactaaaaa ttaaacaaat accctttaag aaattaaaaa aactaaggaa  9060
acatttttct tgtttcgagt agataatgcc agcctgttaa acgccgtcga cgagtctaac  9120
ggacaccaac cagcgaacca gcagcgtcgc gtcgggccaa gcgaagcaga cggcacggca  9180
tctctgtcgc tgcctctgga cccctctcga gagttccgct ccaccgttgg acttgctccg  9240
ctgtcggcat ccagaaattg cgtggcggag cggcagacgt gagccggcac ggcaggcggc  9300
ctcctcctcc tctcacggca ccggcagcta cgggggattc ctttcccacc gctccttcgc  9360
tttcccttcc tcgcccgccg taataaatag acaccccctc cacaccctct ttccccaacc  9420
tcgtgttgtt cggagcgcac acacacacaa ccagatctcc cccaaatcca cccgtcggca  9480
cctccgcttc aaggtacgcc gctcgtcctc cccccccccc ctctctacct tctctagatc  9540
ggcgttccgg tccatgcatg gttagggccc ggtagttcta cttctgttca tgtttgtgtt  9600
agatccgtgt ttgtgttaga tccgtgctgc tagcgttcgt acacggatgc gacctgtacg  9660
tcagacacgt tctgattgct aacttgccag tgtttctctt tggggaatcc tgggatggct  9720
ctagccgttc cgcagacggg atcgatttca tgattttttt tgtttcgttg catagggttt  9780
ggtttgccct tttcctttat ttcaatatat gccgtgcact tgtttgtcgg gtcatctttt  9840
catgcttttt tttgtcttgg ttgtgatgat gtggtctggt tgggcggtcg ttctagatcg  9900
gagtagaatt ctgtttcaaa ctacctggtg gatttattaa ttttggatct gtatgtgtgt  9960
gccatacata ttcatagtta cgaattgaag atgatggatg gaaatatcga tctaggatag  10020
gtatacatgt tgatgcgggt tttactgatg catatacaga gatgcttttt gttcgcttgg  10080
ttgtgatgat gtggtgtggt tgggcggtcg ttcattcgtt ctagatcgga gtagaatact  10140
gtttcaaact acctggtgta tttattaatt ttggaactgt atgtgtgtgt catacatctt  10200
catagttacg agtttaagat ggatggaaat atcgatctag gataggtata catgttgatg  10260
tgggttttac tgatgcatat acatgatggc atatgcagca tctattcata tgctctaacc  10320
ttgagtacct atctattata ataaacaagt atgttttata attattttga tcttgatata  10380
cttggatgat ggcatatgca gcagctatat gtggattttt ttagccctgc cttcatacgc  10440
tatttatttg cttggtactg tttcttttgt cgatgctcac cctgttgttt ggtgttactt  10500
ctgcaggtcg actctagagg atccatggcc actgtgaaca actggctcgc tttctccctc  10560
tccccgcagg agctgccgcc ctcccagacg acggactcca cactcatctc ggccgccacc  10620
gccgaccatg tctccggcga tgtctgcttc aacatccccc aagattggag catgagggga  10680
```

```
tcagagcttt cggcgctcgt cgcggagccg aagctggagg acttcctcgg cggcatctcc  10740
ttctccgagc agcatcacaa ggccaactgc aacatgatac ccagcactag cagcacagtt  10800
tgctacgcga gctcaggtgc tagcaccggc taccatcacc agctgtacca ccagcccacc  10860
agctcagcgc tccacttcgc ggactccgta atggtggcct cctcggccgg tgtccacgac  10920
ggcggtgcca tgctcagcgc ggccgccgct aacggtgtcg ctggcgctgc cagtgccaac  10980
ggcggcggca tcgggctgtc catgattaag aactggctgc ggagccaacc ggcgcccatg  11040
cagccgaggg tggcggcggc tgagggcgcg caggggctct ctttgtccat gaacatggcg  11100
gggacgaccc aaggcgctgc tggcatgcca cttctcgctg gagagcgcgc acgggcgccc  11160
gagagtgtat cgacgtcagc acagggtgga gccgtcgtcg tcacggcgcc gaaggaggat  11220
agcggtggca gcggtgttgc cggcgctcta gtagccgtga gcacggacac gggtggcagc  11280
ggcggcgcgt cggctgacaa cacggcaagg aagacggtgg acacgttcgg gcagcgcacg  11340
tcgatttacc gtggcgtgac aaggcataga tggactggga gatatgaggc acatctttgg  11400
gataacagtt gcagaaggga agggcaaact cgtaagggtc gtcaagtcta tttaggtggc  11460
tatgataaag aggagaaagc tgctagggct tatgatcttg ctgctctgaa gtactggggt  11520
gccacaacaa caacaaattt tccagtgagt aactacgaaa aggagctcga ggacatgaag  11580
cacatgacaa ggcaggagtt tgtagcgtct ctgagaagga agagcagtgg tttctccaga  11640
ggtgcatcca tttacagggg agtgactagg catcaccaac atggaagatg gcaagcacgg  11700
attggacgag ttgcagggaa caaggatctt tacttgggca ccttcagcac ccaggaggag  11760
gcagcggagg cgtacgacat cgcggcgatc aagttccgcg gcctcaacgc cgtcaccaac  11820
ttcgacatga gccgctacga cgtgaagagc atcctggaca gcagcgccct ccccatcggc  11880
agcgccgcca agcgcctcaa ggaggccgag gccgcagcgt ccgcgcagca ccaccacgcc  11940
ggcgtggtga gctacgacgt cggccgcatc gcctcgcagc tcggcgacgg cggagccctg  12000
gcggcggcgt acggcgcgca ctaccacggc gccgcctggc cgaccatcgc gttccagccg  12060
ggcgccgcca gcacaggcct gtaccacccg tacgcgcagc agccaatgcg cggcggcggg  12120
tggtgcaagc aggagcagga ccacgcggtg atcgcggccg cgcacagcct gcaggacctc  12180
caccacctga acctgggcgc ggccggcgcg cacgactttt tctcggcagg gcagcaggcc  12240
gccgccgctg cgatgcacgg cctgggtagc atcgacagtg cgtcgctcga gcacagcacc  12300
ggctccaact ccgtcgtcta caacggcggg gtcggcgaca gcaacggcgc cagcgccgtc  12360
ggcggcagtg gcggtggcta catgatgccg atgagcgctg ccggagcaac cactacatcg  12420
gcaatggtga gccacgagca ggtgcatgca cgggcctacg acgaagccaa gcaggctgct  12480
cagatggggt acgagagcta cctggtgaac gcggagaaca atggtggcgg aaggatgtct  12540
gcatggggga ctgtcgtgtc tgcagccgcg gcggcagcag caagcagcaa cgacaacatg  12600
gccgccgacg tcggccatgg cggcgcgcag ctcttcagtg tctggaacga cacttaagcg  12660
tacgtgccgg cctggctctc cgaaagggcg aattccagca cactggcggc cgttactaga  12720
cccaacctag acttgtccat cttctggatt ggccaactta attaatgtat gaaataaaag  12780
gatgcacaca tagtgacatg ctaatcacta taatgtgggc atcaaagttg tgtgttatgt  12840
gtaattacta gttatctgaa taaaagagaa agagatcatc catatttctt atcctaaatg  12900
aatgtcacgt gtctttataa ttctttgatg aaccagatgc atttcattaa ccaaatccat  12960
atacatataa atattaatca tatataatta atatcaattg ggttagcaaa acaaatctag  13020
tctaggtgtg ttttgcgaat gcggccgcca ccgcggtgga gctcgaattc cggtcgatcc  13080
gatgatcctg agcttctagc ataacttcgt atagcataca ttatacgaag ttatccagat  13140
ctgcccacag caagcacggc ctgaaggagg agatgaccat gaagtaccac atggagggct  13200
gcgtgaacgg ccacaagttc gtgatcaccg gcgagggcat cggctacccc ttcaagggca  13260
agcagaccat caacctgtgc gtgatcgagg gcggccccct gcccttcagc gaggacatcc  13320
tgagcgccgg cttcaagtac ggcgaccgga tcttcaccga gtacccccag gacatcgtgg  13380
actacttcaa gaacagctgc cccgccggct acacctgggg ccggagcttc ctgttcgagg  13440
acggcgccgt gtgcatctgt aacgtggaca tcaccgtgag cgtgaaggag aactgcatct  13500
accacaagag catcttcaac ggcgtgaact tccccgccga cggccccgtg atgaagaaga  13560
tgaccaccaa ctgggaggcc agctgcgaga agatcatgcc cgtgcctaag cagggcatcc  13620
tgaagggcga cgtgagcatg tacctgctgc tgaaggacgg cggccggtac cggtgccagt  13680
tcgacaccgt gtacaaggcc aagagcgtgc ccagcaagat gcccgagtgg cacttcatcc  13740
agcacaagct gctgcgggag gaccggagcg acgccaagaa ccagaagtgg cagctgaccg  13800
agcacgccat cgccttcccc agcgccctgg cctgaagcgg ccgcaaccta gacttgtcca  13860
tcttctggat tggccaactt aattaatgta tgaaataaaa ggatgcacac atagtgacat  13920
gctaatcact ataatgtggg catcaaagtt gtgtgttatg tgtaattact agttatctga  13980
ataaaagaga aagagatcat ccatatttct tatcctaaat gaatgtcacg tgtctttata  14040
attctttgat gaaccagatg catttcatta accaaatcca tatacatata aatattaatc  14100
atatataatt aatatcaatt gggttagcaa aacaaatcta gtctaggtgt gttttgcgaa  14160
ttagcttggt cacccggtcc gggcctagaa ggccagcttg cggccgcccc gggcaacttt  14220
attatacaaa gttgatagat atcggaccga ttaaacttta attcggtccg aagcttgcat  14280
gcctgcagtg cagcgtgacc cggtcgtgcc cctctctaga gataatgagc attgcatgtc  14340
taagttataa aaaattacca catatttttt ttgtcacact tgtttgaagt gcagtttatc  14400
tatctttata catatattta aactttactc tacgaataat ataatctata gtactacaat  14460
aatatcagtg ttttagagaa tcatataaat gaacagttag acatggtcta aaggacaatt  14520
gagtattttg acaacaggac tctacagttt tatcttttta gtgtgcatgt gttctccttt  14580
tttttgcaa atagcttcac ctatataata cttcatccat tttattagta catccattta  14640
gggtttaggg ttaatggttt ttatagacta atttttttag tacatctatt ttattctatt  14700
ttagcctcta aattaagaaa actaaaactc tattttagtt tttttattta ataatttaga  14760
tataaaatag aataaaataa agtgactaaa aattaaacaa atacccttta agaaattaaa  14820
aaaactaagg aaacattttt cttgtttcga gtagataatg ccagcctgtt aaacgccgtc  14880
gacgagtcta acggacacca accagcgaac cagcagcgtc gcgtcgggcc aagcgaagca  14940
gacggcacgg catctctgtc gctgcctctg gacccctctc gagagttccg ctccaccgtt  15000
ggacttgctc cgctgtcggc atccagaaat tgcgtggcgg agcggcagac gtgagccggc  15060
acggcaggcg gcctcctcct cctctcacgg caccggcagc tacgggggat tcctttccca  15120
ccgctccttc gctttccctt cctcgcccgc cgtaataaat agacaccccc tccacaccct  15180
ctttccccaa cctcgtgttg ttcggagcgc acacacacac aaccagatct cccccaaatc  15240
cacccgtcgg cacctccgct tcaaggtacg ccgctcgtcc tccccccccc ccctctctac  15300
cttctctaga tcggcgttcc ggtccatgca tggttagggc ccggtagttc tacttctgtt  15360
catgtttgtg ttagatccgt gtttgtgtta gatccgtgct gctagcgttc gtacacggat  15420
```

```
gcgacctgta cgtcagacac gttctgattg ctaacttgcc agtgtttctc tttggggaat  15480
cctgggatgg ctctagccgt tccgcagacg ggatcgattt catgattttt tttgtttcgt  15540
tgcatagggt ttggtttgcc cttttccttt atttcaatat atgccgtgca cttgtttgtc  15600
gggtcatctt ttcatgcttt tttttgtctt ggttgtgatg atgtggtctg gttgggcggt  15660
cgttctagat cggagtagaa ttctgtttca aactacctgg tggatttatt aattttggat  15720
ctgtatgtgt gtgccataca tattcatagt tacgaattga agatgatgga tggaaatatc  15780
gatctaggat aggtatacat gttgatgcgg gttttactga tgcatataca gagatgcttt  15840
ttgttcgctt ggttgtgatg atgtggtgtg gttgggcggt cgttcattcg ttctagatcg  15900
gagtagaata ctgtttcaaa ctacctggtg tatttattaa ttttggaact gtatgtgtgt  15960
gtcatacatc ttcatagtta cgagtttaag atggatggaa atatcgatct aggataggta  16020
tacatgttga tgtgggtttt actgatgcat atacatgatg gcatatgcag catctattca  16080
tatgctctaa ccttgagtac ctatctatta taataaacaa gtatgtttta taattatttt  16140
gatcttgata tacttggatg atggcatatg cagcagctat atgtggattt ttttagccct  16200
gccttcatac gctatttatt tgcttggtac tgtttctttt gtcgatgctc accctgttgt  16260
ttggtgttac ttctgcaggt cgactttaac ttagcctagg atccacacga caccatgtcc  16320
cccgagcgcc gccccgtcga gatccgcccg gccaccgccg ccgacatggc cgccgtgtgc  16380
gacatcgtga accactacat cgagacctcc accgtgaact tccgcaccga gccgcagacc  16440
ccgcaggagt ggatcgacga cctggagcgc ctccaggacc gctacccgtg gctcgtggcc  16500
gaggtggagg gcgtggtggc cggcatcgcc tacgccggcc cgtggaaggc ccgcaacgcc  16560
tacgactgga ccgtggagtc caccgtgtac gtgtcccacc gccaccagcg cctcggcctc  16620
ggctccaccc tctacaccca cctcctcaag agcatggagg cccagggctt caagtccgtg  16680
gtggccgtga tcggcctccc gaacgacccg tccgtgcgcc tccacgaggc cctcggctac  16740
accgcccgcg gcaccctccg cgccgccggc tacaagcacg gcggctggca cgacgtcggc  16800
ttctggcagc gcgacttcga gctgccggcc ccgccgcgcc cggtgcgccc ggtgacgcag  16860
atctgagtcg aaacctagac ttgtccatct tctggattgg ccaacttaat taatgtatga  16920
aataaaagga tgcacacata gtgacatgct aatcactata atgtgggcat caaagttgtg  16980
tgttatgtgt aattactagt tatctgaata aaagagaaag agatcatcca tatttcttat  17040
cctaaatgaa tgtcacgtgt ctttataatt ctttgatgaa ccagatgcat ttcattaacc  17100
aaatccatat acatataaat attaatcata tataattaat atcaattggg ttagcaaaac  17160
aaatctagtc taggtgtgtt ttgcgaattg cggccgccac cgcggtggag ctcgaattca  17220
ttccgattaa tcgtggcctc ttgctcttca ggatgaagag ctatgtttaa acgtgcaagc  17280
gctactagac aattcagtac attaaaaacg tccgcaatgt gttattaagt tgtctaagcg  17340
tcaatttgtt tacaccacaa tatatcctgc cac                              17373
```

```
SEQ ID NO: 112          moltype = DNA  length = 11111
FEATURE                 Location/Qualifiers
misc_feature            1..11111
                        note = PHP46446
misc_feature            1249..1756
                        note = Rab17 promoter
misc_feature            1757..1851
                        note = Rab17 5' UTR
misc_feature            1890..1913
                        note = attB1
misc_feature            1939..3156
                        note = Cre
misc_feature            3165..3188
                        note = attB2
misc_feature            3203..3520
                        note = PinII term
source                  1..11111
                        mol_type = other DNA
                        organism = synthetic construct
SEQUENCE: 112
gtttacccgc caatatatcc tgtcaaacac tgatagttta aactgaaggc gggaaacgac  60
aatctgatca tgagcggaga attaagggag tcacgttatg acccccgccg atgacgcggg  120
acaagccgtt ttacgtttgg aactgacaga accgcaacgt tgaaggagcc actcagcaag  180
ctggtacgat tgtaatacga ctcactatag ggcgaattga gcgctgttta aacgctcttc  240
aactggaaga gcggttacta ccggctggat ggcggggcct tgatcgtgca ccgccggcgt  300
ccggactaac taactagtcg agctagttac cctatgaggt gacatgaagc gctcacggtt  360
actatgacgg ttagcttcac gactgttggt ggcagtagcg tacgacttag ctatagttcc  420
ggacttaccg ggcccaccgg tggtaccgag ctcgtttaaa cgctcttcaa ctggaagagc  480
ggttaccaga gctggtcacc tttgtccacc aagatggaac tggcgcggct aatttaaatc  540
ctgaggatat cgctatcaac tttgtataga aaagttgggc cgaattcgag ctcggtacgg  600
ccagaatggc ccggaccggg ttaccgaatt cgagctcggt accctgggat ccgatatcga  660
tgggccctgg ccgaagcttg gtcacccggt ccgggcctag aaggccagct tcaagtttgt  720
acaaaaaagc aggctccggc cagaatggcc cggaccgggt taccgaattc gagctcggta  780
ccctgggatc cgatatcgat gggccctggc cgaagcttgg tcacccggtc cgggcctaga  840
aggccgatct cccgggcacc cagctttctt gtacaaagtg gccgttaacg gatcggccag  900
aatggcccgg accgggttac cgaattcgag ctcggtaccc tgggatccga tatcgatggg  960
ccctggccga agcttggtca cccggtccgg gcctagaagg ccagcttcgg ccgccccggg  1020
caactttatt atacaaagtt gatagataaa tcctgaggat ctggtcttcc taaggacccg  1080
ggatatcgga ccgattaaac tttaattcgg tccgacctgg tggcgccgct agcgtatacg  1140
aagttcctat tccgaagttc ctattctcca gaaagtatag gaacttctgt acaataactt  1200
cgtatagcat acattatacg aagttatgcc cgggctggta tttcaaaact atagtatttt  1260
aaaattgcat taacaaacat gtcctaattg gtactcctga gatactatac cctcctgttt  1320
taaaatagtt ggcattatcg aattatcatt ttactcttta atgttttctc ttcttttaat  1380
atattttatg aattttaatg tattttaaaa tgttatgcag ttcgctctgg actttctgc   1440
tgcgcctaca cttgggtgta ctgggcctaa attcagcctg accgaccgcc tgcattgaat  1500
```

-continued

```
aatggatgag caccggtaaa atccgcgtac ccaactttcg agaagaaccg agacgtggcg  1560
ggccgggcca ccgacgcacg gcaccagcga ctgcacacgt cccgccggcg tacgtgtacg  1620
tgctgttccc tcactggccg cccaatccac tcatgcatgc ccacgtacac ccctgccgtg  1680
gcgcgcccag atcctaatcc tttcgccgtt ctgcacttct gctgcctata aatggcggca  1740
tcgaccgtca cctgcttcac caccggcgag ccacatcgag aacacgatcg agcacacaag  1800
cacgaagact cgtttaggag aaaccacaaa ccaccaagcc gtgcaagcac caagcttggt  1860
cacccggtcc gggcctagaa ggccagcttc aagtttgtac aaaaaagcag gcttcgaagg  1920
agatagaacc gatccaccat gtccaacctg ctcacggttc accagaacct tccggctctt  1980
ccagtggacg cgacgtccga tgaagtcagg aagaacctca tggacatgtt ccgcgacagg  2040
caagcgttca gcgagcacac ctggaagatg ctgctctccg tctgccgctc ctgggctgca  2100
tggtgcaagc tgaacaacag gaagtggttc cccgctgagc ccgaggacgt gagggattac  2160
cttctgtacc tgcaagcgcg aggtttgttt ctgcttctac ctttgatata tatataataa  2220
ttatcattaa ttagtagtaa tataatattt caaatatttt tttcaaaata aaagaatgta  2280
gtatatagca attgcttttc tgtagtttat aagtgtgtat attttaattt ataacttttc  2340
taatatatga ccaaaacatg gtgatgccta ggtctggcag tgaagaccat ccagcaacac  2400
cttggacaac tgaacatgct tcacaggcgc tccggcctcc cgcgccccag cgactcgaac  2460
gccgtgagcc tcgtcatgcg ccgcatcagg aaggaaaacg tcgatgccgg cgaaagggca  2520
aagcaggccc tcgcgttcga gaggaccgat ttcgaccagg tccgcagcct gatggagaac  2580
agcgacaggt gccaggacat taggaacctg gcgttcctcg gaattgcata caacacgctc  2640
ctcaggatcg cggaaattgc ccgcattcgc gtgaaggaca ttagccgcac cgacggcggc  2700
aggatgctta tccacattgg caggaccaag acgctcgttt ccaccgcagg cgtcgaaaag  2760
gccctcagcc tcggagtgac caagctcgtc gaacgctgga tctccgtgtc cggcgtcgcg  2820
gacgacccaa acaactacct cttctgccgc gtccgcaaga acggggtggc tgcccctagc  2880
gccaccagcc aactcagcac gagggccttg gaaggtattt tcgaggccac ccaccgcctg  2940
atctacggcg cgaaggatga cagcggtcaa cgctacctcg catggtccgg gcactccgcc  3000
cgcgttggag ctgctaggga catggcccgc gccggtgttt ccatccccga aatcatgcag  3060
gcgggtggat ggacgaacgt gaacattgtc atgaactaca ttcgcaacct tgacagcgag  3120
acgggcgcaa tggttcgcct cctggaagat ggtgactgag ctagacccag ctttcttgta  3180
caaagtggcc gttaacggat ccagacttgt ccatcttctg gattggccaa cttaattaat  3240
gtatgaaata aaaggatgca cacatagtga catgctaatc actataatgt gggcatcaaa  3300
gttgtgtgtt atgtgtaatt actagttatc tgaataaaag agaaagagat catccatatt  3360
tcttatccta aatgaatgtc acgtgtcttt ataattcttt gatgaaccag atgcatttca  3420
ttaaccaaat ccatatacat ataaatatta atcatatata attaatatca attgggttag  3480
caaaacaaat ctagtctagg tgtgttttgc gaattgcggc aagcttcggc cgccccagct  3540
tggtcacccg gtccgggcct agaaggccga tctcccgggc acccagcttt cttgtacaaa  3600
gtggccgtta acggatcggc cagaatggcc cggaccgggt taccgaattc gagctcggta  3660
ccctgggatc gaccgaagct gaccgaagct tgcggccgca cactgatagt ttaaactgaa  3720
ggcgggaaac gacaatctga tcatgagcgg agaattaagg gagtcacgtt atgacccccg  3780
ccgatgacgc gggacaagcc gttttacgtt tggaactgac agaaccgcaa cgttgaagga  3840
gccactcagc cgcgggtttc tggagtttaa tgagctaagc acatacgtca gaaaccatta  3900
ttgcgcgttc aaaagtcgcc taaggtcact atcagctagc aaatatttct tgtcaaaaat  3960
gctccactga cgttccataa attcccctcg gtatccaatt agagtctcat attcactctc  4020
ccgggggatc tcgactctag aggatcgctc aggaaggccg ctgagataga ggcatggcgg  4080
ccaatgcggg cggcggtgga gcgggaggag gcagcggcag cggcagcgtg gctgcgccgg  4140
cggtgtgccg ccccagcggc tcgcggtgga cgccgacgcc ggagcagatc aggatgctga  4200
aggagctcta ctacggctgc ggcatccggt cgcccagctc ggagcagatc cagcgcatca  4260
ccgccatgct gcggcagcac ggcaagatcg agggcaagaa cgtcttctac tggttccaga  4320
accacaaggc ccgcgagcgc cagaagcgcc gcctcaccag cctcgacgtc aacgtgcccg  4380
ccgccggcgc ggccgacgcc accaccagcc aactcggcgt cctctcgctg tcgtcgccgc  4440
cgccttcagg cgcggcgcct ccctcgccca ccctcggctt ctacgccgcc ggcaatggcg  4500
gcggatcggc tgtgctgctg gacacgagtt ccgactgggg cagcagcggc gctgccatgg  4560
ccaccgagac atgcttcctg caggactaca tgggcgtgac ggacacgggc agctcgtcgc  4620
agtggccacg cttctcgtcg tcggacacga taatggcggc ggccgcggcg cgggcggcga  4680
cgacgcgggc gcccgagacg ctccctctct tcccgacctg cggcgacgac ggcggcagcg  4740
gtagcagcag ctacttgccg ttctggggtg ccgcgtccac aactgccggc gccacttctt  4800
ccgttgcgat ccagcagcaa caccagctgc aggagcagta cagcttttac agcaacagca  4860
acagcaccca gctggccggc accggcaacc aagacgtatc ggcaacagca gcagcagccg  4920
ccgccctgga gctgagcctc agctcatggt gctcccctta ccctgctgca gggagtatgt  4980
gagagcaacg cgagctgcca ctgctcttca ctgatgtctc tggaatggaa ggaggaggaa  5040
gtgagcatag cgttggtgcg ttgctgtcaa gggcgaattc acatggttaa cctagacttg  5100
tccatcttct ggattggcca acttaattaa tgtatgaaat aaaaggatgc acacatagtg  5160
acatgctaat cactataatg tgggcatcaa agttgtgtgt tatgtgtaat tactagttat  5220
ctgaataaaa gagaaagaga tcatccatat ttcttatcct aaatgaatgt cacgtgtctt  5280
tataattctt tgatgaacca gatgcatttc attaaccaaa tccatataca tataaatatt  5340
aatcatatat aattaatatc aattgggtta gcaaaacaaa tctagtctag gtgtgttttg  5400
cgaatgcggc cgcgactcta gatcataatc agccatacca cattcgaatg tgagttgatc  5460
cccggcggtg tcccccactg aagaaactat gtgctgtagt atagccgctg cccgctggct  5520
agctagctag ttgagtcatt tagcggcgat gattgagtaa taatgtgtca cgcatcacca  5580
tgcatgggtg gcagtgtcag tgtgagcaat gacctgaatg aacaattgaa atgaaaagaa  5640
aaaagtattg ttccaaatta aacgttttaa ccttttaata ggtttataca ataattgata  5700
tatgttttct gtatatgtct aatttgttat catccattta gatatagaca aaaaaaatct  5760
aagaactaaa acaaatgcta atttgaaatg aagggagtat atattgggat aatgtcgatg  5820
agatccctcg taatatcacc gacatcacac gtgtccagtt aatgtatcag tgatacgtgt  5880
attcacattt gttgcgcgta ggcgtaccca acaattttga tcgactatca gaaagtcaac  5940
ggaagcgagt cgacctcgag gggggcccg gtaccaagat atcaaccgcg gaaagatcta  6000
agcatgcaag ggcccaagtc gacctgcaga agcttcggtc cgggcctaga aggccgatct  6060
cccgggcacc cagctttctt gtacaaagtg gccgttaacg gatcggccag aatggcccgg  6120
accgggttac cgaattcgag ctcggtaccc tgggatcgac cgaagcttgc atgcctgcag  6180
tgcagcgtga cccggtcgtg cccctctcta gagataatga gcattgcatg tctaagttat  6240
```

```
aaaaaattac cacatatttt ttttgtcaca cttgtttgaa gtgcagttta tctatcttta  6300
tacatatatt taaactttac tctacgaata atataatcta tagtactaca ataatatcag  6360
tgttttagag aatcatataa atgaacagtt agacatggtc taaaggacaa ttgagtattt  6420
tgacaacagg actctacagt tttatctttt tagtgtgcat gtgttctcct tttttttgc  6480
aaatagcttc acctatataa tacttcatcc attttattag tacatccatt tagggtttag  6540
ggttaatggt ttttatagac taattttttt agtacatcta ttttattcta ttttagcctc  6600
taaattaaga aaactaaaac tctattttag tttttttatt taataattta gatataaaat  6660
agaataaaat aaagtgacta aaaattaaac aaataccctt taagaaatta aaaaaactaa  6720
ggaaacattt ttcttgtttc gagtagataa tgccagcctg ttaaacgccg tcgacgagtc  6780
taacggacac caaccagcga accagcagcg tcgcgtcggg ccaagcgaag cagacggcac  6840
ggcatctctg tcgctgcctc tggacccctc tcgagagttc cgctccaccg ttggacttgc  6900
tccgctgtcg gcatccagaa attgcgtggc ggagcggcag acgtgagccg gcacggcagg  6960
cggcctcctc ctcctctcac ggcaccggca gctacggggg attcctttcc caccgctcct  7020
tcgctttccc ttcctcgccc gccgtaataa atagacaccc cctccacacc ctctttcccc  7080
aacctcgtgt tgttcggagc gcacacacac acaaccagat ctcccccaaa tccacccgtc  7140
ggcacctccg cttcaaggta cgccgctcgt cctccccccc cccctctct accttctcta  7200
gatcggcgtt ccggtccatg catggttagg gcccggtagt tctacttctg ttcatgtttg  7260
tgttagatcc gtgtttgtgt tagatccgtg ctgctagcgt tcgtacacgg atgcgacctg  7320
tacgtcagac acgttctgat tgctaacttg ccagtgtttc tctttgggga atcctgggat  7380
ggctctagcc gttccgcaga cgggatcgat ttcatgattt tttttgtttc gttgcatagg  7440
gtttggtttg ccctttttcct ttatttcaat atatgccgtg cacttgtttg tcgggtcatc  7500
ttttcatgct ttttttgtc ttggttgtga tgatgtggtc tggttgggcg gtcgttctag  7560
atcggagtag aattctgttt caaactacct ggtggattta ttaattttgg atctgtatgt  7620
gtgtgccata catattcata gttacgaatt gaagatgatg gatggaaata tcgatctagg  7680
ataggtatac atgttgatgc gggttttact gatgcatata cagagatgct ttttgttcgc  7740
ttggttgtga tgatgtggtg tggttgggcg gtcgttcatt cgttctagat cggagtagaa  7800
tactgtttca aactacctgg tgtatttatt aattttggaa ctgtatgtgt gtgtcataca  7860
tcttcatagt tacgagttta agatggatgg aaatatcgat ctaggatagg tatacatgtt  7920
gatgtgggtt ttactgatgc atatacatga tggcatatgc agcatctatt catatgctct  7980
aaccttgagt acctatctat tataataaac aagtatgttt tataattatt ttgatcttga  8040
tatacttgga tgatggcata tgcagcagct atatgtggat ttttttagcc ctgccttcat  8100
acgctattta tttgcttggt actgtttctt ttgtcgatgc tcaccctgtt gtttggtgtt  8160
acttctgcag gtcgactcta gaggatccat ggccactgtg aacaactggc tcgctttctc  8220
cctctccccg caggagctgc cgccctccca gacgacggac tccacactca tctcggccgc  8280
caccgccgac catgtctccg gcgatgtctg cttcaacatc ccccaagatt ggagcatgag  8340
gggatcagag ctttcggcgc tcgtcgcgga gccgaagctg gaggacttcc tcggcggcat  8400
ctccttctcc gagcagcatc acaaggccaa ctgcaacatg atacccagca ctagcagcac  8460
agtttgctac gcgagctcag gtgctagcac cggctaccat caccagctgt accaccagcc  8520
caccagctca gcgctccact tcgcggactc cgtaatggtg gcctcctcgg ccggtgtcca  8580
cgacggcggt gccatgctca gcgcggccgc cgctaacggt gtcgctggcg ctgccagtgc  8640
caacggcggc ggcatcgggc tgtccatgat taagaactgg ctgcggagcc aaccggcgcc  8700
catgcagccg agggtggcgg cggctgaggg cgcgcagggg ctctctttgt ccatgaacat  8760
ggcggggacg acccaaggcg ctgctggcat gccacttctc gctggagagc gcgcacgggc  8820
gcccgagagt gtatcgacgt cagcacaggg tggagccgtc gtcgtcacgg cgccgaagga  8880
ggatagcggt ggcagcggtg ttgccggcgc tctagtagcc gtgagcacgg acacgggtgg  8940
cagcggcggc gcgtcggctg acaacacggc aaggaagacg gtggacacgt tcgggcagcg  9000
cacgtcgatt taccgtggcg tgacaaggca tagatggact gggagatatg aggcacatct  9060
ttgggataac agttgcagaa gggaagggca aactcgtaag ggtcgtcaag tctatttagg  9120
tggctatgat aaagaggaga aagctgctag ggcttatgat cttgctgctc tgaagtactg  9180
gggtgccaca acaacaacaa attttccagt gagtaactac gaaaaggagc tcgaggacat  9240
gaagcacatg acaaggcagg agtttgtagc gtctctgaga aggaagagca gtggtttctc  9300
cagaggtgca tccatttaca ggggagtgac taggcatcac caacatggaa gatggcaagc  9360
acggattgga cgagttgcag ggaacaagga tctttacttg ggcaccttca gcacccagga  9420
ggaggcagcg gaggcgtacg acatcgcggc gatcaagttc cgcggcctca acgccgtcac  9480
caacttcgac atgagccgct acgacgtgaa gagcatcctg gacagcagcg ccctccccat  9540
cggcagcgcc gccaagcgcc tcaaggaggc cgaggccgca gcgtccgcgc agcaccacca  9600
cgccggcgtg gtgagctacg acgtcggccg catcgcctcg cagctcggcg acggcggagc  9660
cctggcggcg gcgtacggcg cgcactacca cggcgccgcc tggccgacca tcgcgttcca  9720
gccgggcgcc gccagcacag gcctgtacca cccgtacgcg cagcagccaa tgcgcggcgg  9780
cgggtggtgc aagcaggagc aggaccacgc ggtgatcgcg gccgcgcaca gcctgcagga  9840
cctccaccac ctgaacctgg gcgcggccgg cgcgcacgac tttttctcgg cagggcagca  9900
ggccgccgcc gctgcgatgc acggcctggg tagcatcgac agtgcgtcgc tcgagcacag  9960
caccggctcc aactccgtcg tctacaacgg cggggtcggc gacagcaacg gcgccagcgc  10020
cgtcggcggc agtggcggtg gctacatgat gccgatgagc gctgccggag caaccactac  10080
atcggcaatg gtgagccacg agcaggtgca tgcacgggcc tacgacgaag ccaagcaggc  10140
tgctcagatg ggtacgaga gctacctggt gaacgcggag aacaatggtg gcggaaggat  10200
gtctgcatgg gggactgtcg tgtctgcagc cgcggcggca gcagcaagca gcaacgacaa  10260
catggccgcc gacgtcggcc atggcggcgc gcagctcttc agtgtctgga acgacactta  10320
agcgtacgtg ccggcctggc tctccgaaag ggcgaattcc agcacactgg cggccgttac  10380
tagacccaac ctagacttgt ccatcttctg gattggccaa cttaattaat gtatgaaata  10440
aaaggatgca cacatagtga catgctaatc actataatgt gggcatcaaa gttgtgtgtt  10500
atgtgtaatt actagttatc tgaataaaag agaaagagat catccatatt tcttatccta  10560
aatgaatgtc acgtgtcttt ataattcttt gatgaaccag atgcatttca ttaaccaaat  10620
ccatatacat ataaatatta atcatatata attaatatca attgggttag caaaacaaat  10680
ctagtctagg tgtgttttgc gaattagctt ggtcacccgg tccgggccta gaaggccagc  10740
ttcggccgcc ccgggcaact ttattataca aagttgatag atcgaataac ttcgtatagc  10800
atacattata cgaagttatc ctgagctgat tccgatgact tcgtaggttc ctagctcaag  10860
ccgctcgtgt ccaagcgtca cttacgatta gctaatgatt acggcatcta ggaccgacta  10920
gctaactaac tagtacgtag aattgtagaa ttaattcatt ccgattaatc gtggcctctt  10980
```

```
gctcttcagg atgaagagct atgtttaaac gtgcaagcgc tactagacaa ttcagtacat  11040
taaaaacgtc cgcaatgtgt tattaagttg tctaagcgtc aatttgttta caccacaata  11100
tatcctgcca c                                                       11111

SEQ ID NO: 113          moltype = DNA  length = 10477
FEATURE                 Location/Qualifiers
misc_feature            1..10477
                        note = PHP48733
misc_feature            1306..1813
                        note = Rab17 promoter
misc_feature            1814..1908
                        note = Rab17 5' UTR
misc_feature            1947..1970
                        note = attB1
misc_feature            1996..3213
                        note = Cre
misc_feature            3222..3245
                        note = attB2
misc_feature            3260..3577
                        note = PinII term
source                  1..10477
                        mol_type = other DNA
                        organism = synthetic construct
SEQUENCE: 113
gtttacccgc caatatatcc tgtcaaacac tgatagttta aactgaaggc gggaaacgac  60
aatctgatca tgagcggaga attaagggag tcacgttatg acccccgccg atgacgcggg  120
acaagccgtt ttacgtttgg aactgacaga accgcaacgt tgaaggagcc actcagcaag  180
ctggtacgat tgtaatacga ctcactatag ggcgaattga gcgctgttta aacgctcttc  240
aactggaaga gcggttacta ccggctggat ggcggggcct tgatcgtgca ccgccggcgt  300
ccggactaac taactagtcg agctagttac cctatgaggt gacatgaagc gctcacggtt  360
actatgacgg ttagcttcac gactgttggt ggcagtagcg tacgacttag ctatagttcc  420
ggacttaccg ggcccaccgg tggtaccgag ctcgtttaaa cgctcttcaa ctggaagagc  480
ggttaccaga gctggtcacc tttgtccacc aagatggaac tggcgcggct aatttaaatc  540
ctgaggatat cgctatcaac tttgtataga aaagttgggc cgaattcgag ctcggtacgg  600
ccagaatggc ccggaccggg ttaccgaatt cgagctcggt accctgggat ccgatatcga  660
tgggccctgg ccgaagcttg gtcacccggt ccgggcctag aaggccagct tcaagtttgt  720
acaaaaaagc aggctccggc cagaatggcc cggaccgggt taccgaattc gagctcggta  780
ccctgggatc cgatatcgat gggccctggc cgaagcttgg tcacccggtc cgggcctaga  840
aggccgatct cccgggcacc cagctttctt gtacaaagtg gccgttaacg gatcggccag  900
aatggcccgg accgggttac cgaattcgag ctcggtaccc tgggatccga tatcgatggg  960
ccctggccga agcttggtca cccggtccgg gcctagaagg ccagcttcgg ccgcccccggg  1020
caactttatt atacaaagtt gatagataaa tcctgaggat ctggtcttcc taaggacccg  1080
ggatatcgga ccgattaaac tttaattcgg tccgacctgg tggcgccgct agcataactt  1140
cgtatagcat acattatacg aagttatcca tatctgaccg gcttaccgaa tgcgtgctcg  1200
ctaccctggg atgcgatttc gatggcccct ggccgaagct ggcatatcgc tatgaccggg  1260
ttagccaatt cgacctcgct accctgggga tgctacgtaa cgcgtctata gtattttaaa  1320
attgcattaa caaacatgtc ctaattggta ctcctgagat actataccct cctgttttaa  1380
aatagttggc attatcgaat tatcatttta ctttttaatg ttttctcttc ttttaatata  1440
ttttatgaat tttaatgtat tttaaaatgt tatgcagttc gctctggact tttctgctgc  1500
gcctacactt gggtgtactg ggcctaaatt cagcctgacc gaccgcctgc attgaataat  1560
ggatgagcac cggtaaaatc cgcgtaccca actttcgaga agaaccgaga cgtggcgggc  1620
cgggccaccg acgcacggca ccagcgactg cacacgtccc gccggcgtac gtgtacgtgc  1680
tgttccctca ctggccgccc aatccactca tgcatgccca cgtacacccc tgccgtggcg  1740
cgcccagatc ctaatccttt cgccgttctg cacttctgct gcctataaat ggcggcatcg  1800
accgtcacct gcttcaccac cggcgagcca catcgagaac acgatcgagc acacaagcac  1860
gaagactcgt ttaggagaaa ccacaaacca ccaagccgtg caagcaccag gcttgggcac  1920
ccgctccggg cttagaaggc cagcttcaag tttgtacaaa aaagcaggct tcgaaggaga  1980
tagaaccgat ccaccatgtc caacctgctc acggttcacc agaaccttcc ggctcttcca  2040
gtggacgcga cgtccgatga agtcaggaag aacctcatgg acatgttccg cgacaggcaa  2100
gcgttcagcg agcacacctg gaagatgctg ctctccgtct gccgctcctg ggctgcatgg  2160
tgcaagctga acaacaggaa gtggttcccc gctgagcccg aggacgtgag ggattacctt  2220
ctgtacctgc aagcgcgagg tttgtttctg cttctacctt tgatatatat ataataatta  2280
tcattaatta gtagtaatat aatatttcaa atattttttt caaaataaaa gaatgtagta  2340
tatagcaatt gcttttctgt agtttataag tgtgtatatt ttaatttata acttttctaa  2400
tatatgacca aaacatggtg atgcctaggt ctggcagtga agaccatcca gcaacacctt  2460
ggacaactga acatgcttca caggcgctcc ggcctcccgc gccccagcga ctcgaacgcc  2520
gtgagcctcg tcatgcgccg catcaggaag gaaaacgtcg atgccggcga aagggcaaag  2580
caggccctcg cgttcgagag gaccgatttc gaccaggtcc gcagcctgat ggagaacagc  2640
gacaggtgcc aggacattag gaacctggcg ttcctcggaa ttgcatacaa cacgctcctc  2700
aggatcgcgg aaattgcccg cattcgcgtg aaggacatta gccgcaccga cggcggcagg  2760
atgcttatcc acattggcag gaccaagacg ctcgtttcca ccgcaggcgt cgaaaaggcc  2820
ctcagcctcg gagtgaccaa gctcgtcgaa cgctggatct ccgtgtccgg cgtcgcggac  2880
gacccaaaca actacctctt ctgccgcgtc cgcaagaacg gggtggctgc ccctagcgcc  2940
accagccaac tcagcacgag ggccttggaa ggtattttcg aggccaccca ccgcctgatc  3000
tacggcgcga aggatgacag cggtcaacgc tacctcgcat ggtccgggca ctccgcccgc  3060
gttggagctg ctagggacat ggcccgcgcc ggtgtttcca tccccgaaat catgcaggcg  3120
ggtggatgga cgaacgtgaa cattgtcatg aactacattc gcaaccttga cagcgagacg  3180
ggcgcaatgg ttcgcctcct ggaagatggt gactgagcta gacccagctt tcttgtacaa  3240
agtggccgtt aacggatgca gacttgtcca tcttctggat tggccaactt aattaatgta  3300
```

-continued

```
tgaaataaaa ggatgcacac atagtgacat gctaatcact ataatgtggg catcaaagtt  3360
gtgtgttatg tgtaattact agttatctga ataaaagaga aagagatcat ccatatttct  3420
tatcctaaat gaatgtcacg tgtctttata attctttgat gaaccagatg catttcatta  3480
accaaatcca tatacatata aatattaatc atatataatt aatatcaatt gggttagcaa  3540
aacaaatcta gtctaggtgt gttttgcgaa ttgcggcaag gttgcgcccg ccccagcttg  3600
gtcagccgct ccgggcttag aaggccgatc tcgcgggcac ccagctttct tctacaaagt  3660
ggccgtttac ggatcggcta gaatgtcccg caccggctta ccgatttgca cctcgctacc  3720
ctgggttcga ccgaagctga ccgatgcttg cgcccgctcg cgaggccggc cacactgata  3780
gtttaaactg aaggcgggaa acgacaatct gatcatgagc ggagaattaa gggagtcacg  3840
ttatgacccc cgccgatgac gcgggacaag ccgttttacg tttggaactg acagaaccgc  3900
aacgattgaa ggagccactc agccgcgggt ttctggagtt taatgagcta agcacatacg  3960
tcagaaacca ttattgcgcg ttcaaaagtc gcctaaggtc actatcagct agcaaatatt  4020
tcttgtcaaa aatgctccac tgacgttcca taaattcccc tcggtatcca attagagtct  4080
catattcact ctcccggcgg atctcgactc tagaggatcg ctcaggaagg ccgctgagat  4140
agagccatgg cggccaatgc gggcggcggt ggagcgggag gaggcagcgg cagcggcagc  4200
gtggctgcgc cggcggtgtg ccgcccccagc ggctcgcggt ggacgccgac gccggagcag  4260
atcaggatgc tgaaggagct ctactacggc tgcggcatcc ggtcgcccag ctcggagcag  4320
atccagcgca tcaccgccat gctgcggcag cacggcaaga tcgagggcaa gaacgtcttc  4380
tactggttcc agaaccacaa ggcccgcgag cgccagaagc gccgcctcac cagcctcgac  4440
gtcaacgtgc ccgccgccgg cgcggccgac gccaccacca gccaactcgg cgtcctctcg  4500
ctgtcgtcgc cgccgccttc aggcgcggcg cctccctcgc ccaccctcgg cttctacgcc  4560
gccggcaatg gcggcggatc ggctgtgctg ctggacacga gttccgactg gggcagcagc  4620
ggcgctgcta tggccaccga gacatgcttc ctgcaggact acatgggcgt gacggacacg  4680
ggcagctcgt cgcagtggcc acgcttctcg tcgtcggaca cgataatggc ggcggccgcg  4740
gcgcgggcgg cgacgacgcg ggcgcccgag acgctccctc tcttcccgac ctgcggcgac  4800
gacggcggca gcggtagcag cagctacttg ccgttctggg gtgccgcgtc cacaactgcc  4860
ggcgccactt cttccgttgc gatccaacag caacaccagc tgcaggagca gtacagcttt  4920
tacagcaaca gcaacagcac ccagctggcc ggcaccggca accaagacgt atcggcaaca  4980
gcagcagcag ccgccgccct ggagctgagc ctcagctcat ggtgctcccc ttaccctgct  5040
gcagggagta tgtgagagca acgcgagctg ccactgctct tcactgatgt ctctggaatg  5100
gaaggaggag gaagtgagca tagcgttggt gcgttgctgt caagggcgaa ttgtaccaca  5160
tggttaacct agacttgtcc atcttctgga ttggccaact taattaatgt atgaaataaa  5220
aggatgcaca catagtgaca tgctaatcac tataatgtgg gcatcaaagt tgtgtgttat  5280
gtgtaattac tagttatctg aataaaagag aaagagatca tccatatttc ttatcctaaa  5340
tgaatgtcac gtgtctttat aattctttga tgaaccagat gcatttcatt aaccaaatcc  5400
atatacatat aaatattaat catatataat taatatcaat tgggttagca aaacaaatct  5460
agtctaggtg tgttttgcgg gtaccattta aattgcgccc gccacggccg tggaggtcgt  5520
attccggtca gcttgcatcc ctgcagtgca gcgtgacccg gtcgtgcccc tctctagaga  5580
taatgagcat tgcatgtcta agttataaaa aattaccaca tattttttt gtcacacttg  5640
tttgaagtgc agtttatcta tctttataca tatatttaaa ctttactcta cgaataatat  5700
aatctatagt actacaataa tatcagtgtt ttagagaatc atataaatga acagttagac  5760
atggtctaaa ggacaattga gtattttgac aacaggactc tacagtttta tcttttagt  5820
gtgcatgtgt tctcctttt ttttgcaaat agcttcacct atataatact tcatccattt  5880
tattagtaca tccatttagg gtttagggtt aatggttttt atagactaat ttttttagta  5940
catctatttt attctatttt agcctctaaa ttaagaaaac taaaactcta ttttagtttt  6000
tttatttaat aatttagata taaaatagaa taaaataaag tgactaaaaa ttaaacaaat  6060
accctttaag aaattaaaaa aactaaggaa acatttttct tgtttcgagt agataatgcc  6120
agcctgttaa acgccgtcga cgagtctaac ggacaccaac cagcgaacca gcagcgtcgc  6180
gtcgggccaa gcgaagcaga cggcacggca tctctgtcgc tgcctctgga cccctctcga  6240
gagttccgct ccaccgttgg acttgctccg ctgtcggcat ccagaaattg cgtggcggag  6300
cggcagacgt gagccggcac ggcaggcggc ctcctcctcc tctcacggca ccggcagcta  6360
cgggggattc ctttcccacc gctccttcgc tttcccttcc tcgcccgccg taataaatag  6420
acaccccctc cacaccctct ttccccaacc tcgtgttgtt cggagcgcac acacacacaa  6480
ccagatctcc cccaaatcca cccgtcggca cctccgcttc aaggtacgcc gctcgtcctc  6540
cccccccccc ctctctacct tctctagatc ggcgttccgg tccatgcatg gttagggccc  6600
ggtagttcta cttctgttca tgtttgtgtt agatccgtgt ttgtgttaga tccgtgctgc  6660
tagcgttcgt acacggatgc gacctgtacg tcagacacgt tctgattgct aacttgccag  6720
tgtttctctt tggggaatcc tgggatggct ctagccgttc cgcagacggg atcgatttca  6780
tgattttttt tgtttcgttg catagggttt ggtttgccct tttcctttat ttcaatatat  6840
gccgtgcact tgtttgtcgg gtcatctttt catgcttttt tttgtcttgg ttgtgatgat  6900
gtggtctggt tgggcggtcg ttctagatcg gagtagaatt ctgtttcaaa ctacctggtg  6960
gatttattaa ttttggatct gtatgtgtgt gccatacata ttcatagtta cgaattgaag  7020
atgatggatg gaaatatcga tctaggatag gtatacatgt tgatgcgggt tttactgatg  7080
catatacaga gatgcttttt gttcgcttgg ttgtgatgat gtggtgtggt tgggcggtcg  7140
ttcattcgtt ctagatcgga gtagaatact gtttcaaact acctggtgta tttattaatt  7200
ttggaactgt atgtgtgtgt catacatctt catagttacg agtttaagat ggatggaaat  7260
atcgatctag gataggtata catgttgatg tgggttttac tgatgcatat acatgatggc  7320
atatgcagca tctattcata tgctctaacc ttgagtacct atctattata ataaacaagt  7380
atgttttata attattttga tcttgatata cttggatgat ggcatatgca gcagctatat  7440
gtggattttt ttagccctgc cttcatacgc tatttatttg cttggtactg tttcttttgt  7500
cgatgctcac cctgttgttt ggtgttactt ctgcaggtcg actctagagg atccatggcc  7560
actgtgaaca actggctcgc tttctccctc tccccgcagg agctgccgcc ctcccagacg  7620
acggactcca cactcatctc ggccgccacc gccgaccatg tctccggcga tgtctgcttc  7680
aacatccccc aagattggag catgaggga tcagagcttt cggcgctcgt cgcggagccg  7740
aagctggagg acttcctcgg cggcatctcc ttctccgagc agcatcacaa ggccaactgc  7800
aacatgatac ccagcactag cagcacagtt tgctacgcga gctcaggtgc tagcaccggc  7860
taccatcacc agctgtacca ccagcccacc agctcagcgc tccacttcgc ggactccgta  7920
atggtggctt cctcggccgg tgtccacgac ggcggtgcca tgctcagcgc ggccgccgct  7980
aacggtgtcg ctggcgctgc cagtgccaac ggcggcggca tcgggctgtc catgattaag  8040
```

```
aactggctgc ggagccaacc ggcgcccatg cagccgaggg tggcggcggc tgagggcgcg  8100
caggggctct ctttgtccat gaacatggcg gggacgaccc aaggcgctgc tggcatgcca  8160
cttctcgctg gagagcgcgc acgggcgccc gagagtgtat cgacgtcagc acagggtgga  8220
gccgtcgtcg tcacggcgcc gaaggaggat agcggtggca gcggtgttgc cggcgctcta  8280
gtagccgtga gcacggacac gggtggcagc ggcggcgcgt cggctgacaa cacggcaagg  8340
aagacggtgg acacgttcgg gcagcgcacg tcgatttacc gtggcgtgac aaggcataga  8400
tggactggga gatatgaggc acatctttgg gataacagtt gcagaaggga agggcaaact  8460
cgtaagggtc gtcaagtcta tttaggtggc tatgataaag aggagaaagc tgctagggct  8520
tatgatcttg ctgctctgaa gtactggggt gccacaacaa caacaaattt tccagtgagt  8580
aactacgaaa aggagctcga ggacatgaag cacatgacaa ggcaggagtt tgtagcgtct  8640
ctgagaagga agagcagtgg tttctccaga ggtgcatcca tttacagggg agtgactagg  8700
catcaccaac atggaagatg gcaagcacgg attggacgag ttgcagggaa caaggatctt  8760
tacttgggca ccttcagcac ccaggaggag gcagcggagg cgtacgacat cgcggcgatc  8820
aagttccgcg gcctcaacgc cgtcaccaac ttcgacatga gccgctacga cgtgaagagc  8880
atcctggaca gcagcgccct ccccatcggc agcgccgcca agcgcctcaa ggaggccgag  8940
gccgcagcgt ccgcgcagca ccaccacgcc ggcgtggtga gctacgacgt cggccgcatc  9000
gcctcgcagc tcggcgacgg cggagccctg gcggcggcgt acggcgcgca ctaccacggc  9060
gccgcctggc cgaccatcgc gttccagccg ggcgccgcca gcacaggcct gtaccacccg  9120
tacgcgcagc agccaatgcg cggcggcggg tggtgcaagc aggagcagga ccacgcggtg  9180
atcgcggccg cgcacagcct gcaggacctc caccacctga acctgggcgc ggccggcgcg  9240
cacgactttt tctcggcagg gcagcaggcc gccgccgctg cgatgcacgg cctgggtagc  9300
atcgacagtg cgtcgctcga gcacagcacc ggctccaact ccgtcgtcta caacggcggg  9360
gtcggcgaca gcaacggcgc cagcgccgtc ggcggcagtg gcggtggcta catgatgccg  9420
atgagcgctg ccggagcaac cactacatcg gcaatggtga gccacgagca ggtgcatgca  9480
cgggcctacg acgaagccaa gcaggctgct cagatggggt acgagagcta cctggtgaac  9540
gcggagaaca atggtggcgg aaggatgtct gcatggggga ctgtcgtgtc tgcagccgcg  9600
gcggcagcag caagcagcaa cgacaacatg gccgccgacg tcgggcatgg cggcgcgcag  9660
ctcttcagtg tctggaacga cacttaagcg tacgtgccgg cctggctctc cgaaagggcg  9720
tattccagca cactggcggc cgttactaga cccaacctag acttgtccat cttctggatt  9780
ggccaactta attaatgtat gaaataaaag gatgcacaca tagtgacatg ctaatcacta  9840
taatgtgggc atcaaagttg tgtgttatgt gtaattacta gttatctgaa taaaagagaa  9900
agagatcatc catatttctt atcctaaatg aatgtcacgt gtctttataa ttctttgatg  9960
aaccagatgc atttcattaa ccaaatccat atacatataa atattaatca tatataatta  10020
atatcaattg ggttagcaaa acaaatctag tctaggtgtg ttttgcgaat tagcttggtc  10080
acccggtccg ggcctagaag gccagcttcg gccgccccgg gcaactttat tatacaaagt  10140
tgatagatcg aataacttcg tatagcatac attatacgaa gttatcctga gctgattccg  10200
atgacttcgt aggttcctag ctcaagccgc tcgtgtccaa gcgtcactta cgattagcta  10260
atgattacgg catctaggac cgactagcta actaactagt acgtagaatt gtagaattaa  10320
ttcattccga ttaatcgtgg cctcttgctc ttcaggatga agagctatgt ttaaacgtgc  10380
aagcgctact agacaattca gtacattaaa aacgtccgca atgtgttatt aagttgtcta  10440
agcgtcaatt tgtttacacc acaatatatc ctgccac                           10477

SEQ ID NO: 114         moltype = DNA  length = 978
FEATURE                Location/Qualifiers
source                 1..978
                       mol_type = genomic DNA
                       organism = Zea mays
CDS                    1..978
SEQUENCE: 114
atggcggcca atgcgggcgg cggtggagcg ggaggaggca gcggcagcgg cagcgtggct  60
gcgccggcgg tgtgccgccc cagcggctcg cggtggacgc cgacgccgga gcagatcagg  120
atgctgaagg agctctacta cggctgcggc atccggtcgc ccagctcgga gcagatccag  180
cgcatcaccg ccatgctgcg gcagcacggc aagatcgagg gcaagaacgt cttctactgg  240
ttccagaacc acaaggcccg cgagcgccag aagcgccgcc tcaccagcct cgacgtcaac  300
gtgcccgccg ccggcgcggc cgacgccacc accagccaac tcggcgtcct ctcgctgtcg  360
tcgccgcctt caggcgcggc gcctccctcg cccaccctcg gcttctacgc cgccggcaat  420
ggcggcggat cggctgggct gctggacacg agttccgact ggggcagcag cggcgctgct  480
atggccaccg agacatgctt cctgcaggac tacatgggcg tgacggacac gggcagctcg  540
tcgcagtggc catgcttctc gtcgtcggac acgataatgg cggcggcggc ggccgcggcg  600
cgggtggcga cgacgcgggc gcccgagaca ctccctctct tcccgacctg cggcgacgac  660
gacgacgacg acagccagcc cccgccgcgg ccgcggcacg cagtcccagt cccggcaggc  720
gagaccatcc gcggcggcgg cggcagcagc agcagctact tgccgttctg ggtgccggt   780
gccgcgtcca caactgccgg cgccacttct tccgttgcga tccagcagca acaccagctg  840
caggagcagt acagctttta cagcaacagc acccagctgg ccggcaccgg cagccaagac  900
gtatcggctt cagcggccgc cctggagctg agcctcagct catggtgctc cccttaccct  960
gctgcaggga gcatgtga                                                978

SEQ ID NO: 115         moltype = AA  length = 325
FEATURE                Location/Qualifiers
source                 1..325
                       mol_type = protein
                       organism = Zea mays
SEQUENCE: 115
MAANAGGGGA GGGSGSGSVA APAVCRPSGS RWTPTPEQIR MLKELYYGCG IRSPSSEQIQ  60
RITAMLRQHG KIEGKNVFYW FQNHKARERQ KRRLTSLDVN VPAAGAADAT TSQLGVLSLS  120
SPPSGAAPPS PTLGFYAAGN GGGSAGLLDT SSDWGSSGAA MATETCFLQD YMGVTDTGSS  180
SQWPCFSSSD TIMAAAAAAA RVATTRAPET LPLFPTCGDD DDDDSQPPPR PRHAVPVPAG  240
ETIRGGGGSS SSYLPFWGAG AASTTAGATS SVAIQQQHQL QEQYSFYSNS TQLAGTGSQD  300
VSASAAALEL SLSSWCSPYP AAGSM                                        325
```

```
SEQ ID NO: 116          moltype = DNA  length = 3727
FEATURE                 Location/Qualifiers
source                  1..3727
                        mol_type = genomic DNA
                        organism = Zea mays
SEQUENCE: 116
atggccactg tgaacaactg gctcgctttc tccctctccc cgcaggagct gccgccctcc  60
cagacgacgg actccacact catctcggcc gccaccgccg accatgtctc cggcgatgtc  120
tgcttcaaca tcccccaaga ttggagcatg aggggatcag agctttcggc gctcgtcgcg  180
gagccgaagc tggaggactt cctcggcggc atctccttct ccgagcagca tcacaaggcc  240
aactgcaaca tgatacccag cactagcagc acagtttgct acgcgagctc aggtgctagc  300
accggctacc atcaccagct gtaccaccag cccaccagct cagcgctcca cttcgcggac  360
tccgtaatgg tggcctcctc ggccggtgtc cacgacggcg gtgccatgct cagcgcggcc  420
gccgctaacg gtgtcgctgg cgctgccagt gccaacggcg gcggcatcgg gctgtccatg  480
atcaagaact ggctgcggag ccaaccggcg cccatgcagc cgagggcggc ggcggctgag  540
ggcgcgcagg ggctctcttt gtccatgaac atggcgggga cgacccaagg cgctgctggc  600
atgccacttc tcgctggaga gcgcgcacgg gcgcccgaga gtgtatcgac gtcagcacag  660
ggtggtgccg tcgtcgtcac ggcgccgaag gaggatagcg gtggcagcgg tgttgccggt  720
gctctagtag ccgtgagcac ggacacgggt ggcagcggcg gcgcgtcggc tgacaacacg  780
gcaaggaaga cggtggacac gttcgggcag cgcacgtcga tttaccgtgg cgtgacaagg  840
taagggggtg gatgaatcaa gtaatcatga aattttgaaa agccattggt aatccaagga  900
actgtcatga tagatttgat tgcatctaga catagttccg atcgaatcaa atgagtaggc  960
caatgtttag cctttgggga tctcgctgat tattaggagt accattgtat tgggcatggt  1020
tgtggtatag tagtagacaa ttaacaaaaa agctaccact tttcaattat tttaggcata  1080
gatggactgg gagatatgag gcacatcttt gggataacag ttgcagaagg gaaggacaaa  1140
ctcgtaaggg tcgtcaaggt atacaaatat aatgcaacat actgtcatta aatatgcttt  1200
ttctgtaagt tttatatttc accaatgatg ttgttattgt taactgacat tgcttcacac  1260
tatcaatttt ggattcggcg caatgatttg tgggattgaa atcaaatctt aaatctacag  1320
tctatttagg tacgcgattt ctctccaact acttaatgca gttcgtttct ccctataacc  1380
atattctttt tcatctcaaa tctcactcga ctcttttttt ttatcttgta ccattgatag  1440
gtggctatga taaagaggag aaagctgcta gggcttatga tcttgctgct ctgaagtact  1500
ggggtcccac aacaacaaca aatttcccag tatgtatatg tagcatccag ttttacttta  1560
ctgaagttca tatctcgtta tgggctataa atatgtatca aatgatgtcc attagctagt  1620
gatctggagt gaaggttcta tagtaaagta aacgctgtgt gcggagtgca gtagcgggag  1680
gtctctcttc tattttctaa gaaaaatgga cattgctgaa attgtactta aagtcgttta  1740
ttttattttt ttgtatttcc aggtgagtaa ctacgaaaag gagctcgagg acatgaagca  1800
catgacaagg caggagtttg tagcgtctct gagaaggtcg gtctaacagc attgattaat  1860
cagtaccacc tctactgaat aaaatctgct gctatttgtt aaattttgag cgaggtcaac  1920
tgcatatttg atcttattag accactgtat atgaatgcag gaagagcagt ggtttctcca  1980
gaggtgcatc catttacagg ggagtgacta ggtatgaatt catatagcta agaacttaac  2040
atcaacaaaa acacacatac acttgggttg atgtggcaga tgcatgcatg gattgaaaat  2100
gtgtgcatgt tgttttactt gaactcgatc tctgtattta taggcatcac caacatggaa  2160
gatggcaagc acggattgga cgagttgcag ggaacaagga tctttacttg ggcaccttca  2220
gtaagtagca aacaaatatg tttttgcatt gtatatagag taccccttgaa tatataaatt  2280
caccacatat acaagcaagt tacagtcaac taacacaatc tcaacgcaac gagaaagcaa  2340
gtgttccagc tgatagtaca catttgtaga ccagccgcat atggttgttt tgtatgcatg  2400
atgactatta aaaatgtgac catcgcatta agtcatgcaa agttgcattg cagtagtaca  2460
ttgcttagtg catgctcctc aagtggcttt tttcaaacct gatcccatgt ctggtgctat  2520
tgttgtctcc cattcacccg tgcatcaggt caaaatagta ccatgcctga ataagaaaaa  2580
caaaacgagc atgcactggc agcagcagac taataaacaa agttccagca tttactaata  2640
aactaattag gctacagcat ccaaaagatt cttccaatta agccacaact gttcatgcat  2700
acatgggtat gccacccagg ataccatgca tgcaccgtgc acgacgaaag cgaaacgctc  2760
gttctcggaa tattagaact gacgaagccg agtgcaacct tctgtcgtgg atgcaggcac  2820
ccaggaggag gcagcggagg cgtacgacat cgcggcgatc aagttccgcg gcctaaacgc  2880
cgtcaccaac ttcgacatga gccgctacga cgtgaagagc atcctggaca gcagcgccct  2940
ccccatcggc agcgccgcca agcgcctcaa ggaggccgag gccgcagcgt ccgcgcagca  3000
ccaccacgcc ggcgtggtga gttacgacgt cggccgcatc gcctcgcagc tcggcgacgg  3060
cggagccctg gcggcggcgt acggcgcgca ctaccacggc gccgcctggc cgaccatcgc  3120
gttccagccg ggcgccgcca ccacaggcct gtaccacccg tacgcgcagc agccaatgcg  3180
cggcggcggg tggtgcaagc aggagcagga ccacgcggtg atcgcggccg cgcacagcct  3240
gcaggacctc caccacctga acctgggcgc ggccggcgcg cacgactttt tctcggcagg  3300
gcagcaggcc gccgccgctg cgatgcacgg cctgggtagc atcgacagtg cgtcgctcga  3360
gcacagcacc ggctccaact ccgtcgtcta caacggcggg gtcggcgaca gcaacggcgc  3420
cagcgccgtc ggcggcagtg gcggtggcta catgatgccg atgagcgctg ccggagcaac  3480
cactacatcg gcaatggtga gccacgagca ggtgcatgca cgggcctacg acgaagccaa  3540
gcaggctgct cagatggggt acgagagcta cctggtgaac gcggagaaca atggtggcgg  3600
aaggatgtct gcatggggga ctgtcgtgtc tgcagccgcg gcggcagcag caagcagcaa  3660
cgacaacatg gccgccgacg tcggccatgg cggcgcgcag ctcttcagtg tctggaacga  3720
cacttaa                                                            3727

SEQ ID NO: 117          moltype = DNA  length = 4325
FEATURE                 Location/Qualifiers
source                  1..4325
                        mol_type = genomic DNA
                        organism = Oryza sativa
SEQUENCE: 117
atgcatatct atcttatata aatatctacc agtgatactg ttgcttagtg ctccaaacct  60
ctcttgacct cttcttcttc ttctcagtta gcttagctta agcttcccct aaccttgagc  120
```

```
tcaccacaac aatggcgact tgatctaaca gagcttaacc aagtagcaaa tcatacatat  180
aaccatagct taattcgcat tgaatcttgt cttgttcagt gtgaatcatc aaccatggcc  240
accatgaaca actggctggc cttctccctc tccccgcagg atcagctccc gccgtctcag  300
accaactcca ctctcatctc cgccgccgcc accaccacca ccgccggcga ctcctccacc  360
ggcgacgtct gcttcaacat cccccaaggt aattaagctc accaatcgat gcatgcattc  420
atgagctaga tatagctagt gttggttggg atttgaagag acatgcatgt ttgattgatt  480
gatttgatgt gcagattgga gcatgagggg atcggagctc tcggcgctcg tcgccgagcc  540
gaagctggag gacttcctcg gcggcatctc cttctcggag cagcagcatc atcacggcgg  600
caagggcggc gtgatcccga gcagcgccgc cgcttgctac gcgagctccg gcagcagcgt  660
cggctacctg taccctcctc caagctcatc ctcgctccag ttcgccgact ccgtcatggt  720
ggccacctcc tcgcccgtcg tcgcccacga cggcgtcagc ggcggcggca tggtgagcgc  780
cgccgccgcc gcggcggcca gtggcaacgg cggcattggc ctgtccatga tcaagaactg  840
gctccggagc cagccggcgc cgcagccggc gcaggcgctg tctctgtcca tgaacatggc  900
ggggacgacg acggcgcagg gcggcggcgc catggcgctc ctcgccggcg caggggagcg  960
aggccggacg acgcccgcgt cagagagcct gtccacgtcg gcgcacggag cgacgacggc  1020
gacgatggct ggtggtcgca aggagattaa cgaggaaggc agcggcagcg ccggcgccgt  1080
ggttgccgtc ggctcggagt caggcggcag cggcgccgtg gtggaggccg gcgcggcggc  1140
ggcggcggcg aggaagtccg tcgacacgtt cggccagaga acatcgatct accgcggcgt  1200
gacaaggtat ttagggtgca attaattaat catctatcta tattttgctc aaaaaagttc  1260
atctactagc tagcttagca caaatcatca tcagtgtaat catatatatt ctttgatgat  1320
ttaactgtgt tgcatgaatt cattcctatt tgatgtttgt gatttggatc ccattttcta  1380
ggatagctat ataggtgata gattgatcat tagatttgta ggatttatca ttatgtcatt  1440
attatgtggg acatgattgt tgtgattaac aaagttgtaa tatcttttgg tttggttata  1500
ggcatagatg gacagggagg tatgaggctc atctttggga caacagctgc agaagagagg  1560
gccaaactcg caagggtcgt caaggtaggc taactagtgc catttaaatc gattaattgt  1620
ttttttatgc tccaatggcg attgatactg atcttgtttc tttttctaat gatcatttcg  1680
ggatcgaatg atcttcctct gtttgatcga acttggcttt tgaatctaca gtctatctag  1740
gtgagtgaga ttccttgaac ctagatgttc tgtttgcgat gcatgtatat attcggtaga  1800
ttgaattatt tgctgatctt tgctttcttg aagtttaatg atcttataaa ttgtaatgct  1860
gataggtggt tatgacaaag aggaaaaagc tgctagagct tatgatttgg ctgctctcaa  1920
atactggggc ccgacgacga cgacaaattt tccggtgtgt ttataattaa tatacagatt  1980
gtgtcacatt gttattttct cactctttta tttgatactg atctagtgta atgatgatta  2040
ctaaaactgt acttaaaggc aatggtttct gtatttttca ggtaaataac tatgaaaagg  2100
agctggagga gatgaagcac atgacaaggc aggagttcgt agcctctttg agaaggttgg  2160
tctctacaat caagatatcc atactatact aattaatttc cttttagatt tatagtaatt  2220
tatctatcgc attgaagtta attaattatc tgatgcttac tgatactaac aaatactgtt  2280
ccttatatgt gcaggaagag cagtggtttc tccagaggtg catccattta ccgtggagta  2340
actaggtaca tatatatatg catcattgta caattaattt ttttaatttt tttagggtaa  2400
aaaatgaaga ctgtgatata gatccattaa tttgatcttg tgtacttgta aatataggca  2460
tcaccagcat gggagatggc aagcaaggat aggaagagtt gcagggaaca aggacctcta  2520
cttgggcacc ttcagtaagt acaaatattc atatttatac tgcaaaacca tataaatcca  2580
tattaataag tatgtccttt ctcattgagt atacaaaata tcatattttc ttggcaagta  2640
caatttattc attcagggca aaatagtagt agtaagaaag aggggtgact cttcaaagaa  2700
cacagagctt acttaagcct gtaactaatt aattaaacta aaaatgtgat ctgcaagtca  2760
tgtcaagttg cattacacca ctaatatata tactctgtgc atgcttgcat gctctcctca  2820
tgtggctagc taccttttca aaccttccat gtctggtgct actcctgtct ccattcacca  2880
ctgcacctgg tcaagatcct cactaattaa gaaacaataa tgcattattt gcagtaaata  2940
atttaactag tgttaatcac attctttgca acacaaacta atcaccaatt aagctagcta  3000
gctagccaaa atgataatct tgcttgcatg cgctaatggt gtgtgtgatg atggtggtgt  3060
cacgcatgca ggcacgcagg aggaggcggc ggaggcgtac gacatcgcgg cgatcaagtt  3120
ccgggggctc aacgccgtca ccaacttcga catgagccgc tacgacgtca agagcatcct  3180
cgacagcgct gccctccccg tcggcaccgc cgccaagcgc ctcaaggacg ccgaggccgc  3240
cgccgcctac gacgtcggcc gcatcgcctc gcacctcggc ggcgacggcg cctacgccgc  3300
gcattacggc caccaccacc actcggccgc cgccgcctgg ccgaccatcg cgttccaggc  3360
ggcggcggcg ccgccgccgc acgccgccgg gctttaccac ccgtacgcgc agccgctgcg  3420
tgggtggtgc aagcaggagc aggaccacgc cgtgatcgcg gcggcgcaca gcctgcagga  3480
tctccaccac ctcaacctcg gcgccgccgc cgccgcgcat gacttcttct cgcaggcgat  3540
gcagcagcag cacggcctcg gcagcatcga caacgcgtcg ctcgagcaca gcaccggctc  3600
caactccgtc gtctacaacg gcgacaatgg cggcggaggc ggcggctaca tcatggcgcc  3660
gatgagcgcc gtgtcggcca cggccaccgc ggtggcgagc agccacgatc acggcggcga  3720
cggcgggaag caggtgcaga tggggtacga cagctacctc gtcggcgcag acgcctacgg  3780
cggcggcggc gccgggagga tgccatcctg ggcgatgacg ccggcgtcgg cgcccggccgc  3840
cacgagcagc agcgacatga ccggagtctg ccatggcgca cagctcttca gcgtctggaa  3900
cgacacataa aaaaaaaact aggttagcca gcttaattag cagggtaaac cactgacaca  3960
attaagccat acttaaatta gggttcatga gatgaccatt aagcaggtta ttatcattaa  4020
tgatgtttaa tttctcaatt agtacttagc tcaaaaggag gggatttctt ctgaaggatg  4080
gtgatggctt gtgaaattga acctggtgtt cttgccatga tttttttttc acaagctgcc  4140
attttggggt tcaggttcag aaggatcctg attattatta accagccata tatatataga  4200
agggtagaaa tggaggtatc ctgcttgtaa attggggcaa tggtagctag agttgatgca  4260
atgaccatgc ttcatgtgat gagaactaat tgtcttcctc tgatcaaatt aagcaggaag  4320
attaa                                                              4325
```

```
SEQ ID NO: 118          moltype = DNA  length = 2079
FEATURE                 Location/Qualifiers
source                  1..2079
                        mol_type = genomic DNA
                        organism = Oryza sativa
CDS                     1..2079
SEQUENCE: 118
```

```
atggccacta tgaacaactg gctcgccttc tcgctctcgc cgcaggacca actcccaccg  60
tcgcagacca atagcactct catctccgct gctgcaacca ccacaaccgc aggcgattcg  120
tcaacgggcg acgtctgctt caacatccct caagactggt ccatgcgcgg aagcgagctt  180
agcgctctcg tcgcggagcc caagttggag gatttcttgg gaggcatctc cttctcggag  240
caacagcatc atcacggcgg aaagggcggt gttatcccaa gctctgctgc cgcatgctat  300
gcaagctccg gctccagcgt gggctacctc taccctccgc cttcatcctc gtcacttcag  360
tttgcagaca gcgtgatggt cgcaacctca tctccagtgg ttgcgcacga tggcgtgagc  420
ggtggcggta tggtctcagc agcagcggct gcagcagctt cgggtaatgg cgggattggc  480
ctctccatga tcaagaactg gctcaggagc caaccggctc cgcaacctgc gcaagcactc  540
agcctgtcga tgaacatggc tggtactact accgctcaag gtggaggcgc aatggcactt  600
ctcgcaggcg ctggcgaaag aggaaggacc acaccagcat ccgagagcct ctctacttcc  660
gcgcacggag ccaccacggc tacaatggct ggcgggagga aagagatcaa cgaggaagga  720
tctggatccg ctggtgccgt ggttgcagtt ggctcagaat caggtggatc cggcgctgtt  780
gttgaagctg gtgccgctgc ggcagcggct cggaagagcg ttgatacttt cggccaaaga  840
acgagcatct acagaggcgt tactcggcac cgctggaccg gcaggtacga ggcacacttg  900
tgggacaaca gctgtcgccg cgagggccaa actaggaagg gaagacaggg aggatatgac  960
aaagaggaga aggctgccag agcgtacgac ctggccgcgt tgaagtactg gggtccaaca  1020
acgacgacca acttcccggt gaacaactac gagaaggagc tggaagagat gaagcacatg  1080
acgcggcagg agttcgtcgc ttctctcagg cgcaagtcat ctggtttctc cagaggtgcg  1140
tcgatctata gaggagttac ccgccaccac cagcacggaa ggtggcaggc aagaatcggg  1200
agagtcgccg gtaacaagga cctgtacttg ggaaccttct cgactcagga ggaggcagcg  1260
gaagcgtatg acattgcggc gatcaagttc cgcggtctca atgccgtgac caacttcgac  1320
atgtcacgct atgatgtcaa gtcgattctg gatagcgctg cgttgcctgt gggaaccgct  1380
gccaaacgcc tcaaggacgc ggaagcagct gccgcgtacg atgttggcag gattgcctca  1440
catctcggtg gagatggagc ttacgctgcc cactacgggc atcatcacca ctctgcagcc  1500
gcagcttggc ctacaatagc attccaagcg gcagcggctc ctcctccaca cgctgctggt  1560
ctttaccatc cgtacgcgca acctctccgc ggttggtgta agcaggaaca agatcatgcg  1620
gtgattgcgg ctgcacacag cttgcaagat ctgcatcacc tcaatctggg agccgcagca  1680
gctgcccatg acttcttctc acaagccatg cagcagcagc atggcctggg cagcatagac  1740
aatgcgtctc tggagcactc caccggatcg aactcggtgg tgtacaatgg agacaacggc  1800
ggaggaggtg gaggttacat catggcacct atgtcagcgg tctctgctac cgctacggcg  1860
gtggcctcat cccacgacca cggtggagac ggcggcaagc aggtccaaat gggctacgac  1920
tcctaccttg tgggagctga cgcttacggc ggaggaggag ctggtcgcat gcctagctgg  1980
gccatgacgc ctgcttctgc tcctgcggct acgagctcgt cggatatgac aggagtgtgt  2040
catggcgccc aactgttctc ggtgtggaat gatacatag                        2079
```

```
SEQ ID NO: 119          moltype = AA  length = 692
FEATURE                 Location/Qualifiers
source                  1..692
                        mol_type = protein
                        organism = Oryza sativa
SEQUENCE: 119
MATMNNWLAF SLSPQDQLPP SQTNSTLISA AATTTTAGDS STGDVCFNIP QDWSMRGSEL  60
SALVAEPKLE DFLGGISFSE QQHHHGGKGG VIPSSAAACY ASSGSSVGYL YPPPSSSSLQ  120
FADSVMVATS SPVVAHDGVS GGGMVSAAAA AAASGNGGIG LSMIKNWLRS QPAPQPAQAL  180
SLSMNMAGTT TAQGGGAMAL LAGAGERGRT TPASESLSTS AHGATTATMA GGRKEINEEG  240
SGSAGAVVAV GSESGGSGAV VEAGAAAAAA RKSVDTFGQR TSIYRGVTRH RWTGRYEAHL  300
WDNSCRREGQ TRKGRQGGYD KEEKAARAYD LAALKYWGPT TTTNFPVNNY EKELEEMKHM  360
TRQEFVASLR RKSSGFSRGA SIYRGVTRHH QHGRWQARIG RVAGNKDLYL GTFSTQEEAA  420
EAYDIAAIKF RGLNAVTNFD MSRYDVKSIL DSAALPVGTA AKRLKDAEAA AAYDVGRIAS  480
HLGGDGAYAA HYGHHHHSAA AAWPTIAFQA AAAPPPHAAG LYHPYAQPLR GWCKQEQDHA  540
VIAAAHSLQD LHHLNLGAAA AAHDFFSQAM QQQHGLGSID NASLEHSTGS NSVVYNGDNG  600
GGGGGYIMAP MSAVSATATA VASSHDHGGD GGKQVQMGYD SYLVGADAYG GGGAGRMPSW  660
AMTPASAPAA TSSSDMTGVC HGAQLFSVWN DT                                692
```

```
SEQ ID NO: 120          moltype = DNA  length = 2088
FEATURE                 Location/Qualifiers
source                  1..2088
                        mol_type = genomic DNA
                        organism = Oryza sativa
CDS                     1..2088
SEQUENCE: 120
atggccacta tgaacaactg gctcgccttc tcgctctcgc cgcaggacca actcccaccg  60
tcgcagacca atagcactct catctccgct gctgcaacca ccacaaccgc aggcgattcg  120
tcaacgggcg acgtctgctt caacatccct caagactggt ccatgcgcgg aagcgagctt  180
agcgctctcg tcgcggagcc caagttggag gatttcttgg gaggcatctc cttctcggag  240
caacagcatc atcacggcgg aaagggcggt gttatcccaa gctctgctgc cgcatgctat  300
gcaagctccg gctccagcgt gggctacctc taccctccgc cttcatcctc gtcacttcag  360
tttgcagaca gcgtgatggt cgcaacctca tctccagtgg ttgcgcacga tggcgtgagc  420
ggtggcggta tggtctcagc agcagcggct gcagcagctt cgggtaatgg cgggattggc  480
ctctccatga tcaagaactg gctcaggagc caaccggctc cgcaacctgc gcaagcactc  540
agcctgtcga tgaacatggc tggtactact accgctcaag gtggaggcgc aatggcactt  600
ctcgcaggcg ctggcgaaag aggaaggacc acaccagcat ccgagagcct ctctacttcc  660
gcgcacggag ccaccacggc tacaatggct ggcgggagga aagagatcaa cgaggaagga  720
tctggatccg ctggtgccgt ggttgcagtt ggctcagaat caggtggatc cggcgctgtt  780
gttgaagctg gtgccgctgc ggcagcggct cggaagagcg ttgatacttt cggccaaaga  840
acgagcatct acagaggcgt tactcggcac cgctggaccg gcaggtacga ggcacacttg  900
tgggacaaca gctgtcgccg cgagggccaa actaggaagg gaagacaggt ctatctagga  960
ggatatgaca aagaggagaa ggctgccaga gcgtacgacc tggccgcgtt gaagtactgg  1020
```

```
ggtccaacaa cgacgaccaa cttcccggtg aacaactacg agaaggagct ggaagagatg  1080
aagcacatga cgcggcagga gttcgtcgct tctctcaggc gcaagtcatc tggtttctcc  1140
agaggtgcgt cgatctatag aggagttacc cgccaccacc agcacggaag gtggcaggca  1200
agaatcggga gagtcgccgg taacaaggac ctgtacttgg gaaccttctc gactcaggag  1260
gaggcagcgg aagcgtatga cattgcggcg atcaagttcc gcggtctcaa tgccgtgacc  1320
aacttcgaca tgtcacgcta tgatgtcaag tcgattctgg atagcgctgc gttgcctgtg  1380
ggaaccgctg ccaaacgcct caaggacgcg gaagcagctg ccgcgtacga tgttggcagg  1440
attgcctcac atctcggtgg agatggagct tacgctgccc actacgggca tcatcaccac  1500
tctgcagccg cagcttggcc tacaatagca ttccaagcgg cagcggctcc tcctccacac  1560
gctgctggtc tttaccatcc gtacgcgcaa cctctccgcg gttggtgtaa gcaggaacaa  1620
gatcatgcgg tgattgcggc tgcacacagc ttgcaagatc tgcatcacct caatctggga  1680
gccgcagcag ctgcccatga cttcttctca caagccatgc agcagcagca tggcctgggc  1740
agcatagaca atgcgtctct ggagcactcc accggatcga actcggtggt gtacaatgga  1800
gacaacggcg gaggaggtgg aggttacatc atggcaccta tgtcagcggt ctctgctacc  1860
gctacggcgg tggcctcatc ccacgaccac ggtggagacg gcggcaagca ggtccaaatg  1920
ggctacgact cctaccttgt gggagctgac gcttacggcg gaggaggagc tggtcgcatg  1980
cctagctggg ccatgacgcc tgcttctgct cctgcggcta cgagctcgtc ggatatgaca  2040
ggagtgtgtc atggcgccca actgttctcg gtgtggaatg atacatag              2088
```

```
SEQ ID NO: 121          moltype = DNA  length = 2133
FEATURE                 Location/Qualifiers
source                  1..2133
                        mol_type = genomic DNA
                        organism = Zea mays
CDS                     1..2133
SEQUENCE: 121
atggccactg tgaacaactg gctcgctttc tccctctccc cgcaggagct gccgccctcc  60
cagacgacgg actccacact catctcggcc gccaccgccg accatgtctc cggcgatgtc  120
tgcttcaaca tcccccaaga ttggagcatg aggggatcag agctttcggc gctcgtcgcg  180
gagccgaagc tggaggactt cctcggcggc atctccttct ccgagcagca tcacaaggcc  240
aactgcaaca tgatacccag cactagcagc acagtttgct acgcgagctc aggtgctagc  300
accggctacc atcaccagct gtaccaccag cccaccagct cagcgctcca cttcgcggac  360
tccgtaatgg tggcctcctc ggccggtgtc cacgacggcg gtgccatgct cagcgcggcc  420
gccgctaacg gtgtcgctgg cgctgccagt gccaacggcg gcggcatcgg gctgtccatg  480
attaagaact ggctgcggag ccaaccggcg cccatgcagc cgagggtggc ggcggctgag  540
ggcgcgcagg ggctctcttt gtccatgaac atggcgggga cgacccaagg cgctgctggc  600
atgccacttc tcgctggaga gcgcgcacgg gcgcccgaga gtgtatcgac gtcagcacag  660
ggtggagccg tcgtcgtcac ggcgccgaag gaggatagcg gtggcagcgg tgttgccggc  720
gctctagtag ccgtgagcac ggacacgggt ggcagcggcg gcgcgtcggc tgacaacacg  780
gcaaggaaga cggtggacac gttcgggcag cgcacgtcga tttaccgtgg cgtgacaagg  840
catagatgga ctgggagata tgaggcacat ctttgggata acagttgcag aagggaaggg  900
caaactcgta agggtcgtca agtctattta ggtggctatg ataaagagga gaaagctgct  960
agggcttatg atcttgctgc tctgaagtac tggggtgcca caacaacaac aaattttcca  1020
gtgagtaact acgaaaagga gctcgaggac atgaagcaca tgacaaggca ggagtttgta  1080
gcgtctctga gaaggaagag cagtggtttc tccagaggtg catccattta caggggagtg  1140
actaggcatc accaacatgg aagatggcaa gcacggattg gacgagttgc agggaacaag  1200
gatctttact tgggcacctt cagcacccag gaggaggcag cggaggcgta cgacatcgcg  1260
gcgatcaagt tccgcggcct caacgccgtc accaacttcg acatgagccg ctacgacgtg  1320
aagagcatcc tggacagcag cgccctcccc atcggcagcg ccgccaagcg cctcaaggag  1380
gccgaggccg cagcgtccgc gcagcaccac cacgccggcg tggtgagcta cgacgtcggc  1440
cgcatcgcct cgcagctcgg cgacggcgga gccctggcgg cggcgtacgg cgcgcactac  1500
cacggcgccg cctggccgac catcgcgttc cagccgggcg ccgccagcac aggcctgtac  1560
cacccgtacg cgcagcagcc aatgcgcggc ggcgggtggt gcaagcagga gcaggaccac  1620
gcggtgatcg cggccgcgca cagcctgcag gacctccacc acctgaacct gggcgcggcc  1680
ggcgcgcacg actttttctc ggcagggcag caggccgccg ccgctgcgat gcacggcctg  1740
ggtagcatcg acagtgcgtc gctcgagcac agcaccggct ccaactccgt cgtctacaac  1800
ggcggggtcg gcgacagcaa cggcgccagc gccgtcggcg gcagtggcgg tggctacatg  1860
atgccgatga gcgctgccgg agcaaccact acatcggcaa tggtgagcca cgagcaggtg  1920
catgcacggg cctacgacga agccaagcag gctgctcaga tggggtacga gagctacctg  1980
gtgaacgcgg agaacaatgg tggcggaagg atgtctgcat gggggactgt cgtgtctgca  2040
gccgcggcgg cagcagcaag cagcaacgac aacatggccg ccgacgtcgg ccatggcggc  2100
gcgcagctct tcagtgtctg gaacgacact taa                              2133
```

```
SEQ ID NO: 122          moltype = AA  length = 710
FEATURE                 Location/Qualifiers
source                  1..710
                        mol_type = protein
                        organism = Zea mays
SEQUENCE: 122
MATVNNWLAF SLSPQELPPS QTTDSTLISA ATADHVSGDV CFNIPQDWSM RGSELSALVA  60
EPKLEDFLGG ISFSEQHHKA NCNMIPSTSS TVCYASSGAS TGYHHQLYHQ PTSSALHFAD  120
SVMVASSAGV HDGGAMLSAA AANGVAGAAS ANGGGIGLSM IKNWLRSQPA PMQPRVAAAE  180
GAQGLSLSMN MAGTTQGAAG MPLLAGERAR APESVSTSAQ GGAVVVTAPK EDSGGSGVAG  240
ALVAVSTDTG GSGGASADNT ARKTVDTFGQ RTSIYRGVTR HRWTGRYEAH LWDNSCRREG  300
QTRKGRQVYL GGYDKEEKAA RAYDLAALKY WGATTTTNFP VSNYEKELED MKHMTRQEFV  360
ASLRRKSSGF SRGASIYRGV TRHHQHGRWQ ARIGRVAGNK DLYLGTFSTQ EEAAEAYDIA  420
AIKFRGLNAV TNFDMSRYDV KSILDSSALP IGSAAKRLKE AEAAASAQHH HAGVVSYDVG  480
RIASQLGDGG ALAAAYGAHY HGAAWPTIAF QPGAASTGLY HPYAQQPMRG GGWCKQEQDH  540
AVIAAAHSLQ DLHHLNLGAA GAHDFFSAGQ QAAAAAMHGL GSIDSASLEH STGSNSVVYN  600
```

-continued

```
GGVGDSNGAS AVGGSGGGYM MPMSAAGATT TSAMVSHEQV HARAYDEAKQ AAQMGYESYL  660
VNAENNGGGR MSAWGTVVSA AAAAAASSND NMAADVGHGG AQLFSVWNDT             710

SEQ ID NO: 123          moltype = DNA  length = 25
FEATURE                 Location/Qualifiers
misc_feature            1..25
                        note = Plasmid linker sequence
source                  1..25
                        mol_type = other DNA
                        organism = synthetic construct
SEQUENCE: 123
tcgaaggaga tagaaccgat ccacc                                        25

SEQ ID NO: 124          moltype =   length =
SEQUENCE: 124
000

SEQ ID NO: 125          moltype = DNA  length = 508
FEATURE                 Location/Qualifiers
source                  1..508
                        mol_type = genomic DNA
                        organism = Zea mays
SEQUENCE: 125
ctatagtatt ttaaaattgc attaacaaac atgtcctaat tggtactcct gagatactat  60
accctcctgt tttaaaatag ttggcattat cgaattatca ttttactttt taatgttttc  120
tcttctttta atatatttta tgaattttaa tgtattttaa aatgttatgc agttcgctct  180
ggacttttct cgtgcgccta cacttgggtg tactgggcct aaattcagcc tgaccgaccg  240
cctgcattga ataatggatg agcaccggta aaatccgcgt acccaacttt cgagaagaac  300
cgagacgtgg cgggccgggc caccgacgca cggcaccagc gactgcacac gtcccgccgg  360
cgtacgtgta cgtgctgttc cctcactggc cgcccaatcc actcatgcat gcccacgtac  420
acccctgccg tggcgcgccc agatcctaat cctttcgccg ttctgcactt ctgctgccta  480
taaatggcgg catcgaccgt cacctgct                                     508

SEQ ID NO: 126          moltype = DNA  length = 558
FEATURE                 Location/Qualifiers
source                  1..558
                        mol_type = genomic DNA
                        organism = Zea mays
SEQUENCE: 126
gtactgtaat atttatatta tatataatta taaactataa tatttcaaaa ctatagtatt  60
ttaaaattgc attaacaaac atgtcctaat tggtactcct gagatactat accctcctgt  120
tttaaaatag ttggcattat cgaattatca ttttactttt taatgttttc tcttctttta  180
atatatttta tgaattttaa tgtattttaa aatgttatgc agttcgctct ggacttttct  240
cgtgcgccta cacttgggtg tactgggcct aaattcagcc tgaccgaccg cctgcattga  300
ataatggatg agcaccggta aaatccgcgt acccaacttt cgagaagaac cgagacgtgg  360
cgggccgggc caccgacgca cggcaccagc gactgcacac gtcccgccgg cgtacgtgta  420
cgtgctgttc cctcactggc cgcccaatcc actcatgcat gcccacgtac acccctgccg  480
tggcgcgccc agatcctaat cctttcgccg ttctgcactt ctgctgccta taaatggcgg  540
catcgaccgt cacctgct                                                558
```